US007045519B2

(12) United States Patent
Nuss et al.

(10) Patent No.: US 7,045,519 B2
(45) Date of Patent: *May 16, 2006

(54) INHIBITORS OF GLYCOGEN SYNTHASE KINASE 3

(75) Inventors: John M. Nuss, Danville, CA (US); Stephen D. Harrison, Albany, CA (US); David B. Ring, Palo Alto, CA (US); Rustum S. Boyce, San Francisco, CA (US); Kirk Johnson, Moraga, CA (US); Keith B. Pfister, San Ramon, CA (US); Savithri Ramurthy, Walnut Creek, CA (US); Lynn Seely, Burlingame, CA (US); Allan S. Wagman, Oakland, CA (US); Manoj C. Desai, Pleasant Hill, CA (US); Barry H. Levine, Lafayette, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/949,035

(22) Filed: Sep. 6, 2001

(65) Prior Publication Data

US 2002/0156087 A1 Oct. 24, 2002

Related U.S. Application Data

(63) Continuation-in-part of application No. 09/336,038, filed on Jun. 18, 1999, now Pat. No. 6,417,185.
(60) Provisional application No. 60/230,480, filed on Sep. 6, 2000, and provisional application No. 60/089,978, filed on Jun. 19, 1998.

(51) Int. Cl.
*A61K 31/506* (2006.01)
*C07D 403/04* (2006.01)

(52) U.S. Cl. .................. 514/235.8; 514/252.4; 514/252.18; 514/252.19; 514/252.2; 514/255.05; 514/263.21; 514/275; 544/122; 544/277; 544/295; 544/296; 544/330; 544/331

(58) Field of Classification Search ............... 544/122, 544/330, 331, 277, 295, 296; 514/235.8, 514/275, 252.4, 252.18, 252.19, 252.2, 255.05, 514/263.21
See application file for complete search history.

(56) References Cited

U.S. PATENT DOCUMENTS

| 4,006,149 | A | 2/1977 | Bonnemann et al. |
|---|---|---|---|
| RE29,640 | E | 5/1978 | Lamm et al. |
| 4,334,912 | A | 6/1982 | Yoshida et al. |
| 4,361,565 | A | 11/1982 | Temple, Jr. et al. |
| 4,532,246 | A | 7/1985 | Ife |
| 4,547,506 | A | 10/1985 | Ife |
| 4,548,940 | A | 10/1985 | Ife |
| 4,554,276 | A | 11/1985 | LaMattina |
| 4,594,421 | A | 6/1986 | Bellani et al. |
| 4,607,106 | A | 8/1986 | Ife |
| 4,659,725 | A | 4/1987 | Ife |
| 4,661,501 | A | 4/1987 | Nakatani et al. |
| 4,665,078 | A | 5/1987 | Sach |
| 4,673,677 | A | 6/1987 | LaMattina |
| 4,711,888 | A | 12/1987 | Walker et al. |
| 4,714,706 | A | 12/1987 | Kisida et al. |
| 4,716,172 | A | 12/1987 | Carmosin et al. |
| 4,745,652 | A | * 5/1988 | Rose et al. ................... 8/409 |
| 4,751,225 | A | 6/1988 | Nishida et al. |
| 4,757,073 | A | 7/1988 | New et al. |
| 4,772,633 | A | 9/1988 | Matsuo et al. |
| 4,791,139 | A | 12/1988 | Bushell et al. |
| 4,814,340 | A | 3/1989 | Kiyoshi et al. |
| 4,835,166 | A | 5/1989 | Kitaura et al. |
| 4,847,259 | A | 7/1989 | Kisida et al. |
| 4,855,286 | A | 8/1989 | Wagner et al. |
| 4,876,256 | A | 10/1989 | Coss et al. |
| 4,879,292 | A | 11/1989 | Nishida et al. |
| 4,898,866 | A | 2/1990 | Schonafinger et al. |
| 4,904,685 | A | 2/1990 | Kitaura et al. |
| 4,906,643 | A | 3/1990 | Van Daele et al. |
| 4,914,116 | A | 4/1990 | Kisida et al. |
| 4,968,340 | A | 11/1990 | Kaku et al. |
| 4,970,222 | A | 11/1990 | Nishida et al. |
| 4,971,982 | A | 11/1990 | Attwood et al. |
| 4,985,560 | A | 1/1991 | Sabb et al. |
| 4,988,700 | A | 1/1991 | Traber et al. |
| 5,001,136 | A | 3/1991 | Walker |

(Continued)

FOREIGN PATENT DOCUMENTS

| DE | 2260827 | 7/1974 |
|---|---|---|
| DE | 2410938 | 9/1974 |

(Continued)

OTHER PUBLICATIONS

US 6,057,286, 5/2000, Harrison et al. (withdrawn)
Cohen and Frame, The renaissance of GSK3, Nature Reviews 2:769–775, 2001.*

(Continued)

*Primary Examiner*—Richard L. Raymond
(74) *Attorney, Agent, or Firm*—Dennis Shelton; Young J. Suh; Alisa A. Harbin

(57) ABSTRACT

New pyrimidine or pyridine based compounds, compositions and methods of inhibiting the activity of glycogen synthase kinase (GSK3) in vitro and of treatment of GSK3 mediated disorders in vivo are provided. The methods, compounds and compositions of the invention may be employed alone, or in combination with other pharmacologically active agents in the treatment of disorders mediated by GSK3 activity, such as diabetes, Alzheimer's disease and other neurodegenerative disorders, obesity, atherosclerotic cardiovascular disease, essential hypertension, polycystic ovary syndrome, syndrome X, ischemia, traumatic brain injury, bipolar disorder, immunodeficiency or cancer.

44 Claims, No Drawings

U.S. PATENT DOCUMENTS

| | | |
|---|---|---|
| 5,002,953 A | 3/1991 | Hindley |
| 5,006,541 A | 4/1991 | Kitaura et al. |
| 5,010,100 A | 4/1991 | Biftu et al. |
| 5,036,088 A | 7/1991 | Kitaura et al. |
| 5,071,860 A | 12/1991 | Alig et al. |
| 5,075,308 A | 12/1991 | Ishikawa et al. |
| 5,082,851 A | 1/1992 | Appelbaum et al. |
| 5,084,456 A | 1/1992 | Guillaumet et al. |
| 5,086,000 A | 2/1992 | Pohlke et al. |
| 5,087,289 A | 2/1992 | Kaku et al. |
| 5,089,514 A | 2/1992 | Hulin |
| 5,118,694 A | 6/1992 | Attwood et al. |
| 5,130,312 A | 7/1992 | Van Daele et al. |
| 5,158,959 A | 10/1992 | Geiger et al. |
| 5,162,362 A | 11/1992 | Geiger et al. |
| 5,194,443 A | 3/1993 | Hindley |
| 5,202,316 A | 4/1993 | Claussner et al. |
| 5,202,321 A | 4/1993 | Hutchinson et al. |
| 5,232,925 A | 8/1993 | Hindley |
| 5,232,945 A | 8/1993 | Hulin |
| 5,250,401 A | 10/1993 | Okada et al. |
| 5,260,445 A | 11/1993 | Hindley |
| 5,302,719 A | 4/1994 | Claussner et al. |
| 5,306,726 A | 4/1994 | Hulin |
| 5,308,840 A | 5/1994 | Sugiyama et al. |
| 5,391,537 A | 2/1995 | Takabe et al. |
| 5,401,766 A | 3/1995 | Geiger et al. |
| 5,403,816 A | 4/1995 | Takabe et al. |
| 5,407,948 A | 4/1995 | Fey et al. |
| 5,411,934 A | 5/1995 | Yoshimura et al. |
| 5,413,999 A | 5/1995 | Vacca et al. |
| 5,418,212 A | 5/1995 | Yoshimura et al. |
| 5,438,074 A | 8/1995 | Hulin |
| 5,478,852 A | 12/1995 | Olefsky et al. |
| 5,521,201 A | 5/1996 | Hindley et al. |
| 5,527,796 A | 6/1996 | Binder et al. |
| 5,534,536 A | 7/1996 | Ohuchida et al. |
| 5,574,031 A | 11/1996 | Abramo et al. |
| 5,589,478 A | 12/1996 | Yamada et al. |
| 5,646,169 A | 7/1997 | Hindley et al. |
| 5,652,240 A | 7/1997 | Abramo et al. |
| 5,654,299 A | 8/1997 | Shenvi et al. |
| 5,658,910 A | 8/1997 | Bjork et al. |
| 5,665,748 A | 9/1997 | Sohda et al. |
| 5,668,140 A | 9/1997 | Schaper et al. |
| 5,688,795 A | 11/1997 | Pfister et al. |
| 5,703,095 A | 12/1997 | Galey et al. |
| 5,708,012 A | 1/1998 | Olefsky |
| 5,726,172 A | 3/1998 | Sparks et al. |
| 5,728,706 A | 3/1998 | Yamada et al. |
| 5,739,333 A | 4/1998 | Yamada et al. |
| 5,741,796 A | 4/1998 | Hartman et al. |
| 5,750,544 A | 5/1998 | Ohuchida et al. |
| 5,753,681 A | 5/1998 | Fujiwara et al. |
| 5,756,525 A | 5/1998 | Hindley et al. |
| 5,760,028 A | 6/1998 | Jadhav et al. |
| 5,760,037 A | 6/1998 | Galey et al. |
| 5,798,375 A | 8/1998 | Tsujita et al. |
| 5,830,896 A | 11/1998 | Perregaard et al. |
| 5,837,707 A | 11/1998 | Perregaard et al. |
| 5,849,914 A | 12/1998 | Dolling et al. |
| 5,859,037 A | 1/1999 | Whitcomb |
| 5,874,451 A | 2/1999 | Glombik et al. |
| 5,902,726 A | 5/1999 | Kliewer et al. |
| 5,916,889 A | 6/1999 | Hohlweg et al. |
| 5,939,439 A | 8/1999 | Anthony et al. |
| 5,942,525 A | 8/1999 | Pennington et al. |
| 5,945,436 A | 8/1999 | Lai et al. |
| 6,020,349 A | 2/2000 | Ankersen et al. |
| 6,024,937 A | 2/2000 | Kasina et al. |
| 6,077,855 A | 6/2000 | Bhatnagar et al. |
| 6,131,402 A * | 10/2000 | Mills, Jr. et al. |
| 6,489,344 B1 * | 12/2002 | Nuss et al. ................. 514/332 |

FOREIGN PATENT DOCUMENTS

| | | |
|---|---|---|
| DE | 2615309 | 3/1977 |
| DE | 2834605 | 2/1980 |
| EP | 0 842 925 A1 | 8/1988 |
| EP | 0 419 035 B1 | 8/1990 |
| EP | 0 446 604 A2 | 2/1991 |
| EP | 0 519 211 A1 | 5/1992 |
| EP | 0 567 133 A1 | 4/1993 |
| EP | 0 576 906 A1 | 6/1993 |
| EP | 0 593 110 A1 | 9/1993 |
| EP | 0 711 757 A1 | 10/1995 |
| EP | 0 710 659 A1 | 11/1995 |
| EP | 0 919 232 A1 | 11/1998 |
| GB | 1384523 | 2/1975 |
| JP | 54041881 | 4/1979 |
| JP | 56139460 | 10/1981 |
| JP | 60036403 | 2/1985 |
| JP | 60038303 | 2/1985 |
| JP | 60215671 | 10/1985 |
| JP | 61001603 | 1/1986 |
| JP | 62051672 | 3/1987 |
| JP | 63270605 | 11/1988 |
| JP | 1228929 | 9/1989 |
| JP | 3034967 | 2/1991 |
| JP | 6041090 | 2/1991 |
| JP | 4001192 | 1/1992 |
| JP | 4078582 | 3/1992 |
| JP | 4261133 | 9/1992 |
| JP | 5158195 | 6/1993 |
| JP | 6041118 | 2/1994 |
| JP | 8062560 | 3/1996 |
| JP | 9059160 | 3/1997 |
| JP | 9151184 | 6/1997 |
| JP | 9157256 | 6/1997 |
| JP | 9194462 | 7/1997 |
| JP | 10029979 | 2/1998 |
| JP | 10072371 | 3/1998 |
| JP | 10226649 | 8/1998 |
| RU | 247954 | 1/1974 |
| WO | WO 88/08416 | 11/1988 |
| WO | WO 91/19702 | 12/1991 |
| WO | WO 92/18498 | 10/1992 |
| WO | WO 93/06118 | 4/1993 |
| WO | WO 93/10254 | 5/1993 |
| WO | WO 93/21166 | 10/1993 |
| WO | WO 94/2001420 | 1/1994 |
| WO | WO 94/05659 | 3/1994 |
| WO | WO 94/12169 | 6/1994 |
| WO | WO 94/13650 | 6/1994 |
| WO | WO 94/25026 | 11/1994 |
| WO | WO 95/03288 | 2/1995 |
| WO | WO 95/07694 | 3/1995 |
| WO | WO 95/07697 | 3/1995 |
| WO | WO 95/21608 | 8/1995 |
| WO | WO 95/30405 | 11/1995 |
| WO | WO 95/31438 | 11/1995 |
| WO | WO95/32710 | 12/1995 |
| WO | WO 9604235 | 2/1996 |
| WO | WO 96/18616 | 6/1996 |
| WO | WO 96/29405 | 9/1996 |
| WO | WO 9705875 A3 | 2/1997 |
| WO | WO 9705875 A2 | 2/1997 |
| WO | WO 97/06167 | 2/1997 |
| WO | WO 97/10819 | 3/1997 |
| WO | WO 97/14681 | 4/1997 |
| WO | WO 97/45141 | 4/1997 |
| WO | WO 97/18811 | 5/1997 |

| | | |
|---|---|---|
| WO | WO 97/22589 | 6/1997 |
| WO | WO 97/22596 | 6/1997 |
| WO | WO 97/23480 | 7/1997 |
| WO | WO 97/24122 | 7/1997 |
| WO | WO 97/25992 | 7/1997 |
| WO | WO 97/36870 | 10/1997 |
| WO | WO 97/40017 A2 | 10/1997 |
| WO | WO 97/40017 A3 | 10/1997 |
| WO | WO 97/31907 | 12/1997 |
| WO | WO 98/02159 | 1/1998 |
| WO | WO 98/02183 | 2/1998 |
| WO | WO 98/05331 | 2/1998 |
| WO | WO 98/15537 | 4/1998 |
| WO | WO 98/15539 | 4/1998 |
| WO | WO 98/16528 A1 | 4/1998 |
| WO | WO 98/17267 | 4/1998 |
| WO | WO 98/20871 | 5/1998 |
| WO | WO 98/24780 A3 | 6/1998 |
| WO | WO 98/24780 A2 | 6/1998 |
| WO | WO 98/24782 A3 | 6/1998 |
| WO | WO 98/24782 A2 | 6/1998 |
| WO | WO 98/25598 | 6/1998 |
| WO | WO 98/25598 A2 | 6/1998 |
| WO | WO 98/28319 | 7/1998 |
| WO | WO 98/29120 | 7/1998 |
| WO | WO 98/36755 | 8/1998 |
| WO | WO 98/37073 | 8/1998 |
| WO | WO 98/37877 | 9/1998 |
| WO | WO 98/38163 | 9/1998 |
| WO | WO 98/39006 | 9/1998 |
| WO | WO 98/42340 | 10/1998 |
| WO | WO 98/43081 | 10/1998 |
| WO | WO 98/44797 | 10/1998 |
| WO | WO 98/45267 | 10/1998 |
| WO | WO 98/51305 | 11/1998 |
| WO | WO 98/55122 | 12/1998 |
| WO | WO 98/57634 | 12/1998 |
| WO | WO 98/57635 | 12/1998 |
| WO | WO 98/57636 | 12/1998 |
| WO | WO 98/57649 | 12/1998 |
| WO | WO 99/00372 | 1/1999 |
| WO | WO 99/03476 | 1/1999 |
| WO | WO 99/03478 | 1/1999 |
| WO | WO 99/08660 | 2/1999 |
| WO | WO 99/18943 | 4/1999 |
| WO | WO 99/18944 | 4/1999 |
| WO | WO 99/25346 | 5/1999 |
| WO | WO 99/27365 | 6/1999 |
| WO | WO 99/27906 | 6/1999 |
| WO | WO 99/30739 | 6/1999 |
| WO | WO 99/42436 | 8/1999 |
| WO | WO 99/48529 | 9/1999 |
| WO | WO 99/65897 | 12/1999 |

OTHER PUBLICATIONS

CAS printout for Parnell et al. (J. Chem. Soc., 1962).*

Aplin, et al., "Effect of Increased Glycogen Synthase Kinase–3 Activity Upon the Maturation of the Amyloid Precursor Protein in Transfected Cells," *Molecular Neuroscience* 8(3):639–643, 1997.

Aplin, et al., "In Vitro Phosphorylation of the Cytoplasmic Domain of the Amyloid Precursor Protein by Glycogen Synthase Kinase–3β," *J. Neurochem.* 67(2):699–707, 1996.

Avruch, "Insulin Signal Transduction Through Protein Kinase Cascades," *Molecular and Cellular Biochemistry* 182:31–48, 1998.

Baum, et al., "Overexpressed Tau Protein in Cultured Cells Is Phosphorylated Without Formation of PHF Implication of Phosphoprotein Phosphatase Involvement," *Brain Res. Mol. Brain Res.* 34:1–17, 1995.

Beals, et al., "Nuclear Export of NF–Atc Enhanced by Glycogen Synthase Kinase–3," *Science* 275:1930–1933, 1997.

Borthwick, et al., "Inhibition of Glycogen Synthase Kinase–3 Insulin in Cultured Human Skeletal Muscle Myoblasts," *Biochem. Biophys. Res. Commun.* 210(3):738–745, 1995.

Brady, et al., "The Activation of Glycogen Synthase by Insulin Switches From Kinase Inhibition to Phosphatase Activation During Adipogenesis in 3T3–L1 Cells," *J. Biol. Chem.* 273(23):14063–14066, 1998.

Brownlees, et al., "Tau Phosphorylation in Transgenic Mice Expressing Glycogen Synthase Kinase–3β Transgenes," *Molec. Neuro.* 8(15):3251–3255, 1997.

Ciudad, et al., "Control of Glycogen Synthase Phosphorylation in Isolated Rat Hepatocytes by Epinephrine, Vasopressin and Glucagon," *Eur. J. Biochem.* 142(3):511–520, 1984.

Cohen, et al., "PDKI, One of the Missing Links in Insulin Signal Transduction?," *FEBS Letters*, 1997, pp. 3–10.

Connor, S.C.,, et al., "Antidiabetic Efficacy of BRL 49653, a Potent Orally Active Insulin Sensitizing Agent, Assessed in the C57BL/KsJ db/db Diabetic Mouse by Non–Invasive $^1$H NMR Studies of Urine," *J. Pharm. Pharmacol.* 49:336–344, 1997.

Cross, et al., "Inhibition of Glycogen Synthase Kinase–3 by Insulin Mediated by Protein Kinase B," *Nature* 378:785–789, 1995.

Cross, et al., "Insulin Activates Protein Kinase B, Inhibits Glycogen Synthase Kinase–3 and Activates Glycogen Synthase by Rapamycin–Insensitive Pathways in Skeletal Muscle and Adipose Tissue," *FEBS Letters*, 1997, pp. 211–215.

Cross, et al., "The Inhibition of Glycogen Synthase Kinase–3 by Insulin or Insulin–Like Growth Factor 1 in the Rat Skeletal Muscle Cell Line L6 Is Blocked by Wortmannin, but Not by Rapamycin: Evidence That Wortmannin Blocks Activation of the Mitogen–Activated Protein Kinase Pathway in L6 Cells Between Ras and Raf," *BioChem. J.* 303:21–26, 1994.

Elgar–Finkelman, et al., "Expression and Characterization of Glycogen Synthase Kinase–3 Mutants and Their Effect on Glycogen Synthase Activity in Intact Cells," *Proc. Nat'l. Acad. Sci. USA* 93:10228–10233, 1996.

Elgar–Finkelman, et al., "Phosphorylation of Insulin Receptor Substrate 1 by Glycogen Synthase Kinase 3 Impairs Insulin Action," *Proc. Nat'l. Acad. Sci. USA* 94:9660–9664, 1997.

Fiol, et al., "Ordered Multisite Protein Phosphorylation Analysis of Glycogen Synthase Kinase 3 Action Using Model Peptide Substrates," *J. Biol. Chem.* 265(11):6061–6065, 1990.

Furnsinn, et al., "More Marked Stimulation by Lithium Than Insulin of the Glycogenic Pathway in Rat Skeletal Muscle," *Am. Phys. Soc.* 1997, pp. 514–520.

Garcia–Perez, et al., "Implication of Cyclin–Dependent Kinases and Glycogen Synthase Kinase–3 in the Phosphorylation of Microtubule–Associated Protein 1B in Developing Neuronal Cells," *J. Neur. Res.* 52:445–452, 1998.

Hegazy, et al., "Inhibitory Effect of Polycations on Phosphorylation of Glycogen Synthase by Glycogen Synthase Kinase 3," *BioChem. Biophys. Acta.* 198:204, 1989.

Hiken, et al., "Rat Skeletal Muscle Glycogen Synthase: Phosphorylation of the Purified Enzyme by Camp –Dependent Arid –Independent Protein Kinases," *Arch BioChem. Biophys.* 236(1):59–71.

Hong, et al., "Lithium Reduces Tau Phosphorylation by Inhibition of Glycogen Synthase Kinase–3," *J. Biol. Chem.* 272(40):25326–25332, 1997.

Hoshi, et al., "Nontoxic Amyloid β Peptide $_{1-42}$ Suppresses Acetylcholine Synthesis," *J. Biol. Chem.* 272(4):2038–2041, 1997.

Hoshi, et al., "Regulation of Mitochondrial Pyruvate Dehydrogenase Activity by Tau Protein Kinase I/Glycogen Synthase Kinase 3beta in Brain," *Proc. Nat'l. Acad. Sci. USA* 93(7):2719–2723, 1996.

Hurel, et al., *BioChem. J.* 1996, pp. 871–877.

Imahori, et al., "Physiology and Pathology of Tau Protein Kinases in Relation to Alzheimer's Disease," *J. BioChem.* 121:179–188, 1997.

Imazu, et al., "Phosphorylation and Inactivation of Liver Glycogen Synthase by Liver Kinases," *J. Biol. Chem.* 259(3):1813–1821, 1984.

Irving, et al., "Tau Phosphorylation in Cells Transfected With Wild–Type or an Alzheimer's Disease Mutant Presenilin 1," *Neuroscience Letters 222, 1977*, pp. 71–74, 1977.

Ishiguro, et al., "Glycogen Synthase Kinase 3 Beta Is Identical to Tau Protein Kinase I Generating Several Epitopes of Paired Helical Filaments," *FEBS*, 1993, pp. 167–172.

Klein, et al., "A Molecular Mechanism for the Effect of Lithium on Development," *Proc. Nat'l. Acad. Sci. USA* 93:8455–8459, 1996.

Lawrence, et al., "Control of Glycogen Synthase by Insulin and Isoproterenol in Rat Adipocytes. Changes in the Distribution of Phosphate in the Synthase Subunit in Response to Insulin and Beta–Adrenergic Receptor Activation," *J. Biol. Chem.* 1986, pp. 669–677.

Lawrence, et al., "New Insights Into the Role and Mechanism of Glycogen Synthase Activation by Insulin," *Diabetes* 46:541–547, 1997.

Liu, et al., "The State of Phosphorylation of Normal Adult Brain Tau, Fetal Tau, and Tau From Alzheimer Paired Helical Filaments at Amino Acid Residue Ser262," *J. Neurochem.* 66(3):1131–1139, 1996.

Lovestone, et al., "Alzheimer's Disease–Like Phosphorylation of the Microtubule–Associated Protein Tau by Glycogen Synthase Kinase–3 in Transfected Mammalian Cells," *Curr. Biol.* 4(12):1077–1086, 1994.

Lovestone, et al., "Phosphorylation of Tau by Glycogen Synthase Kinase–3β in Intact Mammalian Cells: the Effects on the Organization and Stability of Microtubules," *Neuroscience* 73(4):1145–1157, 1996.

Lucas, et al., "Inhibition of GSK–3β Leading to the Loss of Phosphorylated Map–1B Is an Early Event in Axonal Remodeling Induced by WNT–7a or Lithium," *J. Cell Sci.*, 111:1351–1361, 1998.

Lucas, et al., "WNT–7a Induces Axonal Remodeling and Increases Synapsin I Levels in Cerebellar Neurons," *Dev. Biol.* 192:31–44, 1997.

Mandelkow, et al., "Glycogen Synthase Kinase–3 and the Alzheimer–Like State of Microtubule–Associated Protein Tau," *FEBS* 314(3):315–321, 1992.

Mandelkow, et al., "Microtubule–Associated Protein Tau, Paired Helical Filaments, and Phosphorylation," *Ann. N.Y. Acad. Sci.* 695:209–216, 1993.

Mandelkow, et al., "Tau Domains, Phosphorylation, and Interactions With Microtubules," *Neurobiol. Aging* 16(3):355–363, 1995.

Michel, et al., "Characterization of Tau Phosphorylation in Glycogen Synthase Kinase–3β and Cyclin Dependent Kinase–5 Activator (P23) Tranfected Cells," *BBA*, 1998, pp. 177–182.

Moreno, et al., "Glycogen Synthase Kinase 3 Phosphorylation of Different Residues in the Presence of Different Factors: Analysis on Tau Protein," *Molecular and Cellular Biochemistry* 165:47–54, 1996.

Mulot, et al., "PHF–Tau From Alzheimer's Brain Comprises Four Species on SDS–PAGE Which Can Be Mimicked by in vitro Phosphorylation of Human Brain Tau by Glycogen Synthase Kinase–3β," *FEBS Letters*, 1994, pp. 359–364.

Munoz–Montano, et al., "Lithium Inhibits Alzheimer's Disease–Like Tau Protein Phosphorylation in Neurons," *FEBS Letters*, 1997, pp. 183–188.

Pei, et al., "Distribution, Levels, and Activity of Glycogen Synthase Kinase–3 in the Alzheimer Disease Brain," *J. Neuropath. and Exp. Neurol.* 56(1):70–78, 1997.

Shiurba, et al., "Immunocytochemistry of Tau Phosphoserine 413 and Tau Protein Kinase I in Alzheimer Pathology," *Brain Research*, 1996, pp. 119–132.

Singh, et al., "Differential Phosphorylation of Human Tau Isoforms Containing Three Repeats by Several Protein Kinases," *Arch. Biochem. Biophys.* 328(1):43–50, 1996.

Singh, et al., "Protein Kinase C and Calcium/Calmodulin–Dependent Protein Kinase II Phosphorylate Three–Repeat and Four–Repeat Tau Isoforms at Different Rates," *Mol. and Cell. Biochem.* 168:141–148, 1997.

Sivaramakrishnan, et al., "Characterization of Different Forms of Kinase FA From Rabbit Skeletal Muscle," *Adv. Enzyme Regul.* 21:321–330, 1983.

Skurat, et al., "Multiple Mechanisms for the Phosphorylation of C–Terminal Regulatory Sites in Rabbit Muscle Glycogen Synthase Expressed COS Cells," *BioChem. J.* 313:45–50, 1996.

Song, et al., "Tau Protein Kinase I/GSK–3 Beta/Kinase FA in Heparin Phosphorylates Tau on Ser 199, Thr 231, Ser 235, Ser 262, Ser 369, and Ser 400 Sites Phosphorylated in Alzheimer Disease Brain," *J. Protein Chem.* 14(2):95–105, 1995.

Sperber, et al., "Glycogen Synthase Kinase–3 Beta Phosphorylates Tau Protein at Multiple Sites in Intact Cells," *Neurosci. Letters* 197(2):149–153, 1995.

Srivastava, et al., "Potential Mechanisms(s) Involved in the Regulation of Glycogen Synthesis by Insulin," *Molecular and Cellular Biochemistry* 182:135–141, 1998.

Stambolic, et al., "Lithium Inhibits Glycogen Synthase Kinase–3 Activity and Mimics Wingless Signaling in Intact Cells," *Current Biology* 6(12):1664–1668, 1996.

Sutherland, et al., "Inactivation of Glycogen Synthase Kinase–3 Beta by Phosphorylation: New Kinase Connections in Insulin and Growth–Factor Signaling," *BioChem. J.* 296:15–19, 1993.

Takahashi, et al., "Localization and Developmental Changes of Tau Protein Kinase Uglycogen Synthase Kinase–3 Beta in Rat Brain," *J. NeuroChem.* 63(1):245–255, 1994.

Takashima, et al., "Amyloid Beta Peptide Induces Cytoplasmic Accumulation of Amyloid Protein Precursor Via Tau Protein Kinase I/Glycogen Synthase Kinase–3 Beta in Rat Hippocampal Neurons," *Neurosci. Letters* 198(2):83–86, 1995.

Takashima, et al., "Exposure of Rat Hippocampal Neurons to Amyloid Beta Peptide (25–35) Induces the Inactivation of Phosphatidyl Inositol–3 Kinase and the Activation of Tau Protein Kinase I/Glycogen Synthase Kinase–3 Beta," *Neurosci. Letters* 203(1):33–36, 1996.

Ueki, et al., "Potential Role of Protein Kinase B in Insulin–Induced Glucose Transport, Glycogen Synthesis, and Protein Synthesis," *J. Biol. Chem.* 273(9):5315–5322, 1998.

Utton, et al., *J. Biol. Chem.*, 1997, pp. 741–747. [Article Title?].

Van Lint, et al., "A Specific Immunoprecipitation Assay for the Protein Kinase FA/Glycogen Synthase Kinase 3," *Anal. BioChem.* 208(1):132–137, 1993.

Van Weeren, et al., "Essential Role for Protein Kinase B (PKB) in Insulin–Induced Glycogen Synthase Kinase 3 Inactivation," *J. Biol. Chem.* 273(21):13150–13156, 1998.

Wagner, et al., "Cellular Phosphorylation of Tau by GSK–62 Influences Tau Binding to Microtubules and Microtubule Organisation," *J. Cell Sci.* 109:1537–1543, 1996.

Wang, et al., "Inactivation of Rabbit Muscle Glycogen Synthase by Glycogen Synthase Kinase–3. Dominant Role of the Phosphorylation of Ser–640 (Site–3a)," *J. Biol. Chem.* 268(32):23876–23880, 1993.

Wang, et al., "Use of a Synthetic Peptide as a Selective Substrate for Glycogen Synthase Kinase 3," *Anal. BioChem.* 220(2):397–402, 1994.

Woodgett, "Molecular Cloning and Expression of Glycogen Synthase Kinase–3/Factor A," *EMBO J.* 9(8):2431–2438, 1990.

Yamaguchi, et al., "Preferential Labeling of Alzheimer Neurofibrillary Tangles With Antisera for Tau Protein Kinase (TPK) Uglycogen Synthase Kinase –3β and Cyclin–Dependent Kinase 5, a Component of TPK II," *Acta. Neuropathol.* 92:232–241, 1996.

Yang, et al., "Protein Kinase $F_A$/GSK–3 Phosphorylates τ and $Ser^{235}$–Pro and $Ser^{404}$–Pro That Are Abnormally Phosphorylated in Alzheimer's Disease Brain," *J. NeuroChem.* 61(5):1742–1747, 1993.

Yang, et al., "Synergistic Control Mechanism for Abnormal Site Phosphorylation of Alzheimer's Diseased Brain Tau by Kinase FA/GSK–3 Alpha," *BioChem. Biophys. Res. Commun.* 197(2):400–406, 1993.

Zhang, et al., "Mechanisms of Multisite Phosphorylation and Inactivation of Rabbit Muscle Glycogen Synthase," *Arch. BioChem. Biophys.* 304(1):219–225, 1993.

Zheng–Fischhofer, et al., "Sequential Phosphorylation of Tau by Glycogen Synthase Kinase–3β and Protein Kinase A at Thr212 and Ser214 Generates the Alzheimer–Specific Epitope of Antibody AT100 and Requires a Paired–Helical–Filament–Like Conformation," *Eur. J. BioChem.* 252:542–552, 1998.

* cited by examiner

INHIBITORS OF GLYCOGEN SYNTHASE KINASE 3

CROSS-REFERENCES TO RELATED APPLICATIONS

This application claims the benefit of U.S. Provisional Application No. 60/230,480, filed Sep. 6, 2000, and is a continuation-in-part of U.S. application Ser. No. 09/336,038, filed Jun. 18, 1999 (now U.S. Pat. No. 6,417,185), which claims the benefit of U.S. Provisional Application No. 60/089,978, filed Jun. 19, 1998.

FIELD OF THE INVENTION

This invention relates to new pyrimidine and pyridine derivatives that inhibit the activity of glycogen synthase kinase 3 (GSK3) and to pharmaceutical compositions containing the compounds and to the use of the compounds and compositions, alone or in combination with other pharmaceutically active agents. The compounds and compositions provided by the present invention have utility in the treatment of disorders mediated by GSK3 activity, such as diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency and cancer.

BACKGROUND OF THE INVENTION

Glycogen synthase kinase 3 (GSK3) is a serine/threonine kinase for which two isoforms, $\alpha$ and $\beta$, have been identified. Woodgett, *Trends Biochem. Sci.,* 16:177–81 (1991). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signaling molecules include IGF-1 and EGF. Saito et al., *Biochem. J.,* 303:27–31 (1994); Welsh et al., *Biochem. J.* 294:625–29 (1993); and Cross et al., *Biochem. J.,* 303:21–26 (1994).

Agents that inhibit GSK3 activity are useful in the treatment of disorders that are mediated by GSK3 activity. In addition, inhibition of GSK3 mimics the activation of growth factor signaling pathways and consequently GSK3 inhibitors are useful in the treatment of diseases in which such pathways are insufficiently active. Examples of diseases that can be treated with GSK3 inhibitors are described below.

Diabetes.

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the $\beta$ cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parental route. Since GSK3 inhibition stimulates insulin-dependent processes, it is consequently useful in the treatment of type 1 diabetes.

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30–40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK3 inhibition stimulates insulin-dependent processes and is consequently useful in the treatment of type 2 diabetes. Recent data obtained using lithium salts provides evidence for this notion. The lithium ion has recently been reported to inhibit GSK3 activity. Klein et al., *PNAS* 93:8455–9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK3 activity, possibly because of its documented effects on molecular targets other than GSK3. The purine analog 5-iodotubercidin, also a GSK3 inhibitor, likewise stimulates glycogen synthesis and antagonizes inactivation of glycogen synthase by glucagon and vasopressin in rat liver cells. Fluckiger-Isler et al., *Biochem J* 292:85–91 (1993); and Massillon et al., *Biochem J* 299:123–8 (1994). However, this compound has also been shown to inhibit other serine/threonine and tyrosine kinases. Massillon et al., *Biochem J* 299:123–8 (1994).

One of the main goals in the management of patients with diabetes mellitus is to achieve blood glucose levels as close to normal as possible. In general, obtaining normal postprandial blood glucose levels is more difficult than normalizing fasting hyperglycemia. In addition, some epidemiological studies suggest that postprandial hyperglycemia (PPHG) or hyperinsulinemia are independent risk factors for the development of macrovascular complications of diabetes mellitus. Recently, several drugs with differing pharmacodynamic profiles have been developed which target PPHG. These include insulin lispro, amylin analogues, alpha-glucosidase inhibitors and meglitinide analogues. Insulin lispro has a more rapid onset of action and shorter duration of efficacy compared with regular human insulin. In clinical trials, the use of insulin lispro has been associated with improved control of PPHG and a reduced incidence of hypoglycemic episodes. Repaglinide, a meglitinide analogue, is a short-acting insulinotropic agent which, when given before meals, stimulates endogenous insulin secretions and lowers postprandial hyperglycaemic excursions. Both insulin lispro and repaglinide are associated with postprandial hyperinsulinaemia. In contrast, amylin analogues reduce PPHG by slowing gastric emptying and delivery of nutrients to the absorbing surface of the gut. Alpha-glucosidase inhibitors such as acarbose, miglitol and voglibose also reduce PPHG primarily by interfering with the carbohydrate-digesting enzymes and delaying glucose absorption. Yamasaki et al., *Tohoku J Exp Med* 1997 November; 183(3):173–83. The GSK inhibitors of the present invention are also useful, alone or in combination with the agents set forth above, in the treatment of postprandial hyperglycemia as well as in the treatment of fasting hyperglycemia.

Alzheimer's Disease.

GSK3 is also involved in biological pathways relating to Alzheimer's disease (AD). The characteristic pathological features of AD are extracellular plaques of an abnormally processed form of the amyloid precursor protein (APP), so called β-amyloid peptide (β-AP) and the development of intracellular neurofibrillary tangles containing paired helical filaments (PHF) that consist largely of hyperphosphorylated tau protein. GSK3 is one of a number of kinases that have been found to phosphorylate tau protein in vitro on the abnormal sites characteristic of PHF tau, and is the only kinase also demonstrated to do this in living cells and in animals. Lovestone et al., *Current Biology* 4:1077–86 (1994); and Brownlees et al., *Neuroreport* 8: 3251–3255 (1997). Furthermore, the GSK3 kinase inhibitor, LiCl, blocks tau hyperphosphorylation in cells. Stambolic et al., *Current Biology* 6:1664–8 (1996). Thus GSK3 activity may contribute to the generation of neurofibrillary tangles and consequently to disease progression. Recently it has been shown that GSK3β associates with another key protein in AD pathogenesis, presenillin 1 (PS1). Takashima et., *PNAS* 95:9637–9641 (1998). Mutations in the PS1 gene lead to increased production of β-AP, but the authors also demonstrate that the mutant PS1 proteins bind more tightly to GSK3β and potentiate the phosphorylation of tau, which is bound to the same region of PS1.

Interestingly it has also been shown that another GSK3 substrate, β-catenin, binds to PS1. Zhong et al., *Nature* 395:698–702 (1998). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSK3β with mutant PS1 may account for the reduced levels of β-catenin that have been observed in the brains of PS1-mutant AD patients and to the disease related increase in neuronal cell-death. Consistent with these observations, it has been shown that injection of GSK3 antisense but not sense, blocks the pathological effects of β-AP on neurons in vitro, resulting in a 24 hr delay in the onset of cell death. Takashima et al., *PNAS* 90:7789–93. (1993). In these latter studies, the effects on cell-death are preceded (within 3–6 hours of β-AP administration) by a doubling of intracellular GSK3 activity, suggesting that genetic mechanisms may increase GSK3 activity. Further evidence for a role for GSK3 in AD is provided by the observation that the protein expression level (but, in this case, not specific activity) of GSK3 is increased by 50% in postsynaptosomal supernatants of AD vs. normal brain tissue. Pei et al., *J Neuropathol Exp* 56:70–78 (1997). Thus, it is believed that specific inhibitors of GSK3 will act to slow the progression of Alzheimer's Disease.

Other CNS Disorders

In addition to the effects of lithium described above, there is a long history of the use of lithium to treat bipolar disorder (manic depressive syndrome). This clinical response to lithium may reflect an involvement of GSK3 activity in the etiology of bipolar disorder, in which case GSK3 inhibitors could be relevant to that indication. In support of this notion it was recently shown that valproate, another drug commonly used in the treatment of bipolar disorder, is also a GSK3 inhibitor. Chen et al., *J. Neurochemistry* 72:1327–1330 (1999). One mechanism by which lithium and other GSK3 inhibitors may act to treat bipolar disorder is to increase the survival of neurons subjected to aberrantly high levels of excitation induced by the neurotransmitter, glutamate. Nonaka et al., *PNAS* 95: 2642–2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (AML) and multiple sclerosis (MS). Thomas, *J. Am. Geriatr. Soc.* 43: 1279–89 (1995). Consequently GSK3 inhibitors are believed to be a useful treatment in these and other neurodegenerative disorders.

Immune Potentiation

GSK3 phosphorylates transcription factor NF-AT and promotes its export from the nucleus, in opposition to the effect of calcineurin. Beals et al., *Science* 275:1930–33 (1997). Thus, GSK3 blocks early immune response gene activation via NF-AT, and GSK3 inhibitors may tend to permit or prolong activation of immune responses. Thus GSK3 inhibitors are believed to prolong and potentiate the immunostimulatory effects of certain cytokines, and such an effect may enhance the potential of those cytokines for tumor immunotherapy or indeed for immunotherapy in general.

Other Disorders

Lithium also has other biological effects. It is a potent stimulator of hematopoiesis, both in vitro and in vivo. Hammond et al., *Blood* 55: 26–28 (1980). In dogs, lithium carbonate eliminated recurrent neutropenia and normalized other blood cell counts. Doukas et al. *Exp Hematol* 14: 215–221 (1986). If these effects of lithium are mediated through the inhibition of GSK3, GSK3 inhibitors may have even broader applications.

Since inhibitors of GSK3 are useful in the treatment of many diseases, the identification of new inhibitors of GSK3 would be highly desirable.

SUMMARY OF THE INVENTION

It has now been surprisingly discovered that glycogen synthase kinase 3 (GSK3) activity can be inhibited in vitro or in vivo by certain pyrimidine and pyridine based derivatives. Accordingly, the present invention provides new compounds, compositions and methods of inhibiting the activity of GSK3 in vitro and of treatment of GSK3 mediated disorders in vivo. In one aspect, the present invention provides new compounds having GSK3 inhibition activity of the following formula (I):

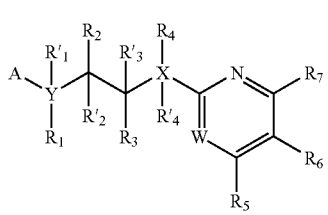

(I)

wherein:
W is optionally substituted carbon or nitrogen;
X and Y are independently selected from the group consisting of nitrogen, oxygen, and optionally substituted carbon;
A is optionally substituted aryl or heteroaryl;
$R_1$, $R'_1$, $R_2$, $R'_2$, $R_3$, $R'_3$, $R_4$ and $R'_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl, and $R'_1$, $R'_2$, $R'_3$ and $R'_4$ are independently selected from the group consisting of hydrogen, and optionally substituted loweralkyl;
$R_5$ and $R_7$ are independently selected from the group consisting of hydrogen, halo, and optionally substituted loweralkyl, cycloalkyl, alkoxy, amino, aminoalkoxy, alkylcarbonylamino, arylcarbonylamino, aralkylcarbonylamino, heteroarylcarbonylamino, heteroaralkylcarbonylamino, cycloimido, heterocycloimido, amidino, cycloamidino, heterocycloamidino, guanidinyl, aryl, biaryl, heteroaryl, heterobiaryl, heterocycloalkyl, and arylsulfonamido;
$R_6$ is selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, beteroaralkylcarbonyl, alkylcarbonyloxy, arylcarbonyloxy, aralkylcarbonyloxy, beteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, heteroarylcarbonylamino cycloamido, cyclothioamido, cycloamidino, heterocycloamidino, cycloimido, heterocycloimido, guanidinyl, aryl, heteroaryl, heterocyclo, heterocycloalkyl, arylsulfonyl and arylsulfonamido;
and the pharmaceutically acceptable salts thereof.

Presently particularly preferred and novel compounds of the invention are provided by the compounds of formulas (IV) and (V):

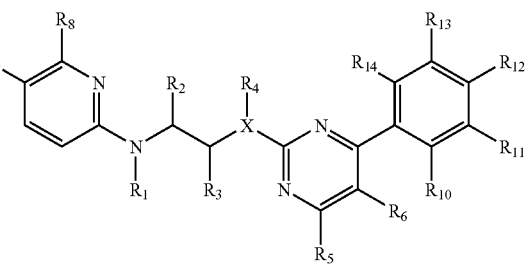

(IV)

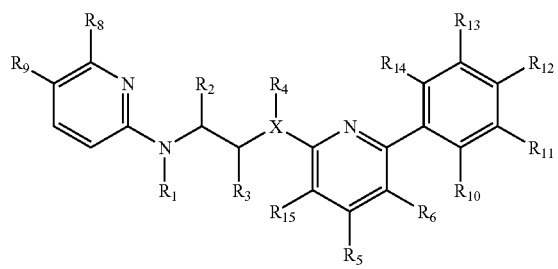

(V)

wherein X, $R_1$–$R_6$, and $R_8$–$R_{14}$ have the meanings described above, and $R_{15}$ is selected from the group consisting of hydrogen, nitro, cyano, amino, alkyl, halo, haloloweralkyl, alkyloxycarbonyl, aminocarbonyl, alkylsulfonyl and arylsulfonyl, and the pharmaceutically acceptable salts thereof.

The methods, compounds and compositions of the invention may be employed alone, or in combination with other pharmacologically active agents in the treatment of disorders mediated by GSK3 activity, such as in the treatment of diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

DETAILED DESCRIPTION OF THE PREFERRED EMBODIMENT

In accordance with the present invention, compounds, compositions and methods are provided for the inhibition of glycogen synthase kinase 3 (GSK3) activity, either in vitro or in vivo. In one aspect, the present invention provides new compounds having GSK3 inhibition activity of the following formula (I):

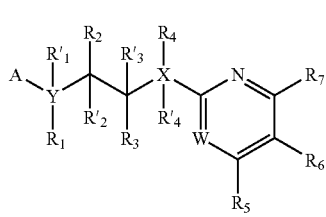

(I)

wherein:
W is optionally substituted carbon or nitrogen;
X and Y are independently selected from the group consisting of nitrogen, oxygen, and optionally substituted carbon;
A is optionally substituted aryl or heteroaryl;
$R_1$, $R'_1$, $R_2$, $R'_2$, $R_3$, $R'_3$, $R_4$ and $R'_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl, and $R'_1$, $R'_2$, $R'_3$ and $R'_4$ are independently selected from the group consisting of hydrogen, and optionally substituted loweralkyl;

$R_5$ and $R_7$ are independently selected from the group consisting of hydrogen, halo, and optionally substituted loweralkyl, cycloalkyl, alkoxy, amino, aminoalkoxy, alkylamino, aralkylamino, heteroaralkylamino, arylamino, heteroarylamino cycloimido, heterocycloimido, amidino, cycloamidino, heterocycloamidino, guanidinyl, aryl, biaryl, heteroaryl, heterobiaryl, heterocycloalkyl, and arylsulfonamido;

$R_6$ is selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, heteraralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroaralkylcarbonylamino, arylcarbonylamino, heteroarylcarbonylamino cycloamido, cyclothioamido, cycloamidino, heterocycloamidino, cycloimido, heterocycloimido, guanidinyl, aryl, heteroaryl, heterocyclo, heterocycloalkyl, arylsulfonyl and arylsulfonamido;

and the pharmaceutically acceptable salts thereof.

In one presently preferred embodiment of the invention, at least one of X and Y is nitrogen. Representative compounds of this group include those compounds in which one of X and Y is nitrogen and the other of X and Y is oxygen or optionally substituted carbon. Preferably, both X and Y are nitrogen.

The constituent A can be an aromatic ring having from 3 to 10 carbon ring atoms and optionally 1 or more ring heteroatoms. Thus, in one embodiment, A can be optionally substituted carbocyclic aryl. Alternatively, A is optionally substituted heteroaryl, such as, for example, substituted or unsubstituted pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, which may substituted with at least one and not more than 3 substitution groups. Representative substitution groups can be independently selected from the group consisting of, for example, nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aminoalkyl and cyanoalkyl.

In a presently particularly preferred embodiment of the invention, A has the formula:

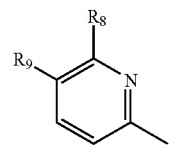

(II)

wherein $R_8$ and $R_9$ are independently selected from the group consisting of hydrogen, hydroxy, nitro, amino, cyano, halo, thioamido, amidino, oxamidino, alkoxyamidino, imidino, guanidinyl, sulfonamido, carboxyl, fomyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthio, aryl and, aralkyl. Most preferably, A is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl.

In other embodiments of the invention at least one of $R_1$, $R'_1$, $R_2$, $R'_2$, $R_3$, $R'_3$, $R_4$, and $R'_4$ may be hydrogen, or unsubstituted or substituted loweralkyl selected from the group consisting of haloloweralkyl, heterocycloaminoalkyl, and loweralkylamino-loweralkyl; or loweralkylaminoloweralkyl. Presently preferred embodiments of the invention include compounds wherein $R_1$, $R'_1$, $R_2$, $R'_2$, $R_3$, $R'_3$ and $R_4$ are hydrogen and $R'_4$ is selected from the group consisting of hydrogen, methyl, ethyl, aminoethyl, dimethylaminoethyl, pyridylethyl, piperidinyl, pyrrolidinylethyl, piperazinylethyl and morpholinylethyl.

Other presently preferred compounds of the invention include compounds of formula (I) wherein at least one of $R_5$ and $R_7$ is selected from the group consisting of substituted and unsubstituted aryl, heteroaryl and biaryl. In presently preferred embodiments, at least one of $R_5$ and $R_7$ is a substituted or unsubstituted moiety of the formula:

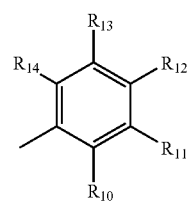

(III)

wherein $R_{10}$, $R_{11}$, $R_{12}$, $R_{13}$, and $R_{14}$ are independently selected from the group consisting of hydrogen, nitro, amino, -cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkylcarbonylamino, heteroaralkylcarbonylamino, arylcarbonylamino, heteroarylcarbonylamino aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyloxyalkyl, and heteroaralkcarbonyloxyalkyl. Presently particularly preferred compounds are obtained wherein $R_{10}$, $R_{11}$, $R_{13}$, and $R_{14}$ are hydrogen and $R_{12}$ is selected from the group consisting of halo, loweralkyl, hydroxy, loweralkoxy, haloloweralkyl, aminocarbonyl, alkylaminocarbonyl and cyano; $R_{11}$, $R_{13}$, and $R_{14}$ are hydrogen and $R_{10}$ and $R_{12}$ are independently selected from the group consisting of halo, loweralkyl, hydroxy, loweralkoxy, haloloweralkyl and cyano; $R_{10}$, $R_{11}$, $R_{13}$, and $R_{14}$ are hydrogen and $R_{12}$ is heteroaryl; $R_{10}$, $R_{11}$, $R_{13}$, and $R_{14}$ are hydrogen and $R_{12}$ is a heterocycloalkyl; and wherein at least one of $R_{10}$, $R_{11}$, $R_{12}$, $R_{13}$, and $R_{14}$ are halo and the remainder of $R_{10}$, $R_{11}$, $R_{12}$, $R_{13}$, and $R_{14}$ are hydrogen. Preferably, at least one of $R_5$ and $R_7$ is selected from the group consisting of dichlorophenyl, difluorophenyl, trifluoromethylphenyl, chlorofluorophenyl, bromochlorophenyl, ethylphenyl, methylchlorophenyl, imidazolylphenyl, cyanophenyl, morphlinophenyl and cyanochlorophenyl.

In representative embodiments of the invention, $R_6$ may be substituted alkyl, such as, for example, aralkyl, hydroxyalkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl; substituted amino such as alkylamino, alkylcarbonylamino, alkoxycarbonylamino, arylalkylamino, arylcarbonylamino, alkylthiocarbonylamino, arylsulfonylamino, heteroarylamino alkylcarbonylamino, arylcarbonylamino, heteroarylcarbonylamino, aralkylcarbonylamino, and heteroaralkylcarbonylamino; or substituted carbonyl such as unsubstituted or substituted aminocarbonyl, alkyloxycarbonyl, aryloxycarbonyl, aralkyloxycarbonyl and alkylaminoalkyloxycarbonyl. In other embodiments, $R_6$ may be selected from the group consisting of amidino, guanidino, cycloimido, heterocycloimido, cycloamido, heterocycloamido, cyclothioamido and heterocycloloweralkyl. In yet other embodiments, $R_6$ may be aryl or heteroaryl, such as, for example, substituted or unsubstituted pyridyl, pyrimidinyl, piperazinyl, thiazolyl, indolyl, imidazolyl, oxadiazolyl, tetrazolyl, pyrazinyl, triazolyl, thienyl, furanyl, quinolinyl, pyrrolyopyridyl, benzothiazolyl, benzopyridyl, benzotriazolyl, and benzimidazolyl. In yet other embodiments, $R_6$ may be a monoketopiperazinyl group having the structure:

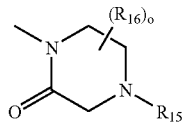

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloarylloweralkyl carbocyclic and heterocyclic; or $R_8$ can be taken with another $R_{16}$ or with $R_{15}$ to form a carbocyclic, heterocyclic or aryl ring; and o is an integer between 1 and 6. In representative embodiments of this aspect of the invention, $R_{15}$ is loweralkyl, such as methyl, ethyl, n-propyl, isopropyl, cyclopropyl, n-butyl, iso-butyl or t-butyl, or $R_{15}$ is taken with $R_{16}$ to form a group having the structure:

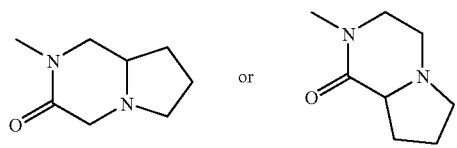

Presently preferred, representative compounds of this group include, for example, 1-[2-{[2-({6-amino-5-[hydroxy(oxido)amino]-2-pyridinyl}amino)ethyl]amino}-4-(2,4-dichlorophenyl)-5-pyrimidinyl]-2-piperazinone, 1-[2-{[2-({6-amino-5-[-hydroxy(oxido)amino]-2-pyridinyl}amino)ethyl]amino}-4-(2,4-dichlorophenyl)-5-pyrimidinyl]-4-ethyl-3-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-methyl-2-piperazinone, 1-[2-{[2-({6-amino-5-[hydroxy(oxido)amino]-2-pyridinyl}amino)ethyl]amino}-4-(2,4-dichlorophenyl)-5-pyrimidinyl]-4-methyl-2-piperazinone, 6-[(2-{[6-(2,4-dichlorophenyl)-5-(4-methyl-2-oxo-1-piperazinyl)-2-pyridinyl]amino}ethyl)amino]nicotinonitrile, 1-[6-{[2-({6-amino-5-[hydroxy(oxido)amino]-2-pyridinyl}amino)ethyl]amino}-2-(4-ethylphenyl)-3-pyridinyl]-4-methyl-2-piperazinone, 6-[(2-{[6-(4-ethylphenyl)-5-(4-methyl-2-oxo-1-piperazinyl)-2-pyridinyl]amino}ethyl)amino]nicotinonitrile, 6-({2-[[6-(4-ethylphenyl)-5-(4-methyl-2-oxo-1-piperazinyl)-2-pyridinyl](methyl)amino]ethyl}amino)nicotinonitrile, 6-[(2-{[4-(2,4-dichlorophenyl)-5-(4-methyl-2-oxo-1-piperazinyl)-2-pyrimidinyl]amino}ethyl)amino]nicotinonitrile, 1-[6-{[2-({6-amino-5-[hydroxy(oxido)amino]-2-pyridinyl}amino)ethyl]amino}-2-(2,4-difluorophenyl)-3-pyridinyl]-4-methyl-2-piperazinone, 4-[6-{[2-({6-amino-5-[hydroxy(oxido)amino]-2-pyridinyl}arnino)ethyl]amino}-3-(4-methyl-2-oxo-1-piperazinyl)-2-pyridinyl]benzonitrile, 1-[6-{[2-({6-amino-5-[hydroxy(oxido)amino]-2-pyridinyl}amino)ethyl]amino}-2-(2,4-dichlorophenyl)-3-pyridinyl]-4-isopropyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-ethyl-2-piperazinone, 1-{6-{[2-({6-amino-5-[hydroxy(oxido)amino]-2-pyridinyl}amino)ethyl]amino}-2-[2-(trifluoromethyl)phenyl]-3-pyridinyl}-4-methyl-2-piperazinone, 1-[6-{[2-({6-amino-5-[hydroxy(oxido)amino]-2-pyridinyl}amino)ethyl]amino}-2-(2-bromophenyl)-3-pyridinyl]-4-methyl-2-piperazinone, 1-[6-{[2-({6-amino-5-[hydroxy(oxido)amino]-2-pyridinyl}amino)propyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)propyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)-1-methylethyl]amino}-2-(2,4-dichlorophenyl)-3-pyridinyl]-4-methyl-2-piperazinone, 1-[6-{[2-({6-amino-5-[hydroxy(oxido)aminol-2-pyridinyl}amino)-1-methylethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)-1,1-dimethylethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)ethyl][2-(1-pyrrolidinyl)ethyl]amino}-2-(2,4-dichlorophenyl)-3-pyridinyl]-4-methyl-2-piperazinone, 1-[6-[3-({6-amino-5-[hydroxy(oxido)amino]-2-pyridinyl}amino)propyl]-2-(2,4-dichlorophenyl)-3-pyridinyl]-4-methyl-2-piperazinone, 1-[6-[[2-({6-amino-5-[hydroxy(oxido)amino]-2-pyridinyl}amino)ethyl](methyl)

amino]-2-(2,4-dichlorophenyl)-3-pyridinyl]-4-methyl-2-piperazinone, 1-[6-[2-({6-amino-5-[hydroxy(oxido)amino]-2-pyridinyl}amino)ethoxy]-2-(2,4-dichlorophenyl)-3-pyridinyl]4-methyl-2-piperazinone, 1-[6-{[2-({6-amino-5-[hydroxy(oxido)amino]-2-pyridinyl}oxy)ethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)ethyl][2-(4-morpholinyl)ethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-cyclopropyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-cyclohexyl-2-piperazinone, 1-[6-{[2-({6-amino-5-[hydroxy(oxido)amino]-2-pyridinyl}amino)ethyl]amino}-2-(4-bromophenyl)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-3,4-dimethyl-2-piperazinone, 1-(2-(2,4-dichlorophenyl)-6-{[2-({5-[hydroxy(oxido)amino]-6-methoxy-2-pyridinyl}amino)ethyl]amino}-3-pyridinyl)-4-methyl-2-piperazinone, 1-(2-(2,4-dichlorophenyl)-6-{[2-({5-[hydroxy(oxido)amino]-2-pyridinyl}amino)ethyl]amino}-3-pyridinyl)-4-methyl-2-piperazinone, 4-[6-{[2-({6-amino-5-[hydroxy(oxido)amino]-2-pyridinyl}amino)ethyl]amino}-3-(4-methyl-2-oxo-1-piperazinyl)-2-pyridinyl]benzamide, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-3(4H)-one, 1-[6-{[2-({6-amino-5-[hydroxy(oxido)amino]-2-pyridinyl}amino)ethyl]amino}-2-(2,4-dichlorophenyl)-3-pyridinyl]-4-(methylsulfonyl)-2-piperazinone, 4-acetyl-1-[6-{[2-({6-amino-5-[hydroxy(oxido)amino]-2-pyridinyl}amino)ethyl]amino}-2-(2,4-dichlorophenyl)-3-pyridinyl]-2-piperazinone, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-3(4H)-one, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-3(4H)-one, 2-[6-{[2-({6-amino-5-[hydroxy(oxido)amino]-2-pyridiny 1-[6-{[2-({6-amino-5-[hydroxy(oxido)amino]-2-pyridinyl}amino)ethyl]amino}-2-(4-methoxyphenyl)-3-pyridinyl]-4-methyl-2-piperazinone, and 1-[6-{[2-({6-amino-5-[hydroxy(oxido)amino]-2-pyridinyl}amino)ethyl]amino}-2-(3-furyl)-3-pyridinyl]-4-methyl-2-piperazinone.

As used herein, representative heterocyclo groups include, for example, those shown below (where the point of attachment of the substituent group, and the other substituent groups shown below, is through the upper left-hand bond). These heterocyclo groups can be further substituted and may be attached at various positions as will be apparent to those having skill in the organic and medicinal chemistry arts in conjunction with the disclosure herein.

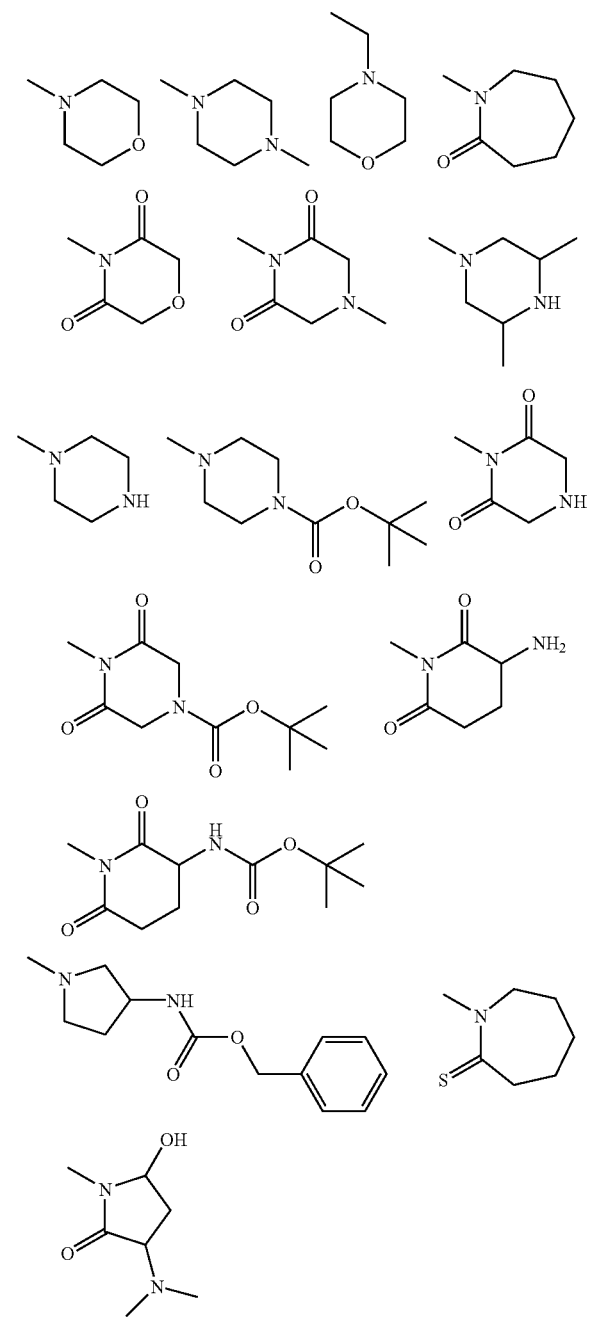

Representative heteroaryl groups include, for example, those shown below. These heteroaryl groups can be further substituted and may be attached at various positions as will be apparent to those having skill in the organic and medicinal chemistry arts in conjunction with the disclosure herein.

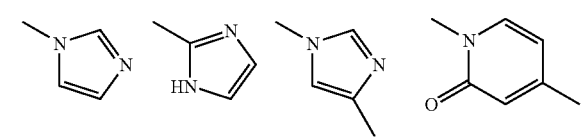

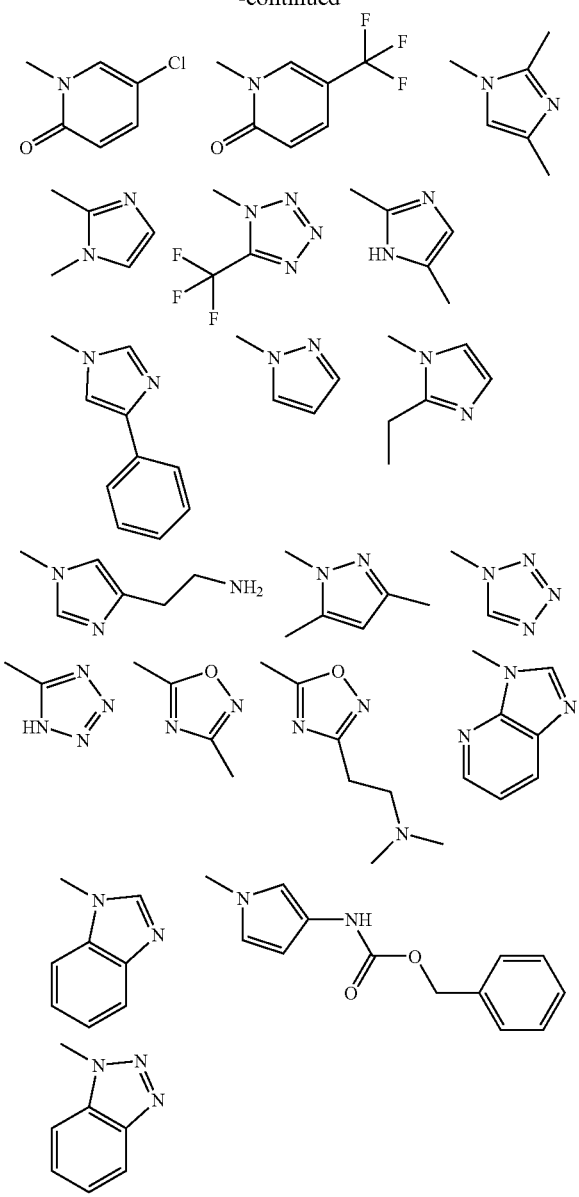

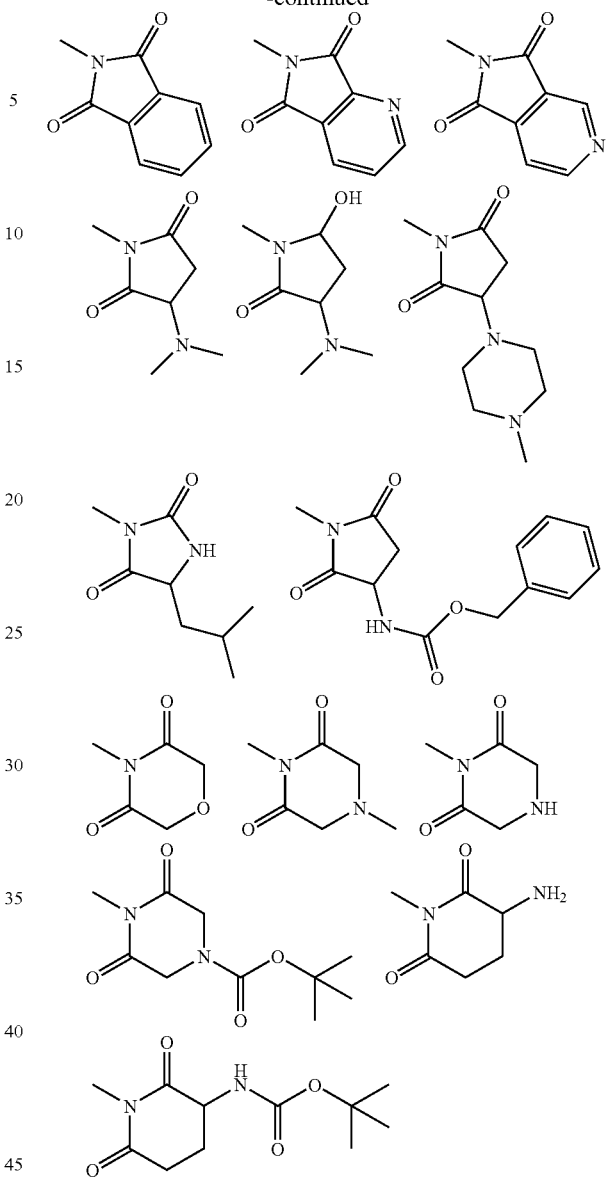

Representative cycloimido and heterocycloimido groups include, for example, those shown below. These cycloimido and heterocycloimido can be further substituted and may be attached at various positions as will be apparent to those having skill in the organic and medicinal chemistry arts in conjunction with the disclosure herein.

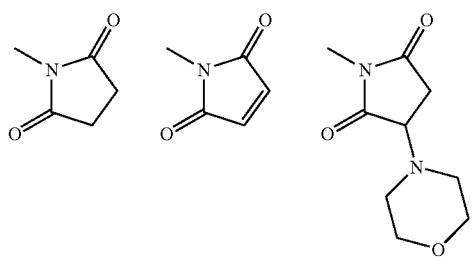

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

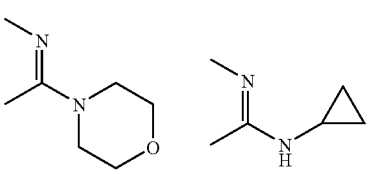

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

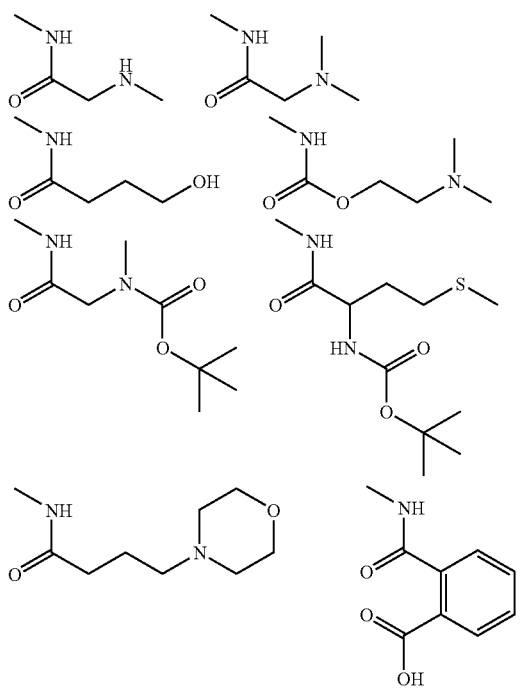

Representative substituted aminocarbonyl groups include, for example, those shown below. These can heterocyclo groups be further substituted as will be apparent to those having skill in the organic and medicinal chemistry arts in conjunction with the disclosure herein.

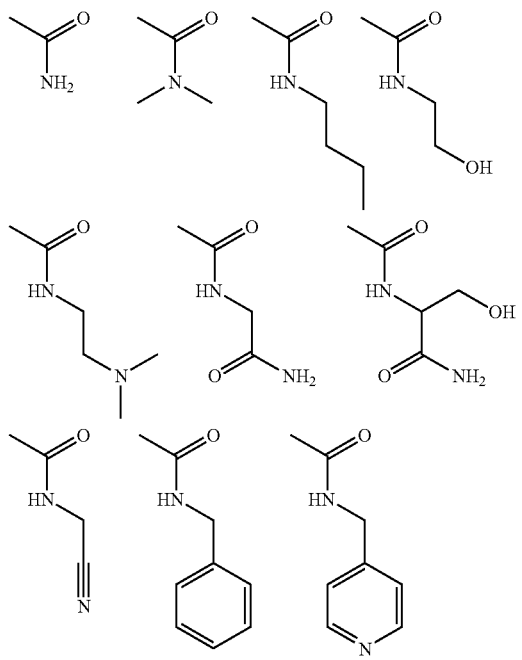

Representative substituted alkoxycarbonyl groups include, for example, those shown below. These alkoxycarbonyl groups can be further substituted as will be apparent to those having skill in the organic and medicinal chemistry arts in conjunction with the disclosure herein.

Presently particularly preferred compounds of the invention include compounds having the structure:

(IV)

wherein X, $R_1$–$R_6$, and $R_8$–$R_{14}$ have the meanings described above, and the pharmaceutically acceptable salts thereof. Presently preferred, representative compounds of this group include, for example, [4-(4-imidazolylphenyl)pyrimidin-2-yl]{2-[(5-nitro(2-pyridyl))amino]ethyl}amine, 4-[5-imidazolyl-2-({2-[(5-nitro(2-pyridyl))amino]ethyl}amino)pyrimidin-4-yl]benzenecarbonitrile, 4-[2-({2-[(6-amino-5-nitro(2-pyridyl))amino]ethyl}amino)-5-imidazolylpyrimidin-4-yl]benzenecarbonitrile, [4-(2,4-dichlorophenyl)-5-imidazolylpyrimidin-2-yl]{2-[(5-nitro(2-pyridyl))amino]ethyl}amine, 4-[2-({2-[(5-nitro-2-pyridyl)amino]ethyl}amino)-7a-hydro-1,2,4-triazolo[1,5-a]pyrimidin-7-yl]benzenecarbonitrile, {2-[(6-amino-5-nitro(2-pyridyl))amino]ethyl}[4-(2,4-dichlorophenyl)-5-imidazolylpyrimidin-2-yl]amine, [4-(2,4-dichlorophenyl)-5-imidazol-2-ylpyrimidin-2-yl]{2-[(5-nitro(2-pyridyl))amino]ethyl}amine, 6-[(2-{[4-(2,4-dichlorophenyl)-5-imidazolylpyrimidin-2-yl]amino}ethyl)amino]pyridine-3-carbonitrile, [5-benzotriazolyl-4-(2,4-dichlorophenyl)pyrimidin-2-yl]{2-[(5-nitro(2-pyridyl))amino]ethyl}amine, [2-({2-[(6-amino-5-nitro(2-pyridyl))amino]ethyl}amino)-4-

(2,4-dichlorophenyl)pyrimidin-5-yl]methan-1-ol, [4-(2,4-dichlorophenyl)-2-({2-[(5-nitro(2-pyridyl))amino]ethyl}amino)pyrimidin-5-yl]methan-1-ol, 2-[2-({2-[(6-amino-5-nitro(2-pyridyl))amino]ethyl}amino)-4-(2,4-dichlorophenyl)pyrimidin-5-yl]isoindoline-1,3-dione, [5-amino-4-(2,4-dichlorophenyl)pyrimidin-2-yl]{2-[(6-amino-5-nitro(2-pyridyl))amino]ethyl}amine, {2-[(6-amino-5-nitro(2-pyridyl))amino]ethyl}[4-(2,4-dichlorophenyl)-5-morpholin-4-ylpyrimidin-2-yl]amine, {2-[(6-amino-5-nitro(2-pyridyl))amino]ethyl}{4-(2,4-dichlorophenyl)-5-[5-(trifluoromethyl)(1,2,3,4-tetraazolyl)]pyrimidin-2-yl}amine, 1-[2-({2-[(6-amino-5-nitro(2-pyridyl))amino]ethyl}amino)-4-(2,4-dichlorophenyl)pyrimidin-5-yl]pyrrolidine-2,5-dione, [4-(2,4-dichlorophenyl)-5-pyrazolylpyrimidin-2-yl]{2-[(5-nitro(2-pyridyl))amino]ethyl}amine, [4-(2,4-dichlorophenyl)-5-(4-methylimidazolyl)pyrimidin-2-yl]{2-[(5-nitro(2-pyridyl))amino]ethyl}amine, [4-(2,4-dichlorophenyl)-5-(2,4-dimethylimidazolyl)pyrimidin-2-yl]{2-[(5-nitro(2-pyridyl))amino]ethyl}amine, 6-[(2-{[4-(2,4-dichlorophenyl)-5-imidazol-2-ylpyrimidin-2-yl]amino}ethyl)amino]pyridine-3-carbonitrile, {2-[(6-amino-5-nitro(2-pyridyl))amino]ethyl}[4-(2,4-dichlorophenyl)-5-(morpholin-4-ylmethyl)pyrimidin-2-yl]amine, {2-[(6-amino-5-nitro(2-pyridyl))amino]ethyl}[4-(2,4-dichlorophenyl)-5-piperazinylpyrimidin-2-yl]amine, {2-[(6-amino-5-nitro(2-pyridyl))amino]ethyl}[4-(4-ethylphenyl)-5-imidazolylpyrimidin-2-yl]amine, 1-[4-(2,4-dichlorophenyl)-2-({2-[(5-nitro(2-pyridyl))amino]ethyl}amino)pyrimidin-5-yl]hydropyridin-2-one, [5-benzimidazolyl-4-(2,4-dichlorophenyl)pyrimidin-2-yl]{2-[(5-nitro(2-pyridyl))amino]ethyl}amine, {2-[(6-amino-5-nitro(2-pyridyl))amino]ethyl}[4-(2,4-dichlorophenyl)-5-imidazolylpyrimidin-2-yl]methylamine, {2-[(6-amino-5-nitro(2-pyridyl))amino]ethyl}[4-(2,4-dichlorophenyl)-5-(4-pyridyl)pyrimidin-2-yl]amine, {2-[(6-amino-5-nitro(2-pyridyl))amino]ethyl}[4-(2,4-dichlorophenyl)-5-(4-methylpiperazinyl)pyrimidin-2-yl]amine, [4-(2,4-dichlorophenyl)-5-(2-methylimidazolyl)pyrimidin-2-yl]{2-[(5-nitro(2-pyridyl))amino]ethyl}amine, {2-[(6-amino-5-nitro(2-pyridyl))amino]ethyl}[4-(2,4-dichlorophenyl)-5-(2-methylimidazolyl)pyrimidin-2-yl]amine, {2-[(6-amino-5-nitro(2-pyridyl))amino]ethyl}[4-(2,4-dichlorophenyl)-5-(4-phenylimidazolyl)pyrimidin-2-yl]amine, {2-[(6-amino-5-nitro(2-pyridyl))amino]ethyl}[4-(2,4-dichlorophenyl)-5-(2,4-dimethylimidazolyl)pyrimidin-2-yl]amine, [4-(2,4-dichlorophenyl)-5-imidazol-2-ylpyrimidin-2-yl](2-{[5-(trifluoromethyl)(2-pyridyl)]amino}ethyl)amine, [4-(2,4-dichlorophenyl)-5-piperazinylpyrimidin-2-yl]{2-[(5-nitro(2-pyridyl))amino]ethyl}amine, [4-(2,4-dichlorophenyl)-5-imidazolylpyrimidin-2-yl][2-(dimethylamino)ethyl]{2-[(5-nitro(2-pyridyl))amino]ethyl}amine, 1-[2-({2-[(6-amino-5-nitro(2-pyridyl))amino]ethyl}amino)-4-(2,4-dichlorophenyl)pyrimidin-5-yl]-4-methylpiperazine-2,6-dione, [4-(2,4-dichlorophenyl)-5-(1-methylimidazol-2-yl)pyrimidin-2-yl]{2-[(5-nitro(2-pyridyl))amino]ethyl}amine, 1-[2-({2-[(6-amino-5-nitro(2-pyridyl))amino]ethyl}amino)-4-(2,4-dichlorophenyl)pyrimidin-5-yl]-3-morpholin-4-ylpyrrolidine-2,5-dione, 1-[4-(2,4-dichlorophenyl)-2-({2-[(5-nitro(2-pyridyl))amino]ethyl}amino)pyrimidin-5-yl]-4-methylpiperazine-2,6-dione, 1-[2-({2-[(6-amino-5-nitro(2-pyridyl))amino]ethyl}amino)-4-(2,4-dichlorophenyl)pyrimidin-5-yl]-3-(dimethylamino)pyrrolidine-2,5-dione, {5-imidazolyl-4-[4-(trifluoromethyl)phenyl]pyrimidin-2-yl}{2-[(5-nitro(2-pyridyl))amino]ethyl}amine, {2-[(6-amino-5-nitro(2-pyridyl))amino]ethyl}[4-(2,4-dichlorophenyl)-5-(1-methylimidazol-2-yl)pyrimidin-2-yl]amine, [4-(2,4-dichlorophenyl)-5-(4-methylpiperazinyl)pyrimidin-2-yl]{2-[(5-nitro(2-pyridyl))amino]ethyl}amine, [4-(2,4-dichlorophenyl)-5-(morpholin-4-ylmethyl)pyrimidin-2-yl]{2-[(5-nitro(2-pyridyl))amino]ethyl}amine, [4-(2,4-dichlorophenyl)-5-(4-methylimidazol-2-yl)pyrimidin-2-yl]{2-[(5-nitro(2-pyridyl))amino]ethyl}amine, {2-[(6-amino-5-nitro(2-pyridyl))amino]ethyl}[4-(2,4-dichlorophenyl)-5-(4-methylimidazol-2-yl)pyrimidin-2-yl]amine, {2-[(6-amino-5-nitro(2-pyridyl))amino]ethyl}[4-(2-chlorophenyl)-5-imidazol-2-ylpyrimidin-2-yl]amine, [4-(2-chloro-4-fluorophenyl)-5-imidazol-2-ylpyrimidin-2-yl]{2-[(5-nitro(2-pyridyl))amino]ethyl}amine, [4-(2,4-dichlorophenyl)-5-imidazolylpyrimidin-2-yl]{2-[(5-nitro(2-pyridyl))amino]ethyl}(2-pyrrolidinylethyl)amine, [4-(2,4-dichlorophenyl)-5-imidazolylpyrimidin-2-yl](2-morpholin-4-ylethyl) {2-[(5-nitro(2-pyridyl))amino]ethyl}amine, 6-[(2-{[4-(2,4-dichlorophenyl)-5-(4-methylimidazol-2-yl)pyrimidin-2-yl]amino}ethyl)amino]pyridine-3-carbonitrile, {2-[(6-amino-5-nitro(2-pyridyl))amino]ethyl}[4-(2-chloro-4-fluorophenyl)-5-imidazol-2-ylpyrimidin-2-yl]amine, [4-(4-ethylphenyl)-5-imidazol-2-ylpyrimidin-2-yl]{2-[(5-nitro(2-pyridyl))amino]ethyl}amine, [5-((1E)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine, N-[4-(2,4-dichlorophenyl)-2-({2-[(5-nitro(2-pyridyl))amino]ethyl}amino)pyrimidin-5-yl]acetamide, [4-(2,4-dichlorophenyl)-5-imidazol-2-ylpyrimidin-2-yl]{2-[(6-methoxy-5-nitro(2-pyridyl))amino]ethyl}amine, 6-[(2-{[4-(2,4-dichlorophenyl)-5-imidazolylpyrimidin-2-yl]methylamino}ethyl)amino]pyridine-3-carbonitrile, 6-[(2-{[4-(2,4-dichlorophenyl)-5-imidazol-2-ylpyrimidin-2-yl]methylamino}ethyl)amino]pyridine-3-carbonitrile, [4-(2,4-dichlorophenyl)-5-imidazol-2-ylpyrimidin-2-yl]methyl{2-[(5-nitro(2-pyridyl))amino]ethyl}amine, 6-[(2-{[4-(2-chloro-4-fluorophenyl)-5-imidazol-2-ylpyrimidin-2-yl]amino}ethyl)amino]pyridine-3-carbonitrile, [4-(4-chlorophenyl)-5-imidazol-2-ylpyrimidin-2-yl]{2-[(5-nitro(2-pyridyl))amino]ethyl}amine, {2-[(6-amino-5-nitro(2-pyridyl))amino]ethyl }[4-(4-chloro-2-methylphenyl)-5-imidazol-2-ylpyrimidin-2-yl]amine, {2-[(6-amino-5-nitro(2-pyridyl))amino]ethyl}[4-(4-bromo-2-chlorophenyl)-5-imidazol-2-ylpyrimidin-2-yl]amine, 6-[(2-{[4-(4-bromo-2-chlorophenyl)-5-imidazol-2-ylpyrimidin-2-yl]amino}ethyl)amino]pyridine-3-carbonitrile, 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione, N-[2-({2-[(6-amino-5-nitro(2-pyridyl))amino]ethyl}amino)-4-(2,4-dichlorophenyl)py Other presently particularly preferred compounds of the invention include compounds having the structure:

(V)

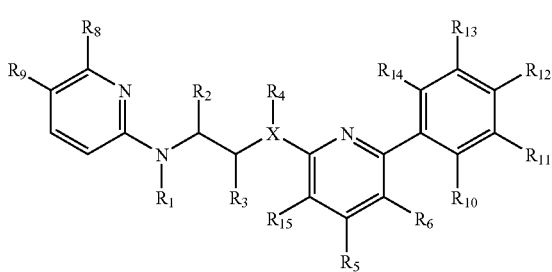

wherein X, $R_1$–$R_6$, and $R_8$–$R_{14}$ have the meanings described above, and $R_{15}$ is selected from the group consisting of hydrogen, nitro, cyano, amino, alkyl, halo, haloloweralkyl, alkyloxycarbonyl, aminocarbonyl, alkylsulfonyl and arylsulfonyl, and the pharmaceutically acceptable salts thereof. Presently preferred, representative compounds of this group include, for example, [6-(2,4-dichlorophenyl)-5-imidazolyl(2-pyridyl)]{2-[(5-nitro(2-pyridyl))amino]ethyl}amine, {2-[(6-amino-5-nitro(2-pyridyl))amino]ethyl}[6-(2,4-dichlorophenyl)-5-imidazolyl(2-pyridyl)]amine, 6-[(2-{[6-(2,4-dichlorophenyl)-5-imidazolyl-2-pyridyl]amino}ethyl)amino]pyridine-3-carbonitrile, {2-[(6-amino-5-nitro(2-pyridyl))amino]ethyl}[6-(2,4-dichlorophenyl)-5-nitro(2-pyridyl)]amine, {2-[(6-amino-5-nitro(2-pyridyl))amino]ethyl}[6-(2,4-dichlorophenyl)-5-(4-methylimidazolyl)(2-pyridyl)]amine, 6-[(2-{[6-(2,4-dichlorophenyl)-5-(4-methylimidazolyl)-2-pyridyl]amino}ethyl)amino]pyridine-3-carbonitrile, and [4-(4-bromo-2-chlorophenyl)-5-imidazol-2-yl-pyrimidin-2-yl]{2-[(5-nitro(2-pyridyl))amino]ethyl}amine.

In another aspect, the invention provides compositions comprising an amount of a compound of formula (I) effective to modulate GSK3 activity in a human or animal subject when administered thereto, together with a pharmaceutically acceptable carrier.

In yet other embodiments, the invention provides methods of inhibiting GSK3 activity in a human or animal subject, comprising administering to the human or animal subject a GSK3 inhibitory amount of a compound of structure (I).

The present invention further provides methods of treating human or animal subjects suffering from GSK3-mediated disorder in a human or animal subject, comprising administering to the human or animal subject a therapeutically effective amount of a compound of formula (I) above, either alone or in combination with other therapeutically active agents.

In yet other embodiments, the present invention provides compounds of formulas I, IV and V, as described above, for use as a pharmaceutical, as well as methods of use of those compounds in the manufacture of a medicament for the treatment of diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency or cancer.

As used above and elsewhere herein the following terms have the meanings defined below:

"Glycogen synthase kinase 3" and "GSK3" are used interchangeably herein to refer to any protein having more than 60% sequence homology to the amino acids between positions 56 and 340 of the human GSK3 beta amino acid sequence (Genbank Accession No. L33801). To determine the percent homology of two amino acid sequences or of two nucleic acids, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). GSK3 was originally identified by its phosphorylation of glycogen synthase as described in Woodgett et al., *Trends Biochem. Sci.*, 16:177–81 (1991), incorporated herein by reference. By inhibiting GSK3 kinase activity, activities downstream of GSK3 activity may be inhibited, or, alternatively, stimulated. For example, when GSK3 activity is inhibited, glycogen synthase may be activated, resulting in increased glycogen production. GSK3 is also known to act as a kinase in a variety of other contexts, including, for example, phosphorylation of c-jun, β-catenin, and tau protein. It is understood that inhibition of GSK3 kinase activity can lead to a variety of effects in a variety of biological contexts. The invention, however, is not limited by any theories of mechanism as to how the invention works.

"GSK3 inhibitor" is used herein to refer to a compound that exhibits an $IC_{50}$ with respect to GSK3 of no more than about 100 μM and more typically not more than about 50 μM, as measured in the cell-free assay for GSK3 inhibitory activity described generally hereinbelow. "$IC_{50}$" is that concentration of inhibitor which reduces the activity of an enzyme (e.g., GSK3) to half-maximal level. Representative compounds of the present invention have been discovered to exhibit inhibitory activity against GSK3. Compounds of the present invention preferably exhibit an $IC_{50}$ with respect to GSK3 of no more than about 10 μM, more preferably, no more than about 5 μM, even more preferably not more than about 1 μM, and most preferably, not more than about 200 nM, as measured in the cell-free GSK3 kinase assay.

"Optionally substituted" refers to the replacement of hydrogen with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl,alkylcarbonyl, arylcarbonyl, aralkylcarbonyl, heteroarylcarbonyl, heteroaralkylcarbonyl, alkylthio, aminoalkyl, cyanoalkyl, and the like.

The substitution group can itself be substituted. The group substituted onto the substitution group can be carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

"Loweralkyl" as used herein refers to branched or straight chain alkyl groups comprising one to ten carbon atoms that are unsubstituted or substituted, e.g., with one or more halogen, hydroxyl or other groups, including, e.g., methyl, ethyl, propyl, isopropyl, n-butyl, t-butyl, neopentyl, trifluoromethyl, pentafluoroethyl and the like.

"Alkylenyl" refers to a divalent straight chain or branched chain saturated aliphatic radical having from 1 to 20 carbon atoms. Typical alkylenyl groups employed in compounds of the present invention are loweralkylenyl groups that have from 1 to about 6 carbon atoms in their backbone. "Alkenyl" refers herein to straight chain, branched, or cyclic radicals having one or more double bonds and from 2 to 20 carbon atoms. "Alkynyl" refers herein to straight chain, branched, or cyclic radicals having one or more triple bonds and from 2 to 20 carbon atoms.

"Loweralkoxy" as used herein refers to RO— wherein R is loweralkyl. Representative examples of loweralkoxy groups include methoxy, ethoxy, t-butoxy, trifluoromethoxy and the like.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Halo" refers herein to a halogen radical, such as fluorine, chlorine, bromine or iodine. "Haloalkyl" refers to an alkyl radical substituted with one or more halogen atoms. The term "haloloweralkyl" refers to a loweralkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Aryl" refers to monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic" refers herein to fused and non-fused cyclic structures in which at least one cyclic structure is aromatic, such as, for example, benzodioxozolo (which has a heterocyclic structure fused to a phenyl group, i.e.

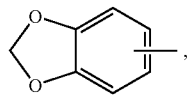

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

"Amino" refers herein to the group —NH$_2$. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "arylcycloalkylamino" refers herein to the group, aryl-cycloalkyl-NH—, where cycloalkyl is a divalent cycloalkyl group. Typically, cycloalkyl has from 3 to 6 backbone atoms, of which, optionally 1 to about 4 are heteroatoms. The term "aminoalkyl" refers to an alkyl group that is terminally substituted with an amino group.

The term "alkoxyalkyl" refers to the group -alk$_1$-O-alk$_2$ where alk$_1$ is alkylenyl or alkenyl, and alk$_2$ is alkyl or alkenyl. The term "loweralkoxyalkyl" refers to an alkoxyalkyl where alk$_1$ is loweralkylenyl or loweralkenyl, and alk$_2$ is loweralkyl or loweralkenyl. The term "aryloxyalkyl" refers to the group -alkylenyl-O-aryl. The term "aralkoxyalkyl" refers to the group -alkylenyl-O-aralkyl, where aralkyl is a loweraralkyl.

The term "alkoxyalkylamino" refers herein to the group —NR—(alkoxylalkyl), where R is typically hydrogen, loweralkyl, or loweralkyl. The term "aminoloweralkoxyalkyl" refers herein to an aminoalkoxyalkyl in which the alkoxyalkyl is a loweralkoxyalkyl.

The term "aminocarbonyl" refers herein to the group —C(O)—NH$_2$. "Substituted aminocarbonyl" refers herein to the group —C(O)—NRR' where R is loweralkyl and R' is hydrogen or a loweralkyl. The term "arylaminocarbonyl" refers herein to the group —C(O)—NRR' where R is an aryl and R' is hydrogen, loweralkyl or aryl. "aralkylaminocarbonyl" refers herein to the group —C(O)—NRR' where R is loweraralkyl and R' is hydrogen, loweralkyl, aryl, or loweraralkyl.

"Aminosulfonyl" refers herein to the group —S(O)$_2$—NH$_2$. "Substituted aminosulfonyl" refers herein to the group —S(O)$_2$—NRR' where R is loweralkyl and R' is hydrogen or a loweralkyl. The term "aralkylaminosulfonlyaryl" refers herein to the group -aryl-S(O)$_2$—NH-aralkyl, where the aralkyl is loweraralkyl.

"Carbonyl" refers to the divalent group —C(O)—.

"Carbonyloxy" refers generally to the group —C(O)—O—,. Such groups include esters, —C(O)—O—R, where R is loweralkyl, cycloalkyl, aryl, or loweralkyl. The term "carbonyloxycycloalkyl" refers generally herein to both an "carbonyloxycarbocycloalkyl" and an "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl, where the aralkyl is loweraralkyl.

The term "sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl, in which the aralkyl is loweraralkyl. The term "sulfonamido" refers herein to —SO$_2$NH$_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl.

As used herein, the term "guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, $(H_2N)_2$C=NH—) and those bonded at either of the nitrogen atoms carrying a formal single bond (the "1-" and/or "3"-positions of the guandine, e.g., $H_2N$—C(=NH)—NH—). The hydrogen atoms at any of the nitrogens can be replaced with a suitable substituent, such as loweralkyl, aryl, or loweraralkyl.

As used herein, the term "amidino" refers to the moieties R—C(=N)—NR'— (the radical being at the "$N^1$" nitrogen) and R(NR')C=N— (the radical being at the "$N^2$" nitrogen), where R and R' can be hydrogen, loweralkyl, aryl, or loweraralkyl.

Compounds of the present invention can be readily synthesized using the methods described herein, or other methods, which are well known in the art. For example, the synthesis of pyrimidines having a wide variety of substituents is comprehensibly reviewed in D. J. Brown, "The Pyrimidines," vol. 54, Wiley (1994), which is incorporated herein by reference. The compounds described herein were synthesized using both solution-phase and resin-based (i.e., solid-phase) techniques.

Pyrimidine based compounds of the present invention can be readily synthesized in solution by reaction of a carbonyl-containing derivative with N,N-dimethylforrnamide dimethyl acetal (DMFDMA). The intermediate enaminoketone that results is then reacted with a guanidine in the presence of an organic solvent and a suitable base such as sodium ethoxide, sodium methoxide, sodium hydroxide or cesium carbonate at various temperatures to give a pyrimidine. This method is generally described in Menozzi et al., *J. Heterocyclic Chem.*, 24:1669 (1987), P. Schenone et al., *J. Heterocyclic Chem.*, 27:295 (1990), R. Paul et al., *J. Med. Chem.*, 36: 2716 (1993) and J. Zimmermann et al., *Arch. Pharm.*, 329:371 (1996), all of which are incorporated herein by reference.

Carbonyl-containing starting reagents that are suitable for use in this reaction scheme include, for example, β-keto esters, alkyl aryl ketones, β-keto sulfones, α-nitro ketones, β-keto nitriles, desoxybenzoins, aryl heteroarylmethyl ketones, and the like. The carbonyl-containing starting reagents can either be purchased or synthesized using known methods.

For example, β-keto esters can be readily synthesized by reaction of an acid chloride or other activated carboxylic acid with potassium ethyl malonate in the presence of triethylamine in accordance with the method described in R. J. Clay et al., *Synthesis*, 1992:290 (1992), which is incorporated herein by reference. Alternatively, the desired β-keto ester can be synthesized by deprotonating an appropriate methyl ketone with a suitable base such as sodium hydride, followed by condensation with diethylcarbonate in accordance with the method described in Sircar et al., *J. Med. Chem.*, 28:1405 (1985), which is incorporated herein by reference.

Likewise, β-keto sulfones and a-nitro ketones can be prepared using known methods, such as those described in N. S. Simpkins, "Sulphones in Organic Synthesis," Pergamon (1993) (β-keto sulfones) and M. Jung et. al., *J. Org. Chem.*, 52:4570 (1987) (α-nitro ketones), both of which are incorporated herein by reference. β-keto nitrites can be readily prepared by reaction of an α-halo ketone with sodium or potassium cyanide.

When the substrate is a doubly activated carbonyl compound (e.g., β-keto ester, β-keto sulfone, β-keto nitrile, and the like) the first condensation is typically conducted with a small excess of DMFDMA in a solvent such as THF at 70–80° C. for several hours. This method is described in more detail in Example 25 hereinbelow (i.e., "Solution Method A").

When a mono-activated substrate such as a methyl ketone is involved, DMFDMA is often used as the solvent at a higher temperature (90–100° C.) for a longer period of time (e.g., overnight). After completion of the condensation reaction, the solvent and excess DMFDMA are removed in vacuo. The resulting solid or oil is dissolved in an appropriate solvent and heated with an equimolar amount of the guanidine and base. This method is described in more detail in Example 60 hereinbelow (i.e., "Solution Method B").

When esters are formed, alkaline or acidic hydrolysis of the resulting pyrimidine yields the corresponding carboxylic acid. This acid can then be further coupled to various alcohols or amines to provide a variety of ester or amide derivatives.

Guanidines employed in the synthesis of invention compounds can be purchased or, alternatively, synthesized by reacting the corresponding amine with a guanidino transfer reagent, such as, for example, benzotriazole carboxamidinium 4-methylbenzenesulfonate. This guanidino transfer reagent is described in A. R. Katritzky et al., 1995, *Synthetic Communications*, 25:1173 (1995), which is incorporated herein by reference. Thus, for example, benzotriazole carboxamidinium 4-methylbenzenesulfonate can be reacted in equimolar quantity with an amine and one equivalent of diisopropyl ethyl amine (DIEA) in acetonitrile at room temperature overnight to yield guanidinium 4-methylbenzenesulfonate upon addition of diethyl ether. Amines containing a nitrogen heterocyclic aryl can be prepared by nucleophilic substitution of a halo-substituted nitrogen heterocyclic aryl with an appropriate diamine, such as, for example, ethylenediamine or propylenediamine. These diamines are particularly suitable for use as reaction solvents at reaction temperatures in the range of about 25° C. to 125° C. The preparation of specialized amines is noted in the Examples provided herein.

Other known synthesis methods can be used to prepare compounds of the present invention. For example, 5-aryl 2-aminopyrimidine can be prepared by reacting a guanidine with a vinamidinium salt, in accordance with the method described in R. M. Wagner and C. Jutz, *Chem. Berichte*, p. 2975 (1971), which is incorporated herein by reference. This method is illustrated in Example 67 hereinbelow (i.e., "Solution Method C").

Similarly, 4-anilo-2-chloropyrimidine can be prepared by reacting aniline with 2,4-dichloropyrimidine. Likewise, an aniline can be treated with a 2,4-dichloropyrimidine to give the 4-anilo-2-chloropyrimidine. Further substitution with a second amine gives 2-amino-4-aminopyrimidine.

In addition to solution-phase synthesis methods, solid-support (including resin-based) synthesis methods can also be used to synthesize compounds of the present invention, especially for parallel and combinatorial synthesis methodologies. For example, the synthesis of tetra-substituted pyrimidines may begin with the loading of an aromatic carboxylic acid aldehyde, such as, for example, 4-formyl benzoic acid, to the amino group of a suitable resin, such as, for example, Rink amide resin (Novabiochem, San Diego, Calif.) ("Resin Method A" which is described in more detail in Example 2). Knoevenagel condensation of a β-keto ester gives an unsaturated intermediate that can be condensed with 1H-pyrazole-1-carboxamidine hydrochloride (Aldrich) in the presence of a suitable base (e.g., potassium carbonate). The intermediate dihydropyrimidine can then be oxidized to the resin bound pyrimidine with 2,3-dichloro-5,6-dicyano-1,4-benzoquinone (DDQ) in benzene. Finally, substitution of the pyrazolo moiety by heating with an amine in 1-methylpyrrolidone (NMP) or other suitable solvent is followed by acidolytic cleavage to give the desired pyrimidine. This synthesis method can be used to generate pyrimidines with a substituent in the 4-position of the pyrimidine ring.

Resin Method B, which is described in detail in Example 3, can be used to synthesize pyrimidines in which the 6-position is unsubstituted. A hydroxymethyl-resin, such as commercially available Sasrin resin (Bachem Biosciences, King of Prussia, Pa.), is treated with triphenylphosphine dibromide in dichloromethane to convert the hydroxymethyl group on the resin to a bromomethyl group, as generally described in K. Ngu et al., *Tetrahedron Letters*, 38:973 (1997), which is incorporated herein by reference. The bromine is then displaced by reaction with a primary amine in NMP (at room temperature or 70–80° C.). The amine is then coupled with the appropriate aromatic compound containing an acetyl group. The coupling can be carried out with PyBOP® (Novabiochem, San Diego, Calif.), and 4-methylmorpholine in NMP.

Resin Method B can also be used to incorporate an amino acid residue into the resulting pyrimidine. For example, amino resin can be coupled to a 9-fluorenylmethoxycarbonyl (FMOC)-protected amino acid using standard peptide synthesis conditions and methods. Further coupling with 4-acetylbenzoic acid followed by reaction with N,N-dimethylformamide dimethyl acetal and cyclization with a guanidine produces a pyrimidine derivative having an amino acid residue incorporated within it.

Pyrimidines having e.g., a carboxamidophenyl group at position 6 and hydrogen at position 5 can be prepared from an amino (i.e., $-NH_2$)-containing resin such as Rink amide resin (Novabiochem, San Diego, Calif.). This method is described in more detail in Example 10 hereinbelow ("Resin Method C").

Compounds of the present invention can also be prepared according to Resin Method D, to produce 2,4-diaminopyrimidines. Resin-bound amine is reacted with a 2,4-dichloropyrimidine to give a resin-bound 6-amino-2-chloropyrimidine. The resin-bound amine can be derived from any suitable primary amine; however, anilines generally are not suitable. Displacement with a second amine and cleavage of the product from the resin gives a 2,4-diaminopyrimidine. For the second displacement, primary or secondary amines that may contain other functional groups, such as unprotected hydroxy groups, are suitable. The resulting dichloropyrimidine may be further substituted, for example, with an ester group at the 5-position. A 2,6-dichloropyridine can be used instead of 2,4-dichloropyrimidine to produce a 2,6-diaminopyridine. This scheme is described in more detail in Examples 17–19 hereinbelow.

Resin Method E can be used to produce a 2,6-diaminopyridine. The method is analogous to Resin Method D except that a 2,6-dichloropyridine is used as the electrophile and the final product is a 2,6-diaminopyridine. Resin Method E is described in more detail in Examples 20–21 hereinbelow.

Resin Method F can be used to synthesize 5-amino substituted compounds of the present invention. Resin-bound amine is reacted with a halomethyl aryl ketone. The resulting resin-bound aminomethyl ketone is then treated with DMFDMA (neat) followed by cyclization with a guanidine to give the 2,5-diamino-6-arylpyrimidine. Resin Method F is described in more detail in Example 22, hereinbelow.

Resin Method G, which is described in more detail in Example 23, can be used to synthesize compounds of the present invention having a carboxyl group at the 5-position.

GSK3 inhibitor compounds of the present invention can be purified using known methods, such as, for example, chromatography, crystallization, and the like.

Compounds of the present invention preferably exhibit inhibitory activity that is relatively substantially selective with respect to GSK3, as compared to at least one other type of kinase. As used herein, the term "selective" refers to a relatively greater potency for inhibition against GSK3, as compared to at least one other type of kinase. Preferably, GSK3 inhibitors of the present invention are selective with respect to GSK3, as compared to at least two other types of kinases. Kinase activity assays for kinases other than GSK3 are generally known. See e.g., Havlicek et al., *J. Med. Chem.*, 40:408–12 (1997), incorporated herein by reference. GSK3 selectivity can be quantitated according to the following: GSK3 selectivity=$IC_{50\ (other\ kinase)} \div IC_{50\ (GSK3)}$, where a GSK3 inhibitor is selective for GSK3 when $IC_{50\ (other\ kinase)} > IC_{50\ (GSK3)}$. Thus, an inhibitor that is selective for GSK3 exhibits a GSK3 selectivity of greater than 1-fold with respect to inhibition of a kinase other than GSK3. As used herein, the term "other kinase" refers to a kinase other than GSK3. Such selectivities are generally measured in the cell-free assay described in Example 265.

Typically, GSK3 inhibitors of the present invention exhibit a selectivity of at least about 2-fold (i.e., $IC_{50\ (other\ kinase)} \div IC_{50\ (GSK3)}$) for GSK3, as compared to another kinase and more typically they exhibit a selectivity of at least about 5-fold. Usually, GSK3 inhibitors of the present invention exhibit a selectivity for GSK3, as compared to at least one other kinase, of at least about 10-fold, desirably at least about 100-fold, and more preferably, at least about 1000-fold.

GSK3 inhibitory activity can be readily detected using the assays described herein, as well as assays generally known to those of ordinary skill in the art. Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function by direct interaction with GSK3 itself, or by other mechanisms, including, for example, interference with GSK3 expression or with post-translational processing required to produce mature active GSK3 or alteration of the intracellular localization of GSK3.

In general, a cell-free GSK3 kinase assay can be readily carried out by: (1) incubating GSK3 with a peptide substrate, radiolabeled ATP (such as, for example, $\gamma^{33}P$- or $\gamma^{32}P$-ATP, both available from Amersham, Arlington Heights, Ill.), magnesium ions, and optionally, one or more candidate inhibitors; (2) incubating the mixture for a period of time to allow incorporation of radiolabeled phosphate into the peptide substrate by GSK3 activity; (3) transferring all or a portion of the enzyme reaction mix to a separate vessel, typically a microtiter well that contains a uniform amount of a capture ligand that is capable of binding to an anchor ligand on the peptide substrate; (4) washing to remove unreacted radiolabeled ATP; then (5) quantifying the amount of $^{33}$P or $^{32}$P remaining in each well. This amount represents the amount of radiolabeled phosphate incorporated into the peptide substrate. Inhibition is observed as a reduction in the incorporation of radiolabeled phosphate into the peptide substrate.

Suitable peptide substrates for use in the cell free assay may be any peptide, polypeptide or synthetic peptide derivative that can be phosphorylated by GSK3 in the presence of an appropriate amount of ATP. Suitable peptide substrates may be based on portions of the sequences of various natural protein substrates of GSK3, and may also contain N-terminal or C-terminal modifications or extensions including spacer sequences and anchor ligands. Thus, the peptide substrate may reside within a larger polypeptide, or may be an isolated peptide designed for phosphorylation by GSK3.

For example, a peptide substrate can be designed based on a subsequence of the DNA binding protein CREB, such as the SGSG-linked CREB peptide sequence within the CREB DNA binding protein described in Wang et al., *Anal. Biochem.*, 220:397–402 (1994), incorporated herein by reference. In the assay reported by Wang et al., the C-terminal serine in the SXXXS motif of the CREB peptide is enzymatically prephosphorylated by cAMP-dependent protein kinase (PKA), a step which is required to render the N-terrninal serine in the motif phosphorylatable by GSK3. As an alternative, a modified CREB peptide substrate can be employed which has the same SXXXS motif and which also contains an N-tertninal anchor ligand, but which is synthesized with its C-terminal serine prephosphorylated (such a substrate is available commercially from Chiron Technologies PTY Ltd., Clayton, Australia). Phosphorylation of the second serine in the SXXXS motif during peptide synthesis eliminates the need to enzymatically phosphorylate that residue with PKA as a separate step, and incorporation of an anchor ligand facilitates capture of the peptide substrate after its reaction with GSK3.

Generally, a peptide substrate used for a kinase activity assay may contain one or more sites that are phosphorylatable by GSK3, and one or more other sites that are phosphorylatable by other kinases, but not by GSK3. Thus, these other sites can be prephosphorylated in order to create a motif that is phosphorylatable by GSK3. The term "prephosphorylated" refers herein to the phosphorylation of a substrate peptide with non-radiolabeled phosphate prior to conducting a kinase assay using that substrate peptide. Such prephosphorylation can conveniently be performed during synthesis of the peptide substrate.

The SGSG-linked CREB peptide can be linked to an anchor ligand, such as biotin, where the serine near the C terminus between P and Y is prephosphorylated. As used herein, the term "anchor ligand" refers to a ligand that can be attached to a peptide substrate to facilitate capture of the peptide substrate on a capture ligand, and which functions to hold the peptide substrate in place during wash steps, yet allows removal of unreacted radiolabeled ATP. An exemplary anchor ligand is biotin. The term "capture ligand" refers herein to a molecule which can bind an anchor ligand with high affinity, and which is attached to a solid structure. Examples of bound capture ligands include, for example, avidin- or streptavidin-coated microtiter wells or agarose beads. Beads bearing capture ligands can be further combined with a scintillant to provide a means for detecting captured radiolabeled substrate peptide, or scintillant can be added to the captured peptide in a later step.

The captured radiolabeled peptide substrate can be quantitated in a scintillation counter using known methods. The signal detected in the scintillation counter will be proportional to GSK3 activity if the enzyme reaction has been run under conditions where only a limited portion (e.g., less than 20%) of the peptide substrate is phosphorylated. If an inhibitor is present during the reaction, GSK3 activity will be reduced, and a smaller quantity of radiolabeled phosphate will thus be incorporated into the peptide substrate. Hence, a lower scintillation signal will be detected. Consequently, GSK3 inhibitory activity will be detected as a reduction in scintillation signal, as compared to that observed in a negative control where no inhibitor is present during the reaction. This assay is described in more detail in Example 265 hereinbelow.

A cell-based GSK3 kinase activity assay typically utilizes a cell that can express both GSK3 and a GSK3 substrate, such as, for example, a cell transformed with genes encoding GSK3 and its substrate, including regulatory control sequences for the expression of the genes. In carrying out the cell-based assay, the cell capable of expressing the genes is incubated in the presence of a compound of the present invention. The cell is lysed, and the proportion of the substrate in the phosphorylated form is determined, e.g., by observing its mobility relative to the unphosphorylated form on SDS PAGE or by determining the amount of substrate that is recognized by an antibody specific for the phosphorylated form of the substrate. The amount of phosphorylation of the substrate is an indication of the inhibitory activity of the compound, i.e., inhibition is detected as a decrease in phosphorylation as compared to the assay conducted with no inhibitor present. GSK3 inhibitory activity detected in a cell-based assay may be due, for example, to inhibition of the expression of GSK3 or by inhibition of the kinase activity of GSK3.

Thus, cell-based assays can also be used to specifically assay for activities that are implicated by GSK3 inhibition, such as, for example, inhibition of tau protein phosphorylation, potentiation of insulin signaling, and the like. For example, to assess the capacity of a GSK3 inhibitor to inhibit Alzheimer's-like phosphorylation of microtubule-associated protein tau, cells may be co-transfected with human GSK3β and human tau protein, then incubated with one or more candidate inhibitors. Various mammalian cell lines and expression vectors can be used for this type of assay. For instance, COS cells may be transfected with both a human GSK3β expression plasmid according to the protocol described in Stambolic et al., 1996, *Current Biology* 6:1664–68, which is incorporated herein by reference, and an expression plasmid such as pSG5 that contains human tau protein coding sequence under an early SV40 promoter. See also Goedert et al., *EMBO J.*, 8:393–399 (1989), which is incorporated herein by reference. Alzheimer's-like phosphorylation of tau can be readily detected with a specific antibody such as, for example, AT8, which is available from Polymedco Inc. (Cortlandt Manor, N.Y.) after lysing the cells. This assay is described in greater detail in the examples, hereinbelow.

Likewise, the ability of GSK3 inhibitor compounds to potentiate insulin signaling by activating glycogen synthase can be readily ascertained using a cell-based glycogen synthase activity assay. This assay employs cells that respond to insulin stimulation by increasing glycogen synthase activity, such as the CHO-HIRC cell line, which overexpresses wild-type insulin receptor (~100,000 binding sites/cell). The CHO-HIRC cell line can be generated as described in Moller et al., *J. Biol. Chem.*, 265:14979–14985 (1990) and Moller et al., *Mol. Endocrinol.*, 4:1183–1191 (1990), both of which are incorporated herein by reference.

The assay can be carried out by incubating serum-starved CHO-HIRC cells in the presence of various concentrations of compounds of the present invention in the medium, followed by cell lysis at the end of the incubation period. Glycogen synthase activity can be detected in the lysate as described in Thomas et al., *Anal Biochem.*, 25:486–499 (1968). Glycogen synthase activity is computed for each sample as a percentage of maximal glycogen synthase activity, as described in Thomas et al., supra, and is plotted as a function of candidate GSK3 inhibitor concentration. The concentration of candidate GSK3 inhibitor that increased glycogen synthase activity to half of its maximal level (i.e., the $EC_{50}$) can be calculated by fitting a four parameter sigmoidal curve using routine curve fitting methods that are well known to those having ordinary skill in the art. This is described in more detail in Example 266, hereinbelow.

GSK3 inhibitors can be readily screened for in vivo activity such as, for example, using methods that are well known to those having ordinary skill in the art. For example, candidate compounds having potential therapeutic activity in the treatment of type 2 diabetes can be readily identified by detecting a capacity to improve glucose tolerance in animal models of type 2 diabetes. Specifically, the candidate compound can be dosed using any of several routes prior to administration of a glucose bolus in either diabetic mice (e.g. KK, db/db, ob/ob) or diabetic rats (e.g. Zucker Fa/Fa or GK). Following administration of the candidate compound and glucose, blood samples are removed at preselected time intervals and evaluated for serum glucose and insulin levels. Improved disposal of glucose in the absence of elevated secretion levels of endogenous insulin can be considered as insulin sensitization and can be indicative of compound efficacy. A detailed description of this assay is provided in the examples, hereinbelow.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, and the like.

In accordance with other embodiments of the present invention, there is provided a composition comprising GSK3-inhibitor compound of the present invention, together with a pharmaceutically acceptable carrier or excipient.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing GSK-3 inhibitor compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrastemal injection, or infusion techniques.

Injectable preparations, for example, sterile injectable aqueous or oleaginous suspensions may, be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

In accordance with yet other embodiments, the present invention provides methods for inhibiting GSK3 activity in a human or animal subject, said method comprising administering to a subject an amount of a GSK3 inhibitor compound having the structure (I), (IV) or (V) (or composition comprising such compound) effective to inhibit GSK3 activity in the subject. Other embodiments provided methods for treating a cell or a GSK3-mediated disorder in a human or animal subject, comprising administering to the cell or to the human or animal subject an amount of a compound or composition of the invention effective to inhibit GSK3 activity in the cell or subject. Preferably, the subject will be a human or non-human animal subject. Inhibition of GSK3 activity includes detectable suppression of GSK3 activity either as compared to a control or as compared to expected GSK3 activity.

Effective amounts of the compounds of the invention generally include any amount sufficient to detectably inhibit GSK3 activity by any of the assays described herein, by other GSK3 kinase activity assays known to those having ordinary skill in the art or by detecting an alleviation of symptoms in a subject afflicted with a GSK3-mediated disorder.

GSK3-mediated disorders that may be treated in accordance with the invention include any biological or medical disorder in which GSK3 activity is implicated or in which the inhibition of GSK3 potentiates signaling through a pathway that is characteristically defective in the disease to be treated. The condition or disorder may either be caused or characterized by abnormal GSK3 activity. Representative GSK3-mediated disorders include, for example, type 2 diabetes, Alzheimer's disease and other neurodegenerative disorders, obesity, atherosclerotic cardiovascular disease, essential hypertension, polycystic ovary syndrome, syndrome X, ischemia, especially cerebral ischemia, traumatic brain injury, bipolar disorder, immunodeficiency, cancer and the like.

Successful treatment of a subject in accordance with the invention may result in the inducement of a reduction or alleviation of symptoms in a subject afflicted with a medical or biological disorder to, for example, halt the further progression of the disorder, or the prevention of the disorder. Thus, for example, treatment of diabetes can result in a reduction in glucose or HbAlc levels in the patient. Likewise, treatment of Alzheimer's disease can result in a reduction in rate of disease progression, detected, for example, by measuring a reduction in the rate of increase of dementia.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be from about 0.1 mg/kg/day to about 100 mg/kg/day, preferably from about 1 mg/kg/day to about 20 mg/kg/day, and most preferably from about 2 mg/kg/day to about 10 mg/kg/day of a GSK3 inhibitor compound of the present invention, which may be administered in one or multiple doses.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of type 2 diabetes include, for example, insulin, troglitazone, rosiglitazone, pioglitazone, glipizide, metformin, sulfonylurea, acarbose, and the like. Representative agents useful in combination with the compounds of the invention for the treatment of Alzheimer's disease include, for example, donepezil, tacrine and the like. Representative agents useful in combination with the compounds of the invention for the treatment of bipolar disease include, for example, lithium salts, valproate, carbamazepine and the like. A representative agent useful in combination with the compounds of the invention for the treatment of stroke is, for example, tissue plasminogen activator.

When additional active agents are used in combination with the compounds of the present invention, the additional active agents may generally be employed in therapeutic amounts as indicated in the PHYSICIANS' DESK REFERENCE (PDR) 53$^{rd}$ Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The foregoing and other aspects of the invention may be better understood in connection with the following representative examples.

EXAMPLES

Example 1

Characterization and Purification Methods

Compounds of the present invention were characterized by high performance liquid chromatography (HPLC) using a Waters Millennium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass- or plastic-backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on a Fisons VG Electrospray Mass Spectrometer. All masses are reported as those of the protonated parent ions.

Nuclear magnetic resonance (NMR) analysis was performed with a Varian 300 MHz NMR (Palo Alto, Calif.). The spectral reference was either TMS or the known chemical shift of the solvent. Some compound samples were run at elevated temperatures (i.e. 75° C.) to promote increased sample solubility.

The purity of some of the invention compounds was assessed by elemental analysis (Desert Analytics, Tucson, Ariz.)

Melting points were determined on a Laboratory Devices Mel-Temp apparatus (Holliston, Mass.).

Preparative separations were carried out using either a Flash 40 chromatography system and KP-Sil, 60A (Biotage, Charlottesville, Va.), a Chromatotron radial chromatography device (Harrison Research, Palo Alto, Calif.), or by HPLC using a C-18 reversed phase column. Typical solvents employed were dichloromethane, methanol, ethyl acetate and triethyl amine.

Example 2

Solid Phase Synthesis of Pyrimidine Compounds

Resin Method A

Step A: Knoevenagel Condensation

A suspension of benzaldehyde-bound resin (1g, 0.52 mmol) in 8 ml of 1:1 alcohol:dioxane was treated with 2.2 mole β-ketoester and 1.3 mmol an amine, e.g., piperidine. The reaction mixture was shaken for 20 hours at room temperature and the resin was then filtered and washed with 4×10 ml dichloromethane (DCM).

Step B: Cyclization and Oxidation to the Pyrimidine Nucleus

The product from Step A (100 mg, 0.052 mmol) was combined with 0.26 mmol of the pyrazole carboxamidine hydrochloride and 0.13 mmol $NaHCO_3$ in 1 ml N-methylpyrrolidinone. The reaction mixture was shaken at 70° C. for 24 hours. Following cooling, the reaction was washed successively with water, methanol, DMF, methylene chloride and ether, then dried. Cleavage of a small amount of resin indicated that the desired dihydropyrimidine was present in high yield.

The dried resin was then taken up in THF and 1.1 eq. of dicyanodichloroquinone (DDQ) was added. The resulting slurry was stirred for 0.5 hours at which time the resin was washed with DMF, 10% $Na_2HCO_3$, $H_2O$, dimethylformamide (DMF), methanol (MeOH), methylene chloride and ether, then dried. Cleavage of a small amount of this resin with trifluoroacetic acid/methylene chloride indicated the presence of a pyrimidine in high yield.

Step C: Amine Displacement and Release from the Solid Support

A suspension of the pyrimidine (50 mg, 0.026 mmol) in 0.75 ml NMP was treated with 1 mmol of an amine and 0.26 mmol acetic acid. The reaction mixture was shaken at 80° C. for 24–48 hours. Following cooling, the resin was washed 4× each with methanol, DMF, and methylene chloride. The resin was then dried and a solution of 5% trifluoroacetic acid in methylene chloride was added. The resin was shaken for 2 hours, then filtered and washed 3× with methylene chloride. The combined filtrates were concentrated, taken up in 1:1 water/acetonitrile and lyophilized to dryness.

The following compounds of the present invention were prepared according to Resin Method A using the ketoester and amine identified in parentheses:

Ethyl 4-(4-carbamoylphenyl)-6-ethyl-2-({2-[(5-nitro(2-pyridyl))amino]ethyl}amino)pyrimidine-5-carboxylate (from ethyl 3-oxo-valerate and 2-(2-aminoethylamino)-5-nitropyridine (dehydration of this compound using trifluoracetic anhydride yielded ethyl 4-(4-cyanophenyl)-6-ethyl-2-({2-[(5-nitro(2-pyridyl)amino]ethyl}amino)pyrimidine-5-carboxylate)

Ethyl 4-(4-carbamoylphenyl)-2-({2-[5-nitro(2-pyridyl))amino]ethyl}amino)-6-(4-pyridyl)pyrimidine-5-carboxylate (from ethyl 3-(4-pyridyl)-3-oxopropionate and 2-(2-aminoethylamino)-5-nitropyridine)

Ethyl 4-(4-carbamoylphenyl)-2-({2-[(5-nitro(2-pyridyl))amino]ethyl}amino)-6-(4-nitrophenyl)pyrimidine-5-carboxylate (from ethyl 3-(4-nitrophenyl)-3-oxoproprionate and 2-(2-aminoethylamino)-5-nitropyridine)

Example 3

Solid Phase Synthesis of Pyrimidine Compounds

Resin Method B

Step 1: Sasrin resin (Bachem Biosciences, 5.0 g, nominal substitution 1.02 mmol/g) was shaken with triphenylphosphine dibromide (2.3 g) in dry dichloromethane (60–70 ml) for 4 hours at room temperature. All solvents and glassware used to carry out this reaction were dry. The resin was washed well with dichloromethane.

Step 2: The resin from Step 1 was then reacted with a primary amine (0.5–1 M) in 1-methylpyrrolidone (NMP) at 70–80° C. for 3–5 hours to produce an aminomethyl resin, which was used immediately after preparation. The resin was then thoroughly washed with dimethylsulfoxide (DMSO) (or DMF) and dichloromethane, then dried in vacuo at room temperature.

Step 3: After drying, the resin was coupled overnight with 4-acetylbenzoic acid using benzotriazole-1-yl-oxy-tris-pyrollidino-phosphonium hexafluorophosphate (PyBop®, which is available from Novabiochem, San Diego, Calif.), 4-methylmorpholine and NMP in accordance with the method described in Example 10 (i.e., "Resin Method C") (except that cleavage of the product from the resin was carried out under more strongly acidic conditions, i.e., typically 20–100% trifluoroacetic acid (TFA) in DCM (e.g., 60% TFA in DCM)).

Other types of resin having a pendant $CH_2OH$ group can also be used in carrying out this method such as, for example, Wang resin (Novabiochem, San Diego, Calif.). It is also possible to load the primary amine onto a solid support by other methods such as, for example, reductive amination of a solid support containing an aldehyde.

Examples 4–9 describe the synthesis of compounds of the present invention pursuant to Resin Method B.

Example 4

Synthesis of N-{(3-bromophenyl)methyl]{4-[2-({3-[(5-nitro(2-pyridyl)amino]propyl}amino)pyrimidin-4-yl]phenyl}carboxamide Step 1: A solution of 2-chloro-5-nitropyridine (3.16 g, 20 mmol) in dry acetonitrile (40 ml) was added dropwise to a solution of 1,3-diaminopropane (5.0 ml) in acetonitrile (20 ml) at room temperature. After 7.5 hour, a yellow solid precipitated in the reaction mixture. The solvent was removed in vacuo and the residue was partitioned between 2.5 M aqueous sodium hydroxide and dichloromethane. The layers were separated and the aqueous portion was extracted 3× with dichloromethane. The combined organic layers were back-extracted with a saturated sodium chloride solution, then dried and concentrated in vacuo using a Buchi rotary evaporator Model R-124 to give (3-aminopropyl)(5-nitro (2-pyridyl))amine as a yellow solid (2.55 g). The amine (1.14 g, 6 mmol) was shaken with benzotriazole carboxamidinium 4-methylbenzenesulfonate (2.0 g, 6 mmol) and diisopropylethyl amine (DIEA) (1.05 ml, 6 mmol) in acetonitrile (10 ml) at room temperature over two days. Dilution with ether gave the amino-{3-[(5-nitro (2-pyridyl))amino] propyl}carboxamidinium 4-methylbenzenesulfonate as a solid.

Step 2: Sasrin resin (10 g) was shaken with triphenylphosphine dibromide (4.5 g) in dry dichloromethane (ca. 80 ml) at room temperature for 4 hours. The resin was washed well with dichloromethane and air-dried briefly. The air-dried resin was divided into 6 equal portions. One portion was heated at 70° C. for 4 hours with a solution of 3-bromobenzylamine (8 mmol) in NMP (12 ml). The resin was washed well with DMF and dichloromethane and dried overnight in vacuo at room temperature. The dried resin was then shaken with a solution of PyBop® (3.12 g, 6 mmol), 4-acetylbenzoic acid (1.0 g, 6 mmol), and 4-methylmorpholine (12 mmol) in NMP (12 ml) at room temperature overnight. The resin was washed with DMF, DMSO and dichloromethane and briefly air-dried. The resin was then heated with N,N-dimethylformamide dimethylacetal (10 ml) at 95° C. for 9 hours. After cooling, the resin was washed with dichloromethane and dried in vacuo at room temperature. The resin (80 mg) was then reacted with 100 mg of the guanidine prepared in Step 1 plus cesium carbonate (160 mg) with NMP (2 ml) at 95° C. overnight, followed by cleavage with 60% TFA in dichloromethane to give N-{(3-bromophenyl)methyl]{4-[2-({3-[(5-nitro(2-pyridyl)amino]propyl}amino)pyrimidin-4-yl]phenyl}carboxamide.

HPLC: 25.31 min (98% pure); MS: $MH^+$=562/564 (1 Br); $C_{26}H_{24}N_7BrO_3$=561/563 g/mol.

Example 5

Synthesis of N-{(3-bromophenyl)methyl]{4-[2-({2-[(5-cyano(2-pyridyl)aminolethyl}amino)pyrimidin-4-yl]phenyl}carboxamide Step 1: 6-Chloronicotinitrile (2.0 g) was treated with ethylenediamine (5 ml). The mixture was then heated at 50° C. for 22 hours. Excess ethylenediamine was removed by rotary evaporation. The residue was partitioned between 2.5 M aqueous sodium hydroxide and dichloromethane. The aqueous layer was extracted 4× more with dichloromethane. The combined organic layers were washed with a saturated sodium chloride solution, dried and then concentrated in vacuo to give 6-[(2-aminoethyl)amino]pyridine-3-carbonitrile as an amber liquid which solidified upon standing. The amine (0.97 g, 6 mmol) was shaken overnight with benzotriazole carboxamidinium 4-methylbenzenesulfonate (2.0 g, 6 mmol) and DIEA (1.05 ml, 6 mmol) in acetonitrile (10 ml). Addition of ether gave amino{2-[(5-cyano(2-pyridyl)amino]ethyl}carboxamidinium 4-methylbenzenesulfonate as a white solid.

Step 2: The guanidine from Step 1 (120 mg) was reacted with the resin prepared as in Example 4, Step 2 (80 mg) in the presence of cesium carbonate (160 mg) in NMP (2 ml) at 90° C. overnight. Treatment of the resin with 60% TFA in dichloromethane gave the title compound.

HPLC: 23.70 min (98% purity)

MS: $MH^+$=528/530 (1 Br) $C_{26}H_{22}N_7BrO$=527/529 g/mole

Example 6

Synthesis of N-[(3-methoxyphenyl)methyl]{4-[2-({2-[(5-nitro(2-pyridyl))aminolethyl}amino)pyrimidin-4-yl]phenyl}carboxamide Step 1: 2-(2-aminoethylamino)-5-nitropyridine (Aldrich Chemical Co., Milwaukee, Wis.) (1.08 g, 6 mol) was shaken with benzotriazole carboxamidinium 4-methylbenzenesulfonate (2.0 gm, 6 mmol) and DIEA (1.05 ml, 6 mmol) in a mixture of acetonitrile (10 ml) and DMF (3 ml) at room temperature overnight. Addition of ether gave amino[2-[(5-nitro(2-pyridyl)amino] ethyl}carboxamidinium 4-methylbenzene-sulfonate as light orange crystals.

Step 2: The Sasrin resin was prepared as described in Step 2 of Example 3. The resin (500 mg) was heated with a solution of 3-methoxybenzylamine (600 μl) in NMP (6 ml) at 70° C. for 4 hours. The resin was then washed with DMF and dichloromethane and then shaken with a solution of PyBop® (1.04 g, 2 mmol), 4-acetylbenzoic acid (0.33 g, 2 mmol), 4-methylmorpholine (4 mmol) in NMP (6 ml) at room temperature overnight. A small aliquot of the resin was treated with 20% TFA in dichloromethane to give the intermediate, (4-acetylphenyl)-N-[(3-methoxyphenyl)methyl]carboxamide (HPLC: 23.94 min (97%); MS; MH$^+$=284 (as required)). The resin was then heated at 95° C. for 7 hours in DMFDMA (5 ml).

After heating, the resin was washed with dichloromethane, then dried in vacuo. Dried resin (120 mg) was reacted with 120 mg of the guanidine prepared in Step 1 plus cesium carbonate (160 mg) in NMP (2 ml) overnight at 90° C. Cleavage with 20% TFA in dichloromethane gave the title compound.

HPLC: 22.32 min (85% pure)
MS: MH$^+$=500 $C_{26}H_{25}N_7O_4$=499 g/mole

Example 7

Synthesis of 4-(2-{[3-(4-nitroimidazolyl)propyl]amino}pyrimidin-4-yl)phenol

Step 1: 4-Nitroimidazole (5.0 g, 44 mol) in DMF:THF (1:1 (v/v), 40 ml) was treated at room temperature with 60% NaH (2.2 g). When hydrogen evolution had ceased, 3-bromopropylphthalimide (11.79 g, 44 mmol) was added, followed by heating at 70° C. overnight. The mixture was cooled, diluted with dichloromethane and carefully quenched with water. At this point the solid product precipitated out to give 2-[3-(4-nitroimidazolyl)propyl]isoindoline-1,3-dione as a white solid, 8.85 g. The solid was refluxed with methanol (60 ml) and anhydrous hydrazine (4 ml) overnight. The mixture was cooled to 4° C., then filtered. The filtrate was concentrated to dryness, then partitioned between dichloromethane and 2.5 M aqueous sodium hydroxide. The organic layer was washed with saturated sodium chloride solution, dried and concentrated in vacuo to give 3-(4-nitroimidazolyl)propylamine as an orange syrup, 2.24 g. The amine, 1.18 g was treated with benzotriazole carboxamidinium 4-methylbenzenesulfonate (2.2 g) and DIEA (1.5 ml) in acetonitrile (8 ml) with shaking at room temperature overnight. Addition of ether gave amino[3-(4-nitroimidazolyl)propyl]carboxamidinium 4-methylbenzenesulfonate as a beige solid.

Step 2: The Sasrin resin (prepared according to Example 3, Step 2) (2.5 g) was heated at 80° C. with 4-hydroxyacetophenone (700 mg) and cesium carbonate (600 mg) in NMP (10 ml) for 24 hours. The resin was then washed with DMF, water, DMF and dichloromethane and dried in vacuo. The dried resin was then heated overnight with DMFDMA (10 ml) at 105° C. The resin was cooled, filtered and washed well with dichloromethane and dried in vacuo. The dried resin (100 mg) was then treated with 100 mg of the guanidine prepared in Step 1, 200 mg of cesium carbonate and 3 ml of NMP at 105° C. for 66 h. The resin was washed with DMSO, acetic acid, water, DMSO and dichloromethane, then shaken with 100% TFA for 1 h, and filtered. The filtrate was concentrated in vacuo and lyophilized to give the title compound.

HPLC: 16.85 min (75% purity)
MS: MH$^+$=341 $C_{16}H_{16}N_6O_3$=340 g/mol

Example 8

Synthesis of 4-[2-({2-[(5-nitro(2-pyridyl))amino]ethyl}amino)-5-phenylpyrimidin-4-yl]phenol Bromomethyl sasrin resin (prepared according to Example 3, Step 2), 0.9 g, was heated with benzyl 4-hydroxyphenyl ketone (1.06 g, 5 mmol) and cesium carbonate (1.6 g) in NMP (8 ml) at 80° C. overnight. The resin was washed serially with DMF, water, DMF and dichloromethane and dried in vacuo. The dried resin was heated with DMFDMA (8 ml) at 100° C. overnight. After cooling the resin was filtered and washed well with dichloromethane, then dried in vacuo. The resin (75 mg) was then reacted with 100 mg of amino {2-[(5-nitro(2-pyridyl))amino]ethyl}carboxamidinium 4-methylbenzenesulfonate and 200 mg of cesium carbonate in NMP (2 ml) at 104° C. for 64 hours. The resin was then washed with DMSO, acetic acid, water, DMSO and dichloromethane. The resin was shaken with 100% TFA at room temperature (1 h). The resin was filtered and the filtrate concentrated in vacuo, then lyophilized to give the title compound.

HPLC: 22.53 min (95% purity)
MS: MH$^+$=429 $C_{23}H_{20}N_6O_3$=428 g/mol

Example 9

Synthesis of [(3-Bromophenyl)methyl]({4-[2-({2-[(5-nitro(2-pyridyl))aminol ethyl}amino)pyrimidine-4-yl]phenyl}sulfonyl)amine Step 1: Sasrin resin (500 mg) substituted with m-bromobenzylamine (according to Step 1 of Example 3) was treated with 4-acetylbenzenesulfonyl chloride (1.1 g, 5 mmol) and DIEA (1.22 ml, 7 mmol) in dichloromethane (10 ml) with shaking at room temperature for 0.5 hours. Then 4-dimethylaminopyridine (122 mg, 1 mmol) was added, followed by shaking overnight at room temperature. The resin was washed well with DMF and dichloromethane, then heated with DMFDMA (10 mL) at 95° C. overnight. The resin was washed well with dichloromethane and dried in vacuo at room temperature.

Step 2: The resin prepared in Step 1 (70 mg) was treated with amino[2-[(5-nitro(2-pyridyl)amino]ethyl}carboxamidinium 4-methylbenzenesulfonate (100 mg) and cesium carbonate (160 mg) in NMP 2 ml) at 95° C. overnight. The resin was serially washed with DMSO, acetic acid, water, DMSO, dichloromethane and then treated with 60% TFA in dichloromethane at room temperature for 0.5 hours. The resin was filtered off and the filtrate was concentrated in vacuo and lyophilized to give the title compound.

HPLC: 26.62 min (100% purity)
MS: MH$^+$=584/586 $C_{24}H_{22}N_7BrO_4S$=583/585 g/mol (1 Br)

The following additional compounds were similarly synthesized according to Resin Method B by varying the guanidine used:

4-(2-{[2-(4-nitrophenyl)ethyl]amino}pyrimidin-4-yl)benzamide
4-{2-[(2-(2-pyridyl)ethyl)amino]pyrimidin-4-yl}benzamide
4-{2-[(4-pyridylmethyl)amino]pyrimidin-4-yl}benzamide
4-[2-({2-[(5-nitro-2-pyridyl)amino]ethyl}amino)pyrimidin-4-yl]benzamide
4-(2-{[2-(pyrimidin-2-ylamino)ethyl]amino}pyrimidin-4-yl)benzamide
4-{2-[(3-imidazol-5-ylethyl)amino]pyrimidin-4-yl}benzamide
4-(2-{[2-(benzothiazol-2-ylamino)ethyl]amino}pyrimidin-4-yl)benzamide
4-{2-[(2-{[5-(trifluoromethyl)-2-pyridyl]amino}ethyl)amino]pyrimidin-4-yl}benzamide
4-[2-({2-[(5-cyano-2-pyridyl)amino]ethyl}amino)pyrimidin-4-yl]benzamide 4-{2-[(2-{[5-(aminothioxomethyl)-2-pyridyl]amino}ethyl)
    amino]pyrimidin-4-yl}benzamide
4-(2-{[(3-bromophenyl)methyl]amino}pyrimidin-4-yl)
    benzamide
4-[2-({[4-(4-fluorophenyl)phenyl]methyl}amino)
    pyrimidin-4-yl]benzamide
4-{2-[4-benzylpiperazinyl]pyrimidin-4-yl}benzamide
4-(2-{[(5-methylpyrazin-2-yl)methyl]amino}pyrimidin-4-
    yl)benzamide
4-{2-[(3-imidazolylpropyl)amino]pyrimidin-4-
    yl}benzamide
4-{2-[(2,2-diphenylethyl)amino]pyrimidin-4-yl}benzamide
4-[2-({[3-(trifluoromethyl)phenyl]methyl}amino)
    pyrimidin-4-yl]benzamide
4-(2-{[(3-nitrophenyl)methyl]amino}pyrimidin-4-yl)
    benzamide
4-{2-[(naphthylmethyl)amino]pyrimidin-4-yl}benzamide
4-(2-{[(4-bromophenyl)methyl]amino}pyrimidin-4-yl)
    benzamide
4-(2-{[(3,5-dichlorophenyl)methyl]amino}pyrimidin-4-yl)
    benzamide
4-(2-{[(3-methoxyphenyl)methyl]amino}pyrimidin-4-yl)
    benzamide
4-[2-({[3-(3-methoxyphenyl)phenyl]methyl}amino)
    pyrimidin-4-yl]benzamide
4-[2-({[3-(3-aminophenyl)phenyl]methyl}amino)
    pyrimidin-4-yl]benzamide
4-{2-[({3-[3-(acetylamino)phenyl]phenyl{methyl)amino]
    pyrimidin-4-yl}benzamide
4-[2-({[4-(3-aminophenyl)phenyl]methyl}amino)
    pyrimidin-4-yl]benzamide
4-(2-{[(3-chlorophenyl)methyl]amino}pyrimidin-4-yl)
    benzamide
4-(2-{[(2,4-dichlorophenyl)methyl]aminol}pyrimidin-4-yl)
    benzamide
4-(2-{[(3-methylphenyl)methyl]amino}pyrimidin-4-yl)
    benzamide
4-(2-{[(3,4-dimethoxyphenyl)methyl]amino}pyrimidin-4-
    yl)benzamide
4-[2-({[4-(trifluoromethyl)phenyl]methyl}amino)
    pyrimidin-4-yl]benzamide
4-(2-{[(4-methoxyphenyl)methyl]amino}pyrimidin-4-yl)
    benzamide
4-(2-{[(4-aminophenyl)methyl]amino}pyrimidin-4-yl)
    benzamide
4-[2-({[3,5-bis(trifluoromethyl)phenyl]methyl}amino)
    pyrimidin-4-yl]benzamide
4-{2-[4-(2-methoxyphenyl)piperazinyl]pyrimidin-4-
    yl}benzamide
4-{2-[({3-[3-(trifluoromethyl)phenyl]phenyl}methyl)
    amino]pyrimidin-4-yl}benzamide
5 4-(2-{[2-(3-methoxyphenyl)ethyl]amino}pyrimidin-4-yl)
    benzamide
4-(2-{[2-(4-fluorophenyl)ethyl]amino}pyrimidin-4-yl)
    benzamide
4-(2-{[(3,4,5-trimethoxyphenyl)methyl]amino}pyrimidin-
    4-yl)benzamide
{4-[2-({2-[({2-[(4-amino-5-cyanopyrimidin-2-yl)amino]
    ethyl}amino)pyrimidin-4-yl]phenyl}-N-[(3-
    bromophenyl)methyl]carboxamide
4-[2-({2-[(4-amino-5-cyanopyrimidin-2-yl)amino]
    ethyl}amino)pyrimidin-4-yl]benzamide
4-[2-({3-[(5-nitro-2-pyridyl)amino]propyl}amino)
    pyrimidin-4-yl]benzamide
4-(2-{[(4-cyanophenyl)methyl]amino}pyrimidin-4-yl)
    benzamide
4-2-[(2-phenylpropyl)amino]pyrimidin-4-yl]benzamide
4-{2-[(2-phenoxyethyl)amino]pyrimidin-4-yl}benzamide
4-(2-{[2-(2,5-dimethoxyphenyl)ethyl]amino}pyrimidin-4-
    yl)benzamide
4-(2-{[(2,6-dimethoxyphenyl)methyl]amino}pyrimidin-4-
    yl)benzamide
4-(2-{[2-(2-methoxyphenyl)ethyl]amino}pyrimidin-4-yl)
    benzamide
4-{2-[(4-phenylbutyl)amino]pyrimidin-4-yl}benzamide
4-{2-[(2-(2H-benzo[3,4-d]1,3-dioxolen-5-yl)ethyl)amino]
    pyrimidin-4-yl}benzamide
4-(2-{[2-(3-chlorophenyl)ethyl]amino}pyrimidin-4-yl)
    benzamide
4-(2-{[2-(2,3-dimethoxyphenyl)ethyl]amino}pyrimidin-4-
    yl)benzamide
4-{2-[(3-phenoxypropyl)amino]pyrimidin-4-yl}benzamide
4-(2-{[3-(4-chlorophenoxy)propyl]amino}pyrimidin-4-yl)
    benzamide
4-(2-{[3-(4-methoxyphenoxy)propyl]amino}pyrimidin-4-
    yl)benzamide
4-(2-{[3-(3-methoxyphenoxy)propyl]amino}pyrimidin-4-
    yl)benzamide
4-(2-{[3-(3-bromophenoxy)propyl]amino}pyrimidin-4-yl)
    benzamide
4-(2-{[3-(2,4-dichlorophenoxy)propyl]amino}pyrimidin-4-
    yl)benzamide
4-[2-({3-[3-(trifluoromethyl)phenoxy]propyl}amino)
    pyrimidin-4-yl]benzamide
4-(2-{[3-(3-methylphenoxy)propyl]amino}pyrimidin-4-yl)
    benzamide
4-(2-{[3-(4-phenylimidazolyl)propyl]amino}pyrimidin-4-
    yl)benzamide
4-(2-{[3-(5,6-dichlorobenzimidazolyl)propyl]
    amino}pyrimidin-4-yl)benzamide
4-(2-{[3-(3,4-dichlorophenoxy)propyl]amino}pyrimidin-4-
    yl)benzamide
4-(2-{[3-(5,6-dimethylbenzimidazolyl)propyl]
    amino}pyrimidin-4-yl)benzamide
4-{2-[(3-(6-quinolyloxy)propyl)amino]pyrimidin-4-
    yl}benzamide
4-{2-[(3-naphthyloxypropyl)amino]pyrimidin-4-
    yl}benzamide
4-(2-{[3-(3-phenylphenoxy)propyl]amino}pyrimidin-4-yl)
    benzamide
4-(2-{[3-(4-nitroimidazolyl)propyl]amino}pyrimidin-4-yl)
    benzamide
4-(2-{[3-(4,5-dichloroimidazolyl)propyl]amino}pyrimidin-
    4-yl)benzamide
4-{2-[(3-benzimidazolylpropyl)amino]pyrimidin-4-yl}-2-
    chlorophenol
4-[2-({3-[4-(2,4-dichlorophenyl)imidazolyl]propyl}amino)
    pyrimidin-4-yl]benzamide
4-[2-({3-[4-(3-methoxyphenyl)imidazolyl]propyl}amino)
    pyrimidin-4-yl]benzamide Example 10

Solid Phase Synthesis of Pyridine Compounds

Resin Method C

Rink amide resin (Novabiochem, San Diego, Calif., nominally 0.46 mmol/g substitution) was deprotected with 20% v/v piperidine in DMF (ca. 60 ml, 0.5 hours, room temperature). The resin was washed thoroughly with DMF and dichloromethane, then treated with 4-acetylbenzoic acid (8 mmol), PyBOP® (8 mmol, Novabiochem), 4-methylmorpholine (12 mmol) and NMP (50 ml) for 8.5 hours at room temperature on a wrist shaker. The resin was washed with DMF and dichloromethane, air dried, and then divided into 3 portions. Each portion was treated with N,N-dimethylformamide dimethyl acetal (ca. 12 ml) with heating at 105° C. overnight (ca. 13 hours). The reactions were allowed to cool and the resin was washed with dichloromethane, then dried in vacuo at room temperature.

For the synthesis of pyrimidines, typically 100 mg of the above dried resin was mixed with 200–300 mg of anhydrous cesium carbonate, 80–200 mg (most usually 100 mg) of the appropriate guanidine as its tosylate salt and 2–3 ml of NMP. This mixture was heated at 90–105° C. for at least 12 hours. In many cases the reactions were allowed to proceed for about 65 hours at this temperature. The resin was cooled, filtered and washed with DMSO, glacial acetic acid, water, DMSO and finally dichloromethane. The product was removed by treatment of the resin with 95:5 v/v dichloromethane/TFA for 0.5–1 hours at room temperature. The resin was then filtered, washed with dichloromethane and the filtrates were concentrated on a rotary evaporator. An aliquot was withdrawn for HPLC analysis and the rest of the sample was lyophilized twice from a 1:1 acetonitrile:water solvent mixture, which usually gave the pyrimidine as a fluffy solid.

Examples 11–16 describe the synthesis of compounds of the present invention pursuant to Resin Method C.

Example 11

Synthesis of 4-(2-{[2-(2-pyridylamino)ethyl]amino}pyrimidin-4-yl)benzamide 2-(2-Aminoethylamino)pyridine (prepared from 2-chloropyridine and ethylenediamine in accordance with the method described in T. Mega et al., 1988, *Bull. Chem. Soc. Japan* 61:4315, which is incorporated herein by reference) (6 mmol) was treated with benzotriazole carboxamidinium 4-methylbenzenesulfonatesulfonate (2.0 g, 6 mmol) and DIEA (1.05 ml, 6 mmol) in anhydrous acetonitrile (10 ml) for 65 hours. Ether (ca. 10 ml) was then added to this mixture. After 8 hours the white solid amino[2-(2-pyridylamino)ethyl]carboxamidinium 4-methylbenzenesulfonate was filtered off and dried in vacuo. The resulting guanidine (200 mg) was reacted with 100 mg of resin (21 hours, 90° C.) according to the method described in Example 10 (Resin method C), to give the title compound.

HPLC: 11.20 min (97% pure)
MS: $MH^+$=335 $C_{18}H_{18}N_6O$=334 g/mol

Example 12

Synthesis of 4-(2-{[2-(2-guinolylamino)ethyl]amino}pyrimidin-4-yl)benzamide

2-Chloroquinoline (7.0 g) was heated at 120° C. under argon with ethylenediamine (50 ml) for 6 hours. The excess ethylenediamine was removed by rotary evaporation (oil pump). The residue was taken up in 2.5 M aqueous sodium hydroxide and extracted 6 times with dichloromethane. The combined organic layers were washed with a small portion of saturated aqueous NaCl, dried over $Na_2SO_4$ and concentrated in vacuo. A portion of the viscous product, 0.55 g (3 mmol) was treated with benzotriazole carboxamidinium 4-methylbenzenesulfonate (1.0 g, 3 mmol), DIEA (0.78 ml, 4.5 mmol) and acetonitrile (8 ml) with shaking at room temperature overnight. Precipitation with ether gave amino[2-(2-quinolylamino)ethyl]carboxamidinium 4-methylbenzenesulfonate. The resulting guanidine (200 mg) was reacted (21 hours, 90° C.) with 100 mg of resin according to the method described in Example 10 (i.e., Resin method C) to give the title compound.

HPLC: 12.04 min (95% pure)
MS: $MH^+$=385 $C_{22}H_{20}N_6O$=384 g/mol

Example 13

Synthesis of 4-[2-({2-[6-methoxy-2-pyridyl)amino[-ethyl}amino)pyrimidin-4-yl]benzamide 2-Chloro-6-methoxypyridine (5.0 g) was heated with ethylenediamine (30 ml) at 120° C. overnight. The excess ethylenediamine was removed by rotary evaporation. The residue was dissolved in a small volume of 2.5 M aqueous sodium hydroxide and extracted thoroughly with dichloromethane. The combined organic layers were washed with saturated aqueous sodium chloride, dried over sodium sulfate and concentrated in vacuo to give (2-aminoethyl)(6-methoxy(2-pyridyl)amine as an orange syrup. The amine (2.58 g) was treated with benzotriazole carboxamidinium 4-methylbenzenesulfonate (0.86 g) and DIEA (0.45 mmol) in acetonitrile (6 ml) and stirred overnight at room temperature. Trituration with ether gave the guanidine, amino-{2-[(6-methoxy(2-pyridyl))amino]ethyl}carboxamidinium 4-methylbenzenesulfonate, as an oil. The oily guanidine (200 mg) was reacted with 100 mg of resin according to Resin Method C (90° C., overnight) to give the title compound.

HPLC: 11.84 min (85% purity)
MS: $MH^+$=365 $C_{19}H_{20}N_6O_2$=364 g/mol

Example 14

Synthesis of 4-{2-[(3-Benzimidazolylpropyl)amino]pyrimidin-4-yl}benzamide

Benzimidazole (2.4 g, 20 mmol) in dry THF (40 ml) was treated at room temperature with 60% NaH in oil (0.96 g). After hydrogen evolution ceased, 3-bromopropylphthalimide (5.36 g, 20 mmol) was added and the mixture heated at 80° C. overnight. The reaction was cooled, diluted with dichloromethane and water and then extracted twice with 5% aqueous potassium carbonate solution. The organic layer was dried over sodium sulfate and concentrated in vacuo to give a beige solid, 4.1 g. The solid was dissolved in methanol (60 ml) and treated with anhydrous hydrazine (4.0 ml), followed by refluxing for 4 hours. The mixture was then cooled to 4° C. for several hours, then filtered. The filtrate was concentrated in vacuo. The residue was partitioned between dichloromethane and 2.5 M aqueous sodium hydroxide. The organic layer was washed with saturated sodium chloride solution, dried over sodium sulfate and concentrated in vacuo to give 3-benzimidazolylpropyl amine as a pale pink oil, 1.1 g. This amine (1.03 g, 6 mmol) was reacted with benzotriazole carboxamidinium 4-methylbenzenesulfonate (2.0 g, 6 mmol) and DIEA (1.39 ml) in acetonitrile (8 ml) overnight at room temperature to give amino(3-benzimidazolylpropyl) carboxamidinium 4-methylbenzenesulfonate which was obtained as a beige solid after repeated trituration with ether. The guanidine (100 mg) was reacted) (65 hours, 105° C.) with 100 mg of resin in accordance with the method described in Example 10 (i.e., Resin Method C) to give the title compound.

HPLC: 12.12 min (95% purity)
MS: $MH^+$=373 $C_{21}H_{20}N_6O$=372 g/mol

Example 15

Synthesis of 4-{2-[(3-(2-napthyloxy)propyl)amino]pyrimidin-4-yl)benzamide

2-Naphthol (2.9 g, 20 mmol) in dry THF (40 ml) was treated with 60% NaH suspension (0.96 g) at room temperature. After hydrogen evolution ceased, 3-bromopropylphthalimide (5.36 g, 20 mmol) was added and the mixture was heated at 80° C. overnight. The reaction was cooled, diluted with ethyl acetate and water. The layers were separated and the aqueous layer extracted 3 times with ethyl acetate. The combined organic layers were then extracted 5 times with 5% aqueous potassium carbonate, dried over sodium sulfate and concentrated in vacuo. The crude product (observed as a single spot by TLC) was taken up in methanol (60 ml), treated with anhydrous hydrazine (4 ml) and refluxed for 3.5 hours. The mixture was cooled to 4° C. for several hours, then filtered. The filtrate was concentrated to dryness, then partitioned between dichloromethane and 2.5 M aqueous sodium hydroxide. The organic layer was washed with saturated sodium chloride solution, dried and concentrated in vacuo to give 3-(2-naphthyloxy)propyl amine as a beige solid, 1.14 g. The amine (1.14 g, 5.7 mmol) was treated with benzotriazole carboxamidinium 4-methylbenzenesulfonate (1.89 g, 5.7 mmol) and DIEA (1.39 ml) in a mixture of acetonitrile (8 ml) and DMF (2 ml) with shaking at room temperature overnight. Precipitation with ether gave amino(3-(2-naphthyloxy)propyl)carboxamidinium 4-methylbenzenesulfonate as a white crystalline solid. This guanidine (100 mg) was reacted (65 hours, 105° C.) with resin (100 mg) in accordance with the method described in Example 10 (i.e., Resin Method C) to give the title compound.

HPLC: 22.52 min (95% purity)
MS: MH$^+$=399 $C_{24}H_{22}N_4O_2$=398 g/mol

Example 16

Synthesis of N-(1-carbamoyl-2-phenylethyl)(4-{2-{(2-(2-pyridyl)ethyl)amino]pyrimidin-4-yl}phenyl)carboxamide This Example provides a variation of Resin Method C in which the pyrimidine is linked to an α-amino acid residue.

Step 1: Rink amide resin (1.5 g) was deprotected with 20% piperidine in DMF (1×0.5 hours). The resin was washed well with DMF and then treated with FMOC (L)-phenylalanine (5.0 mmol), 1-hydroxybenzotriazole (5.0 mmol) and diisopropylcarbodiimide (5.0 mmol) in DMF (10 ml) with shaking at room temperature for 2 hours. The resin was washed with DMF and then treated with 20% piperidine in DMF (1×30 min). The resin was washed well with DMF and then treated with PyBOP® (5 mmol), 4-methylmorpholine (8 mmol) and 4-acetylbenzoic acid (5 mmol) in NMP (10 ml). After 5 hours at room temperature, a negative ninhydrin test indicated completion of the reaction. The resin was washed with DMF and dichloromethane, air-dried and then heated with DMFDMA at 110° C. overnight. The resin was then washed well with dichloromethane and dried in vacuo at room temperature.

Step 2: The resin prepared in Step 1 (150 mg) was treated with amino(2-(2-pyridyl)ethyl)carboxamidinium 4-methylbenzenesulfonate (200 mg) and cesium carbonate (160 mg) in NMP (2 ml) at 85° C. overnight. The resin was washed with DMF and dichloromethane and then treated with 5% TFA in dichloromethane. The resin was filtered off and the filtrate concentrated and lyophilized to give the title compound.

HPLC: 15.08 min (95% purity)
MS: MH$^+$=467 $C_{27}H_{26}N_6O_2$=466 g/mol

The following additional compounds were analogously synthesized according to Resin Method C by varying the guanidine used:

N-benzyl(4-{2-[(2-(2-pyridyl)ethyl)amino]pyrimidin-4-yl}phenyl)carboxamide benzyl {[4-(2-{[2-(2-pyridylamino)ethyl]amino}pyrimidin-4-yl)phenyl]sulfonyl}amine {4-[2-({2-[(5-nitro(2-pyridyl))amino]ethyl}amino)pyrimidin-4-yl]phenyl}-N-benzylcarboxamide {4-[2-({2-[(6-amino-5-nitro(2-pyridyl))amino]ethyl}amino)pyrimidin-4-yl]phenyl}-N-benzylcarboxamide N-[(4-fluorophenyl)methyl]{4-[2-({2-[(5-nitro(2-pyridyl))amino]ethyl}amino)pyrimidin-4-yl]phenyl}carboxamide N-[(3-bromophenyl)methyl]{4-[2-({2-[(5-nitro(2-pyridyl))amino]ethyl}amino)pyrimidin-4-yl]phenyl}carboxamide N-(2-methoxyethyl) {4-[2-({2-[(5-nitro(2-pyridyl))amino]ethyl}amino)pyrimidin-4-yl]phenyl}carboxamide N-(naphthylmethyl){4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-{[3-(trifluoromethyl)phenyl]methyl}carboxamide {4-[2-({2-[(5-nitro(2-pyridyl))amino]ethyl}amino)pyrimidin-4-yl]phenyl}-N-(2-phenylethyl)carboxamide N-[(4-methoxyphenyl)methyl]{4-[2-({2-[(5-nitro(2-pyridyl))amino]ethyl}amino)pyrimidin-4-yl]phenyl}carboxamide N-[(3-methoxyphenyl)methyl]{4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-(oxolan-2-ylmethyl)carboxamide N-[(5-methylpyrazin-2-yl)methyl]{4-[2-({2-[(5-nitro(2-pyridyl))amino]ethyl}amino)pyrimidin-4-yl]phenyl}carboxamide N-(2,2-diphenylethyl){4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-(4-piperidylmethyl)carboxamide N-[2-(2,4-dichlorophenyl)ethyl]{4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-(3-pyridylmethyl)carboxamide N-(3-imidazolylpropyl){4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-(2-thienylmethyl)carboxamide {4-[2-({2-[(5-nitro(2-pyridyl))amino]ethyl}amino)pyrimidin-4-yl]phenyl}-N-[(3-nitrophenyl)methyl]carboxamide N-[(3-methylphenyl)methyl]{4-[2-({2-[(5-nitro(2-pyridyl))amino]ethyl}amino)pyrimidin-4-yl]phenyl}carboxamide {4-[2-({2-[(5-nitro(2-pyridyl))amino]ethyl}amino)pyrimidin-4-yl]phenyl}-N-[(4-sulfamoylphenyl)methyl]carboxamide {4-[2-({2-[(6-amino-5-nitro(2-pyridyl))amino]ethyl}amino)pyrimidin-4-yl]phenyl}-N-[(3-bromophenyl)methyl]carboxamide N-[(3,5-dichlorophenyl)methyl]{4-[2-({2-[(5-nitro(2-pyridyl))amino]ethyl}amino)pyrimidin-4-yl]phenyl}carboxamide N-[(3,4-difluorophenyl)methyl]{4-[2-({2-[(5-nitro(2-pyridyl))amino]ethyl}amino)pyrimidin-4-yl]phenyl}carboxamide N-[(4-bromophenyl)methyl]{4-[2-({2-[(5-nitro(2-pyridyl))amino]ethyl}amino)pyrimidin-4-yl]phenyl}carboxamide N-[(2,3-dimethoxyphenyl)methyl]{4-[2-({2-[(5-nitro(2-pyridyl))amino]ethyl}amino)pyrimidin-4-yl]phenyl}carboxamide N-[(3-fluorophenyl)methyl]{4-[2-({2-[(5-nitro(2-pyridyl))amino]ethyl}amino)pyrimidin-4-yl]phenyl}carboxamide N-[(3-bromophenyl)methyl]{4-[2-({2-[(6-methoxy(2-pyridyl))amino]ethyl}amino)pyrimidin-4-yl]phenyl}carboxamide

[4-(2-{[(3-bromophenyl)methyl]amino}pyrimidin-4-yl)phenyl]-N-[(3-methylphenyl)methyl]carboxamide N-[(3-bromophenyl)methyl]{4-[2-({2-[(5-cyano(2-pyridyl))amino]ethyl}amino)pyrimidin-4-yl]phenyl}carboxamide 4-(2-{[(3-{3-[(methylamino)methyl]phenyl}phenyl)methyl]amino}pyrimidin-4-yl)benzamide N-[(3-bromophenyl)methyl](4-{2-[(3-imidazolylpropyl)amino]pyrimidin-4-yl}phenyl)carboxamide N-[(3-bromophenyl)methyl][4-(2-{[2-(2-quinolylamino)ethyl]amino}pyrimidin-4-yl)phenyl]carboxamide N-[(3-bromophenyl)methyl]{4-[2-({2-[(4-nitrophenyl)amino]ethyl}amino)pyrimidin-4-yl]phenyl}carboxamide N-[(3-bromophenyl)methyl](4-{2-[(2-{[5-(trifluoromethyl)(2-pyridyl)]amino}ethyl)amino]pyrimidin-4-yl}phenyl)carboxamide N-[(3-bromophenyl)methyl][4-(2-{[2-(pyrimidin-2-ylamino)ethyl]amino}pyrimidin-4-yl)phenyl]carboxamide N-[(3-chlorophenyl)methyl]{4-[2-({2-[(5-nitro(2-pyridyl))amino]ethyl}amino)pyrimidin-4-yl]phenyl}carboxamide N-[(3,4-dimethoxyphenyl)methyl]{4-[2-({2-[(5-nitro(2-pyridyl))amino]ethyl}amino)pyrimidin-4-yl]phenyl}carboxamide N-[(3,4-dichlorophenyl)methyl]{4-[2-({2-[(5-nitro(2-pyridyl))amino]ethyl}amino)pyrimidin-4-yl]phenyl}carboxamide

[(3-bromophenyl)methyl]({4-[2-({2-[(5-nitro(2-pyridyl))amino]ethyl}amino)pyrimidin-4-yl]phenyl}sulfonyl)amine N-[(3-iodophenyl)methyl]{4-[2-({2-[(5-nitro(2-pyridyl))amino]ethyl}amino)pyrimidin-4-yl]phenyl}carboxamide

[4-(2-{[2-(2,5-dimethoxyphenyl)ethyl]amino}pyrimidin-4-yl)phenyl]-N-[(3-bromophenyl)methyl]carboxamide N-[(3-bromophenyl)methyl][4-(2-{[2-(3-methoxyphenyl)ethyl]amino}pyrimidin-4-yl)phenyl]carboxamide {4-[2-({2-[(5-nitro(2-pyridyl))amino]ethyl}amino)pyrimidin-4-yl]phenyl}-N-(2-phenylcyclopropyl)carboxamide 3-[2-({2-[(5-nitro-2-pyridyl)amino]ethyl}amino)pyrimidin-4-yl]phenol 4-[2-({2-[(5-nitro-2-pyridyl)amino]ethyl}amino)pyrimidin-4-yl]phenol 4-{2-[(3-phenoxypropyl)amino]pyrimidin-4-yl}phenol 4-(2-{[3-(4-chlorophenoxy)propyl]amino}pyrimidin-4-yl)phenol 4-[2-({2-[(5-nitro(2-pyridyl))amino]ethyl}amino)-5-phenylpyrimidin-4-yl]phenol 4-{2-[(3-benzimidazolylpropyl)amino]pyrimidin-4-yl}phenol 4-{2-[(3-benzimidazolylpropyl)amino]pyrimidin-4-yl}-2-methoxyphenol 4-(2-{[3-(4-nitroimidazolyl)propyl]amino}pyrimidin-4-yl)phenol 4-(2-[3-(2-aminobenzimidazolyl)propyl]amino}pyrimidin-4-yl)phenol 4-(2-{[3-(4,5-dichloroimidazolyl)propyl]amino}pyrimidin-4-yl)phenol Example 17

Solid Phase Synthesis of Pyrimidine Compounds

Resin Method D

A primary amine was loaded onto Sasrin resin as in Example 3 (i.e., Resin Method B). This amine resin was then heated with either 2,4-dichloropyrimidine or ethyl 2,4-dichloropyrimidine-5-carboxylate (200 mg of pyrimidine per 200 mg of amine resin) and cesium carbonate (250 mg) in NMP (3 ml) overnight. The resin was washed with the appropriate solvents (typically DMF or DMSO and dichloromethane) and then reacted with a second amine (e.g., a primary or secondary amine). Second amine displacement was typically conducted at a higher temperature in NMP, for example for 48 hours at 120–130° C. The resin was again washed and treated with 100% TFA for 0.5–1 hours to obtain the 2,4-diaminopyrimidine, which was frequently obtained as a solid after lyophilization from a mixture of acetonitrile and water.

Examples 18–19 describe the synthesis of compounds of the present invention pursuant to Resin Method D.

Example 18

Synthesis of [(3-chlorophenyl)methyl][2-({2-[(5-nitro(2-pyridyl))amino]ethyl}amino)pyrimidin-4-yl]amine Bromomethyl Sasrin resin (prepared as in Step 1 of Example 3, 0.9 g) was heated with 3-chlorobenzylamine (1 ml) in NMP (8 ml) at 80° C. for 1.5 hours, then overnight at room temperature. The resin was washed with DMF and dichloromethane and dried in vacuo. The dried resin (200 mg) was then heated with 2,4-dichloropyrimidine and 250 mg of cesium carbonate in NMP (3 ml) at 80° C. overnight. The resin was washed as before. One half of the resin was heated with 2-(2-aminoethylamino)-5-nitropyridine (180 mg, 1 mmol) in NMP (2 ml) at 125° C. for 66 hours. The resin was washed as before and then treated with 100% TFA for 0.5 hours. The resin was filtered off and the filtrate was concentrated in vacuo, then lyophilized from acetonitrile and water to give the title compound as a yellow solid.

HPLC: 23.46 min (82% purity)

MS: $MH^+$=400 $C_{18}H_{18}ClN_7O_2$=399 g/mol

Example 19

Synthesis of Ethyl-4-{[(3-cyanophenyl)methyl]amino}-2-({2-[(5-nitro(2-pyridyl)amino[ethyl}amino)pyrimidine-5-carboxylate Bromomethyl Sasrin resin (prepared as in Step 1 of Example 3, 1.0 g) was reacted with 4-cyanobenzylamine (1.5 ml) in NMP (8 ml) at 80° C. for 4 hours. The resin was washed with DMF and dichloromethane and dried in vacuo at room temperature. The dried resin (400 mg) was then reacted with ethyl 2,4-dichloropyrimidine-5-carboxylate (prepared according to V. H. Smith and B. E. Christensen, *J. Organic Chem.*, 20: 829 (1955), which is incorporated herein by reference) (400 mg) and cesium carbonate (400 mg) in NMP (4 ml) at 80° C. overnight. The resin was washed as before and dried. The dried resin (200 mg) was then heated with 2-(2-aminoethylamino)-5-nitropyridine (180 mg, 1 mmol) in NMP (2 ml) at 104° C. for 21 hours. The resin was washed with DMSO, glacial acetic acid, water, DMSO, dichloromethane and then treated with 100% TFA to obtain the title compound.

HPLC: 25.27 min (100% purity)

MS: MH$^+$=463 C$_{22}$H$_{22}$N$_8$O$_4$=462 g/mol

The following additional compounds were prepared according to Resin method D using the appropriate amine:

(4-{[(3-bromophenyl)methyl]amino}pyrimidin-2-yl) {2-[(5-nitro(2-pyridyl))amino]ethyl}amine

[(2,4-dichlorophenyl)methyl][2-({2-[(5-nitro(2-pyridyl))amino]ethyl}amino)pyrimidin-4-yl]amine

[(3-methylphenyl)methyl][2-({2-[(5-nitro(2-pyridyl))amino]ethyl}amino)pyrimidin-4-yl]amine

[(3,5-dichlorophenyl)methyl][2-({2-[(5-nitro(2-pyridyl))amino]ethyl}amino)pyrimidin-4-yl]amine Ethyl 4-{[(3-bromophenyl)methyl]amino}-2-({2-[(5-nitro(2-pyridyl))amino]ethyl}amino)pyrimidine-5-carboxylate

[2-({2-[(5-nitro(2-pyridyl))amino]ethyl}amino)pyrimidin-4-yl]benzylamine

[(4-chlorophenyl)methyl][2-({2-[(5-nitro(2-pyridyl))amino]ethyl}amino)pyrimidin-4-yl]amine Ethyl 4-{[(2-chlorophenyl)methyl]amino}-2-({2-[(5-nitro(2-pyridyl))amino]ethyl}amino)pyrimidine-5-carboxylate Ethyl 4-{[(4-cyanophenyl)methyl]amino}-2-({2-[(5-nitro(2-pyridyl))amino]ethyl}amino)pyrimidine-5-carboxylate Example 20

Solid Phase Synthesis of Pyridine Compounds

Resin Method E

An amino resin (for example Sasrin resin loaded with a primary amine as described in Resin Methods B (Example 3) and D (Example 18)) was reacted with, e.g., 2,6-dichloro-3-nitropyridine and cesium carbonate in NMP at temperatures within the range of about 25–50° C. for a period within the range of from about 5 hours to about 24 hours. The resin was then washed with DMF and dichloromethane and heated with a primary amine in NMP at temperatures from 70–100° C. overnight. The resins were washed as described in Example 18, and the pyridine products obtained by treating the resin with 20–100% TFA for 0.5–1 hours (preferably with 80–100% TFA).

Example 21 describes the synthesis of compounds of the present invention pursuant to Resin Method E.

Example 21

Synthesis of {2-[(6-amino-5-nitro(2-pyridyl)amino] ethyl}-{5-nitro-6-[benzylaminol(2-pyridyl)}amine Step 1: 2-Amino-6-chloro-3-nitropyridine (obtained from 2,6-dichloro-3-nitro-pyridine by the method of V. W. von Bebenberg, *Chemiker-Zeitung*, 103:387 (1979), which is incorporated herein by reference) (2.65 g) was treated at room temperature with ethylenediamine (5 ml). The temperature was gradually raised to 100° C. After 4 h the excess ethylenediamine was removed by rotary evaporation. The residue was partitioned between dichloromethane and 2.5 M aqueous sodium hydroxide. The aqueous layer was further extracted 3 times with dichloromethane. The combined organic layers were concentrated in vacuo to give (2-aminoethyl)(6-amino-5-nitro(2-pyridyl))amine as a canary yellow solid.

Step 2: Bromomethyl Sasrin resin, prepared according to Step 1 of Example 3, was heated with benzylamine (2 ml) in NMP (6 ml) at 70° C. for 4 hours. The resin was washed with DMF and dichloromethane and dried in vacuo. The dried resin (100 mg) was heated with 2,6-dichloro-3-nitropyridine (190 mg, 1 mmol) and cesium carbonate (100 mg) in NMP (2 ml) at 50° C. for 5.5 hours. The resin was then washed with water, DMF and dichloromethane. The resin was air dried and then heated with the amine from Step 1 (90 mg) in NMP (2 ml) at 95° C. overnight. The resin was washed with DMSO, acetic acid, water, DMSO, dichloromethane and then treated with 20% TFA to give the title compound.

HPLC: 28.47 min (87% purity)

NMR: (300 MHz, 7/1 acetonitrile-d$_3$/D$_2$O, 75° C.: 8.0 (2H, two overlapping d), 7.2–7.4 (5H, Ph), 5.9 (2H, 2d overlapping), 4.75 (s, 2H), 3.50–3.65 (m, 4H)

The following additional compounds were similarly prepared according to Resin Method E by varying the pyridine and primary amine:

{2-[(5-nitro(2-pyridyl))amino]ethyl}{5-nitro-6-[benzylamino](2-pyridyl)}amine

6-{[2-({5-nitro-6-[benzylamino]-2-pyridyl}amino)ethyl]amino}pyridine-3-carbonitrile {6-[(2-methoxyethyl)amino]-5-nitro(2-pyridyl)}{2-[(5-nitro(2-pyridyl))amino]ethyl}amine (6-{[(2,4-dichlorophenyl)methyl]amino}-5-nitro(2-pyridyl)) {2-[(5-nitro(2-pyridyl))amino]ethyl}amine.

Example 22

Synthesis of 4-[2-({2-[(5-nitro(2-pyridyl))amino] ethyl}amino)-5-[benzylamino]pyrimidin-4-yl [benzenecarbonitrile (Resin Method F)

Benzylamine was reacted with bromomethyl Sasrin resin to give a benzylamine substituted resin as in Step 1 of Example 3. This resin (150 mg) was shaken with 4-cyanophenacylbromide (130 mg), DMF (2 ml) and 2,6-lutidine (200 µl) at room temperature for 6.5 hours. The resin was washed with DMF and dichloromethane and briefly air dried. It was then heated with DMFDMA (3 ml) at 80° C. overnight. The resin was then washed with DMF and dichloromethane and dried in vacuo. The dried resin was heated with amino {2-[(5-nitro(2-pyridyl))amino] ethyl}carboxamidinium 4-methylbenzenesulfonate (120 mg) and cesium carbonate (160 mg) in NMP (2 ml) at 90° C. overnight. The resin was washed with DMF, water, DMF and dichloromethane and then treated with 95:5 TFA:water to give the title compound.

HPLC: 25.61 min (80% pure)

MS: MH$^+$=467 C$_{25}$H$_{22}$N$_8$O$_2$=466 g/mol

Example 23

Solid Phase Synthesis of Pyrimidines (C$_5$= carboxyl)

Resin Method G

A mixture of polystyrene Wang resin (Novabiochem, 0.41 mmol/g, 2.2 g, 1.21 mmol), a β-ketoester (commercially available from Aldrich or Lancaster Chemical, 36.3 mmol) and dimethylaminopyridine (DMAP, 12.1 mmol) in toluene (22 ml) was shaken for 16 hours at 90° C. The resin was filtered and washed with DCM, DMF, DCM, then dried.

A mixture of the dried resin (100 mg, 0.055 mmol), an aldehyde (0.55 mmol), piperidine (0.055 mmol), acetic acid (0.055 mmol) and 3A Molecular Sieves (Aldrich) in DMF (1.0 ml) was shaken for 16 hours at room temperature. The resin was filtered and washed with DMF and DCM, then dried.

To a mixture of the resulting resin (100 mg, 0.055 mmol) and NaHCO$_3$ (12 mg, 0.138 mmol) was added 0.4 M of the appropriate guanidine in DMF (1.0 ml, 0.4 mmol). The mixture was then shaken for 16 hours at 70° C. The resin was then filtered and washed with DMF, water, methanol, DMF, DCM, and dried.

This resin was treated with 0.1 M DDQ in THF (1.1 ml, 0.11 mmol) for 3 hours at room temperature. The resin was filtered and washed with DMF, saturated NaHCO$_3$ (aq), water, methanol, DMF, DCM, then dried. The resin was treated with 95% TFA/water for 1 hour at room temperature, then filtered and washed with DCM. The filtrate and washings were combined and evaporated. The residue was dissolved in acetonitrile/water (1:1) then lyophilized.

In all cases, the product pyrimidines were of purity >80% as determined by HPLC; MS and NMR analysis.

The following compounds were prepared according to Resin Method G using amino{2-[(5-nitro(2-pyridyl)amino] ethyl}carboxamidinium 4-toluene sulfonate as the guanidine source and the β-ketoester and aldehyde indicated in parentheses:

6-(2-Fluorophenyl)-2-({2-[5-nitro(2-pyridyl)amino] ethyl}amino)-4-phenylpyrimidine-5-carboxylic acid (ethyl 3-(4-fluorophenyl)-3-oxoprionate and benzaldehyde)

2-({2-[5-Nitro(2-pyridyl)amino]ethyl}amino)-6-(4-nitrophenyl)-4-phenylpyridine-5-carboxylic acid (ethyl 3-(4-nitrophenyl)-3-oxoprionate and benzaldehyde)

6-Methyl-2-({2-[(5-nitro(2-pyridyl)amino]ethyl}amino)-4-phenylpyrimidine-5-carboxylic acid (ethyl acetoacetate and benzaldehyde)

4,6-bis(4-Nitrophenyl)-2-({2-[5-nitro(2-pyridyl)amino] ethyl}amino)pyridine-5-carboxylic acid (ethyl 3-(4-nitrophenyl)-3-oxoprionate and 4-nitrobenzaldehyde)

2-({2-[5-Nitro(2-pyridyl)amino]ethyl}amino)-6-(4-nitrophenyl)-4-(4-pyridyl)pyrimidine-5-carboxylic acid (ethyl 3-(4-pyridyl)-3-oxoprionate and 4-pyridylcarboxaldehyde)

4-(4-Methoxyphenyl)-2-({2-[5-nitro(2-pyridyl)amino] ethyl}amino)-6-(4-nitrophenyl)pyrimidine-5-carboxylic acid (ethyl 3-(4-nitrophenyl)-3-oxoprionate and 4-methoxybenzaldehyde)

4-(4-Cyanophenyl)-2-({2-[(5-nitro(2-pyridyl)amino] ethyl}amino)-6-(4-nitrophenyl)pyrimidine-5-carboxylic acid (ethyl 3-(4-nitrophenyl)-3-oxoprionate and 4-cyanobenzaldehyde)

2-({2-[(5-Nitro(2-pyridyl))amino]ethyl}amino)-4-(4-nitrophenyl)pyrimidine-5-carboxylic acid (ethyl 3-(4-nitrophenyl)-3-oxoprionate and formaldehyde)

4,6-bis(4-Cyanophenyl)-2-({2-[(5-nitro(2-pyridyl)amino] ethyl}amino)pyrimidine-5-carboxylic acid (ethyl 3-(4-cyanophenyl)-3-oxoprionate and 4-cyanobenzaldehyde)

4-(4-Cyanophenyl)-2-({2-[(5-nitro(2-pyridyl)amino] ethyl}amino)-6-(3-nitrophenyl)pyrimidine-5-carboxylic acid (ethyl 3-(4-cyanophenyl)-3-oxoprionate and 3-nitrobenzaldehyde)

4-(4-Cyanophenyl)-2-({2-[(5-nitro(2-pyridyl)amino] ethyl}amino)-6-phenylpyrimidine-5-carboxylic acid (ethyl 3-(4-cyanophenyl)-3-oxprionate and benzaldehyde)

4-(3-Cyanophenyl)-2-({2-[(5-nitro(2-pyridyl)amino] ethyl}amino)-6-(4-nitrophenyl)pyrimidine-5-carboxylic acid (ethyl 3-(4-nitrophenyl)-3-oxoprionate and 3-cyanobenzaldehyde)

4-(3-Hydroxyphenyl)-2-({2-(5-nitro(2-pyridyl)amino] ethyl}amino)-6-(4-nitrophenyl)pyrimidine-5-carboxylic acid (ethyl 3-(4-nitrophenyl)-3-oxoprionate and 3-hydroxybenzaldehyde)

2-({2-[(5-Nitro(2-pyridyl))amino]ethyl}amino)-4-(3-nitrophenyl)-6-(4-nitrophenyl)pyrimidine-5-carboxylic acid (ethyl 3-(4-nitrophenyl)-3-oxoprionate and 3-nitrobenzaldehyde)

2-({2-[(5-Nitro(2-pyridyl))amino]ethyl}amino)-6-(4-nitrophenyl)-4-(4-quinolyl)pyrimidine-5-carboxylic acid (ethyl 3-(4-nitrophenyl)-3-oxoprionate and 4-quinolinecarboxaldehyde)

2-({2-[(5-Nitro(2-pyridyl))amino]ethyl}amino)-6-(4-nitrophenyl)-4-[4-(trifluoromethyl)phenyl]pyrimidine-5-carboxylic acid (ethyl 3-(4-nitrophenyl)-3-oxoprionate and 4-trifluoromethylbenzaldehyde)

4-({4-Carboxyphenyl)-2-({2-[(5-nitro(2-pyridyl))amino] ethyl}amino)-6-(4-nitrophenyl)pyrimidine-5-carboxylic acid (ethyl 3-(4-nitrophenyl)-3-oxoprionate and 4-carboxybenzaldehyde)

4-Cyclohexyl-2-({2-[(5-nitro(2-pyridyl))amino] ethyl}amino)-6-(4-nitrophenyl)pyrimidine-5-carboxylic acid (ethyl 3-(4-nitrophenyl)-3-oxoprionate and cyclohexanecarboxaldehyde)

4-(4-Cyanophenyl)-6-(4-fluorophenyl)-2-({2-[(5-nitro(2-pyridyl)amino]ethyl}amino)pyrimidine-5-carboxylic acid (ethyl 3-(4-cyanophenyl)-3-oxoprionate and 4-fluorophenylbenzaldehyde)

4-(4-Cyanophenyl)-6-(3-furyl)-2-({2-[(5-nitro(2-pyridyl) amino]ethyl}amino)pyrimidine-5-carboxylate (ethyl 3-(4-cyanophenyl)-3-oxoprionate and 3-furylcarboxaldehyde)

Example 24

Solid Phase Synthesis of Pyrimidines ($C_5$=carboxyl, $C_4$ or $C_6$=H)

Resin Method G

A suspension of resin (Novabiochem, San Diego, USA, 0.51 mmol/g, 100 mg, 0.055 mmol) in DMF-dimethylacetal (1 ml) was shaken for 17 hour at room temperature. The resin was filtered and washed with DCM and ether, then dried.

To a mixture of the resulting dried resin (100 mg, 0.055 mmol) and NaHCO$_3$ (12 mg, 0.138 mmol) was added 0.4 M solution of the appropriate guanidine in DMF (1.0 ml, 0.4 mmol). The mixture was shaken for 16 hours at 70° C. This resin was then filtered and washed successively with DMF, water, MeOH, DMF, DCM, and then dried. The resin was treated with 95% TFA/water for 1 hour at room temperature, then filtered and washed with DCM. The filtrate and washings were combined and evaporated. The residue was dissolved in acetonitrile:water (1:1 v/v) and lyophilized to give a pyrimidine.

The following compounds were prepared according to the above method using N-(3-nitropyridine-6-yl) aminoethylguanidine and the appropriate β-ketoester and aldehyde:

4-methyl-2-({2-[(5-nitro(2-pyridyl)amino]ethyl}amino) pyrimidine-5-carboxylic acid 2-({2-[(5-nitro(2-pyridyl)amino]ethyl}amino)-4-(4-nitrophenyl)pyrimidine-5-carboxylic acid 4-(4-cyanophenyl)-2-({2-[(5-nitro(2-pyridyl))amino]
ethyl}amino)-6-(3-nitrophenyl)pyrimidine-5-carboxylic
acid.

Example 25

Solution Phase Synthesis

Solution Method A

A carbonyl-containing compound (e.g., β-keto esters, β-keto sulfones, β-keto nitriles, α-nitro ketones, and the like) was dissolved in a suitable organic solvent (usually THF) and treated with a slight excess (1.2–2 equivalents) of DMFDMA. The mixture was heated at 60–80° C. for 3–15 hours, most typically 3–5 hours. The reaction mixture was then cooled. When a done on a small scale (0.2–1 mmol) there was no attempt to remove the slight excess of DMFDMA present, rather the cooled mixture was directly added to a mixture of a guanidine (1 equivalent) and an appropriate base (for example, cesium carbonate or 1.2 equivalents of sodium ethoxide in 1 ml of ethanol).

The reaction was then heated at 70–80° C. for 12–24 h. At the conclusion of the reaction the vials were cooled, poured into dichloromethane or ethyl acetate and washed with saturated aqueous sodium bicarbonate solution. The organic layer was concentrated in vacuo and the product was precipitated or crystallized, usually by addition of water to acetonitrile or ethanol solutions of the product. In some cases chromatographic purification was performed, either by semi-preparative HPLC or by radial chromatography using silica gel plates on a Chromatotron (Harrison Research, Palo Alto, Calif.) eluting with mixtures of dichloromethane and methanol. Larger scale reactions were performed in round bottom flasks using typical organic chemistry apparatus.

Examples 31, 35–45, and 50–59 describe the synthesis of compounds of the present invention pursuant to Solution Method A.

Example 26

Synthesis of Ethyl 4-(4-cyanophenyl)-2-{[2-(2-guinolylamino)ethyl]amino}pyrimidine-5-carboxylate Ethyl 3-(4-cyanophenyl)3-oxopropanoate (64 mg, 0.3 mmol) was heated with DMFDMA (50 µl) and dry THF (1 ml) at 70° C. for 3 hours. The cooled mixture was then added to a suspension of amino[2-(2-quinolylamino)ethyl] carboxamidinium 4-methylbenzenesulfonate (prepared according to Example 12), (120 mg, 0.3 mmol) in ethanol (2 ml) containing 0.35 mmol of sodium ethoxide. The reaction was then heated at 80° C. overnight and then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 22.12 min (90% purity)

MS: MH$^+$=439 C$_{25}$H$_{22}$N$_6$O$_2$=438 g/mol

Example 27

Synthesis of Ethyl 4-(6-morpholin-4-yl(3-pyridyl))-2-({2-[(5-nitro(2-pyridyl))amino]ethyl}amino) pyrimidine-5-carboxylate Step 1: Ethyl 6-chloronicotinate (5.0 g) and morpholine (10 ml) were mixed and then heated to 100° C. In less than 5 minutes at this temperature, a thick paste formed. Acetonitrile (15 ml) was added and heating was continued overnight at 90° C. The mixture was cooled, diluted with water and extracted with ethyl acetate. The organic layer was dried and concentrated in vacuo to give ethyl 6-morpholin-4-ylpyridine-3-carboxylate as a white solid.

NMR (300 MHz, CDCl$_3$: 8.80 (s, 1H), 8.05 (d, 1H), 6.60 (d, 1H), 4.35 (q, 2H), 3.80 (m, 4H), 3.65 (m, 4H), 1.35 (t, 3H).

The solid was refluxed in a mixture of THF and aqueous potassium hydroxide for 2 hours. The THF was removed in vacuo and the aqueous layer was extracted with ethyl acetate. The aqueous layer was then acidified with acetic acid. A white solid precipitated out and was washed with water and dried to give 6-morpholin-4-ylpyridine-3-carboxylic acid.

NMR (300 MHz, DMSO-d$_6$) 8.65 (s, 1H), 7.95 (d, 1H), 6.85 (d, 1H), 3.70 (m, 4H), 3.60 (m, 4H)

Step 2: The acid described in Step 1 was converted to the β-keto ester as follows. The acid (5.6 g., 27 mmol) in dry THF (100 ml) was treated at room temperature with oxalyl chloride (40 mmol) followed by several drops of DMF. The mixture was then refluxed for 2 hours. The solvent was removed in vacuo to give a yellow solid acid chloride. Potassium ethyl malonate (Aldrich Chemical Co., 9.2 g, 54 mmol) and anhydrous magnesium chloride (6.48 g) were mixed in dry acetonitrile (100 ml). Then triethylamine (6 ml) was added and the mixture stirred at room temperature for 4 hours. An additional 3 ml of triethylamine was added, followed by addition of the acid chloride dissolved in 50 ml of dry acetonitrile. The mixture stirred overnight at room temperature, then the solvent was removed in vacuo. The residue was treated with toluene (ca. 200 ml) and then sufficient 25% aqueous HCl was added to dissolve the residue entirely. The mixture was shaken and organic and aqueous layers separated. The toluene layer was washed with water. The combined aqueous layers were then washed twice with toluene. The organic layers were discarded. The pH of the aqueous layer was adjusted to pH 7 by addition of solid sodium carbonate. The aqueous layer was then extracted with toluene. Concentration of the toluene layer in vacuo gave ethyl 3-(6-morpholin-4-yl)(3-pyridyl)-3-oxopropanoate as a yellow solid.

Step 3: The β-keto ester from Step 2 (83 mg, 0.3 mmol) was heated with DMFDMA (50 µl) and dry THF (1 ml) at 70° C. for 3 hours. The cooled mixture was then added to a suspension of amino[2-[(5-nitro(2-pyridyl)amino] ethyl}carboxamidinium 4-methylbenzenesulfonate (120 mg, 0.3 mmol) in ethanol (2 ml) containing 0.35 mmol of sodium ethoxide. The reaction was then heated at 80° C. overnight and then concentrated in vacuo. The residue was dissolved in dichloromethane, then washed with saturated aqueous sodium bicarbonate. This organic layer was then concentrated in vacuo, then redissolved in acetonitrile. Addition of water gave a precipitate which was filtered off and dried to give the title compound.

HPLC: 18.77 min (98%)

MS: MH$^+$=495 C$_{23}$H$_{26}$N$_8$O$_5$=494 g/mol

Example 28

Synthesis of Ethyl 2-({2-[(6-amino-5-nitro(2-pyridyl))amino]ethyl}amino)-4-(4-cyanophenyl) pyrimidine-5-carboxylate To a solution of ethyl 3-(4-cyanophenyl)-3-oxopropionate (63 mg, 0.3 mmol) in THF (1 ml) was added DMFDMA (50

μl). The solution was heated at 70° C. for 3 hours and then added to a mixture of amino[2-[(5-nitro(2-pyridyl)amino]ethyl}carboxamidinium 4-methylbenzenesulfonate (123 mg, 0.3 mmol), ethanol (1 ml) and 1.0 M sodium ethoxide (0.35 ml). This mixture was heated at 80° C. overnight. The reaction was cooled, diluted with dichloromethane and washed with aqueous sodium bicarbonate. The organic layer was concentrated in vacuo, the dissolved in acetonitrile. The product was precipitated with water to give the title compound.

HPLC: 25.21 min

MS: $MH^+$=449 $C_{21}H_{20}N_8O_4$=448 g/mol

NMR (DMSO-d6): 1.02 (t, 3H), 3.60 (m, 4H), 4.10 (q, 2H), 5.95 (d, 1H), 7.60 (d, 2H), 7.85 (d, 2H), 7.90 (d, 1H), 8.80 (s, 1H)

Example 29

Synthesis of ethyl 2-({2-[(6-amino-5-nitro(2-pyridyl))amino]ethyl}amino)-4-(4-morpholin-4-ylphenyl)pyrimidin-5-carboxylate To a solution of ethyl 3-(4-morpholinophenyl)3-oxopropanoate (70 mg, 0.3 mmol) in THF (1 ml) was added DMFDMA (60 μl). The solution was heated at 70° C. for 3 hours, then added to a mixture of amino[2-(6-amino-5-nitro(2-pyridyl)amino]ethyl}carboxamidinium 4-methylbenzenesulfonate (123 mg, 0.3 mmol), ethanol (1 ml) and 1.0 M sodium ethoxide (0.35 ml). The mixture was heated at 80° C. overnight, then cooled, diluted with dichloromethane and washed with saturated aqueous sodium bicarbonate solution. The organic layer was concentrated in vacuo, dissolved in acetonitrile and the product precipitated with water to give the title compound.

HPLC: 22.37 min. (85% purity)

MS: $MH^+$=509 $C_{24}H_{28}N_8O_5$=508 g/mol

NMR (DMSO-$d_6$): 1.05 (t, 3H), 3.3 (m, 4H), 3.60 (m, 4H), 3.78 (m, 4H), 4.15 (q, 2H), 5.95 (d, 1H), 6.90 (d, 2H), 7.45 (d, 2H), 7.95 9d, 1H), 8.60 (s, 1H)

Example 30

Synthesis of Ethyl 2-({2-[(6-amino-5-nitro(2-pyridyl)amino]ethyl}amino)-4-(2,4-dichlorophenyl)pyrimidine-5-carboxylate To a solution of ethyl 3-(2,4-dichlorophenyl)-3-oxopropionate (78 mg, 0.3 mmol) in THF (2 ml) was added DMFDMA (70 μl). The solution was heated 3 hours at 70° C., then cooled and added to a suspension of amino[2-(6-amino-5-nitro(2-pyridyl)amino]ethyl}carboxamidinium 4-methylbenzenesulfonate (123 mg, 0.3 mmol), dry ethanol (1 ml) and 1.0 M sodium ethoxide (0.35 ml). This mixture was heated at 80° C. overnight. The mixture was cooled, diluted with dichloromethane and then extracted with saturated aqueous sodium bicarbonate. The organic layer was concentrated in vacuo and the residual oil was dissolved in acetonitrile. Addition of water gave the title compound as a yellow solid.

Example 31

Synthesis of Ethyl 4-(4-cyanophenyl)-2-({2-[(5-nitro(2-pyridyl))amino]ethyl}amino)pyrimidine-5-carboxylate To a solution of ethyl 3-(4-cyanophenyl)-3-oxopropionate (65 mg, 0.3 mmol) in THF (1 ml) was added DMFDMA (50 μl). The solution was heated at 70° C. for 3 hours. The solution was then added to a mixture of amino[2-[(5-nitro(2-pyridyl)amino]ethyl}carboxamidimium 4-methylbenzenesulfonate (120 mg, 0.3 mmol), dry ethanol (1 ml) and 1.0 M sodium ethoxide (0.35 ml). The mixture was heated at 80° C. overnight. The mixture was cooled, diluted with dichloromethane and washed with saturated aqueous sodium bicarbonate. The organic layer was concentrated in vacuo, then dissolved in acetonitrile. The solid product was precipitated by addition of water to give the title compound.

HPLC: 28.05 min. (95% pure)

Example 32

Synthesis of 2-((2-((5-nitro(2-pyridyl)amino)ethyl)amino)-4-(4-cyanophenyl)pyrimidine-5-carboxylate To a suspension of 1.0 g (2.3 mmol) of ethyl 4-(4-cyanophenyl)-2-({2-[(5-nitro(2-pyridyl)amino]ethyl}amino)pyrimidine-5-carboxylate (prepared as described in Example 31) in 1:1 methanol/water was added 1.5 mnmol of sodium hydroxide and the solution warmed to 60° C. for 45 minutes. During this time the reaction became homogenous. After cooling the mixture, the pH was adjusted to about 5.0 at which time the desired acid precipitated from solution. This solid was collected and dried to give 890 mg (2.2 numol, 98% yield) of 2-((2-((5-nitro(2-pyridyl)amino)ethyl)amino)-4-(4-cyanophenyl)pyrimidine-5-carboxylate as a light yellow powder.

Example 33

Synthesis of 2-(dimethylamino)ethyl 4-(4-cyanophenyl)-2-({2-[(5-nitro(2-pyridyl)amino]ethyl{amino)pyrimidine-5-carboxylate 2-((2-((5-nitro(2-pyridyl)amino)ethyl)amino)-4-(4-cyanophenyl)pyrimidine-5-carboxylate (300 mg, 0.74 mmol) (prepared as described in Example 32) was suspended in 5 ml of 2-(dimethylamino)ethanol at room temperature. O-Benzotriazole-N,N,N',N'-tetramethyluronium-hexafluoro-phosphate (HBTU) (Advance Chem Tech, Louisville, Ky.) was then added in one portion and the mixture stirred for 18 hours at room temperature. The resulting clear solution was poured onto an ice water mixture and extracted thoroughly with ethyl acetate. The aqueous layer was back extracted with ethyl acetate 2×. The combined organic layers were then dried with sodium sulfate and concentrated in vacuo. HPLC and NMR analysis indicated that the desired compound, 2-(dimethylamino)ethyl 2-((2-((5-nitro(2-pyridyl)amino)ethyl)amino)-4-(4-cyanophenyl)pyrimidine-5-carboxylate, was formed in quantitative yield (>95%).

By substituting an alcohol or amine for the 2-(dimethylamino)ethanol indicated above, the following additional compounds of the present invention were similarly synthesized (the alcohol or amine employed is indicated in parentheses):

tert-Butyl 4-(4-cyanophenyl)-2-({2-[(5-nitro(2-pyridyl))amino]ethyl}amino)pyrimidine-5-carboxylate (tert-butyl alcohol)

Methyl 4-(4-cyanophenyl)-2-({2-[((5-nitro(2-pyridyl))amino]ethyl}amino)pyrimidine-5-carboxylate (methanol)

Butyl 4-(4-cyanophenyl)-2-({2-[(5-nitro(2-pyridyl))amino]ethyl}amino)pyrimidine-5-carboxylate (n-butanol)

Phenylmethyl 4-(4-cyanophenyl)-2-({2-[(5-nitro(2-pyridyl))amino]ethyl}amino)pyrimidine-5-carboxylate (benzyl alcohol)

N-Butyl[4-(4-cyanophenyl)-2-({2-[(5-nitro(2-pyridyl))amino]ethyl}amino)pyrimidin-5-yl]carboxamide (n-butylamine)

[4-(4-Cyanophenyl)-2-({2-[(5-nitro(2-pyridyl))amino]ethyl}amino)pyrimidin-5-yl]-N-benzylcarboxamide (benzylamine)

[4-(4-Cyanophenyl)-2-({2-[(5-nitro(2-pyridyl))amino]ethyl}amino)pyrimidin-5-yl]-N,N-dimethylcarboxamide (dimethylamine)

N-(Cyanomethyl)[4-(4-cyanophenyl)-2-({2-[(5-nitro(2-pyridyl)amino]ethyl}amino)pyrimidin-5-yl]carboxamide (aminoacetonitrile)

N-(tert-Butyl)[4-(4-cyanophenyl)-2-({2-[(5-nitro(2-pyridyl)amino]ethyl}amino)pyrimidin-5-yl]carboxamide (t-butylamine)

N-[2-(Dimethylamino)ethyl][4-(4-cyanophenyl)-2-({2-[(5-nitro(2-pyridyl)amino]ethyl}amino)pyrimidin-5-yl]carboxamide 38564 (2-(dimethylamino)ethyl amine)

[4-(4-Cyanophenyl)-2-({2-[(5-nitro(2-pyridyl))amino]ethyl}amino)pyrimidin-5-yl]-N-(2-hydroxyethyl)carboxamide (2-aminoethanol)

4-[5-(Morpholin-4-ylcarbonyl)-2-({2-[(5-nitro(2-pyridyl))amino]ethyl}amino)pyrimidin-4-yl]benzenecarbonitrile (morpholine)

[4-(4-Cyanophenyl)-2-({2-[(5-nitro(2-pyridyl))amino]ethyl}amino)pyrimidin-2-yl]-N-methylcarboxamide (methylamino)

N-(2-Aminoethyl)[4-(4-cyanophenyl)-2-({2-[(5-nitro(2-pyridyl)amino]ethyl}amino)pyrimidin-5-yl]carboxamide (ethylenediamine)

4-[2-({2-[(5-nitro(2-pyridyl))amino]ethyl}amino)-5-(piperazinylcarbonyl)pyrimidin-4-yl]benzenecarbonitrile (piperazine)

4-(4-Cyanophenyl)-2-({2-[5-nitro(2-pyridyl)amino]ethyl}amino)pyrimidine-5-carboxamide (ammonia)

N-(Carbamoylmethyl)[4-(4-cyanophenyl)-2-({2-[(5-nitro(2-pyridyl))amino]ethyl}amino)pyrimidin-5-yl]carboxamide (glycinamide)

[4-(4-cyanophenyl)-2-({2-[(5-nitro(2-pyridyl))amino]ethyl}amino)pyrimidin-5-yl]-N-(4-pyridylmethyl)carboxamide 2-Hydroxyethyl 4-(4-cyanophenyl)-2-({2-[(5-nitro(2-pyridyl))amino]ethyl}amino)pyrimidine-5-carboxylate (ethylene glycol)

N-(1-Carbamoyl-2-hydroxyethyl)[4-(4-cyanophenyl)-2-({2-[(5-nitro(2-pyridyl))amino]ethyl}amino)pyrimidin-5-yl]carboxamide (serinamide)

Example 34

Synthesis of 4-[5-(3-methyl(1,2,4-oxadiazol-5-yl))-2-({2-[(5-nitro(2-pyridyl))amino]ethyl}amino)pyrimidin-4-yl]benzenecarbonitrile To a mixture of ethyl 4-(4-cyanophenyl)-2-({2-[(5-nitro(2-pyridyl))amino]ethyl}amino)pyrimidine-5-carboxylate (0.069 mmol, prepared as described in Example 31) and triethylamine (19.3 µl, 0.14 mmol) in THF (1 ml) was added isobutyl chloroformate (13.4 µl, 0.14 mmol). After stirring at room temperature overnight, the appropriate amidoximine (0.14 mmol) (prepared according to C. D. Bedfore et al., *J Med. Chem.* 20:2174–2183 (1986), which is incorporated herein by reference) was added and the mixture stirred at 70° C. for 6 hours. After stirring an additional 72 hours at room temperature, the reaction was filtered, the solid washed successively with methanol and water, and dried under vacuum to give the desired oxadiazole, 4-[5-(3-methyl(1,2,4-oxadiazol-5-yl))-2-({2-[(5-nitro(2-pyridyl))amino]ethyl}amino)pyrimidin-4-yl]benzene-carbonitrile. The following additional compounds were prepared according to this method by using the appropriate amidoximine:

4-[5-{3-[2-(dimethylamino)ethyl](1,2,4-oxadiazol-5-yl)-2-({2-[(5-nitro(2-pyridyl))amino]ethyl}amino)pyrimidin-4-yl)

(2-{5-[2-({2-[(6-amino-5-nitro(2-pyridyl)amino]ethyl}amino)-4-(2,4-dichlorophenyl)pyrimidin-5-yl](1,2,4-oxadiazol-3-yl)}ethyl)dimethylamine Example 35

Synthesis of Ethyl 4-(4-morpholin-4-ylphenyl)-2-({2-[(5-nitro(2-pyridyl))amino]ethyl}amino)pyrimidine-5-carboxylate To a solution of ethyl 3-(4-morpholinophenyl)3-oxopropionate (193 mg, 0.7 mmol) in THF (1 ml) was added DMFDMA(140 µl). The solution was heated at 70° C. for 3 hours. This solution was added to a mixture of amino[2-[(5-nitro(2-pyridyl)amino]ethyl}carboxamidinium 4-methylbenzenesulfonate (280 mg, 0.7 mmol), ethanol (1 ml) and 1.0 M sodium ethoxide (0.82 ml). The mixture was heated at 80° C. overnight. The cooled mixture was diluted with dichloromethane and extracted with saturated aqueous sodium bicarbonate. The organic layer was concentrated in vacuo, then dissolved in acetonitrile. The product was precipitated as an orange solid (126 mg) by addition of water to give the title compound.

HPLC 25.25 min (95% purity)

NMR (DMSO-d6): 1.15 (t, 3H), 3.20 (m, 4H), 3.60 (br. s, 4H), 3.78 (m, 4H), 4.05 (q, 2H), 6.59 (d, 1H), 6.95 (d, 2H), 7.40 (d, 2H), 8.0 (m, 1H), 8.60 (s, 1H), 8.90 (d, 1H)

MS: MH$^+$=494 C$_{24}$H$_{27}$N$_7$O$_5$=493 g/mol

Example 36

Synthesis of Ethyl 4-((4-imidazolylphenyl)-2-({2-[(5-nitro(2-pyridyl))amino]ethyl}amino)pyrimidine-5-carboxylate To a solution of ethyl 3-[4-(imidazol-1-yl)phenyl]3-oxopropanoate (78 mg, 0.3 mmol) (prepared according to I. Sircar et al., *J. Med. Chem.*, 28:1405 (1985), which is incorporated herein by reference) in THF (1 ml) was added DMFDMA (50 µl). The solution was heated at 70° C. for 3 hours. The solution was then added to a mixture of amino [2-[(5-nitro(2-pyridyl)amino]ethyl}carboxamidinium 4-methylbenzenesulfonate (120 mg, 0.3 nmmol), ethanol (1 ml) and 1.0 M sodium ethoxide (0.35 ml). The mixture was heated at 80° C. overnight, cooled, diluted with dichloromethane and washed with saturated aqueous sodium bicarbonate solution. The organic layer was concentrated in vacuo, redissolved in acetonitrile and then the product was precipitated by addition of water as a yellow solid to give the title compound.

HPLC: 18.50 min. (95% purity)

MS: MH$^+$=475 C$_{23}$H$_{22}$N$_8$O$_4$=474 g/mol

NMR (DMSO-d6): 1.05 (t, 3H), 3.62 (br. s, 4H), 4.10 (q, 2H), 6.58 (d, 1H), 7.15 (s, 1H), 7.60 (d, 2H), 7.70 (d, 2H), 7.75 (s, 1H), 7.85 (br s, 1H), 7.9–8.1 (m, 2H), 8.25 (s, 1H), 8.75 (s, 1H), 8.90 (s, 1H)

Example 37

Synthesis of Ethyl 2-({2-[(5-nitro-(2-pyridyl))amino]ethyl}amino)-4-(4-(1,3-oxazol-5-yl)phenyl)pyrimidine-5-carboxylate Step 1: Methyl 4-formylbenzoate (Aldrich Chemical Co., St. Louis, Mo.) (5.0 g, 30.5 mmol), anhydrous potassium carbonate (4.55 g, 33 mmol) and p-toluenesulfonylmethyl isocyanide (TOSMIC, Aldrich Chemical Co.) (6.83 g, 30.5 mmol) were refluxed in methanol (100 ml) for 3.5 hours. The mixture was then concentrated to dryness in vacuo. The residue was dissolved in ethyl acetate, washed twice with water, dried and concentrated in vacuo to give methyl 4-(1,3-oxazol-5-yl)benzoate as a beige solid (4.95 g).

(NMR (300 MHz, CDCl$_3$: 8.10 (d, 2H), 7.98 (s, 1H), 7.75 (d, 2H), 7.48 (s, 3H), 3.94 (s, 3H)).

The above ester was heated at reflux for 2 hours in a mixture of 1 M aqueous potassium hydroxide and 50 ml THF. The THF was removed in vacuo and the solution cooled, then acidified with 50% HCl to give 4-(1,3-oxazol-5-yl)benzoic acid as a white solid.

NMR (300 MHz, DMSO-d6; 8.52 (s, 1H), 8.05 (d, 2H), 7.82–7.9, m, 3H).

The dried acid above was refluxed in neat thionyl chloride until all of the solid had dissolved. The thionyl chloride was removed by rotary evaporation (with hexane). The crude acid chloride was then dried in vacuo briefly. Meanwhile, potassium ethyl malonate (11.1 g, 65 mmol) and anhydrous magnesium chloride (7.7 g, 81 mmol) in dry acetonitrile (150 ml) were treated with triethylamine (5.15 ml, 37 mmol). The mixture was stirred for 3 hours at room temperature, then an additional 1 ml of triethylamine was added, followed by a solution of the acid chloride prepared above in dry acetonitrile (50 ml). The reaction was stirred overnight at room temperature. The mixture was concentrated to dryness in vacuo and then partitioned between toluene and 0.25 M aqueous HCl. The organic layer was washed with water, dried and concentrated to give crude ethyl 3-(4-(1,3-oxazol-5-yl)phenyl)-3-oxopropanoate. The crude product was purified by silica gel chromatography (hexanes/ethyl acetate).

Step 2. To a solution of ethyl 3-(4-(1,3-oxazol-5-yl)phenyl)-3-oxopropanoate (76 mg, 0.3 mmol) in THF (1 ml) was added DMFDMA (60 µl). The solution was heated at 70° C. for 3 hours. This solution was added to a mixture of amino[2-[(5-nitro(2-pyridyl)amino]ethyl}carboxamidinium 4-methylbenzenesulfonate (120 mg, 0.3 mmol), ethanol (1 ml) and 1.0 M sodium ethoxide (0.35 ml). The mixture was heated at 80° C. overnight, cooled, diluted with dichloromethane and washed with saturated sodium bicarbonate solution. The organic layer was concentrated in vacuo, redissolved in acetonitrile and the product precipitated with water to give the title compound as an orange solid.

HPLC: 26.75 min. (90% purity)

NMR (DMSO-d$_6$): 1.05 (t, 3H), 3.65 (br. s, 4H), 4.10 (q, 2H), 6.58 (d, 1H), 7.58 (d, 2H), 7.70 (s, 1H), 7.75 (d, 2H), 7.82 (br. s, 1H), 7.95–8.10 (m, 2H), 8.40 (s, 1H), 8.75 (s, 1H), 8.85 (s, 1H)

Example 38

Synthesis of Ethyl 4-(4-(2-furyl)phenyl)-2-({2-[(5-nitro(2-pyridyl))amino]ethyl}amino)pyrimidine-5-carboxylate Step 1: Ethyl 4-iodobenzoate (2.76 g, 10 mmol) and 2-furylboronic acid (Frontier Scientific, 1.12 g, 10 mmol)) were mixed with bis (triphenylphosphine)palladium dichloride (100 mg) in 1,2-dimethoxyethane (20 ml) and 2 M aqueous sodium carbonate (20 ml). The mixture was bubbled with argon gas, then heated at 80° C. under argon overnight. The mixture was cooled, diluted with ethyl acetate, then washed with water. The organic layer was dried and concentrated in vacuo to give a crude solid ester. This material was taken up in a mixture of THF and 1 M aqueous potassium hydroxide and refluxed for 2.5 hours. The THF was removed by rotary evaporation and the aqueous layer acidified with acetic acid. Cooling to 4° C. resulted in the precipitation of 4-(2-furyl)benzoic acid as a brown solid (1.49 g)

(NMR (300 MHz, DMSO-d6: 8.10 (d, 2H), 7.90 (m, 3H), 7.24 (d, 1H), 6.75 (dd, 1H)).

Step 2: The acid from Step 1 was converted to the acid chloride by refluxing in a mixture of oxalyl chloride (1.3 ml), THF (20 ml) and several drops of DMF. Small portions of oxalyl chloride were added until the reaction was homogeneous. Reflux continued for 0.5 hours, then the solvent was removed in vacuo to give the crude acid chloride. Meanwhile, potassium ethyl malonate (2.7 g) was reacted with anhydrous magnesium chloride (1.9 g) and triethylamine (2.21 ml) in dry acetonitrile (50 ml) at room temperature for 3 hours. Triethylamine (1 ml) was added, followed by addition of a solution of the acid chloride in acetonitrile. The mixture was then stirred overnight at room temperature, then concentrated to dryness. The residue was partitioned between toluene and 10% aqueous HCl. The organic layer was washed with 10% HCl and water, dried and was then concentrated to give crude ethyl 3-(4-(2-furyl)phenyl)-3-oxopropanoate as a solid.

Step 3: The β-keto ester prepared in Step 2 (76 mg, 0.3 mmol) was dissolved in dry THF (2 ml) and heated with DMFDMA (60 µl) at 70° C. for 4 hours. This solution was then added to a mixture of amino[2-[(5-nitro(2-pyridyl)amino]ethyl}carboxamidinium 4-methylbenzenesulfonate (120 mg, 0.3 mmol) and cesium carbonate (160 mg) and then heated at 80° C. overnight to give ethyl 4-(4-(2-furyl)phenyl)-2-({2-[(5-nitro(2-pyridyl))amino]ethyl}amino)pyrimidine-5-carboxylate.

HPLC: 32.05 min (80% purity)

MS: MH$^+$=476 C$_{24}$H$_{23}$N$_6$O$_5$=475 g/mol

Example 39

Synthesis of Ethyl 4-(4-cyanophenyl)-2-({2-[(4-methyl-5-nitro(2-pyridyl))amino]ethyl}amino)pyrimidine-5-carboxylate Step 1: 2-Chloro-4-methyl-5-nitropyridine (2.0 g, 11.5 mmol) in acetonitrile (10 ml) was added dropwise to ethylenediamine (2.5 ml) in acetonitrile (10 ml). The mixture was stirred overnight at room temperature. The solvent was removed by rotary evaporation and the residue was partitioned between dichloromethane and 2.5 M aqueous sodium hydroxide. The aqueous layer was further extracted 4 times with dichloromethane. The combined organic layers were washed with a saturated sodium chloride solution, dried and concentrated in vacuo to give (2-aminoethyl)(4-methyl-5-nitro(2-pyridyl))amine as an orange solid (1.74 g).

Step 2: The amine from Step 1 (1.2 g, 6 mmol) was shaken with benzotriazole carboxamidinium 4-methylbenzenesulfonate (2.0 g, 6 mmol) and DIEA (1.05 ml, 6 mmol) in dry acetonitrile (10 ml) at room temperature overnight. Addition of ether resulted in the precipitation of amino{2-[(4-methyl-5-nitro(2-pyridyl))amino]ethyl}carboxamidinium 4-methylbenzenesulfonate as a yellow solid.

Step 3: Ethyl 3-(4-cyanophenyl)-3-oxopropanoate (64 mg, 0.3 mmol) in THF (1 ml) and DMFDMA (0.3 mmol) was heated at 70° C. for 3 hours. The solution was added to a mixture of the guanidine from Step 2 (123 mg, 0.3 mmol), 1.0 M sodium ethoxide in ethanol (0.35 ml) and ethanol (1 ml). The mixture was then heated overnight at 80° C., cooled, diluted with dichloromethane, then washed with saturated sodium bicarbonate solution. The organic layer was concentrated in vacuo, redissolved in acetonitrile and the product precipitated with water.

HPLC: 27.63 min (85% pure)

MS: MH$^+$=448 $C_{22}H_{21}N_7O_4$=447 g/mol

Example 40

Synthesis of 2-({2-[(5-nitro(2-pyridyl)amino] ethyl}amino)-4-phenylpyrimidine-5-carbonitrile 3-Oxo-3-phenylpropanenitrile (44 mg, 0.3 mmol) in THF (1 ml) and DMFDMA (50 µl) was heated at 70° C. for 3 hours. This solution was added to a mixture of amino[2-[(5-nitro(2-pyridyl)amino]ethyl}carboxamidinium 4-methylbenzenesulfonate (120 mg, 0.3 mrol), 1.0 M sodium ethoxide in ethanol (0.35 ml) and dry ethanol (1 ml) and heated at 80° C. overnight, then concentrated in vacuo. The residue was then taken up in dichloromethane and washed with a saturated aqueous sodium bicarbonate solution. The organic layer was concentrated in vacuo. The residue was taken up in acetonitrile. Addition of water gave a precipitate which was filtered off and dried to give the title compound.

HPLC: 13.87 min (95% pure)

Example 41

Synthesis of {2-[(5-nitro(2-pyridyl))amino]ethyl}-(5-nitro-4-phenylpyrimidin-2-yl)amine 2-Nitro-1-phenylethan-1-one (50 mg, 0.3 mmol) was heated in THF (1 ml) and DMFDMA (50 µl) for 3 h at 70° C. This solution was added to a mixture of amino[2-[(5-nitro(2-pyridyl)amino]ethyl}carboxamidinium 4-methylbenzenesulfonate (120 mg, 0.3 mmol), 1.0 M sodium ethoxide in ethanol (0.35 ml) and dry ethanol (1 ml), heated at 80° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 15.33 min (100% purity)

MS: MH$^+$=382 $C_{17}H_{15}N_7O_4$=381 g/mol

Example 42

Synthesis of (5-Nitro-4-phenylpyrimidin-2-yl)[2-(2-pyridylamino)ethyl]amine

2-Nitro-1-phenylethan-1-one (50 mg, 0.3 mmol) was heated in THF (1 ml) and DMFDMA (50 µl) for 3 hours at 70° C. This solution was added to a mixture of amino[2-(2-pyridyl)amino)ethyl}carboxamidinium 4-methylbenzenesulfonate (105 mg, 0.3 mmol), 1.0 M sodium ethoxide in ethanol (0.35 ml) and dry ethanol (1 ml), heated at 80° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 19.66 min (100% purity)

MS: MH$^+$=337 $C_{17}H_{16}N_6O_2$=336 g/mol

Example 43

Synthesis of Ethyl 4-(4-cyanophenyl)-2-[(2-{[5-(trifluoromethyl)(2-pyridyl)]amino}ethyl)amino] pyrimidine-5-carboxylate Step 1: 2-Chloro-5-(trifluoromethyl)pyridine (5.0 g) was heated with ethylenediamine (20 ml) at 120° C. overnight. The excess ethylenediamine was removed by rotary evaporation and the residue was partitioned between dichloromethane and 2.5 M aqueous sodium hydroxide. The aqueous layer was extracted 5 times further with dichloromethane. The combined organic layers were washed with a saturated aqueous sodium chloride solution, dried, then concentrated in vacuo to give (2-aminoethyl)[5-(trifluoromethyl)(2-pyridyl)]amine as an orange oil.

Step 2: The amine from Step 1 (1.1 g, 5.36 numol) was treated with benzotriazole carboxamidinium 4-methylbenzenesulfonate (1.78 g, 5.36 mmol) and DIEA (0.93 ml, 5.36 mmol) in acetonitrile (6 ml) with shaking at room temperature overnight. Addition of ether gave amino (2-{[5-(trifluoromethyl)(2-pyridyl)]amino}ethyl) carboxamidinium 4-methylbenzenesulfonate as a white solid.

Step 3: Ethyl 3-(4-cyanophenyl)-3-oxopropanoate (64 mg, 0.3 mmol) was heated in THF (1 ml) with DMFDMA (50 µl) at 70° C. for 4 hours. This solution was added to a mixture of the guanidine from Step 2 (123 mg, 0.3 mmol), 1.0 M sodium ethoxide in ethanol (0.35 ml) and dry ethanol (1 ml). This mixture was heated at 80° C. overnight, then concentrated in vacuo. The residue was taken up in dichloromethane and washed with a saturated aqueous sodium bicarbonate solution. The organic layer was concentrated in vacuo. The residue was taken up in acetonitrile. Addition of water gave a precipitate that was filtered off and dried to give the title compound.

HPLC: 24.46 min (85% purity)

MS: MH$^+$=457 $C_{22}H_{19}N_6O_2F_3$=456 g/mol

Example 44

Synthesis of [4-(2,4-dichlorophenyl)-5-imidazolylpyrimidin-2-yl]{2-[(5-nitro(2-pyridyl))amino]ethyl}amine Step 1. 2,4-Dichlorophenacyl chloride (1.42 g, 6.4 mmol) and imidazole (1.18 g, 16 mmol) were heated in toluene (40 ml) at 75° C. for 2.25 hours. The mixture was concentrated to dryness in vacuo. The residue was dissolved in dichloromethane and washed with 5% aqueous potassium carbonate solution and water, dried and concentrated in vacuo. The crude product was purified by passage over a pad of silica gel, eluting with 5% methanol in dichloromethane to give 1-(2,4-dichlorophenyl)-2-imidazolylethan-1-one as an orange oil.

Step 2: The product of Step 1 (95 mg) was heated with DMFDMA (2 ml) at 105° C. for 9 hours. The solvent was removed in vacuo and the residue was dissolved in dry THF (2 ml) and added to a mixture of amino[2-[(5-nitro(2-pyridyl)amino]ethyl}carboxamidinium 4-methylbenzenesulfonate (100 mg, 0.3 mmol) and cesium carbonate (200 mg). The mixture was heated overnight at 80° C., then concentrated in vacuo. The residue was taken up in dichloromethane and washed with saturated aqueous sodium bicarbonate. The organic layer was concentrated in vacuo. The product was purified by radial chromatography on silica gel.

HPLC: 22.48 min (96% purity)

MS: MH$^+$=471–473 (cluster, 2 Cl) $C_{20}H_{16}Cl_2N_8O_2$=471 g/mol

Example 45

4-[2-({2-[(6-amino-5-nitro(2-pyridyl))amino] ethyl}amino)-5-imidazolylpyrimidin-4-yl] benzenecarbonitrile Step 1: 4-Cyanophenacyl bromide (0.72 g, 3.2 mmol) and imidazole (0.55 g, 8 mmol) were heated at 75° C. in toluene (20 ml) for 2.5 hours. The mixture was concentrated to dryness in vacuo. The residue was dissolved in dichloromethane and washed with a 5% aqueous potassium carbonate solution and water, dried and concentrated in vacuo to give a pink solid (0.35 g). This method is a variation of the one described in Sakurai et al., 1996, *Chem. Pharm. Bull.* 44:1510, which is incorporated herein by reference.

Step 2: 1-(4-Cyanophenyl)-2-imidazolylethan-1-one (from Step 1, 63 mg, 0.3 mmol) was heated with DMFDMA (2 ml) at 105° C. for 9 hours. The solvent was removed in vacuo and the residue was dissolved in dry THF (2 ml) and added to a mixture of amino[2-[(6-amino-5-nitro(2-pyridyl)) amino]ethyl}carboxamidinium 4-methylbenzene-sulfonate (105 mg, 0.3 mmol) and cesium carbonate (200 mg). The mixture was heated overnight at 80° C., then concentrated in vacuo. The residue was taken up in dichloromethane and washed with a saturated aqueous sodium bicarbonate solution. The organic layer was concentrated in vacuo. The residue was crystallized from ethanol/water to give yellow needles.

HPLC: 17.68 min (100% purity)
MS: $MH^+$=443 $C_{21}H_{18}N_{10}O_2$=442 g/mol

Example 46

Synthesis of [4-(2,4-dichlorophenyl)-5-imidazol-2-ylpyrimidin-2-yl]{2-[(5-nitro(2-pyridyl)amino]ethyl}amine A solution of 1-(2,4-dichlorophenyl)-2-imiazol-2-ylethan-1-one (prepared from the appropriate acid chloride and 2-methylimidazole according to the procedure described in Macco et al., *J Org. Chem.*, 20:252 (1985), which is incorporated herein by reference) and DMFDMA (10 ml/mmol of ketone) was stirred at reflux for 12 hours. After concentration of this solution, the resulting solid was redissolved in DMF (10 ml/mmol). $Cs_2CO_3$(3 mmol) and (2-(5-nitro(2-pyridyl)amino]ethyl)carboxamidinium 4-methylbenzenesulfonate (1.5 mrol) were added, and the mixture stirred for 8 hours at 100° C. The mixture was cooled, filtered and the filtrate diluted with ethyl acetate and washed with saturated aqueous sodium bicarbonate. Concentration of the organic layers yielded [4-(2,4-dichlorophenyl)-5-imidazol-2-ylpyrimidin-2-yl]{2-[(5-nitro(2-pyridyl)amino]ethyl}amine.

Example 47

Synthesis of [2-[(6-amino-5-nitro(2-pyridyl))amino]ethyl}[4-(2,4-dichlorophenyl)-5-imidazol-2-ylpyrimidin-2-yl]amine A solution of 1-(2,4-dichlorophenyl)-2-imiazol-2-ylethan-1-one (prepared from the appropriate acid chloride and 2-methylimidazole according to the procedure described in Macco et al., *J. Org. Chem.*, 20:252 (1985), which is incorporated herein by reference) and DMFDMA (10 ml/mmol of ketone) was stirred at reflux for 12 hours. After concentration of this solution, the resulting solid was redissolved in DMF (10 ml/mmol). $Cs_2CO_3$(3 mmol) and (2-(6-amino-5-nitro(2-pyridyl)amino)ethyl)carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded [2-[(6-amino-5-nitro (2-pyridyl))amino]ethyl}[4-(2,4-dichlorophenyl)-5-imidazol-2-ylpyrimidin-2-yl]amine.

Example 48

Synthesis of 4-[5-imidazol-2-yl-2-({2-[(5-nitro(2-pyridyl)amino]ethyl}amino)pyrimidin-4-yl]benzenecarbonitrile A solution of 4-(2-midazol-2-ylacetyl)benzenecarbonitrile (prepared from the appropriate acid chloride and 2-methylimidazole according to the procedure described in Macco et al., *J. Org. Chem.*, 20:252 (1985) and DMFDMA (10 ml/mmol of ketone) was stirred at reflux for 12 hours. After concentration of this solution, the resulting solid was redissolved in DMF (10 ml/mmol). $Cs_2CO_3$(3 mmol) and (2-(5-nitro(2-pyridyl)amino]ethyl) carboxamidinium 4-methylbenzenesulfonate (1.5 minol) were added, and the mixture stirred for 8 hours at 100° C. The mixture was cooled, filtered and the filtrate diluted with ethyl acetate and washed with saturated aqueous sodium bicarbonate. Concentration of the organic layers yielded 4-[5-imidazol-2-yl-2-({2-[(5-nitro(2-pyridyl)amino]ethyl}amino)pyrimidin-4-yl]benzenecarbonitrile.

Example 49

Synthesis of 4-[2-({2-[(6-amino-5-nitro(2-pyridyl))amino]ethyl}amino)-5-imidazol-2-ylpyrimidin-4-yl]benzenecarbonitrile A solution of 4-(2-midazol-2-ylacetyl)benzenecarbonitrile (prepared from the appropriate acid chloride and 2-methylimidazole according to the procedure described in Macco et al., *J Org. Chem.*, 20:252 (1985) and DMFDMA (10 ml/mmol of ketone) was stirred at reflux for 12 hours. After concentration of this solution, the resulting solid was redissolved in DMF (10 ml/mmol). $Cs_2CO_3$(3 mmol) and (2-(6-amino-5-nitro(2-pyridyl)amino)ethyl) carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded 4-[2-({2-[(6-amino-5-nitro(2-pyridyl))amino]ethyl}amino)-5-imidazol-2-ylpyrimidin-4-yl]benzenecarbonitrile.

Example 50

Synthesis of Ethyl 2-({2-[(5-nitro(2-pyridyl))amino]ethyl}amino)-4-(4-pyridyl)pyrimidine-5-carboxylate This compound was prepared from ethyl 3-oxo-3-(4-pyridyl)propanoate and amino[2-[(5-nitro(2-pyridyl)amino]ethyl}carboxamidinium 4-methylbenzenesulfonate in accordance with Solution Method A.

HPLC: 17.78 min (90% purity)
NMR(300 MHz, 5/1 acetonitrile-$d_3$/$D_2O$): 8.85 (d, 1H), 8.82 (s, 1H), 8.80 (d, 2H), 8.01 (dd, 1H), 7.38 (d, 2H), 6.43 (d, 1H), 4.10 (q, 2H), 3.60–3.80 (m, 4H), 1.06 (t, 3H).

Example 51

Synthesis of Ethyl 4-(3-nitrophenyl)-2-{[2-(2-pyridylamino)ethyl]amino}pyrimidine-5-carboxylate This compound was prepared from ethyl 3-oxo-3-(3-nitrophenyl)propanoate and amino[2-(2-pyridylamino)ethyl]carboxamidinium 4-methylbenzenesulfonate in accordance with Solution Method A.

HPLC: 21.25 min (90% purity)
MS: $MH^+$=409 $C_{20}H_{19}N_6O_4$=408 g/mol

Example 52

Synthesis of Ethyl 2-({2-[(5-nitro(2-pyridyl))amino]ethyl}amino)-4-[4-(trifluoromethoxy)phenyl]pyrimidine-5-carboxylate This compound was prepared from ethyl 3-oxo-3-(4-trifluoromethoxyphenyl)propanoate and amino[2-[(5-nitro(2-pyridyl)amino]ethyl}carboxamidinium 4-methylbenzenesulfonate in accordance with Solution Method A.

HPLC: 22.50 min (91% purity)
MS: $MH^+=493$ $C_{21}H_{19}N_6O_5F_3=472$ g/mol

Example 53

Synthesis of Ethyl 4-(3,4-difluorophenyl)-2-({2-[(5-nitro(2-pyridyl))amino]ethyl}amino)pyrimidine-5-carboxylate This compound was prepared from ethyl 3-oxo-3-(3,4-difluorophenyl)propanoate and amino[2-[(5-nitro(2-pyridyl)amino]ethyl}carboxamidinium 4-methylbenzenesulfonate in accordance with Solution Method A.

HPLC: 17.96 min (100% purity)
MS: $MH^+=445$ $C_{20}H_{18}N_6O_4F_2=444$ g/mol

Example 54

Synthesis of Ethyl 4-[4-(methylsulfonyl)phenyl]-2-({2-[(5-nitro(2-pyridyl))amino]ethyl}amino)pyrimidine-5-carboxylate This compound was make from ethyl 3-(4-methylsulfonylphenyl)-3-oxopropanoate and amino[2-[(5-nitro(2-pyridyl)amino]ethyl}carboxamidinium 4-methylbenzenesulfonate in accordance with Solution Method A.

HPLC: 11.21 min (100% purity)
MS: $MH^+=487$ $C_{21}H_{22}N_6O_6S=486$ g/mol

Example 55

Synthesis of Ethyl 4-(4-methylthiophenyl)-2-({2-[(5-nitro(2-pyridyl))amino]ethyl}amino)pyrimidine-5-carboxylate This compound was prepared from ethyl 3-(4-methylthiophenyl)-3-oxopropanoate and amino[2-[(5-nitro(2-pyridyl)amino]ethyl}carboxamidinium 4-methylbenzenesulfonate in accordance with Solution Method A.

HPLC: 17.26 min (92% purity)
MS: $MH^+=455$ $C_{21}H_{22}N_6O_4S=454$ g/mol

Example 56

Synthesis of Ethyl 4-[4-(dimethylamino)phenyl]-2-({2-[(5-nitro(2-pyridyl))amino]ethyl}amino)pyrimidine-5-carboxylate This compound was prepared from ethyl 3-(4-dimethylaminophenyl)-3-oxopropanoate and amino[2-[(5-nitro(2-pyridyl)amino]ethyl}carboxamidinium 4-methylbenzenesulfonate in accordance with Solution Method A.

HPLC: 9.0 min (90% purity)
MS: $MH^+=452$ $C_{22}H_{25}N_7O_4=451$ g/mol

Example 57

Synthesis of Ethyl 2-({2-[(6-amino-5-nitro(2-pyridyl))amino]ethyl}amino)-4-(4-cyanophenyl)pyrimidine-5-carboxylate This compound was prepared from ethyl 3-(4-cyanophenyl)-3-oxopropanoate and amino{2-[(6-amino-5-nitro(2-pyridyl))amino]ethyl}carboxamidinium 4-methylbenzene-sulfonate in accordance with Solution Method A.

HPLC: 25.21 min (83% purity)
MS: $MH^+=449$ $C_{21}H_{20}N_8O_4=448$ g/mol

Example 58

Synthesis of Ethyl 4-(4-imidazolylphenyl)-2-({2-[(5-nitro(2-pyridyl))amino]ethyl}amino)pyrimidine-5-carboxylate This compound was prepared from ethyl 3-[4-(1-imidazolyl)phenyl]-3-oxopropanoate and amino[2-[(5-nitro(2-pyridyl)amino]ethyl}carboxamidinium 4-methylbenzenesulfonate in accordance with Solution Method A.

HPLC: 18.50 min (91% purity)
MS: $MH^+=475$ $C_{23}H_{22}N_8O_4=474$ g/mol

Example 59

Synthesis of Ethyl 4-(4-ethylphenyl)-2-({2-[(5-nitro(2-pyridyl))amino]ethyl}amino)pyrimidine-5-carboxylate This compound was prepared from ethyl 3-(4-ethylphenyl)-3-oxopropanoate and amino[2-[(5-nitro(2-pyridyl)amino]ethyl}carboxamidinium 4-methylbenzenesulfonate in accordance with Solution Method A.

HPLC: 32.45 min (95% purity)
MS: $MH^+=437$ $C_{22}H_{24}N_6O_4=436$ g/mol

The following additional compounds were prepared according to Solution Method A using the appropriate carbonyl containing compound and guanidine.

Ethyl 4-(2-furyl)-2-[(2-(2-pyridyl)ethyl)amino]pyrimidine-5-carboxylate

Ethyl 4-(3-nitrophenyl)-2-[(2-(2-pyridyl)ethyl)amino]pyrimidine-5-carboxylate

Ethyl 4-(4-fluorophenyl)-2-[(2-(2-pyridyl)ethyl)amino]pyrimidine-5-carboxylate

Ethyl 4-(4-methoxyphenyl)-2-[(2-(2-pyridyl)ethyl)amino]pyrimidine-5-carboxylate

Ethyl 4-(4-cyanophenyl)-2-[(2-(2-pyridyl)ethyl)amino]pyrimidine-5-carboxylate 2-({2-[(5-nitro(2-pyridyl))amino]ethyl}amino)-4-(4-nitrophenyl)pyrimidine-5-carboxylic acid Ethyl 4-(4-fluorophenyl)-2-({2-[(5-nitro(2-pyridyl))amino]ethyl}amino)pyrimidine-5-carboxylate Ethyl 2-({2-[(5-nitro(2-pyridyl))amino]ethyl}amino)-4-(3-quinolyl)pyrimidine-5-carboxylate Ethyl 2-({2-[(5-nitro(2-pyridyl))amino]ethyl}amino)-4-(3-nitrophenyl)pyrimidine-5-carboxylate Methyl 2-({2-[(5-nitro(2-pyridyl))amino]ethyl}amino)-4-(3-pyridyl)pyrimidine-5-carboxylate Ethyl 2-({2-[(5-nitro(2-pyridyl))amino]ethyl}amino)-4-(4-nitrophenyl)pyrimidine-5-carboxylate Ethyl 4-[3,5-bis(trifluoromethyl)phenyl]-2-({2-[(5-nitro(2-pyridyl))amino]ethyl}amino)pyrimidine-5-carboxylate Ethyl 2-({2-[(5-nitro(2-pyridyl))amino]ethyl}amino)-4-[4-(trifluoromethyl)phenyl]pyrimidine-5-carboxylate Ethyl 2-({2-[(5-nitro(2-pyridyl))amino]ethyl}amino)-4-[3-(trifluoromethyl)phenyl]pyrimidine-5-carboxylate Ethyl 4-(5-bromo(3-pyridyl))-2-({2-[(5-nitro(2-pyridyl))amino]ethyl}amino)pyrimidine-5-carboxylate Ethyl 4-(2,4-difluorophenyl)-2-({2-[(5-nitro(2-pyridyl))amino]ethyl}amino)pyrimidine-5-carboxylate Ethyl 4-(2,4-dichlorophenyl)-2-({2-[(5-nitro(2-pyridyl))amino]ethyl}amino)pyrimidine-5-carboxylate
Ethyl 4-(4-cyanophenyl)-2-{[2-(pyrimidin-2-ylamino)ethyl]amino}pyrimidine-5-carboxylate
Ethyl 4-(4-methoxyphenyl)-2-({2-[(5-nitro(2-pyridyl))amino]ethyl}amino)pyrimidine-5-carboxylate
Ethyl 4-(3-cyanophenyl)-2-({2-[(5-nitro(2-pyridyl))amino]ethyl}amino)pyrimidine-5-carboxylate
Ethyl 4-(4-cyanophenyl)-2-({2-[(4-nitrophenyl)amino]ethyl}amino)pyrimidine-5-carboxylate
Ethyl 4-(3-fluorophenyl)-2-({2-[(5-nitro(2-pyridyl))amino]ethyl}amino)pyrimidine-5-carboxylate
Ethyl 4-(3,5-dichlorophenyl)-2-({2-[(5-nitro(2-pyridyl))amino]ethyl}amino)pyrimidine-5-carboxylate
4-[5-(methylsulfonyl)-2-({2-[(5-nitro(2-pyridyl))amino]ethyl}amino)pyrimidin-4-yl]benzenecarbonitrile
Ethyl 2-({2-[(5-nitro(2-pyridyl))amino]ethyl}amino)-4-(4-sulfamoylphenyl)pyrimidine-5-carboxylate
Ethyl 4-(4-chlorophenyl)-2-({2-[(5-nitro(2-pyridyl))amino]ethyl}amino)pyrimidine-5-carboxylate
Ethyl 4-(4-bromophenyl)-2-({2-[(5-nitro(2-pyridyl))amino]ethyl}amino)pyrimidine-5-carboxylate
Ethyl 4-naphthyl-2-({2-[(5-nitro(2-pyridyl))amino]ethyl}amino)pyrimidine-5-carboxylate
Ethyl 2-({2-[(5-nitro(2-pyridyl))amino]ethyl}amino)-4-(4-phenylphenyl)pyrimidine-5-carboxylate
Ethyl 4-(2H-benzo[3,4-d]1,3-dioxolen-5-yl)-2-({2-[(5-nitro(2-pyridyl))amino]ethyl}amino)pyrimidine-5-carboxylate
Ethyl 4-(4-butoxyphenyl)-2-({2-[(5-nitro(2-pyridyl))amino]ethyl}amino)pyrimidine-5-carboxylate
6-[(2-{[4-(4-cyanophenyl)-5-(ethoxycarbonyl)pyrimidin-2-yl]amino}ethyl)amino]pyridine-3-carboxylic acid
tert-Butyl 4-(4-cyanophenyl)-2-({2-[(5-nitro(2-pyridyl))amino]ethyl}amino)pyrimidine-5-carboxylate
tert-Butyl 6-[(2-{[4-(4-cyanophenyl)-5-(ethoxycarbonyl)pyrimidin-2-yl]amino}ethyl)amino]pyridine-3-carboxylate
Methyl 4-(4-cyanophenyl)-2-({2-[(5-nitro(2-pyridyl))amino]ethyl}amino)pyrimidine-5-carboxylate
Methyl 6-[(2-{[4-(4-cyanophenyl)-5-(ethoxycarbonyl)pyrimidin-2-yl]amino}ethyl)amino]pyridine-3-carboxylate
Ethyl 4-(4-cyanophenyl)-2-[(2-{[5-(morpholin-4-ylcarbonyl)(2-pyridyl)]amino}ethyl)amino]pyrimidine-5-carboxylate
Ethyl 4-(4-cyanophenyl)-2-[(2-{[5-(N-ethylcarbamoyl)(2-pyridyl)]amino}ethyl)amino]pyrimidine-5-carboxylate
4-[5-nitro-2-({2-[(5-nitro(2-pyridyl))amino]ethyl}amino)pyrimidin-4-yl]benzenecarbonitrile
Ethyl 4-(4-cyanophenyl)-2-{[2-({5-nitro-6-[benzylamino](2-pyridyl)}amino)ethyl]amino}pyrimidine-5-carboxylate
Ethyl 4-[4-(4-methylpiperazinyl)phenyl]-2-({2-[(5-nitro(2-pyridyl))amino]ethyl}amino)pyrimidine-5-carboxylate
Ethyl 2-({2-[(5-cyano(2-pyridyl))amino]ethyl}amino)-4-(4-cyanophenyl)pyrimidine-5-carboxylate
Ethyl 4-(4-cyanophenyl)-2-[(2-{[6-(methylamino)-5-nitro(2-pyridyl)]amino}ethyl)amino]pyrimidine-5-carboxylate
Ethyl 2-({2-[(5-nitro(2-pyridyl))amino]ethyl}amino)-4-(4-(1,3-oxazol-5-yl)phenyl)pyrimidine-5-carboxylate
Ethyl 2-({2-[(4-amino-5-nitropyrimidin-2-yl)amino]ethyl}amino)-4-(4-cyanophenyl)pyrimidine-5-carboxylate
Ethyl 2-({2-[(6-amino-5-nitro(2-pyridyl))amino]ethyl}amino)-4-(4-(1,3-oxazol-5-yl)phenyl)pyrimidine-5-carboxylate
Ethyl 4-[4-(methylethyl)phenyl]-2-({2-[(5-nitro(2-pyridyl))amino]ethyl}amino)pyrimidine-5-carboxylate
Ethyl 4-[4-(tert-butyl)phenyl]-2-({2-[(5-nitro(2-pyridyl))amino]ethyl}amino)pyrimidine-5-carboxylate
Ethyl 4-(3,4-dichlorophenyl)-2-({2-[(5-nitro(2-pyridyl))amino]ethyl}amino)pyrimidine-5-carboxylate
Ethyl 4-(3,4-dimethoxyphenyl)-2-({2-[(5-nitro(2-pyridyl))amino]ethyl}amino)pyrimidine-5-carboxylate
Ethyl 4-[4-(diethylamino)phenyl]-2-({2-[(5-nitro(2-pyridyl))amino]ethyl}amino)pyrimidine-5-carboxylate
2-({2-[(5-nitro(2-pyridyl))amino]ethyl}amino)-4-(2,4,6-trichlorophenyl)pyrimidine-5-carboxylic acid
Ethyl 4-(4-methylphenyl)-2-({2-[(5-nitro(2-pyridyl))amino]ethyl}amino)pyrimidine-5-carboxylate
Ethyl 4-(2-naphthyl)-2-({2-[(5-nitro(2-pyridyl))amino]ethyl}amino)pyrimidine-5-carboxylate
Ethyl 4-(3,4-dimethylphenyl)-2-({2-[(5-nitro(2-pyridyl))amino]ethyl}amino)pyrimidine-5-carboxylate
Ethyl 2-({2-[(4-amino-5-cyanopyrimidin-2-yl)amino]ethyl}amino)-4-(4-cyanophenyl)pyrimidine-5-carboxylate
4-(2-methoxyphenyl)-2-({2-[(5-nitro(2-pyridyl))amino]ethyl}amino)pyrimidine-5-carboxylic acid
Ethyl 4-(4-cyanophenyl)-2-{[2-(3-methoxyphenyl)ethyl]amino}pyrimidine-5-carboxylate
2-({2-[(6-amino-5-nitro(2-pyridyl))amino]ethyl}amino)-4-(3,4-dichlorophenyl)pyrimidine-5-carbonitrile
4-(3,4-dichlorophenyl)-2-({2-[(5-nitro(2-pyridyl))amino]ethyl}amino)pyrimidine-5-carbonitrile
Ethyl 2-({2-[(5-nitro(2-pyridyl))amino]ethyl}amino)-4-(4-(1,2,4-triazol-4-yl)phenyl)pyrimidine-5-carboxylate
2-({2-[(6-amino-5-nitro(2-pyridyl))amino]ethyl}amino)-4-(2,4-dichlorophenyl)pyrimidine-5-carbonitrile
4-(2,4-dichlorophenyl)-2-({2-[(5-nitro(2-pyridyl))amino]ethyl}amino)pyrimidine-5-carbonitrile
2-({2-[(6-amino-5-nitro(2-pyridyl))amino]ethyl}amino)-4-(2,4-dichlorophenyl)pyrimidine-5-carboxylic acid
Ethyl 2-({2-[(5-amino(2-pyridyl))amino]ethyl}amino)-4-(4-cyanophenyl)pyrimidine-5-carboxylate Example 60

Solution Phase Synthesis

Solution Method B

A ketone with a $CH_2$ or $CH_3$ group adjacent to the carbonyl group was heated in neat N,N-dimethylformamide dimethyl acetal (DMFDMA) at 90–110° C. for 5 to 24 hours, usually 8 to 14 hours. The excess DMFDMA was then removed by rotary evaporation to give the intermediate enaminoketone as an oil or solid. This intermediate could be crystallized if desired, but was usually used in crude form in the next reaction step. The enaminoketone was dissolved in an appropriate solent such as THF, ethanol, isopropanol or for syntheses where a higher reaction temperature was desired, in NMP (ca. 1–2 ml of solvent for 0.3–1 mmol of starting ketone).

This solution was then added to a mixture of a guanidine (1 equivalent) and a suitable base such as sodium ethoxide (freshly prepared), cesium carbonate or powdered sodium hydroxide. The usual combinations were cesium carbonate in THF or sodium ethoxide in ethanol or sodium hydroxide in isopropanol or cesium carbonate in NMP, although other base and/or solvent combinations can be used. The reaction was then heated at 80–125° C. (depending on the boiling point of the solvent) for 12 to 66 hours.

Small scale (i.e., 0.2–1 mmol) reactions were conducted in screw cap vials. The vials were placed into predrilled thermostated aluminum blocks (Digi-Block, Laboratory Devices, Holliston, Mass.) and shaken on a gyrotary shaker (Lab-Line Model G-2). After completion of the reaction, the vials were cooled, and their contents poured into dichloromethane or ethyl acetate, then washed with saturated aqueous sodium bicarbonate solution. The organic layer was concentrated in vacuo and the product was precipitated or crystallized, usually by addition of water to acetonitrile or ethanol solutions of the product. In some cases chromatographic purification was performed, either by semi-preparative HPLC or by radial chromatography using silica gel plates on a Chromatotron (Harrison Research, Palo Alto, Calif.) eluting with mixtures of dichloromethane and methanol. Larger scale reactions were performed in round bottom flasks using typical organic chemistry apparatus.

Examples 61–66 describe the synthesis of compounds prepared pursuant to Solution Method B.

Example 61

Synthesis of [2-(2-pyridylamino)ethyl](4-(3-pyridyl) pyrimidin-2-yl)amine

3-Acetylpyridine (0.5 mmol) was heated with DMFDMA (300 μl) at 90° C. for 8.5 hours. The solvent was removed by rotary evaporation. The residue was dissolved in isopropanol (2 ml) and added to 170 mg (0.5 mmol) of amino[2-(2-pyridylamino)ethyl]carboxamidinium 4-methylbenzenesulfonate and powdered sodium hydroxide (70 mg). The mixture was heated at 85° C. overnight, then concentrated in vacuo. The residue was taken up in dichloromethane and washed with a saturated aqueous sodium bicarbonate solution. The organic layer was concentrated in vacuo. The residue was taken up in acetonitrile. Addition of water gave a precipitate that was filtered off and dried to give the title compound.

HPLC: 9.9 min(100% purity)

NMR (300 MHz, 5/1 acetonitrile-$d_3$/$D_2O$, 75° C.): 9.20 (s, 1H), 8.65 (d, 1H), 8.2–8.4 (m, 2H), 7.94 (d, 1H), 7.50 (dd, 1H), 7.38 (t, 1H), 7.10 (d, 1H), 6.50 (m, 2H), 3.70 (t, 2H), 3.50 (t, 2H)

Example 62

Synthesis of (5-Ethyl-4-phenylpyrimid-2-yl)[2-(2-pyridylamino)ethyl]amine

Butyrophenone (0.5 mmol) was heated with DMFDMA (300 μl) at 90° C. for 8.5 hours. The solvent was removed by rotary evaporation. The residue was dissolved in isopropanol (2 ml) and added to 170 mg (0.5 mmol) of amino[2-(2-pyridylamino)ethyl]carboxamidinium 4-methylbenzenesulfonate and powdered sodium hydroxide (70 mg). The mixture was heated at 90° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 17.46 min (98% purity)

MS: $MH^+$=320 $C_{18}H_{21}N_5$=319 g/mol

Example 63

Synthesis of [2-(2,5-dimethoxyphenyl)ethyl](4-(3-pyridyl)pyrimidin-2-yl)amine

Step 1: 2,5-Dimethoxyphenethylamine (1.08 g, 6 mmol) was shaken with benzotriazole carboxamidinium 4-methylbenzenesulfonate (2.0 g, 6 mmol) and DIEA (1.05 ml, 6 mmol) in dry acetonitrile (10 ml) at room temperature overnight. Addition of ether resulted in the precipitation of amino[2-(2,5-dimethoxyphenyl) ethyl]carboxamidinium 4-methylbenzenesulfonate as a white solid.

Step 2: 3-Acetylpyridine (37 mg, 0.3 imol) was heated at 100° C. in DMFDMA (1 ml) for 8 hours. The solvent was removed by rotary evaporation and the residue was dissolved in dry THF (2 ml) and added to a mixture of cesium carbonate (160 mg) and 120 mg (0.3 mmol) of the guanidine prepared in Step 1. The mixture was then heated at 80° C. overnight, then concentrated in vacuo. The residue was then taken up in dichloromethane and washed with a saturated aqueous sodium bicarbonate solution. The organic layer was concentrated in vacuo. The residue was taken up in ethanol (2 ml). Addition of water gave a precipitate which was filtered off and dried to give the title compound.

HPLC: 18.03 min (100% purity)

MS: $MH^+$=337 $C_{19}H_{20}N_4O_2$=336 g/mol

Example 64

Synthesis of [4-(4-Morpholin-4-ylphenyl)pyrimidin-2-yl]{2-[(5-nitro(2-pyridyl))amino]ethyl}amine 4-Morpholinoacetophenone (0.633 g, 2.5 mmol) was heated at 100° C. in 4 ml of DMFDMA for 9 hours. The mixture was concentrated to a viscous oil by rotary evaporation. The oil was redissolved in isopropanol (10 ml) and treated with amino[2-[(5-nitro(2-pyridyl)amino]ethyl}carboxamidinium 4-methylbenzenesulfonate (1.0 g, 2.5 inmol) and powdered sodium hydroxide (200 mg). This mixture was heated at 80° C. overnight. The cooled mixture was diluted with dichloromethane and washed with saturated aqueous sodium bicarbonate solution. The organic layer was concentrated in vacuo, the dissolved in acetonitrile. The product was precipitated by addition of water. The brown solid was recrystalized from isopropanol to give the title compound.

M.P. 223–225° C. (with decomposition)

Elemental Analysis; $C_{21}H_{23}N_7O_3$. 0.7 $H_2O$ requires C, 58.10; H, 5.66; N, 22.59; found C, 58.02; H, 5.30N; 22.39;

HPLC: 20.85 min (100% purity)

MS: $MH^+$=422 g/mol (FW=421)

NMR (DMSO-$d_6$): 3.30 (m, 4H), 3.60 (m, 4H), 3.75 (m, 4H), 6.58 (d, 1H), 6.95 (m, 3H), 8.00 (d, 2H), 8.10 (d, 1H), 8.25 (d, 1H), 8.90 (s, 1H)

Example 65

Synthesis of [4-(2,4-dichlorophenyl)-5-ethylpyrimid-2-yl]{2-[(5-nitro(2-pyridyl))amino] ethyl}amine Step 1: A mixture of 2,4-dichlorobenzoyl chloride (4.5 g) and copper (I) iodide (200 mg) in dry THF (30 ml) was cooled to −20° C. under argon. Then a solution of n-propyl magnesium chloride (2 M in ether, 11.0 ml) was added dropwise. Ten minutes after addition was complete, the cooling bath was removed and the mixture stirred for 1 hour. Water was carefully added, followed by extraction with toluene. The toluene layer was washed with dilute HCl, water, saturated sodium bicarbonate solution, dried and concentrated in vacuo to give 1-(2,4-dichlorophenyl)butan-1-one (4.0 g).

Step 2: The ketone from Step 1 (108 mg, 0.5 mmol) was heated at 95° C. overnight with DMFDMA (1.5 ml). The solvent was removed in vacuo and the residue was dissolved in dry ethanol (2 ml) and added to a mixture of amino[2-[(5-nitro(2-pyridyl)amino]ethyl}carboxamidinium 4-methylbenzenesulfonate (200 mg), 1.0 M sodium ethoxide (0.6 ml) and dry ethanol (2 ml). This mixture was heated at 85° C. overnight, then concentrated in vacuo, redissolved in dichloromethane and washed with saturated sodium bicarbonate solution. The organic layer was concentrated in vacuo. The residue was purified by chromatography on silica gel using 10% methanol in dichloromethane to give an oily product. Lyophilization from acetonitrile/water gave the title compound as a solid.

HPLC: 29.56 (85% purity)

MS: MH$^+$=433 C$_{19}$H$_{18}$N$_6$Cl$_2$O$_2$=432 g/mol

Example 66

Synthesis of [4-(4-imidazolylphenyl)pyrimidin-2-yl] {2-[(5-nitro(2-pyridyl))amino]ethyl}amine 4-(1-Imidazolyl)acetophenone (57 mg, 0.3 mmol) was heated with DMFDMA (1 ml) for 8 hours at 105° C. The solvent was removed in vacuo and the residue was dissolved in dry THF (2 ml) and added to a mixture of amino[2-[(5-nitro(2-pyridyl)amino]ethyl}carboxamidinium 4-methylbenzenesulfonate (120 mg, 0.3 mmol) and cesium carbonate (200 mg) and heated overnight at 80° C., then concentrated in vacuo, redissolved in dichloromethane and washed with a saturated sodium bicarbonate solution. The organic layer was concentrated in vacuo. The residue was purified by crystallization to give the title compound.

HPLC: 15.17 min (100% purity)

NMR (300 Mhz, DMSO-d$_6$): 8.90 (s, 1H), 8.38 (d, 1H), 8.30 (s, 1H), 8.22 (d, 2H), 8.05 (d, 1H), 7.75 (d, 2H), 7.20 (s, 1H), 7.15 (d, 1H), 6.58 (d, 1H), 3.60 (m, 4H).

The following additional compounds were similarly prepared according to Solution Method B by varying the ketone and guanidine used:

(4-phenylpyrimidin-2-yl)(2-(2-pyridyl)ethyl)amine
4-(2-{[2-(2-pyridylamino)ethyl]amino}pyrimidin-4-yl) benzenecarbonitrile
(4-phenylpyrimidin-2-yl) [2-(2-pyridylamino)ethyl]amine
4-{2-[(2-(2-pyridyl)ethyl)amino]pyrimidin-4-yl}benzenecarbonitrile
[4-(4-nitrophenyl)pyrimidin-2-yl][2-(2-pyridylamino)ethyl] amine
[4-(4-imidazolylphenyl)pyrimidin-2-yl][2-(2-pyridylamino) ethyl]amine
[4-(3,4-difluorophenyl)pyrimidin-2-yl][2-(2-pyridylamino) ethyl]amine
[2-(2-pyridylamino)ethyl]{4-[4-(trifluoromethoxy)phenyl] pyrimidin-2-yl}amine
[4-(2,4-dichlorophenyl)pyrimidin-2-yl][2-(2-pyridylamino) ethyl]amine
[4-(4-chlorophenyl)-5-methylpyrimidin-2-yl][2-(2-pyridylamino)ethyl]amine
[4-(4-methyl-1-phenylpyrazol-3-yl)pyrimidin-2-yl][2-(2-pyridylamino)ethyl]amine
3-[2-({2-[(5-nitro-2-pyridyl)amino]ethyl}amino)pyrimidin-4-yl]benzenecarbonitrile
[4-(2,4-dimethyl(1,3-thiazol-5-yl))pyrimidin-2-yl]{2-[(5-nitro(2-pyridyl))amino]ethyl}amine
{2-[(5-nitro(2-pyridyl))amino]ethyl}(4-pyrazin-2-ylpyrimidin-2-yl)amine
[4-phenyl-5-benzylpyrimidin-2-yl][2-(2-pyridylamino) ethyl]amine
4-[2-({2-[(5-nitro-2-pyridyl)amino]ethyl}amino)pyrimidin-4-yl]benzenesulfonamnide
{4-[4-(4,5-dichloroimidazol-2-yl)phenyl]pyrimidin-2-yl}{2-[(5-nitro(2-pyridyl))amino]ethyl}amine
4-(2-{[2-(2,5-dimethoxyphenyl)ethyl]amino}pyrimidin-4-yl)benzenecarbonitrile
[2-(2,5-dimethoxyphenyl)ethyl](4-(3-pyridyl)pyrimidin-2-yl)amine
[4-(4-benzimidazolylphenyl)pyrimidin-2-yl]{2-[(5-nitro(2-pyridyl))amino]ethyl}amine
4-[5-imidazolyl-2-({2-[(5-nitro(2-pyridyl))amino] ethyl}amino)pyrimidin-4-yl]benzenecarbonitrile
4-[2-({2-[(6-amino-5-nitro(2-pyridyl))amino]ethyl}amino)-5-imidazolylpyrimidin-4-yl]benzenecarbonitrile
[4-(2,4-dichlorophenyl)-5-imidazolylpyrimidin-2-yl]{2-[(5-nitro(2-pyridyl))amino]ethyl}amine
{2-[(6-amino-5-nitro(2-pyridyl))amino]ethyl}[4-(2,4-dichlorophenyl)-5-imidazolylpyrimidin-2-yl]amine
[4-(2,4-dimethylphenyl)-5-imidazolylpyrimidin-2-yl]{2-[(5-nitro(2-pyridyl))amino]ethyl}amine
ethyl 4-[2-({2-[(5-nitro-2-pyridyl)amino]ethyl}amino) pyrimidin-4-yl]benzoate
4-(2-{[3-(4-phenylimidazolyl)propyl]amino}pyrimidin-4-yl)benzenecarbonitrile
(3-benzimidazolylpropyl)[4-(4-imidazolylphenyl) pyrimidin-2-yl]amine
N-{4-[2-({2-[(5-nitro-2-pyridyl)amino]ethyl}amino) pyrimidin-4-yl]phenyl}acetamide Example 67

Synthesis of [5-(4-(Fluorophenyl)pyrimidin-2-yl]{2-[(5-nitro(2-pyridyl))amino]ethyl}amine Solution Method C Step 1: Dry DMF (22 ml) was cooled to 0° C. under argon. Phosphorous oxychloride (9.2 g) was added dropwise to the cooled DMF. The mixture was removed from the cooling bath and stirring continued for 1 hour. Then, 4-fluorophenylacetic acid (3.08 g, 20 mnmol) was added as a solid and the mixture was heated at 85° C. for 6 hours. After the mixture was cooled to room temperature it was poured onto approximately 100 g of ice with stirring. A solution of sodium perchlorate monohydrate (3.66 g) in water (10 ml) was added. The precipitated solid was filtered, washed with water and dried in vacuo to give [(2-E,Z)-3-(dimethylamino)-2-(4-fluorophenyl)prop-2-enylidene] dimethyl-ammonium perchlorate. This procedure is described in Church et al., *J. Org. Chem.*, 60:3750 (1995), which is incorporated herein by reference.

Step 2: The vinylogous amidinium salt obtained in Step 1 (100 mg, 0.3 mmol) was treated with dry ethanol (2 ml) and amino{2-[(5-nitro(2-pyridyl)amino]ethyl}carboxamidinium 4-methylbenzenesulfonate (180 mg, 0.45 mmol). Then, 0.45 ml of a 1.0 M solution of sodium ethoxide in ethanol was added and the mixture was shaken 0.5 hours at room temperature. Another 0.3 ml of sodium ethoxide solution was added, followed by heating at 70° C. for 2 hours. The solvent was removed in vacuo. The residue was partitioned between dichloromethane and water. The organic layer was dried and concentrated in vacuo, then the resulting residue was dissolved in acetonitrile. Addition of water to the residue/acetonitrile mixture caused the title compound to precipitate as an orange solid.

HPLC: 18.49 min (80% purity)

NMR (300 MHz, DMSO-d$_6$: 8.90 (d, 1H), 8.60 (s, 2H), 8.12 (dd, 1H), 7.65 (m, 2H), 7.24 (m, 2H), 6.60 (d, 1H), 3.58 (m, 4H)

Example 68

Synthesis of Ethyl 4-[(2,4-dichlorophenyl)amino]-2-({2-[(5-nitro(2-pyridyl)amino]ethyl}amino) pyrimidine-5-carboxylate Solution Method D Step 1: Ethyl 2,4-dichloropyrimidine-5-carboxylate (0.49 g, 2 mmol) and 2,4-dichloroaniline (0.33 g, 2 mmol) and DIEA (0.35 ml, 2 mmol) in acetonitrile (6 ml) were heated at 80° C. for 36 hours. The mixture was cooled and the crystalline product, ethyl 4-[(2,4-dichlorophenyl)amino]-2-chloropyrimidine-5-carboxylate, 0.54 g was filtered off.

NMR (300 MHz, CDCl$_3$): 8.90 (s, 1H), 8.44 (d, 1H), 7.45 (d, 1H), 7.32 (dd, 1H), 4.45 (q, 2H), 1.45 (t, 3H)].

Step 2: The pyrimidine from Step 1 (69 mg, 0.2 mmol) was heated with DIEA (100 µL), and (2-aminoethyl)(5-nitro (2-pyridyl))amine (36 mg, 0.2 mmol) in NMP (3 ml) at 105° C. for 14 hours. The reaction was cooled, poured into water and extracted with ethyl acetate. The organic layer was separated, washed with water, dried, then concentrated in vacuo. The crude product was purified by radial chromatography on silica gel, followed by crystallization from a mixture of acetonitrile, methanol and water to give colorless crystals.

HPLC: 30.32 min (>95% purity)

MS: MH$^+$=492–494 (cluster) $C_{20}H_{19}N_7O_4Cl_2$=492 g/mol

Example 69

Synthesis of tert-Butyl 6-[(2-{[4-(4-cyanophenyl)-5-ethoxycarbonyl)pyrimidin-2-yl]amino}ethyl)amino] pyridine-3-carboxylate Step 1: 6-Chloro-pyridine-3-carboxylic acid (5.6 g, 36 mmol) was treated with 1,1'-carbonyldiimidazole (6.93 g, 42 mmol) in DMF (40 ml) at 40° C. for 1 hour. Then, t-butanol (9.5 ml, 0.11 mol) and 1,8-Diazabicyclo[5.4.0]undec-7-ene (DBU) (5.38 ml, 36 mmol) were added and heating continued overnight. The mixture was cooled to room temperature and diluted with ether (300 ml). The mixture was extracted once with water. The aqueous layer was back-extracted twice with dichloromethane. The combined organic layers were washed with a saturated aqueous citric acid solution, dried and concentrated in vacuo to give a cream colored solid (7.07 g).

(NMR (300 MHz, CDCl$_3$): 8.92 (d, 1H), 8.20 (dd, 1H), 7.40 (d, 1H), 1.60 (s, 9H)).

The tert-butyl 6-chloropyridine-3-carboxylate was heated with ethylenediamine (20 ml) at 80° C. overnight. The solvent was removed in vacuo. The residue was partitioned between dichloromethane and 2.5 M aqueous sodium hydroxide solution. The aqueous layer was extracted a further three times with dichloromethane. The combined organic layers were washed with water, dried and concentrated in vacuo to give tert-butyl 6-[(2-aminoethyl)amino] pyridine-3-carboxylate.

NMR (300 MHz, CDCl$_3$): 8.70 (s, 1H), 7.95 (d, 1H), 6.40 (d, 1H), 3.42 (m, 2H), 2.96 (m, 2H), 1.70 (s, 9H)

Step 2: t-Butyl 6-[(2-aminoethyl)amino]pyridine-3-carboxylate (1.42 g, 6 mmol), benzotriazole carboxamidinium 4-methylbenzenesulfonate (2.0 g, 6 mmol) and DIEA (1.05 ml, 6 mmol) were shaken in a mixture of dry acetonitrile (10 ml) and DMF (2 ml) overnight. Ether was added, followed by cooling 4 days at 4° C. The solid was filtered off and dried in vacuo to give tert-butyl 6-{[(2-(amidinoammonium)ethyl]amino}pyridine-3-carboxylate 4-methylbenzenesulfonate (1.87 g).

NMR (300 MHz, DMSO-d$_6$: 8.55 (br s, 1H), 7.80 (d, 1H), 7.55 (d, 2H), 7.10 (d, 2H), 6.50 (d, 1H), 3.50 (m, 2H), 3.30 (m, 2H), 2.30 (s, 3H), 1.52 (s, 9H).

Step 3: Ethyl 3-(4-cyanophenyl)-3-oxopropanoate (217 mg, 1.0 mmol) was heated with DMFDMA (200 µl) in dry THF (2 ml) at 70° C. for 5.5 hours. To the cooled solution was added tert-butyl 6-{[(2-(amidinoammonium)ethyl] amino}pyridine-3-carboxylate 4-methylbenzenesulfonate (451 mg, 1.0 mmol) along with dry ethanol (4 ml) and 1.0 M sodium ethoxide in ethanol (1.2 ml). The mixture was heated at 80° C. overnight. The solvents were removed in vacuo. The residue was partitioned between dichloromethane and the saturated aqueous sodium bicarbonate solution. The organic layer was concentrated in vacuo. The residue was dissolved in acetonitrile. Addition of water gave the title compound as a solid (230 mg).

HPLC: 25.90 min (80% purity)

MS: MH$^+$=489 $C_{26}H_{28}N_6O_4$=488 g/mol

Example 70

Synthesis of 6-[(2-{[4-(4-cyanophenyl)-5-ethoxycarbonyl)pyrimidin-2-yl]amino}ethyl)amino] pyridine-3-carboxylic Acid tert-Butyl 6-[(2-{[4-(4-cyanophenyl)-5-ethoxycarbonyl) pyrimidin-2-yl]amino}ethyl)amino]pyridine-3-carboxylate (prepared in Example 62, 220 mg) was shaken with 100% TFA for 1 hour at room temperature. The TFA was removed in vacuo. The residue was dissolved in acetonitrile and water was added. No precipitate formed. Several drops of concentrated ammonium hydroxide were added. Then glacial acetic acid was added dropwise until white solid formed. The mixture was then filtered to give the title compound as a white solid (180 mg, after drying).

MS: MH$^+$=433 $C_{22}H_{20}N_6O_4$=432 g/mol

NMR (300 MHZ, DMSO-d$_6$): 8.80 (s, 1H), 8.58 (s, 1H), 7.85 (d, 2H), 7.80 (m, 1H), 7.60 (d, 2H), 6.50 (d, 1H), 4.05 (q, 2H), 3.55 (m, 4H), 1.05 (t, 3H).

Example 71

Synthesis of Methyl 6-[(2-{[4-(4-cyanophenyl)-5-ethoxycarbonyl)pyrimidin-2-yl]amino}ethyl)amino] pyridine-3-carboxylate Step 1: 6-[(2-{[4-(4-cyanophenyl)-5-ethoxycarbonyl) pyrimidin-2-yl]amino}ethyl)amino]pyridine-3-carboxylic acid (prepared in Example 70, 120 mg) was dissolved in thionyl chloride (3 ml) and then warmed at 50° C. for 0.5 hours. The solvent was removed in vacuo to give crude ethyl 2-({2-[(5-(chlorocarbonyl)(2-pyridyl))amino]ethyl}amino)-4-(4-cyanophenyl)pyrimidine-5-carboxylate. This compound was dissolved in dry dichloromethane (4 ml).

Step 2: The acid chloride solution prepared in Step 1 (1.0 ml) was treated with dry methanol (1 ml). After standing approximately 1 hour at room temperature, the solvent was removed in vacuo to give the title compound.

HPLC: 20.90 min (95% purity)

MS: MH$^+$=447 $C_{23}H_{22}N_6O_4$=446 g/mol

Example 72

Synthesis of Ethyl 4-(4-cyanophenyl)-2-[(2-{[5-(morpholin-4-ylcarbonyl)(2-pyridyl)]amino}ethyl) amino]pyrimidine-5-carboxylate The solution of ethyl 2-({2-[(5-(chlorocarbonyl)(2-pyridyl))amino]ethyl}amino)-4-(4-cyanophenyl) pyrimidine-5-carboxylate in dichloromethane prepared in Step 1 of Example 71 (1.0 ml) was treated at room temperature with a solution of morpholine (150 µL) in dichloromethane (1 ml). After 1 hour the solvent was removed in vacuo to give the title compound.

HPLC: 19.63 min (96% purity)

MS: MH$^+$=502 $C_{26}H_{27}N_7O_4$=501 g/mol.

Example 73

Synthesis of Ethyl 4-(4-cyanophenyl-2-{[2-({5-nitro-6[benzylamino](2-pyridyl)}amino)ethyl] amino}pyrimidine-5-carboxylate Step 1: 6-Chloro-3-nitro(2-pyridyl))benzylamine was prepared in accordance with the method described in von Bebenberg, *Chemiker-Zeitung*, 103:387 (1979), which is incorporated herein by reference. This amine (1.8 g) was heated with ethylenediamine (5 ml) in acetonitrile (15 ml) at 100° C. for 3.5 hours. The solvent was removed in vacuo and the residue was partitioned between dichloromethane and 2.5 M aqueous sodium hydroxide solution. The aqueous layer was extracted 3× further with dichloromethane. The combined organic layers were washed with a saturated sodium chloride solution, dried and concentrated in vacuo to give a yellow solid.

NMR (300 MHz, CDCl$_3$): 8.10 (d, 1H), 7.2–7.4 (m, 5H), 5.80 (s, 1H), 4.80 (AB q, 2H), 3.42 (m, 2H), 2.85 (m, 2H).

Step 2: The amine from Step 1 (1.31 g) was treated with benzotriazole carboxamidinium 4-methylbenzenesulfonate (1.52 g) and DIEA (800 μl) in acetonitrile (15 ml) at room temperature overnight. The mixture was diluted with ether, then filtered to give the guanidine, amino[2-({5-nitro-6-[benzylamino](2-pyridyl)}amino)ethyl]carboxamidinium 4-methylbenzenesulfonate, as a yellow solid.

NMR (300 MHz, DMSO-d$_6$): 8.02 (d, 1H), 7.72 (d, 2H), 7.30–7.40 (m, 5H), 7.10 (d, 2H), 6.00 (d, 1H), 4.78 (AB q, 2H), 3.50 (m, 2H), 3.30 (m, 2H), 2.25 (s, 3H).

Step 3: Ethyl 3-(4-cyanophenyl)-3-oxopropanoate (65 mg, 0.3 mmol) was heated with DMFDMA (60 μL) in THF (1 ml) at 70° C. for 3 h. This solution was then added to a mixture of the guanidine prepared in Step 2 (150 mg, 0.3 mmol), dry ethanol (1 ml) and 1.0 M sodium ethoxide in ethanol (0.35 ml) and heated at 80° C. overnight. The solvents were removed in vacuo. The residue was partitioned between dichloromethane and saturated aqueous sodium bicarbonate solution. The organic layer was concentrated in vacuo. The residue was dissolved in acetonitrile. Addition of water gave the title compound as a yellow solid.

HPLC: 34.06 min (98% purity)

MS: MH$^+$=539 C$_{28}$H$_{26}$N$_8$O$_4$=538 g/mol

Example 74

Preparation of [4-(2,4-dichlorophenyl)-5-imidazol-2-ylpyrimidin-2-yl]{2-[(5-nitro(2-pyridyl))amino]ethyl}amine

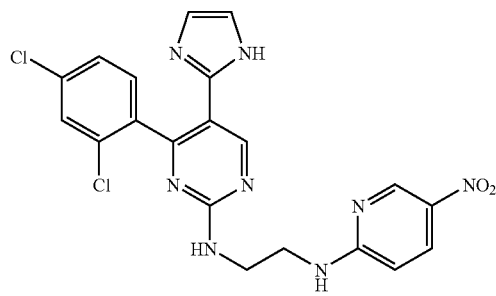

1. Preparation of 1-(2,4-dichlorophenyl)-2-imidazol-2-ylethan-1-one.

A solution of 2,4-dichlorobenzoyl chloride (9.75 M) in dichloromethane (75 ml) was added dropwise over 30 minutes to a stirred solution of 2-methylimidazole (2) (0.49 M) in dichloromethane (500 ml) and N,N-diisopropylethylamine (Hünig's base) (136 ml). (Ref. Macco, A. A.; Godefroi, E. F.; Drouen, J. J. M., *J. Org. Chem.* 1975, 40, 252–255.) The reaction mixture was cooled during the addition using an ice-water bath. The reaction mixture was then heated to reflux for 3.5 hours. A thick reddish black mixture forms. To dilute the thick heterogeneous reaction, additional dichloromethane (100–200 ml) was added as needed to maintain stirring. On cooling dichloromethane (500 ml) was added, and the solution was transferred to a separatory funnel. The organic layer was washed with distilled water (3×200 ml). An emulsion formed that breaks apart on sitting for 15 minutes or by filtering. The wet organic layer was directly concentrated under reduced pressure without drying. The solid product was then dried in vacuo for several hours.

To the dry solid (described above) was added a solution (2:1 v/v, 500–600 ml) of gla. acetic acid and aq. con. HCl. The mixture was then stirred at reflux for ca. 75 min. The acetic acid was removed via rotary evaporator. Distilled water (800 ml) and benzene (400 ml) were added to the solid residue which was vigorously stirred for 15 min. The solids were filtered off, and the filtrate was transferred to a separatory funnel. After the organic layer was discarded, the aqueous layer was washed with benzene (4×150 ml). The aqueous layer was transferred to a large beaker (4 L) and diluted with isopropyl ether (100 ml). The stirred mixture was basified (pH 7–8) by careful addition of sodium bicarbonate which leads to the formation of a white solid. After 2 hours of additional stirring the desired solid was filtered, washed with distilled water (3×60 ml), isopropyl ether (2×60 ml), and dried in vacuo overnight giving 1-(2,4-dichlorophenyl)-2-imidazol-2-ylethan-1-one in 56% yield.

2. Preparation of (2Z)-1-(2,4-dichlorophenyl)-3-(dimethylamino)-2-imidazol-2-ylprop-2-en-1-one.

A mixture of 1-(2,4-dichlorophenyl)-2-imidazol-2-ylethan-1-one (0:39 M) in N,N-dimethylformamide dimethyl acetal (DMFDMA) (150 ml) was stirred for 2.5 h at 70–75° C. The DMFDMA was then removed under reduced pressure and dried under high vacuum for several hours giving an orange-yellow solid 4 in quantitative yield. The product (2Z)-1-(2,4-dichlorophenyl)-3-(dimethylamino)-2-imidazol-2-ylprop-2-en-1-one was typically used without further purification.

3. Preparation of amino{2-[(5-nitro(2-pyridyl))amino]ethyl}carboxamidine, hydrochloride.

A mixture of 2-(2-aminoethylamino)-5-nitropyridine (0.47 M) (purchased from Aldrich, or made by reacting ethylene diamine with 2-chloro-5-nitropyridine as per the procedure in example {2-[(6-amino-5-nitro(2-pyridyl))amino]ethyl}[4-(2,4-dichlorophenyl)-5-imidazol-2-ylpyrimidin-2-yl]amine or example 6-[(2-{[4-(2,4-dichlorophenyl)-5-(4-methylimidazol-2-yl)pyrimidin-2-yl]amino}ethyl)amino]pyridine-3-carbonitrile) and 1H-pyrazole-1-carboxamidine hydrochloride (0.47 M) in acetonitrile (500 ml) were stirred overnight (ca. 20 h) at 70–80° C. Upon cooling, a yellow precipitate was collected by filtration. The yellow solid was washed thoroughly with acetonitrile (3×100 ml), ethyl ether (3×100 ml), and dried overnight in vacuo resulting in 87% yield of amino{2-[(5-nitro(2-pyridyl))amino]ethyl}carboxamidine, hydrochloride.

4. Preparation of [4-(2,4-dichlorophenyl)-5-imidazol-2-ylpyrimidin-2-yl]{2-[(5-nitro(2-pyridyl))amino]ethyl}amine.

A solution of sodium ethoxide (0.59 M) dissolved in abs. ethanol (100 ml) was added to a stirred mixture of (2Z)-1-(2,4-dichlorophenyl)-3-(dimethylamino)-2-imidazol-2-ylprop-2-en-1-one (0.23 M) and amino{2-[(5-nitro(2-pyridyl))amino]ethyl}carboxamidine, hydrochloride (0.23 M) in abs. ethanol (260 ml). The reaction was stirred at room temperature for 15 min. and then at 75–80° C. for 2.5 hours. On cooling a yellow precipitate was collected by filtration. The filtrate was stored for possible further isolation and purification of the product. The solid product was washed with abs. ethanol (3×50 ml), distilled water (3×50 ml), and ethyl ether (3×50 ml). The yellow solid was dried overnight in vacuo giving 52.7% yield of final product [4-(2,4-dichlorophenyl)-5-imidazol-2-ylpyrimidin-2-yl]{2-[(5-nitro (2-pyridyl))amino]ethyl}amine.

HPLC: 20.9 min (>95% purity)
MS: M+H=471 ($C_{20}H_{16}C_{12}N_8O_2$+H=471)

Example 75

Preparation of {2-[(4-amino-5-nitro(2-pyridyl)) amino]ethyl}[4-(2,4-dichlorophenyl)-5-imidazol-2-ylpyrimidin-2-yl]amine

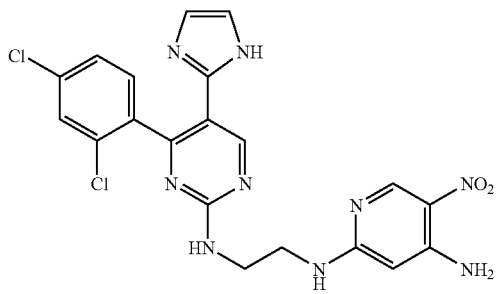

{2-[(4-amino-5-nitro(2-pyridyl))amino]ethyl}[4-(2,4-dichlorophenyl)-5-imidazol-2-ylpyrimidin-2-yl]amine was prepared using the general method for [4-(2,4-dichlorophenyl)-5-imidazol-2-ylpyrimidin-2-yl]{2-[(5-nitro (2-pyridyl))amino]ethyl}amine (see Example 74) with the exceptions noted below.

1. Preparation of 2-(2-aminoethyl)amino-6-amino-5-nitropyridine.

A mixture of 2-amino-6-chloro-3-nitropyridine (0.52 M) in acetonitrile (70 ml), and ethylene diamine (40 ml) were stirred overnight (ca. 20 h) at 75–80° C. under argon. The ethylene diamine was removed under reduced pressure. The residual solution was basified with 1M sodium hydroxide solution (50 ml). The aqueous solution was saturated with sodium chloride and extracted with a solution of 95% ethyl acetate and 5% methanol (3×150 ml) and with a solution of 95% acetonitrile and 5% methanol (3×150 ml). The organic extracts were combined and extracted with a saturated sodium chloride solution (2×75 ml). The organic layer was dried with sodium sulfate, filtered, and concentrated under reduced pressure. The crude yellow solid was triturated with ether (2×25 ml) and dried overnight in vacuo resulting in 2-(2-aminoethyl)amino-6-amino-5-nitropyridine in 99% yield.

2. Preparation of amino{2-[(6-amino-5-nitro(2-pyridyl)) amino]ethyl}carboxamidine, hydrochloride.

A mixture of 2-(2-aminoethyl)amino-6-amino-5-nitropyridine (0.44 M), 1H -pyrazole-1-carboxamidine hydrochloride (0.44 M) in acetonitrile (75 ml) were stirred overnight (ca. 24 h) at 75–80° C. Upon cooling, a yellow precipitate was collected by filtration. The yellow solid was washed thoroughly with acetonitrile (3×50 ml), ethyl ether (3×50 ml), and dried overnight in vacuo giving amino{2-[(6-amino-5-nitro(2-pyridyl))amino]ethyl}carboxamidine as the HCl salt in 82% yield.

3. Preparation of {2-[(4-amino-5-nitro(2-pyridyl))amino] ethyl}[4-(2,4-dichlorophenyl)-5-imidazol-2-ylpyrimidin-2-yl]amine.

A solution of sodium ethoxide (0.5 M) dissolved in abs. ethanol (8 ml) was added to a stirred mixture of (2Z)-1-(2, 4-dichlorophenyl)-3-(dimethylamino)-2-imidazol-2-ylprop-2-en-1-one (0.57 M), amino{2-[(6-amino-5-nitro(2-pyridyl))amino]ethyl}carboxamidine, hydrochloride (0.58 M), and abs. ethanol (7 ml). The reaction was then heated to 75–80° C. for 2.5 hours. On cooling a yellow precipitate was collected by filtration. The filtrate was stored for possible further isolation and purification of final product. The solid product was washed with abs. ethanol (3×10 ml), distilled water (3×10 ml), and ethyl ether (3×10 ml). The yellow solid was dried overnight in vacuo giving {2-[(4-amino-5-nitro (2-pyridyl))amino]ethyl}[4-(2,4-dichlorophenyl)-5-imidazol-2-ylpyrimidin-2-yl]aminein 70% yield.

HPLC: 18.7 min (>95% purity)
MS: M+H=486.2 ($C_{20}H_{17}Cl_2N_9O_2$+H=486)

Example 76

Preparation of 6-[(2-{[4-(4-cyanophenyl)-5-imidazolylpyrimidin-2-yl]amino}ethyl)amino] pyridine-3-carbonitrile

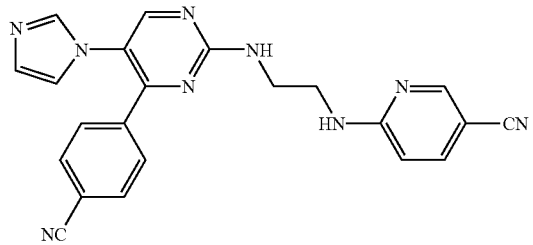

1. Preparation of 4-(2-imidazolylacetyl)benzenecarbonitrile.

A stirred solution of 4-(2-chloroacetyl) benzenecarbonitrile (0.5 M) and imidazole (1.5 M) in $CH_3CN$ (200 ml) were heated for 14 hours at 60° C. The product was stripped of solvent under reduced pressure. The residue was diluted with dichloromethane (250 ml) and water (100 ml), and the mixture was stirred for 30 min. After filtering off a solid impurity, the aqueous layer was removed and discarded. The organic layer was washed sequentially with water (60 ml), sat. aq. $NaHCO_3$ (60 ml), water (60 ml), brine (60 ml), dried with $Na_2SO_4$, filtered, and concentrated under reduced pressure. The dark colored oil was dried overnight in vacuo giving 4-(2-imidazolylacetyl) benzenecarbonitrile in 90% yield.

2. Preparation of 4-[(2E)-3-(dimethylamino)-2-imidazolylprop-2-enoyl]benzene-carbonitrile.

A mixture of 4-(2-imidazolylacetyl)benzenecarbonitrile (0.30 M) and N,N-dimethylformamide dimethyl acetal (DMFDMA) (80 ml) was stirred for 12 h at 75° C. The DMFDMA was then removed under reduced pressure and dried under high vacuum for several hours giving an orange-yellow solid 4-[(2E)-3-(dimethylamino)-2-imidazolylprop-2-enoyl]benzenecarbonitrile in quantitative yield. The enaminone product was typically used without further purification.

3. Preparation of amino {2-[(5-cyano(2-pyridyl))amino] ethyl}carboxamidine, hydrochloride).

The preparation of the material amino{2-[(5-cyano(2-pyridyl))amino]ethyl}carboxamidine, hydrochloride can be found in the procedures for the preparation of 6-[(2-{[4-(2,4-dichlorophenyl)-5-(4-methylimidazol-2-yl)pyrimidin-2-yl]amino}ethyl)amino]pyridine-3-carbonitrile.

4. Preparation of 6-[(2-{[4-(4-cyanophenyl)-5-imidazolylpyrimidin-2-yl]amino}ethyl)amino]pyridine-3-carbonitrile.

A solution of sodium ethoxide (0.66 M) dissolved in abs. ethanol (8 ml) was added to a stirred mixture of 4-[(2E)-3-(dimethylamino)-2-imidazolylprop-2-enoyl]benzenecarbonitrile (0.33 M), amino{2-[(5-cyano(2-pyridyl))amino]ethyl}carboxamidine, hydrochloride (0.33 M), and abs. ethanol (15 ml). The reaction was then heated to 75–80° C. for 2.5 hours. On cooling the reaction was diluted with ethyl acetate (400 ml) washed with sat. aq. NaHCO₃ (100 ml), distilled water (2×100 ml), brine (100 ml), dried with Na₂SO₄, filtered, and concentrated. The crude product was purified by flash chromatography over silica gel. The column was run starting with 1:1 ethyl acetate to hexane, then ethyl acetate which was used until all of the fast moving impurities had been removed. The product was eluted with 1.5% methanol in ethyl acetate. The column is monitored by TLC using 5% methanol in ethyl acetate as the solvent system. The proper fractions were condensed. The off-white solid was dried overnight in vacuo giving 6-[(2-{[4-(4-cyanophenyl)-5-imidazolylpyrimidin-2-yl]amino}ethyl)amino]pyridine-3-carbonitrile in 40% yield.

HPLC: 18.9 min (>95% purity)
MS: M+H=473.1 ($C_{22}H_{17}N_9$+H=473)

Example 77

Preparation of (tert-butoxy)-N-(2-{[4-(4-cyanophenyl)-5-imidazolylpyrimidin-2-yl]amino}ethyl)carboxamide 1. Preparation of N-(2-aminoethyl)(tert-butoxy)carboxamide.

A solution of tert-butyl[(tert-butyl)oxycarbonyloxy]formate (Boc₂O) (181g, 830 mmol) in dichloromethane (1 L) was added slowly to a mechanically stirred solution of ethylene diamine (250 g, 4.16 mol) in dichloromethane (2.5 L) at room temperature. After 24 hours, the reaction solution was washed with water (3×500 ml), Brine (500 ml), dried with Na₂SO₄, filtered, and concentrated under reduced pressure. The pure product N-(2-aminoethyl)(tert-butoxy)carboxamide was obtained in 50% yield.

2. Preparation of N-[2-(amidinoamino)ethyl](tert-butoxy)carboxamide, hydrochloride.

Portions of solid 1H-pyrazole-1-carboxamidine hydrochloride (91.10 g, 624 mmol)) are added to a stirred solution of N-(2-aminoethyl)(tert-butoxy)carboxamide (100 g, 624 imol) in CH₃CN (1 L) at 80° C. After 24 hours, the reaction was stripped of solvent under reduced pressure. The residue was triturated with ether (3 x 100 ml), and dried in vacuo. The guanidine N-[2-(amidinoamino)ethyl](tert-butoxy)carboxamide, hydrochloride was obtained in over 100% yield containing a small amount of pyrazole. The guanidine was used without further purification.

3. Preparation of (tert-butoxy)-N-(2-{[4-(4-cyanophenyl)-5-imidazolylpyrimidin-2-yl]amino}ethyl)carboxamide.

4-[(2E)-3-(dimethylamino)-2-imidazolylprop-2-enoyl]benzenecarbonitrile (8.0g, 30.0 mmol) in NMP (5 ml) was added to a stirred mixture of N-[2-(amidinoamino)ethyl](tert-butoxy)carboxamide, hydrochloride (13.8 g, 45 =mol)) and Cs₂CO₃ (11.72, 36.0 mmol) in NMP (15 ml). The reaction was heated to 100° C. for 48 hours. The reaction was followed by HPLC. Upon completion, the reaction was partitioned with water (50 ml) and dichloromethane (250 ml). The organic layer was separated and washed with water (2×50 ml), brine (50 ml), dried Na₂SO₄, filtered, and concentrated under reduced pressure. The product was purified by flash chromatography eluting with 10% methanol in dichloromethane. After stripping off the solvents and drying in vacuo, 10.08 g of (tert-butoxy)-N-(2-{[4-(4-cyanophenyl)-5-imidazolylpyrimidin-2-yl]amino}ethyl)carboxamide was obtained as a dark red glass in 83% yield.

Example 78

Preparation of 4-{5-imidazolyl-2-[(2-{[5-(trifluoromethyl)(2-pyridyl)]amino}ethyl)amino]pyrimidin-4-yl}benzenecarbonitrile

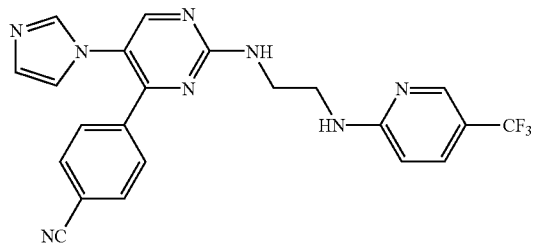

4-{5-imidazolyl-2-[(2-{[5-(trifluoromethyl)(2-pyridyl)]amino}ethyl)amino]pyrimidin-4-yl}benzenecarbonitrile was prepared using the general method for 6-[(2-{[4-(4-cyanophenyl)-5-imidazolylpyrimidin-2-yl]amino}ethyl)amino]pyridine-3-carbonitrile (60406) (see Example 76) with the exceptions noted below.

1. Preparation of N-(2-aminoethyl)(tert-butoxy)carboxamide.

A solution of tert-butyl [(tert-butyl)oxycarbonyloxy]formate (Boc₂O) (0.83 M) in dichloromethane (1 L) was added slowly (3 h) to a mechanically stirred solution of ethylene diamine (1.66 M) in dichloromethane (2.5 L) at room temperature. After 24 hours, the reaction solution was washed with water (3×500 ml), brine (500 ml), dried with Na₂SO₄, filtered, and concentrated under reduced pressure. The pure N-(2-aminoethyl)(tert-butoxy)carboxamide was obtained in 50% yield.

2. Preparation of N-[2-(amidinoamino)ethyl](tert-butoxy)carboxamide, hydrochloride.

Portions of solid 1H-pyrazole-1-carboxamnidine hydrochloride (91.10 g, 624 mmol)) are added to a stirred solution of N-(2-aminoethyl)(tert-butoxy)carboxamide (0.62 M) in CH₃CN (1 L) at 80° C. After 24 hours, the reaction was stripped of solvent under reduced pressure. The residue was triturated with ether (3×100 ml), and dried in vacuo. The N-[2-(amidinoamino)ethyl](tert-butoxy)carboxamide, hydrochloride was obtained in over 100% yield containing a small amount of pyrazole. The N-[2-(amidinoamino)ethyl](tert-butoxy)carboxamide, hydrochloride was used without further purification.

3. Preparation of (tert-butoxy)-N-(2-{[4-(4-cyanophenyl)-5-imidazolylpyrimidin-2-yl]amino}ethyl)carboxatnide.

4-[(2E)-3-(dimethylamino)-2-imidazolylprop-2-enoyl]benzenecarbonitrile (6 M) in NMP (5 ml) was added to a stirred mixture of N-[2-(amidinoamino)ethyl](tert-butoxy)carboxarnide, hydrochloride (3 M) and Cs₂CO₃ (2.4) in NMP (15 ml). The reaction was heated to 100° C. for 48 hours. The reaction was followed by HPLC. Upon completion, the reaction was partitioned with water (50 ml) and dichloromethane (250 ml). The organic layer was separated and washed with water (2×50 ml), brine (50 ml), dried Na₂SO₄, filtered, and concentrated under reduced pressure.

The product was purified by flash chromatography eluting with 10% methanol in dichloromethane. After stripping off the solvents and drying in vacuo, (tert-butoxy)-N-(2-{[4-(4-cyanophenyl)-5-imidazolylpyrimidin-2-yl]amino}ethyl)carboxamide was obtained as a dark red glass in 83% yield.

4. Preparation of 4-{2-[(2-aminoethyl)amino]-5-imidazolylpyrimidin-4-yl}benzenecarbonitrile.

Aqueous 3M HCl (15–30 ml) was added to a stirred solution of (tert-butoxy)-N-(2-{[4-(4-cyanophenyl)-5-imidazolylpyrimidin-2-yl]amino}ethyl)carboxamide (0.15 M) in CH₃CN (50 ml) at room temperature until the reaction became slightly turbid. After 16 hours, the reaction was partitioned between dichloromethane (200 ml) and 1M HCl (200 ml). The layers were separated, and the aqueous layer was extracted with dichloromethane (3×200 ml). The aqueous layer was basified carefully with solid NaHCO₃ to pH 7–8. A solid forms which can be filtered and dissolved in CH₃CN (100 ml). The organic solution is washed with sat. aq. NaHCO₃ (50 ml), brine (50 ml), dried with Na₂SO₄, filtered, and concentrated. The crude product was purified by flash chromatography over silica gel. The column was eluted first with a 1:1 mixture of dichloromethane/methanol followed by a mixture of 5% TEA/10% water/85% methanol to elute the product. The proper fractions were condensed. The dark yellow glass was dried overnight in vacuo giving 4-{2-[(2-aminoethyl)amino]-5-imidazolylpyrimidin-4-yl}benzenecarbonitrile in 89% yield.

5. Preparation of 4-{5-imidazolyl-2-[(2-{[5-(trifluoromethyl)(2-pyridyl)]amino}ethyl)amino]pyrimidin-4-yl}benzenecarbonitrile.

A mixture of 4-{2-[(2-aminoethyl)amino]-5-imidazolylpyrimidin-4-yl}benzene-carbonitrile (30 mg, 0.098 mmol), 2-chloro-5-(trifluoromethyl)pyridine (18 mg, 0.098 mmol), and Hünig's base (70 uL, 0.4 mmol) in DMA (500 uL) were heated to 80° C. After stirring for 12 hours, the reaction was diluted with ethyl acetate (10 ml) and extracted with sat. aq. NaHCO₃ (2×5 ml), water (3×5 ml), brine (5 ml), dried with Na₂SO₄, filtered, and concentrated. The product was purified by preparative HPLC using a reverse phase column and a water/acetonitrile gradient. The product 4-{5-imidazolyl-2-[(2-{[5-(trifluoromethyl)(2-pyridyl)]amino}ethyl)amino]pyrimidin-4-yl}benzenecarbonitrilewas obtained as a off-white solid in 5% yield.

HPLC: 16.3 min (>95% purity)
MS: M+H=451.2 (C₂₂H₁₇F₃N₈+H=451)

Example 79

Preparation of 4-{5-imidazolyl-2-[(2-{[(4-nitrophenyl)sulfonyl]amino}ethyl)amino]pyrimidin-4-yl}benzenecarbonitrile A mixture of 4-{2-[(2-aminoethyl)amino]-5-imidazolylpyrimidin-4-yl}benzene-carbonitrile (30 mg, 0.098 mmol), chloro(4-nitrophenyl)sulfone (22 mg, 0.1 nmuol), and Hünig's base (70 uL, 0.4 mmol) in DMA (500 uL) were heated to 80° C. After stirring for 12 hours, the reaction was diluted with ethyl acetate (10 ml) and extracted with sat. aq. NaHCO₃ (2×5 ml), water (3×5 ml), brine (5 ml), dried with Na₂SO₄, filtered, and concentrated. The resulting product, 4-{5-imidazolyl-2-[(2-{[(4-nitrophenyl) sulfonyl]amino}ethyl)amino]pyrimidin-4-yl}benzenecarbonitrile weighing 27 mg (56% yield) was approximately 90% pure by LCMS and HPLC.

Example 80

Preparation of N-(2-{[4-(4-cyanophenyl)-5-imidazolylpyrimidin-2-yl]amino}ethyl)(3-nitrophenyl)carboxamide A mixture of 4-{2-[(2-aminoethyl)amino]-5-imidazolylpyrimidin-4-yl}benzene-carbonitrile (30 mg, 0.098 mmol), 3-nitrobenzoic acid (17 mg, 0.1 mmol), 1-(3-dimethylaminopropyl)-3-ethylcarbodiimide hydrochloride (EDC) (19 mg, 0.1 mmol), 1-bydroxybenzotriazole hydrate (HOBT) (14 mg, 0.1 mmol), and 4-dimethylaminopyridine (DMAP) (12 mg, 0.1 mmol) in DMA (500 uL) were stirred at room temperature. After 12 hours, the reaction was diluted with ethyl acetate (10 ml) and extracted with sat. aq. NaHCO₃ (2×5 ml), water (3×5 ml), brine (5 ml), dried with Na₂SO₄, filtered, and concentrated. The resulting product, N-(2-{[4-(4-cyanophenyl)-5-imidazolylpyrimidin-2-yl]amino}ethyl)(3-nitrophenyl)carboxamide weighing 32 mg (70% yield) was approximately 95% pure by LCMS and HPLC.

Example 81

Preparation of [5-amino-4-(2,4-dichlorophenyl)pyrimidin-2-yl]{2-[(6-amino-5-nitro(2-pyridyl))amino]ethyl}amine

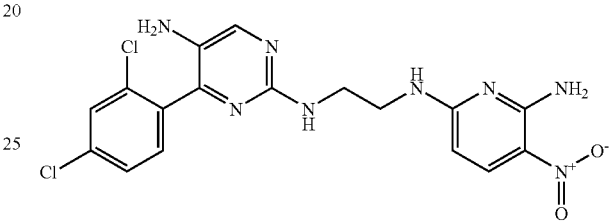

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of Cs₂CO₃ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in neat N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline 1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl)) amino]ethyl}carboxamidine, and 3 mmol of Cs₂CO₃ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid was heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mnol of hydrazine were stirred in ethanol at 75° C. for two hours and the resulting product, [5-amino-4-(2,4-dichlorophenyl)pyrimidin-2-yl]{2-[(6-amino-5-nitro(2-pyridyl))amino]ethyl}amine was purified by column chromatography eluting with 5–10% methanol/methylene chloride.

HPLC: 5.704min. (100% purity)
MS:MH$^+$=435.1

Example 82

Preparation of {2-[(6-amino-5-nitro(2-pyridyl))amino]ethyl}[4-(2,4-dichlorophenyl)-5-morpholin-4-ylpyrimidin-2-yl]amine

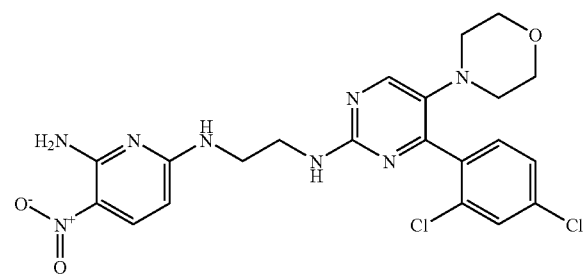

1. Preparation of 1-(2,4-dichlorophenyl)-2-morpholin-4-ylethan-1-one 1 mmol of 2,4-dichlorophenacyl chloride in DMF was added drop wise to 10 mnmol morpholine in DMF at room temperature for fourteen hours. The reaction mixture was concentrated in vacuo and diluted with water and ethyl acetate. The solution was extracted three times with ethyl acetate, dried over sodium sulfate, and purified by column chromatography eluting with 50% ethyl acetate and 50% hexane to obtain 1-(2,4-dichlorophenyl)-2-morpholin-4-ylethan-1-one.

2. Preparation of (2E)-1-(2,4-dichlorophenyl)-3-(dimethylamnino)-2-morpholin-4-ylprop-2-en-1-one 1 mmol of 1-(2,4-dichlorophenyl)-2-morpholin-4-ylethan-1-one was heated to 80° C. in N,N-dimethylformamidedimethyl acetal for six hours. The reaction mixture was concentrated in vacuo and purified by trituration with diethyl ether to obtain (2E)-1-(2,4-dichlorophenyl)-3-(dimethylamino)-2-morpholin-4-ylprop-2-en-1-one.

3. Preparation of {2-[(6-amino-5-nitro(2-pyridyl))amino]ethyl}[4-(2,4-dichlorophenyl)-5-morpholin-4-ylpyrimidin-2-yl]amine 1 mmol of (2E)-1-(2,4-dichlorophenyl)-3-(dimethylamino)-2-morpholin-4-ylprop-2-en-1-one, 1 mmol of amino{2-[(6-amino-5-nitro(2-pyridyl))amino]ethyl}carboxamidine, and 3 mmol of Cs$_2$CO$_3$ were dissolved in DMF and heated to 90° C. for fourteen hours. The reaction mixture was concentrated in vacuo and diluted with water and ethyl acetate. The solution was extracted three times with ethyl acetate and purified by column chromatography eluting with 5–10% methanol/methylene chloride to obtain{2-[(6-amino-5-nitro(2-pyridyl))amino]ethyl}[4-(2,4-dichlorophenyl)-5-morpholin-4-ylpyrimidin-2-yl]amine.

HPLC: 9.367min. (100% purity)
MS: MH$^+$=505

Example 83

Preparation of 1-[2-({2-[(6-amino-5-nitro(2-pyridyl))amino]ethyl}amino)-4-(2,4-dichlorophenyl)pyrimidin-5-yl]pyrrolidine-2,5-dione

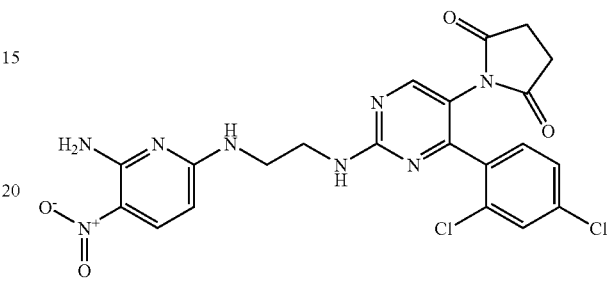

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of Cs$_2$CO$_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in neat N,N-dimethylformamidedimethyl acetal for six hours. The reaction mixture is concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl))amino]ethyl}carboxamidine, and 3 mmol of Cs$_2$CO$_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid is heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and then purified by column chromatography eluting with 5–10% methanol/methylene chloride to obtain [5-amino-4-(2,4-dichlorophenyl)pyrimidin-2-yl]{2-[(6-amino-5-nitro(2-pyridyl))amino]ethyl}amine.

6. Preparation of 1-[2-({2-[(6-amino-5-nitro(2-pyridyl))amino]ethyl}amino)-4-(2,4-dichlorophenyl)pyrimidin-5-yl]pyrrolidine-2,5-dione 1 mmol of [5-amino-4-(2,4-dichlorophenyl)pyrimidin-2-yl]{2-[(6-amino-5-nitro(2-pyridyl))amino]ethyl}amine, and 2 mmol of succinic acid, 4 mmol of HBTU, and 5 mmol of N,N-diisopropylethylamine were added to solution and stirred for six hours at room temperature. The reaction mixture was concentrated in vacuo and diluted with water and ethyl acetate. The solution was extracted three times with ethyl acetate, dried over sodium sulfate, and purified by column chromatography 5–10% methanol/methylene chloride to obtain 1-[2-({2-[(6-amino-5-nitro(2-pyridyl))amino]ethyl}amino)-4-(2,4-dichlorophenyl)pyrimidin-5-yl]pyrrolidine-2,5-dione.

HPLC: 8.917min. (100% purity)
MS: MH+=517.1

Example 84

Preparation of {2-[(6-amino-5-nitro(2-pyridyl))amino]ethyl}[4-(2,4-dichlorophenyl)-5-piperazinylpyrimidin-2-yl]amine

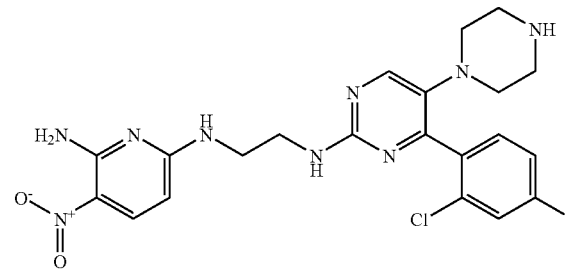

1. Preparation of tert-butyl 4-[2-(2,4-dichlorophenyl)-2-oxoethyl]piperazinecarboxylate 1 mmol of 2,4-dichlorophenacyl chloride in DMF was added drop wise to 1.2 mmol of tert-butyl piperazinecarboxylate and 1.2 mmol $Cs_2CO_3$ in DMF at room temperature for fourteen hours. The reaction mixture was concentrated in vacuo and diluted with water and ethyl acetate. The solution was extracted three times with ethyl acetate, dried over sodium sulfate, and purified by column chromatography eluting with 50% ethyl acetate and 50% hexane to obtain tert-butyl 4-[2-(2,4-dichlorophenyl)-2-oxoethyl]piperazinecarboxylate.

2. Preparation of tert-butyl 4-{2-(2,4-dichlorophenyl)-1-[(dimethylamino)methylene]-2-oxoethyl}piperazinecarboxylate 1 mmol of tert-butyl 4-[2-(2,4-dichlorophenyl)-2-oxoethyl]piperazinecarboxylate was heated to 80° C. in neat N,N-dimethylformamidedimethyl acetal for six hours. The reaction mixture was concentrated in vacuo and purified by trituration with diethyl ether to obtain tert-butyl 4-{2-(2,4-dichlorophenyl)-1-[(dimethylamino)methylene]-2-oxoethyl}piperazinecarboxylate.

3. Preparation of tert-butyl 4-[2-({2-[(6-amino-5-nitro(2-pyridyl))amino]ethyl}amino)-4-(2,4-dichlorophenyl)pyrimidin-5-yl]piperazinecarboxylate 1 mmol of tert-butyl 4-{2-(2,4-dichlorophenyl)-1-[(dimethylamino)methylene]-2-oxoethyl}piperazinecarboxylate, 1 mmol of amino{2-[(5-nitro(2-pyridyl))amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate, dried over sodium sulfate, and purified by column chromatography eluting with 5–10% methanolmethylene chloride to obtain tert-butyl 4-[2-({2-[(6-amino-5-nitro(2-pyridyl))amino]ethyl}amino)-4-(2,4-dichlorophenyl)pyrimidin-5-yl]piperazinecarboxylate.

4. Preparation of {2-[(6-amino-5-nitro(2-pyridyl))amino]ethyl}[4-(2,4-dichlorophenyl)-5-piperazinylpyrimidin-2-yl]amine 1 mmol of tert-butyl 4-[2-({2-[(6-amino-5-nitro(2-pyridyl))amino]ethyl}amino)-4-(2,4-dichlorophenyl)pyrimidin-5-yl]piperazinecarboxylate was heated to 60° C. 3M HCl in MeOH for one hour and concentrated in vacuo to obtain {2-[(6-amino-5-nitro(2-pyridyl))amino]ethyl}[4-(2,4-dichlorophenyl)-5-piperazinylpyrimidin-2-yl]amine.

HPLC: 5.27min. (100% purity)
MS: MH+=504.2

Example 85

Preparation of {2-[(6-amino-5-nitro(2-pyridyl))amino]ethyl}[4-(4-ethylphenyl)-5-imidazolylpyrimidin-2-yl]amine

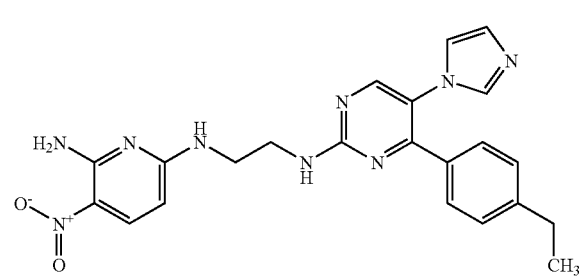

1. Preparation of 2-bromo-1-(4-ethylphenyl)ethan-1-one 20 mmol of 1-(4-ethylphenyl)ethan-1-one, 1 ml conc. HCl were mixed in 20 ml diethyl ether at 0° C. under nitrogen. To this solution a solution of 20 mmol $Br_2$ in 20 ml chloroform was added drop wise and left for four hours and then concentrated in vacuo to obtain 2-bromo-1-(4-ethylphenyl)ethan-1-one.

2. Preparation of 1-(4-ethylphenyl)-2-imidazolylethan-1-one 1 mmol of 2-bromo-1-(4-ethylphenyl)ethan-1-one in acetonitrile was added drop wise to 5.5 mmol imidazoline in acetonitrile at room temperature for fourteen hours. The reaction mixture was concentrated in vacuo and diluted with water and ethyl acetate. The solution was extracted three times with ethyl acetate and dried over sodium sulfate to obtain 1-(4-ethylphenyl)-2-imidazolylethan-1-one.

3. Preparation of (2E)-3-(dimethylamino)-1-(4-ethylphenyl)-2-imidazolylprop-2-en-1-one 1 mmol of 1-(4-ethylphenyl)-2-imidazolylethan-1-one was heated to 80° C. in N,N-dimethylformamidedimethyl acetal for six hours and concentrated in vacuo to obtain (2E)-3-(dimethylamino)-1-(4-ethylphenyl)-2-imidazolylprop-2-en-1-one.

4. Preparation of{2-[(6-amino-5-nitro(2-pyridyl))amino]ethyl}[4-(4-ethylphenyl)-5-imidazolylpyrimidin-2-yl]amine 1 mmol of (2E)-3-(dimethylamino)-1-(4-ethylphenyl)-2-imidazolylprop-2-en-1-one, 1 mmol of amino{2-[(6-amino-5-nitro(2-pyridyl))amino]ethyl}carboxamidine, and 3 mmol of $Cs_2CO_3$ was dissolved in DMF and heated to 90° C. for fourteen hours. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain {2-[(6-amino-5-nitro(2-pyridyl))amino]ethyl}[4-(4-ethylphenyl)-5-imidazolyl-pyrimidin-2-yl]amine.

HPLC: 7.733min. (100% purity)
MS: $MH^+$=446.2

Example 86

Preparation of {2-[(6-amino-5-nitro(2-pyridyl))amino]ethyl}[4-(2,4-dichlorophenyl)-5-(4-pyridyl)pyrimidin-2-yl]amine

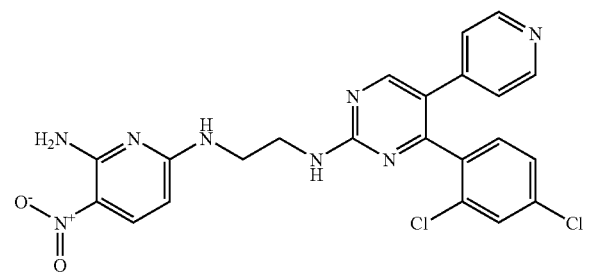

1-(2,4-dichlorophenyl)-2-(4-pyridyl)ethan-1-one was synthesized as in Suzuki et al., "Facile dibenzoylation of picoline," *J HeterocycL. Chem.* 22(6):1487–9 (1985). 1 mmol of 1-(2,4-dichlorophenyl)-2-(4-pyridyl)ethan-1-one was heated to 80° C. in neat DMF-DMA for six hours. The reaction mixture was concentrated in vacuo and the residue was purified by trituration with diethyl ether. using amino{2-[(6-amino-5-nitro(2-pyridyl))amino]ethyl}carboxamidine hydrochloride (160mg, 0.58mmol, 1 eq) and the enaminone (2E)-1-(2,4-dichlorophenyl)-3-(dimethylamino)-2-(4-pyridyl)prop-2-en-1-one (202mg, 0.58mmol) and $Cs_2CO_3$ (246mg, 1.3eq) in 5ml DMF at 95° C. for 6h. It was worked up by concentration in vacuo and extraction into ethyl acetate to yield a crude product that was purified by column chromatography, eluting with 10% methanol in methylene chloride to yield {2-[(6-amino-5-nitro(2-pyridyl))amino]ethyl}[4-(2,4-dichlorophenyl)-5-(4-pyridyl)pyrimidin-2-yl]amine as a yellow powder after lyophilization.

HPLC: 6.32 min(100%)
MS:$MH^+$=497

Example 87

Preparation of {2-[(6-amino-5-nitro(2-pyridyl))amino]ethyl}{4-(2,4-dichlorophenyl)-5-[5-(trifluoromethyl)(1,2,3,4-tetraazolyl)]pyrimidin-2yl}amine

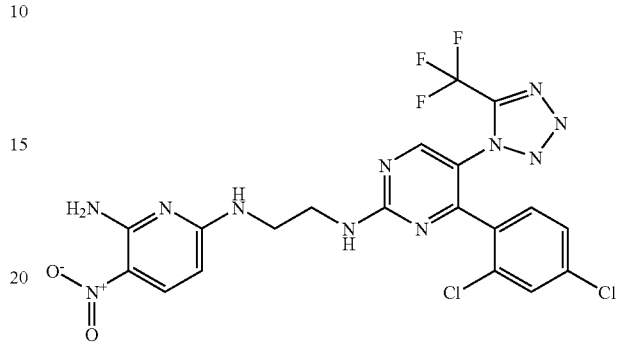

Trifluoromethyl tetrazole was made according to the procedure published in *Tetrahedron Letters* 38(7):1257–1260. A mixture of tetrachlorosilane (5mmol) and sodium azide (15mmol) in dry acetonitrile (10 ml) and trifluoromethyl acetamide (5mmol) was refluxed and stirred with the exclusion of moisture. The reaction mixture was poured into ice cold sodium carbonate solution and extracted with chloroform (3×20 ml). The solvent was distilled off under reduced pressure to yield trifluoromethyl tetrazole (MS:MH–=136.7) which was used without further purification. Trifluromethyl tetrazole (1 mmol), $Cs_2CO_3$ (1.3 mmol) and 1-(2,4-dichlorophenyl)-2-chloroethan-1-one (1 mmol) were refluxed in DMF(2ml) overnight. The reaction mixture was cooled and concentrated in vacuo, and then extracted into ethyl acetate and dried over sodium sulfate. The extract was further purified by column chromatography on silica gel to yield 1-(2,4-dichlorophenyl)-2-[5-(trifluoromethyl)(1,2,3,4-tetraazolyl)]ethan-1-one. 1 mmol of 1-(2,4-dichlorophenyl)-2-[5-(trifluoromethyl)(1,2,3,4-tetraazolyl)]ethan-1-one was heated to 80° C. in neat DMF-DMA for six hours. The reaction mixture was concentrated in vacuo and purified by trituration with diethyl ether. 1 mmol of the above enaminone, 1 mmol of amino{2-[(6-amino-5-nitro(2-pyridyl))amino]ethyl}carboxamidine hydrochloride and 3 mmol of $Cs_2CO_3$ were dissolved in DMF and heated to 90° C. for fourteen hours. The reaction mixture was concentrated in vacuo and extracted into ethyl acetate and the residue after solvent evaporation was purified by column chromatography eluting with 5–10% methanol in methylene chloride to yield{2-[(6-amino-5-nitro(2-pyridyl))amino]ethyl}{4-(2,4-dichlorophenyl)-5-[5-(trifluoromethyl)(1,2,3,4-tetraazolyl)]pyrimidin-2-yl}amine as a yellow powder after lyophilization.

MS:$MH^+$=556.0,
HPLC: 10.77min (98.3%)

Example 88

Preparation of {2-[(6-amino-5-nitro(2-pyridyl))amino]ethyl}[4-(2,4-dichlorophenyl)-5-(4-methylpiperazinyl)pyrimidin-2-yl]amine

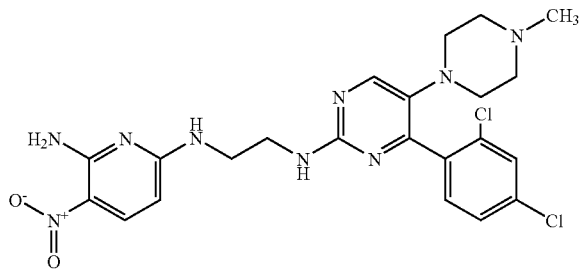

1-(2,4-dichlorophenyl)-2-chloroethan-1-one(1 mmol) and methylpiperazine (4 mmol) in 8ml DMF was stirred for 8h at room temperature. The reaction mixture was concentrated in vacuo and extracted into ethyl acetate and the organic layer was washed with water and dried with sodium sulfate. The residue after concentration in vacuo was purified by column chromatography eluting with 10% methanol in methylene chloride to yield 1-(2,4-dichlorophenyl)-2-(4-methylpiperazinyl)ethan-1-one. The ethanone was taken up in DMF-DMA and heated to 80° C. for 6h. The reaction mixture was cooled and concentrated in vacuo and the residue containing the enaminone was purified by column chromatography. 1 mmol of the enaminone obtained above, 1 mmol of amino{2-[(6-amino-5-nitro(2-pyridyl))amino]ethyl}carboxamidine hydrochloride and 3 mmol of $Cs_2CO_3$ was suspended in DMF and heated to 90° C. for fourteen hours. The reaction was cooled and concentrated in vacuo. The residue was partitioned between water and ethyl acetate and the layers separated. The organic layers were dried with sodium sulfate and after solvent removal were chromatographed on silica gel eluting with 5–10% methanol in methylene chloride to obtain {2-[(6-amino-5-nitro(2-pyridyl))amino]ethyl}[4-(2,4-dichlorophenyl)-5-(4-methylpiperazinyl)pyrimidin-2-yl]amine as a yellow powder after lyophilization.

LC RT 5.193 min (95.3%)
MS:MH$^+$=518.2

Example 89

Preparation of [4-(2,4-dichlorophenyl)-5-(4-methylpiperazinyl)pyrimidin-2-yl]{2-[(5-nitro(2-pyridyl))amino]ethyl}amine

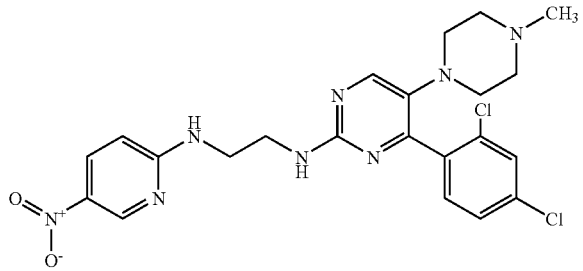

1-(2,4-dichlorophenyl)-2-chloroethan-1-one(1mmol) and methylpiperazine(4 mmol) in 8ml DMF was stirred for 8h at room temperature. The reaction mixture was then concentrated in vacuo and extracted into ethyl acetate and the organic layer was washed with water and dried with sodium sulfate. The residue after concentration in vacuo was purified by column chromatography eluting with 10% methanol in methylene chloride to yield 1-(2,4-dichlorophenyl)-2-(4-methylpiperazinyl)ethan-1-one. 1-(2,4-dichlorophenyl)-2-(4-methylpiperazinyl)ethan-1-one was heated to 80° C. in neat DMF-DMA for six hours. The reaction mixture was concentrated in vacuo and the residue obtained was purified by trituration with diethyl ether to yield the enaminone. 1 mmol of the enaminone obtained above, 1mmol of amino{2-[(5-nitro(2-pyridyl))amino]ethyl}carboxamidine hydrochloride and 1.3 mmol of $Cs_2CO_3$ were dissolved in DMF and heated to 90° C. for fourteen hours. The reaction mixture was cooled to room temperature and concentrated in vacuo. Water was added and then extracted 3× with ethyl acetate. The combined organic layers were dried with sodium sulfate. The residue after solvent evaporation was purified by column chromatography eluting with 5–10% methanol in methylene chloride to yield [4-(2,4-dichlorophenyl)-5-(4-methylpiperazinyl)pyrimidin-2-yl]{2-[(5-nitro(2-pyridyl))amino]ethyl}amine as a yellow powder after lyophilization.

HPLC 5.933min (>95%)
MS:MH$^+$=503.1

Example 90

Preparation of 4-[6-imidazolyl-2-({2-[(5-nitro(2-pyridyl))aminolethyl}amino)pyrimidin-4-yl]benzenecarbonitrile According to the procedure of Wierenga (*Heterocycles*, 23:1687 (1985)), 9.45 g (0.034 mol) of S-methyl isourea nitrate, 13.57g (0.062 mol) of ethyl 3-(4-cyanophenyl)-3-oxopropanoate and 8.0 g (0.142 mol) of potassium hydroxide were suspended in 40 ml water and the heterogeneous mixture stirred for 18 h. The mixture was then filtered, and the solid washed with copious amounts of water. The solid was dried, and recrystalized from 5% dimethylformamide/ethanol to afford 2.47 g (34%) of 4-(2-amino-4-oxo-1,3-oxazin-6-yl)benzenecarbonitrile as a colorless solid.

A solution of 44 ml DMF, 3.81 g (17.89 mmol) 4-(2-amino-4-oxo-1,3-oxazin-6-yl)benzenecarbonitrile and 8.57 g (53.63 mmol) of N-(2-aminoethyl) (tert-butoxy) carboxamide were heated to 50° C. for 3 h. The reaction was then concentrated in vacuo (0.5 mm Hg) and the resulting yellow solid triturated with cold ethanol. The resulting suspension was filtered and the solid washed with copious amounts of ethanol. This gave 4.51 g (71%) of (tert-butoxy)-N-(2-{[6-(4-cyanophenyl)-4-hydroxypyrimidin-2-yl]amino}ethyl)carboxamide as a white solid.

To a solution of 4.01 g (11.2 mmol) of (tert-butoxy)-N-(2-{[6-(4-cyanophenyl)-4-hydroxypyrimidin-2-yl]amino}ethyl)carboxamide, 4.82 g (13.5 mmol) of N-phenyltrifluorosulfonimide in 40 mL pyridine was added 4.03 g (12.4 mmol) of anhydrous cesium carbonate. The resulting suspension was stirred at room temperature for 18 h. and then partitioned between ethyl acetate and water. The aqueous layer was extracted thoroughly with ethyl acetate and the combined organics washed with 5% aqueous hydrochloric acid, water, and brine. Concentration and chromatography (silica gel, ether, Rf=0.40) gave1.50 g of 2-({2-[(tert-butoxy)carbonylamino]ethyl}amino)-6-(4-cyanophenyl)pyrimidin-4-yl (trifluoromethyl)sulfonate as a gelatinous solid. 2-({2-[(tert-butoxy)carbonylamino] ethyl}amino)-6-(4-cyanophenyl)pyrimidin-4-yl (trifluoromethyl)sulfonate (134 mg, 0.275 mmol) was dissolved in a 2 M solution of imidazole in N-methylpyrrolidinone and the resulting solution heated to 90° C. for 18 h. The solution was cooled, water added and the suspension extracted thoroughly with ethyl acetate. Concentration of the combined organic layers gave a crude solid which was chromatographed (silica gel, 0.5% ammonium hydroxide/5% methanol/methylene chloride) to afford 66 mg of (tert-butoxy)-N-(2-{[4-(4-cyanophenyl)-6-imidazolyl-4-ylpyrimidin-2-yl]amino]ethyl)carboxamide as a off white solid.

Removal of the tert-butoxy protecting group was accomplished in the following manner: the (tert-butoxy)-N-(2-{[4-(4-cyanophenyl)-6-imidazolyl-4-ylpyrimidin-2-yl]amino}ethyl)carboxamide produced as described above was dissolved in anhydrous trifluoroacetic acid (2 mL) and stirred at room temperature for 2 h. Concentration gave 47.8 mg of 4-{2-[(2-aminoethyl)amino]-6-imidazolyl-4-ylpyrimidin-4-yl}benzene-carbonitrile as its (2×) trifluoroacetate salt.

The 4-{2-[(2-aminoethyl)amino]-6-imidazolyl-4-ylpyrimidin-4-yl}benzene-carbonitrile trifluoroacetate produced as described above (48 mg, 0.074 mmol) was dissolved in 0.5 mL acetonitrile and 2-chloro-5-nitropyridine (12 mg, 0.074 m-mol) added. The mixture was heated to 80° C. for 18 h and then concentrated. Chromatography of the residue (silica gel, 5% methanol/methylene chloride) afforded 5.1 mg (15%) of 4-[6-imidazolyl-2-({2-[(5-nitro(2-pyridyl))amino]ethyl}amino)pyrimidin-4-yl]benzenecarbonitrile as a light yellow solid.

HPLC [Method AZ-S]7.25 min (100%), 1HNMR;
MS: (m+H)/z, 428.

Example 91

Preparation of 4-[6-morpholin-2-({2-[(5-nitro(2-pyridyl))amino]ethyl}amino)pyrimidin-4-yl]benzenecarbonitrile 2-({2-[(tert-butoxy)carbonylamino]ethyl}amino)-6-(4-cyanophenyl)pyrimidin-4-yl (trifluoromethyl)sulfonate (134 mg, 0.275 mmol) was dissolved in a 2 M solution of morpholine in acetonitrile and the resulting solution heated to 90° C. for 18h. The solution was cooled, water added and the suspension extracted thoroughly with ethyl acetate. Concentration of the combined organic layers gave a crude solid which was chromatographed (silica gel, 2% methanol/methylene chloride) to afford 234 mg of (tert-butoxy)-N-(2-{[4-(4-cyanophenyl)-6-morpholin-4-ylpyrimidin-2-yl]amino}ethyl)carboxamide as a off white solid. Removal of the tert-butoxy protecting group was accomplished in the following manner: the (tert-butoxy)-N-(2-{[4-(4-cyanophenyl)-6-morpholin-4-ylpyrimidin-2-yl]amino}ethyl)carboxamide produced as described above was dissolved in anhydrous hydrogen chloride in dioxane (2 mL of a 2M solution) and stirred at room temperature for 2 h. Concentration gave 134 mg of 4-{2-[(2-aminoethyl)amino]-6-imidazolyl-4-ylpyrimidin-4-yl}benzenecarbonitrile as its (2x) hydrochloride salt.

The 4-{2-[(2-aminoethyl)amino]-6-morpholin-4-ylpyrimidin-4-yl}benzene-carbonitrile trifluoroacetate produced above (50 mg, 0.14 mmol) was dissolved in 0.25 mL acetonitrile and 2-chloro-5-nitropyridine (22 mg, 0.074 mmol) added. The mixture was heated to 80° C. for 18 h and then concentrated. Chromatography of the residue (silica gel, 5% methanol/methylene chloride) afforded 5.1 mg (15%) of 4-[6-morpholin-2-({2-[(5-nitro(2-pyridyl))amino]ethyl}amino)pyrimidin-4-yl]benzenecarbonitrile as a light yellow solid.

HPLC [Method AZ-S]7.20 min (100%), 1HNMR;
MS: (m+H)/z, 447.

Example 92

Preparation of [5-benzotriazolyl-4-(2,4-dichlorophenyl)pyrimidin-2-yl]{2-[(5-nitro(2-pyridyl))amino[ethyl}amine

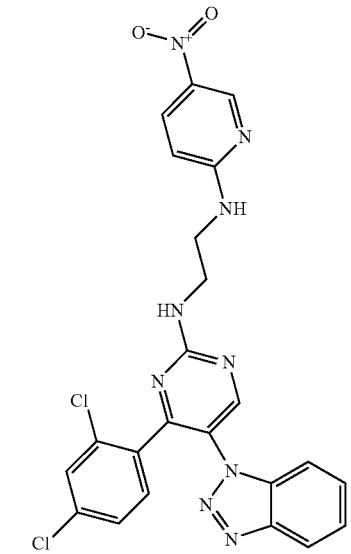

A solution of 1-(2,4-dichlorophenyl)-2-chloroethan-1-one (10.0 g, 44.63 mmol), benzotriazole (10.6 g, 89.3 mmol) and triethylamine (9.0 g, 89.3 mmol) in 140 mL acetonitrile was refluxed for 18h. The acetonitrile was removed in vacuo, and the residue dissolved in ethyl acetate. Water was added and the water layer extracted twice with ethyl acetate. The combined organics were washed with brine, dried and concentrated to give 13.2 g of a light brown solid. Recrystallization from ethyl acetate gave 4.8 g (35.%) of a colorless solid identified as 2-benzotriazolyl-1-(2,4-dichlorophenyl)ethan-1-one.

2-benzotriazolyl-1-(2,4-dichlorophenyl)ethan-1-one was dissolved in dimethyl-formamide dimethyl acetal (5 mL) and the solution refluxed for 8 h. Evaporation of the solvent gave 2-benzotriazolyl-1-(2,4-dichlorophenyl)-3-(dimethylamino)prop-2-en-1-one as an air sensitive red solid which was used in the next step without further purification.

2-benzotriazolyl-1-(2,4-dichlorophenyl)-3-(dimethylamino)prop-2-en-1-one was dissolved in 64 mL N-methylpyrrolidinone and 6.82 g (20.9 mmol) of cesium carbonate and 4.19 g (16.12 mmol) of amino{2-[(5-nitro(2-pyridyl))amino]ethyl}carboxamidine hydrochloride added. The resulting suspension was heated at 100° C. for 118h. The reaction was then cooled and partitioned between ethyl acetate and water. The aqueous layer was extracted with ethyl acetate, and the combined organic layers washed twice with water and once with brine. Concentration of the combined organic layers gave a yellow solid which was recrystallized from 5% ethyl acetate/methanol to afford 4.25 g (65%) of [5-benzotriazolyl-4-(2,4-dichlorophenyl)pyrimidin-2-yl]{2-[(5-nitro(2-pyridyl))amino]ethyl}amine as a light yellow solid.

HPLC [Method AZ-S]11.56 min (100%), 1HNMR;
MS: (m+H)/z, 522.

Example 93

Preparation of [4-(2,4-dichlorophenyl)-5-piperazinylpyrimidin-2-yl]{2-[(5-nitro(2-pyridyl))amino]ethyl}amine

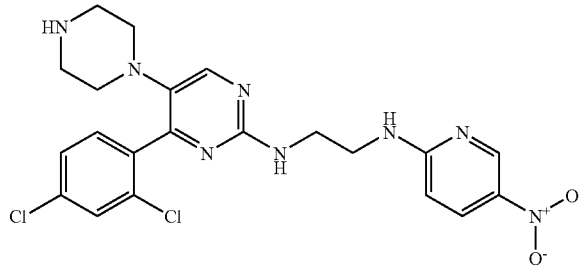

1. Preparation of tert-butyl 4-[2-(2,4-dichlorophenyl)-2-oxoethyl]piperazinecarboxylate 1 mmol of 2,4-dichlorophenacyl chloride in DMF was added drop wise to 1. mmol of tert-butyl piperazinecarboxylateand 1.2 mmol $Cs_2CO_3$ in DMF at room temperature for fourteen hours. The reaction mixture was concentrated in vacuo and diluted with water and ethyl acetate. The solution was extracted three times with ethyl acetate, dried over sodium sulfate, and purified by column chromatography eluting with 50% ethylacetate and 50% hexane to obtain tert-butyl 4-[2-(2,4-dichlorophenyl)-2-oxoethyl]piperazinecarboxylate.

2. Preparation of tert-butyl 4-{2-(2,4-dichlorophenyl)-1-[(dimethylamino)methylene]-2-oxoethyl}piperazinecarboxylate 1 mmol of tert-butyl 4-[2-(2,4-dichlorophenyl)-2-oxoethyl]piperazinecarboxylate was heated to 80° C. in neat N,N-dimethylformamidedimethyl acetal for six hours. The reaction mixture was concentrated in vacuo and purified by trituration with diethyl ether to obtain tert-butyl 4-{2-(2,4-dichlorophenyl)-1-[(dimethylamino)methylene]-2-oxoethyl}piperazinecarboxylate.

3. Preparation of tert-butyl 4-[4-(2,4-dichlorophenyl)-2-({2-[(5-nitro(2-pyridyl))amino]ethyl}amino)pyrimidin-5-yl]piperazinecarboxylate 1 mmol of tert-butyl 4-{2-(2,4-dichlorophenyl)-1-[(dimethylamino)methylene]-2-oxoethyl}piperazinecarboxylate, 1 mmol of amino{2-[(5-nitro(2-pyridyl))amino]ethyl}carboxamidine, and 3 MMol of $Cs_2CO_3$ was dissolved in DMF and heated to 90° C. for fourteen hours. The reaction mixture was concentrated in vacuo and diluted with water and ethyl acetate. The solution was extracted three times with ethyl acetate, dried over sodium sulfate, and purified by column chromatography eluting with 5–10% methanol/methylene/chloride to obtain tert-butyl 4-[4-(2,4-dichlorophenyl)-2-({2-[(5-nitro(2-pyridyl))amino]ethyl}amino)pyrimidin-5-yl]piperazinecarboxylate.

4. Preparation of [4-(2,4-dichlorophenyl)-5-piperazinylpyrimidin-2-yl]{2-[(5-nitro(2-pyridyl))amino]ethyl}amine 1 mmol of tert-butyl 4-[4-(2,4-dichlorophenyl)-2-({2-[(5-nitro(2-pyridyl))amino]ethyl}amino)pyrimidin-5-yl]piperazinecarboxylate is heated to 60° C. 3M HCl in MeOH for one hour and concentrated in vacuo to obtain [4-(2,4-dichlorophenyl)-5-piperazinylpyrimidin-2-yl]{2-[(5-nitro(2-pyridyl))amino]ethyl}amine.

HPLC: 7.683 min. (100% purity)
MS: $MH^+$=489.1

Example 94

Preparation of 1-[2-({2-[(6-amino-5-nitro(2-pyridyl))amino]ethyl}amino)-4-(2,4-dichlorophenyl)pyrimidin-5-yl]-4-methylpiperazine-2,6-dione

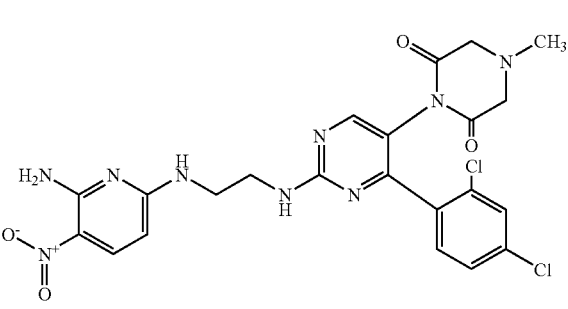

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl))amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid was heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and then purified by column chromatography eluting with 5–10% methanol/ methylene chloride to obtain [5-amino-4-(2,4-dichlorophenyl)pyrimidin-2-yl]{2-[(6-amino-5-nitro(2-pyridyl))amino]ethyl}amine.

6. Preparation of 1-[2-({2-[(6-amino-5-nitro(2-pyridyl))amino]ethyl}amino)-4-(2,4-dichlorophenyl)pyrimidin-5-yl]-4-methylpiperazine-2,6-dione 1 mmol of [5-amino-4-(2,4-dichlorophenyl)pyrimidin-2-yl]{2-[(6-amino-5-nitro(2-pyridyl))amino]ethyl}amine, and 2 mmol of methyliminodiacetic acid, 4 mmol of HBTU, and 5 mmol of N,N-diisopropylethylamine were added to solution and stirred for six hours at room temperature. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain 1-[2-({2-[(6-amino-5-nitro(2-pyridyl))amino]ethyl}amino)-4-(2,4-dichlorophenyl)pyrimidin-5-yl]-4-methylpiperazine-2,6-dione.

HPLC: 7.560min. (99% purity)
MS: MH$^+$=546.1

Example 95

Preparation of 1-[2-({2-[(6-amino-5-nitro(2-pyridyl))amino]ethyl}amino)-4-(2,4-dichlorophenyl)pyrimidin-5-yl]-3-morpholin-4-ylpyrrolidine-2,5-dione

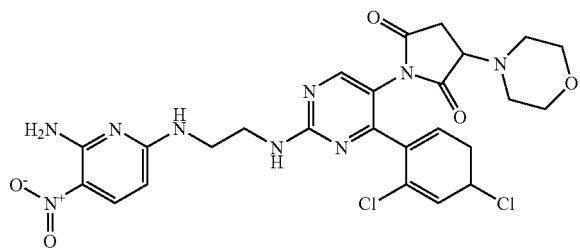

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of Cs$_2$CO$_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl))amino]ethyl}carboxamidine, and 3 mmol of Cs$_2$CO$_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid is heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours. The reaction was concentrated and purified by column chromatography 5–10% methanol/methylene chloride to obtain [5-amino-4-(2,4-dichlorophenyl)pyrimidin-2-yl]{2-[(6-amino-5-nitro(2-pyridyl))amino]ethyl}amine.

5. Preparation of 1-[2-({2-[(6-amino-5-nitro(2-pyridyl))amino]ethyl}amino)-4-(2,4-dichlorophenyl)pyrimidin-5-yl]-3-pyrroline-2,5-dione 1 mmol of [5-amino-4-(2,4-dichlorophenyl)pyrimidin-2-yl]{2-[(6-amino-5-nitro(2-pyridyl))amino]ethyl}amine, and 2 mmol of malaic anhydride are stirred at room temperature for four hours. 2 mmol of HBTU, and 3 mmol of N,N-diisopropylethylamine were added to solution and left for six hours at room temperature. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain 1-[2-({2-[(6-amino-5-nitro(2-pyridyl))amino]ethyl}amino)-4-(2,4-dichlorophenyl)pyrimidin-5-yl]-3-pyrroline-2,5-dione.

6. Preparation of 1-[2-({2-[(6-amino-5-nitro(2-pyridyl))amino]ethyl}amino)-4-(2,4-dichlorophenyl)pyrimidin-5-yl]-3-morpholin-4-ylpyrrolidine-2,5-dione Large excess of morpholine was added to clean fractions of 1-[2-({2-[(6-amino-5-nitro(2-pyridyl))amino]ethyl}amino)-4-(2,4-dichlorophenyl)pyrimidin-5-yl]-3-pyrroline-2,5-dione concentrated in vacuo, and purified by column chromatography eluting with 5–10% methanol/methylene chloride to obtain 1-[2-({2-[(6-amino-5-nitro(2-pyridyl))amino]ethyl}amino)-4-(2,4-dichlorophenyl)pyrimidin-5-yl]-3-morpholin-4-ylpyrrolidine-2,5-dione.

HPLC: 8.133 min. (100% purity)

MS: MH$^+$=602.2

Example 96

Preparation of 1-[4-(2,4-dichlorophenyl)-2-({2-[(5-nitro(2-pyridyl))amino]ethyl}amino)pyrimidin-5-yl]-4-methylpiperazine-2,6-dione

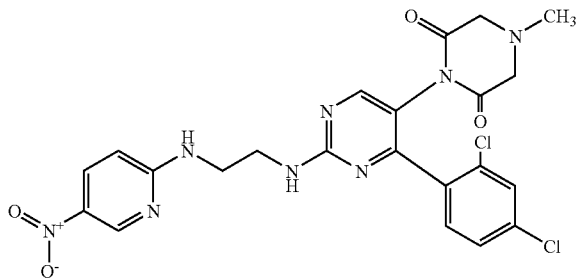

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione is heated to 80° C. in neat N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[4-(2,4-dichlorophenyl)-2-({2-[(5-nitro(2-pyridyl))amino]ethyl}amino)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino {2-[(5-nitro(2-pyridyl))amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[4-(2,4-dichlorophenyl)-2-({2-[(5-nitro(2-pyridyl))amino]ethyl}amino)pyrimidin-5-yl]carbamoyl}benzoic acid.

4. Preparation of 2-[4-(2,4-dichlorophenyl)-2-({2-[(5-nitro(2-pyridyl))amino]ethyl}amino)pyrimidin-5-yl]isoindoline-1,3-dione 1 mmol of 2-{N-[4-(2,4-dichlorophenyl)-2-({2-[(5-nitro(2-pyridyl))amino]ethyl}amino)pyrimidin-5-yl]carbamoyl}benzoic acid was heated to 120° C. in acetic acid for four hours and then concentrated in vacuo to obtain 2-[4-(2,4-dichlorophenyl)-2-({2-[(5-nitro(2-pyridyl))amino]ethyl}amino)pyrimidin-5-yl]isoindoline-1,3-dione.

5. Preparation of [5-amino-4-(2,4-dichlorophenyl)pyrimidin-2-yl]{2-[(5-nitro(2-pyridyl))amino]ethyl}amine 1 mmol of 2-[4-(2,4-dichlorophenyl)-2-({2-[(5-nitro(2-pyridyl))amino]ethyl}amino)pyrimidin-5-yl]isoindoline-1,3-dione and 20 mmol of hydrazine were stirred in ethanol at 75° C. for two hours and then purified by column chromatography eluting with 5–10% methanol/methylene chloride to obtain [5-amino-4-(2,4-dichlorophenyl)pyrimidin-2-yl]{2-[(5-nitro(2-pyridyl))amino]ethyl}amine.

6. Preparation of 1-[4-(2,4-dichlorophenyl)-2-({2-[(5-nitro(2-pyridyl))amino]ethyl{amino)pyrimidin-5-yl]-4-methylpiperazine-2,6-dione 1 mmol of [5-amino-4-(2,4-dichlorophenyl)pyrimidin-2-yl]{2-[(5-nitro(2-pyridyl))amino]ethyl}amine, and 2 mmol of methyliminodiacetic acid, 4 mmol of HBTU, and 5 mmol of N,N-diisopropylethylamine were added to solution and stirred for six hours at room temperature. The reaction mixture was concentrated in vacuo and diluted with water and ethyl acetate. The solution was extracted three times with ethyl acetate, dried over sodium sulfate, purified by column chromatography eluting with 5–10% methanol/methylene chloride to obtain 1-[4-(2,4-dichlorophenyl)-2-({2-[(5-nitro(2-pyridyl))amino]ethyl}amino)pyrimidin-5-yl]-4-methylpiperazine-2,6-dione.

HPLC: 12.850 min. (100% purity)
MS: $MH^+$=531.2

Example 97

Preparation of 1-[2-({2-[(6-amino-5-nitro(2-pyridyl))amino]ethyl}amino)-4-(2,4-dichlorophenyl)pyrimidin-5-yl]-3-(dimethylamino)pyrrolidine-2,5-dione

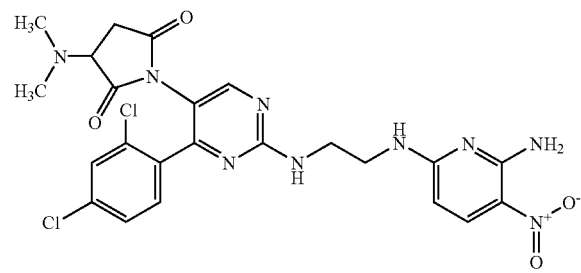

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and the purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in neat N,N-dimethylformatidedimethyl acetal for six hours. The reaction mixture was concentrated in vano and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mm of amino{2-[(6-amino-5-nitro(2-pyridyl))amino]ethyl}carboxamnidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sufate to obtain 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl})amino)-4-(2,4-dichlorophenyl)pyrimidin-5-yl]carbamoyl}benzoic acid was heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and then purified by column chromatography eluting with 5–10% methanol/methylene chloride to obtain [5-amino-4-(2,4-dichlorophenyl)pyrimidin-2-yl]{2-[(6-amino-5-nitro(2-pyridyl))amino]ethyl}amine.

6. Preparation of 1-[2-({2-[(6-amino-5-nitro(2-pyridyl))amino]ethyl}amino)-4-(2,4-dichlorophenyl)pyrimidin-5-yl]-3-pyrroline-2,5-dione 1 mmol of [5-amino-4-(2,4-dichlorophenyl)pyrimidin-2-yl]{2-[(6-amino-5-nitro(2-pyridyl))amino]ethyl}amine, and 2 mmol of malaic anhydride were stirred at room temperature for four hours. 2 mmol of HBTU, and 3mmol of N,N-diisopropylethylamine were added to the solution and left for six hours at room temperature. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain 1-[2-({2-[(6-amino-5-nitro(2-pyridyl))amino]ethyl}amino)-4-(2,4-dichlorophenyl)pyrimidin-5-yl]-3-pyrroline-2,5-dione.

7. Preparation of 1-[2-({2-[(6-amino-5-nitro(2-pyridyl))amino]ethyl}amino)-4-(2,4-dichlorophenyl)pyrimidin-5-yl]-3-(dimethylamino)pyrrolidine-2,5-dione A large excess of dimethylamine was added to clean fractions of 1-[2-({2-[(6-amino-5-nitro(2-pyridyl))amino]ethyl}amino)-4-(2,4-dichlorophenyl)pyrimidin-5-yl]-3-pyrroline-2,5-dione concentrated in vacuo.

HPLC: 5.215 min. (95% purity)
MS: MH+=560.2

Example 98

Preparation of {2-[(6-amino-5-nitro(2-pyridyl))amino]ethyl}[6-(2,4-dichlorophenyl)-5-imidazolyl(2-pyridyl)]amine

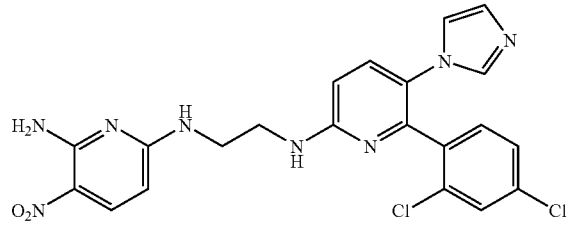

1. Preparation of 1-(2,4-dichlorophenyl)-2-imidazolylethan-1-one.

A stirred solution of 1-(2,4-dichlorophenyl)-2-chloroethan-1-one (0.95 M) and imidazole (2.68 M) in CH$_3$CN (500 ml) were heated for 14–16 hours at 75° C. The product was stripped of solvent under reduced pressure. The residue was diluted with dichloromethane (1 L) and water (400 ml), and the mixture was stirred for 30 min. After filtering off a solid impurity, the aqueous layer was removed and discarded. The organic layer was washed sequentially with water (300 ml), sat. aq. NaHCO$_3$ (300 ml), water (300 ml), brine (200 ml), dried with Na$_2$SO$_4$, filtered, and concentrated under reduced pressure. The reddish black oil was dried overnight in vacuo giving 1-(2,4-dichlorophenyl)-2-imidazolylethan-1-one in 90% yield.

2. Preparation of ethyl 5-(2,4-dichlorophenyl)-4-imidazolyl-5-oxopentanoate.

1-(2,4-dichlorophenyl)-2-imidazolylethan-1-one (0.80 M) was dissolved with heating as necessary in a stirred mixture of THF (250 ml) and abs. ethanol (250 ml). After cooling to room temperature, potassium hydroxide (0.20 M) was added followed by a dropwise addition of ethyl acrylate (45.8 ml) via addition funnel over 10 min. A room temperature water bath was used to cool the exothermic reaction for the first 30 min. After stirring for 14–16 hours, the reaction was neutralized with gla. acetic acid (10 ml) and concentrated under reduced pressure. The residual dark reddish black slurry was dissolved in abs. ethanol (100 ml) and concentrated again under reduced pressure giving ethyl 5-(2,4-dichlorophenyl)-4-imidazolyl-5-oxopentanoate (2) in 108% yield. The crude material is contaminated with potassium salts and is used without further purification.

3. Preparation of 6-(2,4-dichlorophenyl)-5-imidazolyl-1,3,4-trihydropyridin-2-one.

A mixture of ethyl 5-(2,4-dichlorophenyl)-4-imidazolyl-5-oxopentanoate (0.51 M) was dissolved in gla. acetic acid (245 ml), toluene (135 ml), and abs. ethanol (405 ml). Ammonium acetate (3.07 M) and flame dried 4A powder molecular sieves (145 g) were added to the stirred solution. The resulting mixture was stirred for 44–46 hours at 90–95° C. under argon. After 24 hours of heating, additional reagents were added including ammonium acetate (0.51 M), acetic acid (41 ml), and flame dried 4A powder molecular sieves (24 g). On cooling methanol (200 ml) was added with stirring for 15 minutes. The sieves were filtered and washed with methanol (2×150 ml). The filtrate was concentrated under reduce pressure. To the crude material was added dichloromethane (1.5 L). The organic layer was then washed until basic, with 5–10% sodium hydroxide solution (3×500 ml). The organic layer was then washed with distilled water (3×400 ml), saturated sodium chloride solution (300 ml), dried with sodium sulfate, filtered, and concentrated under reduce pressure. The reddish orange solid was dried in vacuo giving 102 g of crude product. A solution of 2% methanol in ethyl acetate (90–110 ml) was added to the crude product. The resulting solid was collected by filtration and washed with ethyl acetate (2×100 ml). The off white solid was dried in vacuo to give 6-(2,4-dichlorophenyl)-5-imidazolyl-1,3,4-trihydropyridin-2-one in 60% yield.

4. Preparation of 6-(2,4-dichlorophenyl)-5-imidazolylhydropyridin-2-one.

A mixture of 6-(2,4-dichlorophenyl)-5-imidazolyl-1,3,4-trihydropyridin-2-one (0.21 M), selenium(IV) oxide (0.63), and gla. acetic acid (400 ml) was stirred for 10 hours at 105–110° C. under argon. The acetic acid was removed under reduced pressure. Methanol (500 ml) was added. After mixing, the solution was filtered to remove selenium residue. To the methanolic solution, lead(II) acetate trihydrate (99 g) and distilled water (50 ml) were added and stirred for 1 hour. The mixture was filtered through a celite plug (0.25–0.5 inches). The solution was concentrated under reduced pressure. The crude material was purified by a silica gel column. The product was eluted with ethyl acetate and a slowly increasing gradient of methanol reaching a final concentration of 8%. The proper fractions were concentrated under reduced pressure and dried in vacuo. The solid was further purified by trituration with a small volume of 1:1 methanol and ethyl acetate. The off-white solid was dried in vacuo to give 6-(2,4-dichlorophenyl)-5-imidazolylhydropyridin-2-one in 68% yield.

5. Preparation of [2-(2,4-dichlorophenyl)-6-chloro-3-pyridyl]imidazole.

To the dry solid 6-(2,4-dichlorophenyl)-5-imidazolylhydropyridin-2-one (2.40 M) was added N,N-dimethylacetamide (6 drops) followed by phosphorous oxychloride (20 ml). The reaction mixture was stirred for 18–20 hours at 105–110° C. under argon. The phosphorous oxychloride was removed under reduced pressure. The crude product was taken up in dichloromethane (75 ml), and the solvent was removed under vacuum. The sticky solid was dried to a free flowing solid in vacuo 3–4 hour giving [2-(2,4-dichlorophenyl)-6-chloro-3-pyridyl]imidazole in 167% yield. The crude material is contaminated with phosphorous residue and is used with out further purification.

6. Preparation of (2-aminoethyl)[6-(2,4-dichlorophenyl)-5-imidazolyl(2-pyridyl)]amine.

The crude material above, [2-(2,4-dichlorophenyl)-6-chloro-3-pyridyl]imidazole was cooled under argon to −78° C. with dry ice acetone. With argon continually flushing through the system, ethylene diamine (200 ml) was added very carefully monitoring the release of gas and heat. After completing the addition, the reaction mixture was stirred for 5–6 hours at 105–110° C. under argon. Upon cooling, the ethylene diamine was removed under reduced pressure and dried in vacuo for 2–3 hours. To the residual material was added acetonitrile (100 ml) and saturated sodium bicarbonate solution (250–300 ml). To the stirred mixture above, sodium bicarbonate solid was added until the mixture was fully saturated. After 30 min., acetonitrile (300–350 ml) was added to the saturated aqueous solution. The mixture was stirred and the layers were separated saving both aqueous and organic portions. The aqueous layer was extracted with acetonitrile (4×250 ml). The organic layers were combined and washed with saturated sodium chloride solution (100 ml), dried with sodium sulfate, filtered, concentrated, and dried in vacuo. The residue was dissolved in methanol (70–90 ml). The mixture was filtered to remove residual salt, and concentrated under reduced pressure. The off-white solid was dried in vacuo giving (2-aminoethyl)[6-(2,4-dichlorophenyl)-5-imidazolyl(2-pyridyl)]amine in 97% yield based on the initial amount of 6-(2,4-dichlorophenyl)-5-imidazolylhydropyridin-2-one used. The material contains minimal amounts of salt and was used without further purification.

7. Preparation of {2-[(6-amino-5-nitro(2-pyridyl))amino]ethyl}[6-(2,4-dichlorophenyl)-5-imidazolyl(2-pyridyl)]amine.

A mixture of (2-aminoethyl)[6-(2,4-dichlorophenyl)-5-imidazolyl(2-pyridyl)]amine (0.14 M), 6-chloro-3-nitro-2-pyridylamine (0.14 M), N-N-dimethylacetamide (40 ml), and Hünig's base (2.5 ml) was stirred for 12 hours at 85–90° C. under argon. Ethylene diamine (3.8 ml) was added to remove the unreacted chloropyridine, and the mixture was stirred for an additional 0.75–1 hour at 85–90° C. under argon. After cooling, the reaction was diluted with ethyl acetate (500–600 ml), extracted with saturated sodium bicarbonate (4×200 ml), distilled water (3×150 ml), saturated sodium chloride (150 ml). The organic layer was dried with sodium sulfate briefly (2–3 minutes) so as not to initiate precipitation of the product. The organic layer was filtered, concentrated, and dried in vacuo. To cause precipitation of the product, a minimal amount of methanol (3–5 ml) was added followed with the addition of an equal volume of ethyl acetate. The mixture was allowed to age for 2–3 hours. The solid was collected by filtration, washed with minimal 1:1 methanol/ethyl acetate (5 ml), and a finally 100% ethyl acetate (2×10 ml). The yellow solid was dried in vacuo to give {2-[(6-amino-5-nitro(2-pyridyl))amino]ethyl}[6-(2,4-dichlorophenyl)-5-imidazolyl(2-pyridyl)]aminein 61% yield.

HPLC: 19.8 min (>95% purity)
MS: M+H=485 ($C_{21}H_{18}C_{12}N_8O_2$+H=485)

Example 99

Preparation of 6-[(2-{[4-(2,4-dichlorophenyl)-5-(4-methylimidazol-2-yl)pyrimidin-2-yl]amino}ethyl)amino]pyridine-3-carbonitrile

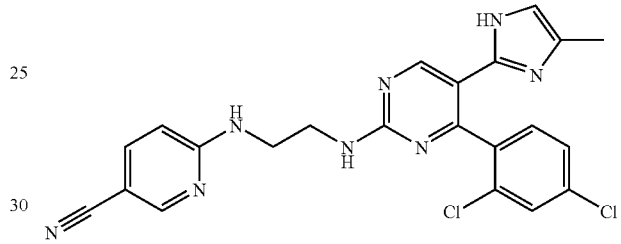

6-[(2-{[4-(2,4-dichlorophenyl)-5-(4-methylimidazol-2-yl)pyrimidin-2-yl]amino}ethyl)amino]pyridine-3-carbonitrile was prepared using the general method for [4-(2,4-dichlorophenyl)-5-imidazol-2-ylpyrimidin-2-yl]{2-[(5-nitro(2-pyridyl))amino]ethyl}amine with the exceptions noted below.

1. Preparation of 1-(2,4-dichlorophenyl)-2-(4-methylimidazol-2-yl)ethan-1-one.

A solution of 2,4-dichlorobenzoyl chloride (7.24 M) in dichloromethane (25 ml) was added dropwise over 20 minutes to a stirred solution of 2,4-dimethylimidazole (0.80 M) in dichloromethane (75 ml) and N,N-diisopropylethylamine (Hünig's base) (34 ml). The reaction mixture was cooled during the addition using a water bath. The reaction mixture was then heated to reflux for 5 hours. The reaction can turn a darker color. The product was stripped of solvent under reduced pressure, and the resulting solid was dried in vacuo for one hour.

To the dry solid (described above) was added a solution (2:1 v/v, 120 ml) of gla. acetic acid and aq. con. HCl. The mixture was then stirred at reflux for ca. 90 min. The acetic acid was removed via rotary evaporator. Upon cooling, distilled water (200 ml) and toluene (100 ml) were added to the solid residue, which was vigorously stirred for 30 min. The solids were filtered, rinsed with 50 ml distilled water, and discarded. The filtrate was transferred to a separatory funnel. After the organic layer was discarded, the aqueous layer was washed with toluene (2×100 ml). The aqueous layer was transferred to a large beaker (2 L) and diluted with isopropyl ether (50 ml). The stirred mixture was basified (pH 7–8) by careful addition of sodium bicarbonate which leads to the formation of a sticky white solid. Dichloromethane (200 ml) was added and stirring continued for 10 min. The organic layer was separated and the aqueous layer was again extracted with dichloromethane (100 ml). The organic layers were combined and washed with sat. aq. NaHCO$_3$ (100 ml), distilled water (100 ml), brine (100 ml), dried with Na$_2$SO$_4$, filtered, concentrated, and dried in vacuo giving 1-(2,4-dichlorophenyl)-2-(4-methylimidazol-2-yl)ethan-1-one in 46% yield.

2. Preparation of (2Z)-1-(2,4-dichlorophenyl)-3-(dimethylamino)-2-(4-methylimidazol-2-yl)prop-2-en-1-one.

A mixture of 1-(2,4-dichlorophenyl)-2-(4-methylimidazol-2-yl)ethan-1-one (0.33 M) and N,N-dimethylformamide-dimethyl acetal (DMFDMA) (25 ml) was stirred for 2.5 h at 70–75° C. The DMFDMA was then removed under reduced pressure and dried under high vacuum for several hours giving a light orange solid in quantitative yield. The enaminone product (2Z)-1-(2,4-dichlorophenyl)-3-(dimethylamino)-2-(4-methylimidazol-2-yl)prop-2-en-1-one was typically used without further purification.

3. Preparation of 6-[(2-aminoethyl)amino]pyridine-3-carbonitrile.

A mixture of 2-chloro-5-cyanopyridine (0.60 M) in acetonitrile (120 ml) and ethylene diamine (85 ml) were stirred overnight (ca. 16 h) at 75–80° C. under argon. The ethylene diamine was removed under reduced pressure and then dried in vacuo for 2–3 h. The residual solution was basified with 1M sodium hydroxide solution (~100 ml). The aqueous solution was saturated with sodium chloride and extracted with a solution of 95% ethyl acetate and 5% methanol (3×150 ml) and with a solution of 95% acetonitrile and 5% methanol (3×150 ml). The organic extracts were combined and extracted with a saturated sodium chloride solution (2×70 ml). The organic layer was dried with sodium sulfate, filtered, and concentrated under reduced pressure. The crude white to tan solid was triturated with ether (2×50 ml) and dried overnight in vacuo resulting in 78% yield of 6-[(2-aminoethyl)amino]pyridine-3-carbonitrile.

4. Preparation of amino {2-[(5-cyano(2-pyridyl))amino]ethyl}carboxamidine, hydrochloride.

A mixture of 6-[(2-aminoethyl)amino]pyridine-3-carbonitrile (0.47 M), 1H-pyrazole-1-carboxamidine hydrochloride (0.47 M), and acetonitrile (120 ml) were stirred ca. 24 h at 75–80° C. Upon cooling, a precipitate was collected by filtration. The white solid was washed thoroughly with acetonitrile (2×100 ml), ethyl ether (3×100 ml), and dried overnight in vacuo giving amino{2-[(5-cyano(2-pyridyl))amino]ethyl}carboxamidine as the HCl salt in 82% yield.

5. Preparation of 6-[(2-{[4-(2,4-dichlorophenyl)-5-(4-methylimidazol-2-yl)pyrimidin-2-yl]amino}ethyl)amino]pyridine-3-carbonitrile.

A solution of sodium ethoxide (0.58 M) dissolved in abs. ethanol (15 ml) was added to a stirred mixture of (2Z)-1-(2,4-dichlorophenyl)-3-(dimethylamino)-2-(4-methylimidazol-2-yl)prop-2-en-1-one (0.41 M), amino{2-[(5-cyano(2-pyridyl)) amino]ethyl}carboxamidine, hydrochloride (0.43 M), and abs. ethanol (20 ml). The reaction was then heated to 75–80° C. for 2.5 hours. On cooling the reaction was diluted with ethyl acetate (400 ml) washed with sat. aq. NaHCO$_3$ (100 ml), distilled water (2×100 ml), brine (100 ml), dried with Na$_2$SO$_4$, filtered, and concentrated. The crude product (~50% purity) was purified by flash chromatography over silica gel. The column was run starting with 1:1 ethyl acetate to hexane, then ethyl acetate which was used until all of the fast moving impurities had been removed. The product was eluted with 1.5% methanol in ethyl acetate. The column is monitored by TLC using 5% methanol in ethyl acetate as the solvent system. The product has UV activity in the long wave length region and "glows" blue on the unstained TLC plate. The proper fractions were condensed. The off-white solid was dried overnight in vacuo giving 6-[(2-{[4-(2,4-dichlorophenyl)-5-(4-methylimidazol-2-yl)pyrimidin-2-yl]amino}ethyl) amino]pyridine-3-carbonitrile in 28% yield.

HPLC: 20.7 min (>99% purity)
MS: M+H=465.3 (C$_{22}$H$_{18}$C$_{12}$N$_8$+H=465)

Example 100

Preparation of [5-((1E)-1-aza-2-morpholin-4-ylprop-1-enyl)-4-(2,4-dichlorophenyl)pyrimidin-2yl]{2-[(6-amino-5-nitro(2-pyridyl))amino]ethyl}amine

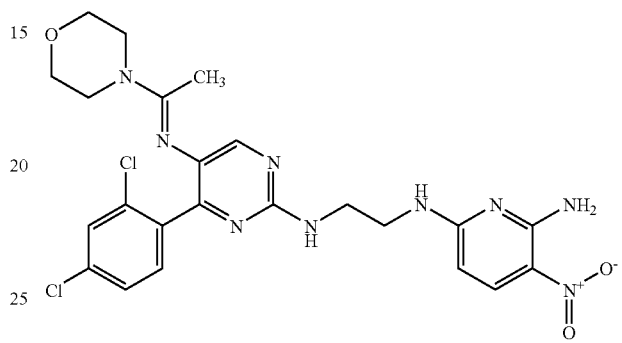

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of Cs$_2$CO$_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl)) amino]ethyl}amino)-4-(2,4-dichlorophenyl)pyrimidin-5-yl] carbamoyl}benzoic acid 1 mmol of 2-{2-(2,4-dichlorophenyl)-1-[(dimethylamino) methylene]-2-oxoethyl}isoindoline-1,3-dione, 1 mmol of amino{2-[(6-amino-5-nitro(2-pyridyl))amino] ethyl}carboxamidine, and 3 mmol of Cs$_2$CO$_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain 2-{N-[2-({2-[(6-amino-5-nitro(2-pyridyl))amino] ethyl}amino)-4-(2,4-dichlorophenyl)pyrimidin-5-yl] carbamoyl}benzoic acid.

4. Preparation of 2-[2-({2-[(6-amino-5-nitro(2-pyridyl)) amino]ethyl}amino)-4-(2,4-dichlorophenyl)pyrimidin-5-yl] isoindoline-1,3-dione 1 mmol of 2-{N-[2-({2-[(6-amino-5-nitro(2-pyridyl)) amino]ethyl}amino)-4-(2,4-dichlorophenyl)pyrimidin-5-yl]

carbamoyl}benzoic acid was heated to 120° C. in acetic acid for four hours and concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and purified by column chromatography eluting with 5–10% methanol/methylene chloride to obtain [5-amino-4-(2,4-dichlorophenyl)pyrimidin-2-yl]{2-[(6-amino-5-nitro(2-pyridyl))amino]ethyl}amine.

6. Preparation of N-[2-({2-[(6-amino-5-nitro(2-pyridyl))amino]ethyl}amino)-4-(2,4-dichlorophenyl)pyrimidin-5-yl]acetamide 1 mmol of [5-amino-4-(2,4-dichlorophenyl)pyrimidin-2-yl]{2-[(6-amino-5-nitro(2-pyridyl))amino]ethyl}amine and 1 mmol of acetic anhydride were stirred at room temperature for four hours in THF. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain N-[2-({2-[(6-amino-5-nitro(2-pyridyl))amino]ethyl}amino)-4-(2,4-dichlorophenyl)pyrimidin-5-yl]acetamide.

7. Preparation of 1-{[2-({2-[(6-amino-5-nitro(2-pyridyl))amino]ethyl}amino)-4-(2,4-dichlorophenyl)pyrimidin-5-yl]amino}ethane-1-thione 1 mmol of N-[2-({2-[(6-amino-5-nitro(2-pyridyl))amino]ethyl}amino)-4-(2,4-dichlorophenyl)pyrimidin-5-yl]acetamide and 2 mmol of Lawesson's reagent were stirred in 2 ml of DME at 80° C. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain 1-{[2-({2-[(6-amino-5-nitro(2-pyridyl))amino]ethyl}amino)-4-(2,4-dichlorophenyl)pyrimidin-5-yl]amino}ethane-1-thione.

8. Preparation of [5-((1Z)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine 1 mmol of 1-{[2-({2-[(6-amino-5-nitro(2-pyridyl))amino]ethyl}amino)-4-(2,4-dichlorophenyl)pyrimidin-5-yl]amino}ethane-1-thione was heated to 90° C. in morpholine and purified by column chromatography eluting with 5–10% methanol/methylene chloride to obtain [5-((1 Z)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine.

HPLC: 9.75 min. (100% purity)

MS: MH$^+$=546.3

Example 101

Preparation of [4-(2,4-dichlorophenyl)-5-imidazol-2-ylpyrimidin-2-yl]{2-[(6-methoxy-5-nitro(2-pyridyl))amino]ethyl}amine

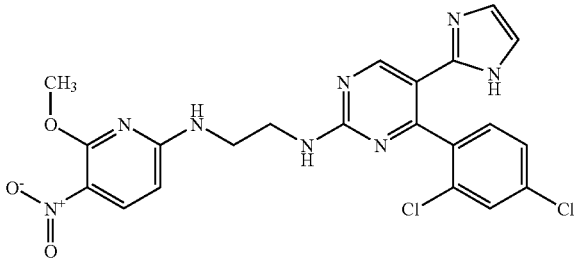

1. Preparation of 6-chloro-2-methoxy-3-nitro-pyridine

To a suspension of sodium hydride (684 mg, 28.49 mmol) in xylene (100 ml), methanol (0.98 ml, 25.9 mmol) in xylene (30 ml) was added under nitrogen. The mixture was stirred for 20 min. A solution of 2,6-dichloro-3-nitropyridine (5.0g, 25.9mmo) in xylene (100 ml) was added to the reaction mixture and stirred at room temperature overnight. Water (50 ml) was added and the organic layer was separated. The organics was washed with water (1×50 ml) and brine (2×50 ml), dried, and concentrated in vacuo. The crude product was purified by flash chromatography (10:1 methylene chloride and acetone) to provide the desired compound, 6-chloro-2-methoxy-3-nitro-pyridine, as the only isomer as light yellow solid (90%).

2. Preparation of [4-(2,4-dichlorophenyl)-5-imidazol-2-ylpyrimidin-2-yl]{2-[(6-methoxy-5-nitro(2-pyridyl))amino]ethyl}amine To a solution of [4-(2,4-dichlorophenyl)-5-imidazol-2-ylpyrimidin-2-ylethylamine (20 mg, 0.04 mmol) in DMF (1 ml), 2-methoxy-3-nitro-6-chloro-pyridine (8.3 mg, 0.04 mmol) and diisopropylethyl amine (31 μl, 0.18 mmol) were added. The reaction mixture was stirred for 12 hours at 80° C. The crude mixture was concentrated in vacuo and subjected to column chromatography (10% methanol in methylene chloride) to afford [4-(2,4-dichlorophenyl)-5-imidazol-2-ylpyrimidin-2-yl]{2-[(6-methoxy-5-nitro(2-pyridyl))amino]ethyl}amine as bright yellow solid.

HPLC: 3.1 min (100% pure)

MS: MH+=501 C21H18C12N8O3=500 g/mol

Example 102

Preparation of [4-(2,4-dichlorophenyl)-5-imidazolylpyrimidin-2-yl]{2-[(6-methoxy-5-nitro(2-pyridyl))amino]ethyl}amine

[4-(2,4-dichlorophenyl)-5-imidazolylpyrimidin-2-yl]{2-[(6-methoxy-5-nitro(2-pyridyl))amino]ethyl}amine was prepared from [4-(2,4-dichlorophenyl)-5-imidazol-1-ylpyrimidin-2-ylethylamine in accordance to the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 3.2 min (100% pure)

MS: MH+=501 C21H18C12N8O3=500 g/mol

Example 103

Preparation of 6-[(2-{[4-(2,4-dichlorophenyl)-5-imidazol-2-ylpyrimidin-2-yl]amino}ethyl)aminol-3-nitropyridin-2-ol

[4-(2,4-dichlorophenyl)-5-imidazol-2-ylpyrimidin-2-yl]{2-[(6-methoxy-5-nitro(2-pyridyl)amino]ethyl}amine (7 mg, 0.01 mmol) was treated with hydrobromic acid (100?1) and acetic acid (100?1) and stirred at 100° C. overnight. The mixture was concentrated in vacuo and lyophilized to give 6-[(2-{[4-(2,4-dichlorophenyl)-5-imidazol-2-ylpyrimidin-2-yl]amino}ethyl)amino]-3-nitropyridin-2-ol as a dark brown solid.

HPLC: 2.7 min (100% pure)
MS: MH+=487 C20H16C12N8O3=486 g/mol

Example 104

Preparation of 6-[(2-{[4-(2,4-dichlorophenyl)-5-imidazolylpyrimidin-2-yl]amino}ethyl)amino]-3-nitropyridin-2-ol 6-[(2-{[4-(2,4-dichlorophenyl)-5-imidazolylpyrimidin-2-yl]amino}ethyl)amino]-3-nitropyridin-2-ol was prepared from [4-(2,4-dichlorophenyl)-5-imidazol-1-ylpyrimidin-2-yl]{2-[(6-methoxy-5-nitro(2-pyridyl)amino]ethyl}amine (7mg, 0.01 mmol) by following the same procedure as described for the preparation of 6-[(2-{[4-(2,4-dichlorophenyl)-5-imidazol-2-ylpyrimidin-2-yl]amino}ethyl)amino]-3-nitropyridin-2-ol.

HPLC: 2.46 min (100% pure)
MS: MH+=487 C20H16C12N8O3=486 g/mol

Example 105

Preparation of 1-{6-[(2-{[4-(2,4-dichlorophenyl)-5-imidazolylpyrimidin-2-yl]amino}ethyl)amino]-3-pyridyl}ethan-1-one 1-{6-[(2-{[4-(2,4-dichlorophenyl)-5-imidazolylpyrimidin-2-yl]amino}ethyl)amino]-3-pyridyl}ethan-1-one was prepared from [4-(2,4-dichlorophenyl)-5-imidazol-1-ylpyrimidin-2-yl]ethylamine and 1-(6-chloro-3-pyridyl)ethanone (prepared as described in Tetrahedron 48:9233 (1992)) in accordance to the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

Example 106

Preparation of [4-(2,4-dichlorophenyl)-5-imidazol-2-ylpyrimidin-2-yl](2-{[5-(iminomethoxymethyl)(2-pyridyl)]amino}ethyl)amine And 6-[(2-{[4-(2,4-dichlorophenyl)-5-imidazol-2-ylpyrimidin-2-yl]amino}ethyl)amino]pyridine-3-carboxamide

[4-(2,4-dichlorophenyl)-5-imidazol-2-ylpyrimidin-2-yl]{2-[(5-cyano(2-pyridyl)amino]ethyl}amine (20 mg, 0.04 mmol) was treated with saturated solution of methanolic ammonia (1 ml) and ammonium chloride (10 mg) and stirred at 60° C. overnight. The crude product was purified by column chromatography (10% methanol in methylene chloride) to provide the title compounds as white powder.

HPLC: 2.38 min (100% pure)
MS: MH+=484 C22H20C12N7O=483 g/mol
HPLC: 1.94 min (100% pure)
MS: MH+=469 C22H20C12N7O=468 g/Mol

Example 107

Preparation of {6-[(2-{[4-(2,4-dichlorophenyl)-5-imidazol-2-ylpyrimidin-2-yl]amino}ethyl)amino](3-pyridyl)}iminomethylhydroxylamine A solution of [4-(2,4-dichlorophenyl)-5-imidazol-2-ylpyrimidin-2-yl]{2-[(5-cyano(2-pyridyl)amino]ethyl}amine (20 mg, 0.04 mmol) in aqueous ethanol(50?l of water in 500 ?l ethanol) was treated with hydoxylamine hydrochloride (3.0 mg, 0.04 mmol) and diisopropylethyl amine (16 ?l, 0.08 mmol). The reaction mixture was stirred overnight under reflux, and concentrated in vacuo. The residue was taken up in ethylacetate and washed with brine and concentrated. The crude mixture was subjected to column chromatography (10% methanol in methylene chloride) to give{6-[(2-{[4-(2,4-dichlorophenyl)-5-imidazol-2-ylpyrimidin-2-yl]amino}ethyl)amino](3-pyridyl)}iminomethylhydroxylamine.

HPLC: 2.16 min (100% pure)
MS: MH+=484 C21H19OC12N9O=483 g/mol

Example 108

Preparation of {6-[(2-{[4-(2,4-dichlorophenyl)-5-imidazolylpyrimidin-2-yl]amino}ethyl)amino](3-pyridyl)}iminomethylhydroxylamine {6-[(2-{[4-(2,4-dichlorophenyl)-5-imidazolylpyrimidin-2-yl]amino}ethyl)amino](3-pyridyl)}iminomethylhydroxylamine was prepared from [4-(2,4-dichlorophenyl)-5-imidazol-1-ylpyrimidin-2-yl]ethylamine in accordance to the procedure described for the preparation of {6-[(2-{[4-(2,4-dichlorophenyl)-5-imidazol-2-ylpyrimidin-2-yl]amino}ethyl)amino](3-pyridyl)}iminomethylhydroxylamine.

HPLC: 2.19 min (100% pure)
MS: MH+=484 C21H19OC12N9O=483 g/mol

Example 109

Preparation of 6-[(2-{[4-(2,4-dichlorophenyl)-5-imidazol-2-ylpyrimidin-2-yl]amino}ethyl)amino]pyridine-3-carboxamidine A solution of [4-(2,4-dichlorophenyl)-5-imidazol-2-ylpyrimidin-2-yl]{2-[(5-cyano(2-pyridyl)amino]ethyl}amine (20 mg, 0.04 mmol) in saturated solution of methanoic ammonia was stirred at 60° C. for 48 h. The product was purified from the crude using reverse phase column chromatography to give 6-[(2-{[4-(2,4-dichlorophenyl)-5-imidazol-2-ylpyrimidin-2-yl]amino}ethyl)amino]pyridine-3-carboxamidine.

HPLC: 2.14 min (100% pure)
MS: MH+=468 C21H19C12N9=467 g/mol

Example 110

Preparation of [4-(2,4-dichlorophenyl)-5-imidazol-1-ylpyrimidin-2-yl]{2-[(4-cyano (2-pyridyl)amino]ethyl}amine

[4-(2,4-dichlorophenyl)-5-imidazol-1-ylpyrimidin-2-yl]{2-[(4-cyano(2-pyridyl)amino]ethyl}amine was prepared from [4-(2,4-dichlorophenyl)-5-imidazol-2-ylpyrimidin-2-yl]ethylamine and 2-chloro-4-cyanopyridine in accordance to the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 2.79 min (100% pure)
MS: MH+=451 C21H16C12N8=450 g/mol

Example 111

Preparation of {6-[(2-{[4-(2,4-dichlorophenyl)-5-imidazol-2-ylpyrimidin-2-yl]amino}ethyl)amino]-3-nitro(2-pyridyl)}dimethylamine 1. Preparation of 6-chloro-2-dimethylamino-3-nitro pyridine A mixture of 2,6-dichloro-3-nitropyridine (1.9 g, 10 mmole) and potassium carbonate (1.66 g, 12 mmole) in 30 ml of tetrahydrofuran was stirred at 0° C. for 5 min. A solution of dimethylamine/tetrahydrofuran (2 M, 6 ml, 12 mmole) was added dropwise to the reaction mixture over 40 min. After stirring for 5 min at 0° C., the mixture was warmed to room temperature and stirred overnight. The reaction mixture was filtered and the filtrate was collected and concentrated under reduced pressure. The crude product was purified by flash chromatography, eluting with 87% hexane: 13% ethyl acetate to give 6-chloro-2-dimethylamino-3-nitro pyridine (1.05 g).

HPLC: 11.18 min (90% pure)

MS: MH+=202.1 C7H8C1N3O2=201 g/mol

2. Preparation of {6-[(2-{[4-(2,4-dichlorophenyl)-5-imidazol-2-ylpyrimidin-2-yl]amino}ethyl)amino]-3-nitro(2-pyridyl)}dimethylamine {6-[(2-{[4-(2,4-dichlorophenyl)-5-imidazol-2-ylpyrimidin-2-yl]amino}ethyl)amino]-3-nitro(2-pyridyl)}dimethylamine was prepared from [4-(2,4-dichlorophenyl)-5-imidazol-2-ylpyrimidin-2-ylethylamine and 6-chloro-2-dimethylamino-3-nitro pyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11.5 min (85% pure)

MS: MH+=514.2 C22H21C12N9O2=513 g/mol

Example 112

Preparation of {6-[(2-{[4-(2,4-dichlorophenyl)-5-imidazolylpyrimidin-2-yl]amino}ethyl)amino]-3-nitro(2-pyridyl)}dimethylamine {6-[(2-{[4-(2,4-dichlorophenyl)-5-imidazolylpyrimidin-2-yl]amino}ethyl)amino]-3-nitro(2-pyridyl)}dimethylamine was prepared from [4-(2,4-dichlorophenyl)-5-imidazol-1-ylpyrimidin-2-ylethylamine and 6-chloro-2-dimethylamino-3-nitro pyridine in accordance with the procedure described above for the preparation of [4-(2,4-dichlorophenyl)-5-imidazol-2-ylpyrimidin-2-yl]{2-[(6-methoxy-5-nitro(2-pyridyl)) amino]ethyl}amine.

HPLC: 11.6 min (85% pure)

MS: MH+=514.3 C22H21C12N9O2=513 g/mol

Example 113

Preparation of [4-(2,4-dichlorophenyl)-5-imidazol-2-ylpyrimidin-2-yl](2-{[6-(methylamino)-5-nitro(2-pyridyl)]amino}ethyl)amine 1. Preparation of 6-chloro-2-methylamino-3-nitro-pyridine 6-chloro-2-methylamino-3-nitro-pyridine was prepared in accordance to the procedure described above for the preparation of 6-chloro-2-dimethylamino-3-nitro pyridine by using solution of methyl amine. The crude product was purified by flash chromatography, eluting with 90% hexane: 10% ethyl acetate to 16 (300 mg).

HPLC: 12.06 min (85% pure)

MS: MH+=188.1 C6H6C1N3O2 187 g/mol

Preparation of [4-(2,4-dichlorophenyl)-5-imidazol-2-ylpyrimidin-2-yl](2-{[6-(methylamino)-5-nitro(2-pyridyl)]amino}ethyl)amine

[4-(2,4-dichlorophenyl)-5-imidazol-2-ylpyrimidin-2-yl](2-{[6-(methylamino)-5-nitro(2-pyridyl)]amino}ethyl)amine was prepared from [4-(2,4-dichlorophenyl)-5-imidazol-2-ylpyrimidin-2-ylethylamine and 6-chloro-2-methylamino-3-nitro-pyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11 min (85% pure)

MS: MH+=500.3 C21H19C12N9O2 499 g/mol

Example 114

Preparation of [4-(2,4-dichlorophenyl)-5-imidazolylpyrimidin-2-yl](2-{[6-(methylamino)-5-nitro(2-pyridyl)]amino}ethyl)amine

[4-(2,4-dichlorophenyl)-5-imidazolylpyrimidin-2-yl](2-{[6-(methylamino)-5-nitro(2-pyridyl)]amino}ethyl)amine was prepared from [4-(2,4-dichlorophenyl)-5-imidazol-1-ylpyrimidin-2-ylethylamine and 6-chloro-2-methylamino-3-nitro-pyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11.3 min (85% pure)

MS: MH+=500.3 C21H19C12N9O2 499 g/mol

Example 115

Preparation of 2,6-dichloropyridine-3-carboxamide; 2,6-dichloropyridine-3-carbonitrile; and 6-chloro-2-methoxypyridine-3-carbonitrile 1. Preparation of 2,6-dichloropyridine-3-carboxamide A mixture of 2,6-dichloro-3-carboxypyridine (5.73 g, 30 mmole) and N-methylmorpholine (3.6 ml, 33 mmole) in dichloromethane (100 ml) was stirred in an ice-bath for 5 min. Isopropyl chloroformate (4.28 ml, 33 mmole) was added the reaction mixture at 0° C. The reaction mixture was stirred for 30 min and then bubbled with pure ammonia gas for 2 min. and stirred overnight at room temperature. The crude was concentrated under reduced pressure and sodium bisulfate (0.5 M, 35 ml) was added with stirring. The aqueous solution was extracted with ethyl acetate (3×40 ml). The organics was washed with water and brine and dried with sodium sulfate to give yellow crude product (6.3g, 50% pure).

Preparation of 2,6-dichloropyridine-3-carbonitrile

To a mixture of 2,6-dichloro-3-acetamidopyridine (6.3 g, 55% pure) and pyridine (4.93 ml, 61 mmole) in dichloromethane (100 ml), trifluoroacetic anhydride (4.23 ml, 30 mmole) was added. The reaction mixture was stirred at room temperature overnight and concentrated under reduced pressure. The crude product was purified by flash chromatography, eluting with 85% hexane: 15% ethyl acetate to give a pale yellow product (1.77 g, 90%).

HPLC: 10.26 min (90% pure)

MS: MH+=172.9 C6H2C12N2 171.9 g/mol

Preparation of 6-chloro-2-methoxypyridine-3-carbonitrile 6-chloro-2-methoxypyridine-3-carbonitrile was prepared from 2,6-dichloro-pyridine-3-carboxamide in accordance with the procedure described above for the preparation of 6-chloro-2-methoxy-3-nitro-pyridine.

HPLC: 11.37 min (80% pure)

MS: MH+=169.1 C7H5C1N2O 168 g/mol

Example 116

Preparation of 6-[(2-{[4-(2,4-dichlorophenyl)-5-imidazolylpyrimidin-2-yl]amino}ethyl)amino]-2-methoxypyridine-3-carbonitrile 6-[(2-{[4-(2,4-dichlorophenyl)-5-imidazolylpyrimidin-2-yl]amino}ethyl)amino]-2-methoxypyridine-3-carbonitrile was prepared from [4-(2,4-dichlorophenyl)-5-imidazol-1-ylpyrimidin-2-ylethylamine and 6-chloro-2-methoxypyridine-3-carbonitrile in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11.8 min (85% pure)
MS: MH+=481.2 C22H18Cl2N8O 480 g/mol

Example 117

Preparation of 6-[(2-{[4-(2,4-dichlorophenyl)-5-imidazol-2-ylpyrimidin-2-yl]amino}ethyl)amino]-2-methoxypyridine-3-carbonitrile 6-[(2-{[4-(2,4-dichlorophenyl)-5-imidazol-2-ylpyrimidin-2-yl]amino}ethyl)amino]-2-methoxypyridine-3-carbonitrile was prepared from [4-(2,4-dichlorophenyl)-5-imidazol-2-ylpyrimidin-2-ylethylamine and 6-chloro-2-methoxypyridine-3-carbonitrile in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11.37 min (80% pure)
MS: MH+=169.1 C7H5Cl1N2O 168 g/mol

Example 118

Preparation of N-{6-[(2-{[4-(2,4-dichlorophenyl)-5-imidazol-2-ylpyrimidin-2-yl]amino}ethyl)amino]-3-nitro-2-pyridyl}acetamide 1. Preparation of N-(6-chloro-3-nitro-2-pyridyl)acetamide To a suspension of sodium hydride (120 mg, 5 mmole) in tetrahydrofuran(10 ml), a solution of 2-amino-3-nitro-6-chloropyridine (870 mg, 5 mmole) in 20 ml of tetrahydrofuran (20 ml) was added. The reaction mixture was stirred at room temperature for 30 min. A solution of acetic anhydride (377 μl, 6 mmole) in tetrahydrofuran (10 ml) was added and stirred at room temperature overnight. The reaction mixture was quenched with water and concentrated under reduced pressure. The crude product was dissolved in dichloromethane and washed with brine. The organic layer was dried with sodium sulfate and then concentrated under vacuo. The crude was purified by flash chromatography, eluting 78% hexane: 22% ethyl acetate to give a yellow product (88 mg).

HPLC: 6.36 min and 9.78 min (88% pure)
MS: MH+=215.9 C7H6Cl1N3O3 215 g/mol

2. Preparation of N-{6-[(2-{[4-(2,4-dichlorophenyl)-5-imidazol-2-ylpyrimidin-2-yl]amino}ethyl)amino]-3-nitro-2-pyridyl}acetamide N-{6-[(2-{[4-(2,4-dichlorophenyl)-5-imidazol-2-ylpyrimidin-2-yl]amino}ethyl)amino]-3-nitro-2-pyridyl}acetamide was prepared from [4-(2,4-dichlorophenyl)-5-imidazol-2-ylpyrimidin-2-ylethylamine and N-(6-chloro-3-nitro-2-pyridyl)acetamide in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 10.6 min (85% pure)
MS: MH+=528.2 C22H19Cl2N9O3 527 g/mol

Example 119

Preparation of N-{6-[(2-{[4-(2,4-dichlorophenyl)-5-imidazolylpyrimidin-2-yl]amino}ethyl)amino]-3-nitro-2-pyridyl}acetamide N-{6-[(2-{[4-(2,4-dichlorophenyl)-5-imidazolylpyrimidin-2-yl]amino}ethyl)amino]-3-nitro-2-pyridyl}acetamide was prepared from [4-(2,4-dichlorophenyl)-5-imidazol-1-ylpyrimidin-2-ylethylamine and N-(6-chloro-3-nitro-2-pyridyl)acetamide in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 10.8 min (85% pure)
MS: MH+=528.2 C22H19Cl2N9O3 527 g/mol

Example 120

Preparation of {6-[(2-{[4-(2,4-dichlorophenyl)-5-imidazol-2-ylpyrimidin-2-yl]amino}ethyl)amino]-3-nitro(2-pyridyl)}(methylsulfonyl)amine 1. Preparation of (6-chloro-3-nitro(2-pyridyl))(methylsulfonyl)amine (6-chloro-3-nitro(2-pyridyl))(methylsulfonyl)amine was prepared from 2-amino-3-nitro-6-chloropyridine and methane sulphonyl chloride in accordance with the procedure described above for the preparation of N-(6-chloro-3-nitro-2-pyridyl)acetamide.

HPLC: 8.08 min (90% pure)
MS: MH+=251.9 C6H6Cl1N3O4S 251 g/mol

2. Preparation of {6-[(2-{[4-(2,4-dichlorophenyl)-5-imidazol-2-ylpyrimidin-2-yl]amino}ethyl)amino]-3-nitro(2-pyridyl)}(methylsulfonyl)amine {6-[(2-{[4-(2,4-dichlorophenyl)-5-imidazol-2-ylpyrimidin-2-yl]amino}ethyl)amino]-3-nitro(2-pyridyl)}(methylsulfonyl)amine was prepared from [4-(2,4-dichlorophenyl)-5-imidazol-2-ylpyrimidin-2-ylethylamine and (6-chloro-3-nitro(2-pyridyl))(methylsulfonyl)amine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 10.8 min (85% pure)
MS: MH+=564 C21H19Cl2N9O4S 563 g/mol

Example 121

Preparation of {6-[(2-{[4-(2,4-dichlorophenyl)-5-imidazolylpyrimidin-2-yl]amino}ethyl)amino]-3-nitro(2-pyridyl)}(methylsulfonyl)amine {6-[(2-{[4-(2,4-dichlorophenyl)-5-imidazolylpyrimidin-2-yl]amino}ethyl)amino]-3-nitro(2-pyridyl)}(methylsulfonyl)amine was prepared from [4-(2,4-dichlorophenyl)-5-imidazol-1-ylpyrimidin-2-ylethylamine and (6-chloro-3-nitro(2-pyridyl))(methylsulfonyl)amine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 11.1 min (85% pure)
MS: MH+=564 C21H19Cl2N9O4S 563 g/mol

Example 122

Preparation of (2-{6-[(2-{[4-(2,4-dichlorophenyl)-5-imidazol-2-ylpyrimidin-2-yl]amino}ethyl)amino]-3-nitro(2-pyridyloxy)}ethyl)dimethylamine 1. Preparation of [2-(6-chloro-3-nitro(2-pyridyloxy))ethyl]dimethylamine

[2-(6-chloro-3-nitro(2-pyridyloxy))ethyl]dimethylamine was prepared from 2,2-dimethylaminoethanol in accordance to the procedure described above for the preparation of 6-chloro-2-methoxy-3-nitro-pyridine.

HPLC: 4.9 min (65% pure)

MS: MH+=246.1 C9H12C1N3O3 245 g/mol

2. Preparation of (2-{6-[(2-{[4-(2,4-dichlorophenyl)-5-imidazol-2-ylpyrimidin-2-yl]amino}ethyl)amino]-3-nitro(2-pyridyloxy)}ethyl)dimethylamine (2-{6-[(2-{[4-(2,4-dichlorophenyl)-5-imidazol-2-ylpyrimidin-2-yl]amino}ethyl)amino]-3-nitro(2-pyridyloxy)}ethyl)dimethylamine was prepared from [4-(2,4-dichloro-phenyl)-5-imidazol-2-ylpyrimidin-2-ylethylamine and [2-(6-chloro-3-nitro(2-pyridyloxy))-ethyl]dimethylamine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 8.5 min (85% pure)

MS: MH+=558.3 C24H25C12N9O3 557.1 g/mol

Example 123

Preparation of (2-{6-[(2-{[4-(2,4-dichlorophenyl)-5-imidazolylpyrimidin-2-yl]amino}ethyl)amino]-3-nitro(2-pyridyloxy)}ethyl)dimethylamine (2-{6-[(2-{[4-(2,4-dichlorophenyl)-5-imidazolylpyrimidin-2-yl]amino}ethyl)amino]-3-nitro(2-pyridyloxy)}ethyl)dimethylamine was prepared from [4-(2,4-dichlorophenyl)-5-imidazol-1-ylpyrimidin-2-ylethylamine and [2-(6-chloro-3-nitro(2-pyridyloxy))ethyl]dimethylamine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC: 8.3 min (85% pure)

MS: MH+=558.3 C24H25C12N9O3 557.1 g/mol

Example 124

Preparation of (1 Z)-1-aza-2-(6-chloro(3-pyridyl))-1-methoxyprop-1-ene

To a solution of 5-(2-chloropyidinyl)oxime methyl ether (540 mg, 3.2 mmole) in acetonitrile(9 ml), ethylene diamine (2.8 ml, 42 mmole) was added. The reaction mixture was stirred at 85° C. overnight, concentrated under vacuo. The crude product was dissolved in aqueous sodium hydroxide (1 M, 15 ml) and extracted with ethyl acetate and a mixture of acetonitrile/methanol (10:1). The organic extract was dried with sodium sulfate to give (1Z)-1-aza-2-(6-chloro(3-pyridyl))-1-methoxyprop-1-ene as an yellow oil (547 mg, 75%).

HPLC: 1.8 min (75% pure)

MS: MH+=195.1 C9H14N4O 194.1 g/mol

Example 125

Preparation of (2-{[5-((1Z)-2-aza-2-methoxy-1-methylvinyl)(2-pyridyl)]amino}ethyl)[4-(2,4-dichlorophenyl)-5-imidazolylpyrimidin-2-yl]amine (2-{[5-((1Z)-2-aza-2-methoxy-1-methylvinyl)(2-pyridyl)]amino}ethyl)[4-(2,4-dichlorophenyl)-5-imidazolylpyrimidin-2-yl]amine was prepared from the guanidine (which was made from [2-(6-chloro-3-nitro(2-pyridyloxy))ethyl]dimethylamine and the corresponding eneaminone).

HPLC: 9.3 min (85% pure)

MS: MH+=483.2 C22H20C12N8O 482 g/mol

Example 126

Preparation of {2-[(6-amino-5-nitro(2-pyridyl))amino]ethyl}[4-(2,4-dichlorophenyl)-5-imidazolylpyrimidin-2-yl]amine {2-[(6-amino-5-nitro(2-pyridyl))amino]ethyl}[4-(2,4-dichlorophenyl)-5-imidazolyl-pyrimidin-2-yl]amine was prepared from [4-(2,4-dichlorophenyl)-5-imidazol-1-ylpyrimidin-2-ylethylamine and 2-chloro-5-nitro-6-aminopyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 6.15 min (100%)

MS (m+H/z), 486.

Example 127

Preparation of 6-[(2-{[4-(2,4-dichlorophenyl)-5-imidazolylpyrimidin-2-yl]amino}ethyl)amino]pyridine-3-carbonitrile 6-[(2-{[4-(2,4-dichlorophenyl)-5-imidazolylpyrimidin-2-yl]amino}ethyl)amino]pyridine-3-carbonitrile was prepared from [4-(2,4-dichlorophenyl)-5-imidazolylpyrimidin-2-ylethylamine and 2-chloro-5-cyanopyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 5.94 min (100%);

MS (m+H/z), 451.

Example 128

Preparation of [4-(2,4-dichlorophenyl)-5-imidazolylpyrimidin-2-yl]{2-[(5-methyl (7a-hydro-1,2,4-triazolo[1,5-a]pyrimidin-7-yl))amino]ethyl}amine

[4-(2,4-dichlorophenyl)-5-imidazolylpyrimidin-2-yl]{2-[(5-methyl(7a-hydro-1,2,4-triazolo[1,5-a]pyrimidin-7-yl))amino]ethyl}amine was prepared from [4-(2,4-dichlorophenyl)-5-imidazol-1-ylpyrimidin-2-ylethylamine and 7-methyl-9-chloro-1,2,4-triazolo(1,5-a)pyrimidine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 5.80 min (70%);

MS (m+H/z), 481.

Example 129

Preparation of [4-(2,4-dichlorophenyl)-5-imidazolylpyrimidin-2-yl]{2-[(5-trifluoromethyl(2-pyridyl))amino]ethyl}amine

[4-(2,4-dichlorophenyl)-5-imidazolylpyrimidin-2-yl]{2-[(5-trifluoromethyl(2-pyridyl))amino]ethyl}amine was prepared from [4-(2,4-dichlorophenyl)-5-imidazol-1-ylpyrimidin-2-ylethylamine and 2-chloro-5-trifluoromethylpyridine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC. [Method AZ-S], 7.62 min (60%);

MS (m+H/z), 494.

Example 130

Preparation of 4-(2,4-dichlorophenyl)-5-imidazolylpyrimidin-2-yl]{2-[(5-nitro(1,3-thiazol-2-yl))amino]ethyl}amine 4-(2,4-dichlorophenyl)-5-imidazolylpyrimidin-2-yl]{2-[(5-nitro(1,3-thiazol-2-yl))amino]ethyl}amine was prepared from [4-(2,4-dichlorophenyl)-5-imidazol-1-ylpyrimidin-2-ylethylamine and 2-chloro-5-nitro-thiazole in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 7.14 min (100%);

MS (m+H/z), 477.

Example 131

Preparation of [4-(2,4-dichlorophenyl)-5-imidazolylpyrimidin-2-yl]{2-[(6-chloropyrimidin-4-yl)amino]ethyl}amine

[4-(2,4-dichlorophenyl)-5-imidazolylpyrimidin-2-yl]{2-[(6-chloropyrimidin-4-yl)amino]ethyl}amine was prepared from [4-(2,4-dichlorophenyl)-5-imidazol-1-ylpyrimidin-2-ylethylamine and 4,6-dichloropyrimidine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 7.43 min (80%);

MS (m+H/z), 461.

Example 132

Preparation of [4-(2,4-dichlorophenyl)-5-imidazolylpyrimidin-2-yl]{2-[(6-chlorobenzothiazo 1-2-yl)amino]ethyl}amine

[4-(2,4-dichlorophenyl)-5-imidazolylpyrimidin-2-yl]{2-[(6-chlorobenzothiazo 1-2-yl)amino]ethyl}amine was prepared from [4-(2,4-dichlorophenyl)-5-imidazol-1-ylpyrimidin-2-ylethylamine and 2,6-dichlorobenzothiazole in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 8.23 min (100%);

MS (m+H/z), 516.

Example 133

Preparation of [4-(2,4-dichlorophenyl)-5-imidazolylpyrimidin-2-yl]{2-[(3-nitro (2-thienyl))amino]ethyl}amine

[4-(2,4-dichlorophenyl)-5-imidazolylpyrimidin-2-yl]{2-[(3-nitro(2-thienyl))amino]ethyl}aamine was prepared from [4-(2,4-dichlorophenyl)-5-imidazol-1-ylpyrimidin-2-ylethylamine and 2-chloro-3-nitrothiophene in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 9.50 min (75%);

MS (m+H/z), 495.

Example 134

Preparation of 4-amino-2-[(2-{[4-(2,4-dichlorophenyl)-5-imidazolylpyrimidin-2-yl]amino}eth yl)amino]pyrimidine-5-carbonitrile 4-amino-2-[(2-{[4-(2,4-dichlorophenyl)-5-imidazolylpyrimidin-2-yl]amino}ethyl)amino]pyrimidine-5-carbonitrile was prepared from [4-(2,4-dichlorophenyl)-5-imidazol-1-ylpyrimidin-2-ylethylamine and 2-chloro-4-amino-5-cyanopyrimidine in accordance with the procedure described above for the preparation of [4-(2,4-dichlorophenyl)-5-imidazol-2-ylpyrimidin-2-yl]{2-[(6-methoxy-5-nitro(2-pyridyl))amino]ethyl}amine.

HPLC [Method AZ-S], 6.00 min (70%);

MS (m+H/z), 467.

Example 135

Preparation of {2-[(6-amino-5-nitro(2-pyridyl))amino]ethyl}[6-(2,4-dichlorophenyl)-5-nitro(2-pyridyl)]amine

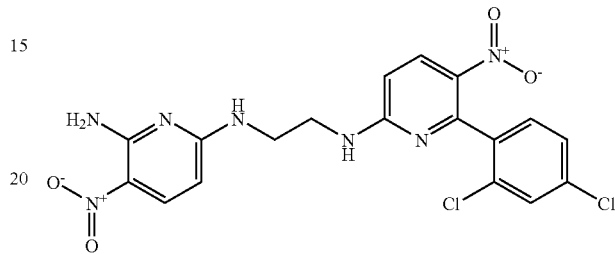

1. Preparation of 2-(2,4-dichlorophenyl)-6-chloro-3-nitropyridine 1 mmol 2,6-dichloro-3-nitropyridine, 1.05 mmol of 2,4-dichlorobenzeneboronic acid, and 3 mmol of $Na_2CO_3$, were dissolved in 1.5 ml THF and 0.5 ml water and purged with nitrogen. 0.05 mmol of [1,1'-Bis(diphenylphosphino)ferrocene]dichloro-palladium(II) was added to reaction and stirred at room temperature under nitrogen for fourteen hours. The reaction mixture was concentrated in vacuo and diluted with water and ethyl acetate. The solution was extracted three times with ethyl acetate, dried over sodium sulfate, and purified by column chromatography eluting with 10% ethylacetate 90% hexanes to obtain 2-(2,4-dichlorophenyl)-6-chloro-3-nitropyridine.

2. Preparation of (2-aminoethyl)(6-amino-5-nitro(2-pyridyl))amine 1 mmol of 2-amino-6-chloro-3-nitropyridine and 15 mmol of 1,2-diaminoethane were stirred at reflux for fourteen hours. The reaction mixture was concentrated in vacuo and solution of 1.5 mmol of NaOH in water was added. This solution was extracted twice with 95%/5% methylene chloride/methanol. The aqueous was then saturated with salt and extracted twice with 95%/5% acetonitrile/methanol and then finally extrated twice with 95%/5% ethylacetate/methanol. All organic fractions were combined and dried over sodium sulfate to obtain (2-aminoethyl)(6-amino-5-nitro(2-pyridyl))amine.

3. Preparation of {2-[(6-amino-5-nitro(2-pyridyl))amino]ethyl}[6-(2,4-dichlorophenyl)-5-nitro(2-pyridyl)]amine 1 mmol of 2-(2,4-dichlorophenyl)-6-chloro-3-nitropyridine was taken with 2 mmol of (2-aminoethyl)(6-amino-5-nitro(2-pyridyl))amine and 3 mmol of N,N-diisopropylethylamine in 2 ml of DMF at 80° C. for two hours. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain {2-[(6-amino-5-nitro(2-pyridyl))amino]ethyl}[6-(2,4-dichlorophenyl)-5-nitro(2-pyridyl)]amine.

HPLC: 8.698 min. (100% purity)

MS: MH+=464.1

Example 136

Preparation of 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione

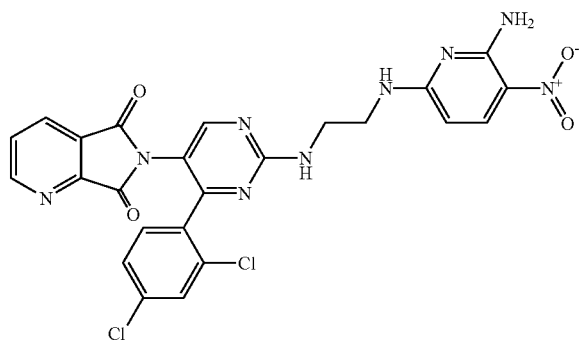

1. Preparation of 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and then purified by trituration with diethyl ether to obtain 2-[2-(2,4-dichlorophenyl)-2-oxoethyl]isoindoline-1,3-dione.

2. Preparation of 2-{2-(2,4-dichlorophenyl)-1-[(dimethylamino)methylene]-2-oxoethyl}isoindoline-1,3-dione 1 mmol of 2-[2-(2,4-dichlcrophenyl)-2-oxoethyl]isoindoline-1,3-dion was heated to 80° C. in neat N,N-dimethylformamidedimethyl acetal for six hours. The reaction mixture was concentrated in vacuo and purified by trituration with diethyl ether to obtain 2-{2-(2,4-dichlorophenyl)-1-[(dimethylamino)methylene]-2-oxoethyl}isoindoline-1,3-dione.

3. Preparation of 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino {2-[(6-amino-5-nitro(2-pyridyl))amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate to obtain of 2-{N-[2-({2-[(6-amino-5-nitro(2-pyridyl))amino]ethyl}amino)-4-(2,4-dichlorophenyl)pyrimidin-5-yl]carbamoyl}benzoic acid.

4. Preparation of 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid was heated to 120° C. in acetic acid for four hours and then concentrated in vacuo to obtain 2-[2-({2-[(6-amino-5-nitro(2-pyridyl))amino]ethyl}amino)-4-(2,4-dichlorophenyl)pyrimidin-5-yl]isoindoline-1,3-dione.

5. Preparation of [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and then purified by column chromatography eluting with 5–10% methanol/methylene chloride to obtain [5-amino-4-(2,4-dichlorophenyl)pyrimidin-2-yl]{2-[(6-amino-5-nitro(2-pyridyl))amino]ethyl}amine.

6. Preparation of 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione 1 mmol of [5-amino-4-(2,4-dichlorophenyl)pyrimidin-2-yl]{2-[(6-amino-5-nitro(2-pyridyl))amino]ethyl}amine, and 2 mmol of furano[3,4-b]pyridine-5,7-dione were stirred at room temperature for four hours. 2 mmol of HBTU, and 3 mmol of N,N-diisopropylethylamine were added to solution and left for six hours at room temperature. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride to obtain 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione.

HPLC: 7.829 min. (97.32% purity)
MS: MH+=566.0

Example 137

Preparation of [6-(2,4-dichlorophenyl)-5-imidiazol-2-yl(2-pyridyl)]{2-[(5-nitro(2-pyridyl))amino]ethyl}amine

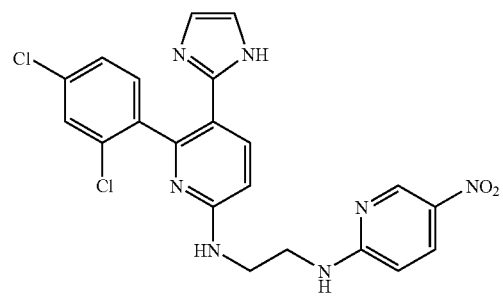

1. Preparation of 1-(2,4-dichlorophenyl)-2-imidazol-2-ylethan-1-one.

The preparation of the material 1-(2,4-dichlorophenyl)-2-imidazol-2-ylethan-1-one can be found in the precedures for the preparation of [4-(2,4-dichlorophenyl)-5-imidazol-2-ylpyrimidin-2-yl]{2-[(5-nitro(2-pyridyl))amino]ethyl}amine.

2. Preparation of 2-(2-aminoethylamino)-5-nitropyridine.

The preparation of the material 6-[(2-aminoethyl)amino]pyridine with various substitutents on the pyridine can be found in the precedures for the preparation of [4-(2,4-dichlorophenyl)-5-imidazol-2-ylpyrimidin-2-yl]{2-[(5-nitro(2-pyridyl))amino]ethyl}amine, Example 74, and its analogues.

3. Preparation of methyl 2-phenylthiopropanoate.

A solution of methyl-2-bromopropionate (6.13 M) in abs. ethanol (25 ml) was added slowly (~1 h) to a stirred solution of thiophenol (107 M), KOH (107 M) in abs. ethanol (90 ml) at room temperature. After 12 h, the reaction was filtered and stripped of solvent under reduced pressure. The resulting slurry was partitioned with water (150 ml) and ether (100 ml). The aqueous layer was extracted with ether (3×100 ml). The combined organic layers were washed with 1 M NaOH (2×50 ml), water (2×50 ml), brine (100 ml), dried with $Mg_2SO_4$, filtered, and concentrated under reduced pressure. Drying in vacuo for 2–3 hours results in methyl 2-phenylthiopropanoate as a clear oil in 90% yield and >99% purity. (see analogous procedure in Warren, S.; et. al. *J Chem. Soc. Perkin Trans. I* 1986, 1939–1945.)

4. Preparation of methyl 2-(phenylsulfinyl)propanoate.

A solution of mCPBA (57–86% active) in dry ether (200 ml, ~0.25 g per ml) was added dropwise to a stirred solution of methyl 2-phenylthiopropanoate (0.34 M) in dry ether (400 ml) at 0° C. The reaction was followed by TLC eluting with 10% ethyl acetate in hexane. After all of the starting material had been consumed, the reaction was concentrated under reduced pressure. The residue was dissolved in ether (150 ml) and dichloromethane (400 ml). The organics were washed with 1 M $Na_2S_2O_3$ (2×80 ml), sat. aq. $Na_2CO_3$ (4×100 ml), brine (100 ml), and dried with $Na_2SO_4$. After removing the volatile organics, of methyl 2-(phenylsulfinyl) propanoate was obtained in 99% yield and 99% purity.

5. Preparation of methyl 2-phenylthioprop-2-enoate.

A mixture of methyl 2-(phenylsulfinyl)propanoate (0.17 M) in dichloromethane (800 ml), acetic anhydride (20 ml), and methanesulfonic acid (1.5 ml) were heated at 40° C. for 18 h. The reaction was concentrated under reduced pressure in a water bath that was held at a constant 35° C. The residue was partitioned with water (200 ml) and ether (100 ml). The aqueous layer was extracted with ether (3×50 ml). The combined organic layers were washed with water (50 ml), sat. aq. $Na_2CO_3$ (3×30 ml), brine (30 ml), and dried with $MgSO_4$. After filtration, the product was stripped of solvent under reduced pressure at <35° C. The product was purified by eluting through a short column of silica gel using a 10% ethyl acetate in hexane mixture as eluent. Upon concentration, methyl 2-phenylthioprop-2-enoate was isolated in 50% yield.

6. Preparation of methyl 5-(2,4-dichlorophenyl)-4-imidazol-2-yl-5-oxo-2-phenylthiopentanoate.

A solution (1 M) of tert-butoxide in tert-butanol (54.9 ml) was added to a stirred solution of 1-(2,4-dichlorophenyl)-2-imidazol-2-ylethan-1-one (0.11 M) and methyl 2-phenylthioprop-2-enoate (0.14 M) dissolved in dichloromethane (300 ml) and methanol (200 ml) at room temperature. The reaction, which developed a dark color, was typically stirred overnight (ca. 16 h) under argon. The reaction was monitored by TLC using 5% methanol in dichloromethane as the solvent system. Additional methyl 2-phenylthioprop-2-enoate was added as needed to consume all of the starting 1-(2,4-dichlorophenyl)-2-imidazol-2-ylethan-1-one. The reaction was quenched by the addition of sat. aq. $NH_4Cl$ (~100 ml). The mixture was transferred to a separatory funnel and diluted with ethyl acetate (300 ml). The aqueous layer was removed and the organic layer was washed with sat. aq. $NH_4Cl$ (3×100 ml), brine (100 ml), and dried with $Na_2SO_4$. After filtration and evaporation, the residue was purified by flash chromatography over silica gel. The column was eluted starting with 100% dichloromethane to remove the non-polar methyl 2-phenylthioprop-2-enoate. The product was eluted with 3% methanol in dichloromethane. After drying overnight in vacuo, methyl 5-(2,4-dichlorophenyl)-4-imidazol-2-yl-5-oxo-2-phenylthiopentanoate as a deep red glass was obtained in 71% yield. A further 10% yield of product could be obtained by resubmitting side product contaminated fractions to a second purification by flash chromatography.

7. Preparation of 6-(2,4-dichlorophenyl)-5-imidazol-2-yl-3-phenylthio-1,3,4-trihydropyridin-2-one.

A solution was made of methyl 5-(2,4-dichlorophenyl)-4-imidazol-2-yl-5-oxo-2-phenylthiopentanoate (0.33 M), gla. acetic acid (21 ml), abs. ethanol (63 ml), toluene (21 ml) by heating the mixture to 90° C. To the stirred solution, $NH_4OAc$ (1.97 M) and 4 Å molecular sieves (15 g) were added. After 24 h of heating, another portion of both $NH_4OAc$ (1.97 M) and 4 Å molecular sieves (15 g) were added. After 48 h, the reaction had come to completion as determined by HPLC. The reaction is diluted with ethyl acetate (500 ml), filtered, and washed with sat. aq. $NaHCO_3$ (4×250 ml) and brine (200 ml). The organic layer was dried with $Na_2SO_4$ and concentrated under reduced pressure. The residue was redissolved in EtOAc and concentrated under reduced pressure. The residue was taken up in a minimal amount of EtOAc to precipitate the product. The remaining product could be purified by flash chromatography over silica gel. The column was eluted using 100% ethyl acetate. After concentration, the product was dried in vacuo, The product 6-(2,4-dichlorophenyl)-5-imidazol-2-yl-3-phenylthio-1,3,4-trihydropyridin-2-one obtained from both precipitation and chromatography gave a tan solid in 89% yield.

8. Preparation of 6-(2,4-dichlorophenyl)-5-imidazol-2-ylhydropyridin-2-one.

Dichloromethane (~150 ml) was added carefully so as not to cause precipitation to a solution of 6-(2,4-dichlorophenyl)-5-imidazol-2-yl-3-phenylthio-1,3,4-trihydropyridin-2-one (0.17 M) in THF (40 ml). A solution of mCPBA (2.85 g, ~16.5 mmol; 65–85% active) in dichloromethane (50 mg per 1 ml) is added dropwise to the stirred solution of phenylthiol above at −20° C. After adding approximately 1 equivalent of oxidant, the reaction was allowed to warm to room temperature. Additional mCPBA is titrated into the reaction until all of the starting material is gone as judged by TLC eluting in 5% MeOH in dichloromethane ($R_f$ of the product is ~0.1). As the reaction nears completion, the elimination product starts to precipitate out of solution as a gum. Upon completion, the reaction is stirred for an additional 30 min. Triethylamine (4 ml; 2 eq. based on mCPBA) is added to the reaction which causes the reaction to go completely clear for approximately 1 min. followed by nearly complete precipitation of the product as an off-white solid. The solid is filtered and washed with dichloromethane (3×30 ml). The product was dried in vacuo resulting in of 6-(2,4-dichlorophenyl)-5-imidazol-2-ylhydropyridin-2-one in 93% yield.

9. Preparation of 6-(2,4-dichlorophenyl)-5-{1-[(trifluoromethyl)sulfonyl]imidazol-2-yl}-2-pyridyl (trifluoromethyl)sulfonate.

Trifluoromethanesulfonic anhydride (1.61 ml, 9.78 mmol) was added to a stirred suspension of 6-(2,4-dichlorophenyl)-5-imidazol-2-ylhydropyridin-2-one (500 mg, 1.63 mmol) in pyridine (10 ml) at −10° C. After 30 min., the reaction was allowed to warm to room temperature. Stirring continued until all of the solid starting material had been dissolved and reacted as determined by HPLC. The reaction was diluted with dichloromethane (500 ml) and washed sequentially with sat. aq. $NaHCO_3$ (3×100 ml), water (2×100 ml), sat. aq. $NaHCO_3$ (100 ml), brine, dried with $Na_2SO_4$, filtered and concentrated under reduced pressure. The residue was purified over a short column of silica gel eluting with 25% ethyl acetate in hexanes to remove the non-polar product from baseline material. After removing the solvents and drying in vacuo, the product 6-(2,4-dichlorophenyl)-5-{1-[(trifluoromethyl)sulfonyl]imidazol-2-yl}-2-pyridyl (trifluoro-methyl)sulfonate was obtained as a slightly yellow clear glass weighting 874 mg in 95% yield.

10. Preparation of [6-(2,4-dichlorophenyl)-5-imidazol-2-yl (2-pyridyl)]{2-[(5-nitro(2-pyridyl))amino]ethyl}amine.

A suspension of (2-aminoethyl)(5-nitro(2-pyridyl))amine (255 mg, 1.40 mmol) in N,N-dimethylacetamide (3 ml) containing dry powdered 4 Å molecular sieves (50 mg) was added to a suspension of 6-(2,4-dichlorophenyl)-5-{1-[(trifluoromethyl)sulfonyl]imidazol-2-yl}-2-pyridyl (trifluoromethyl)sulfonate (200 mg, 0.35 mmol) in N,N-dimethylacetamide (3 ml) containing dry powdered 4 Å molecular sieves (50 mg). After stirring at 40° C. for 24 h, ethylenediamine (0.5 ml) and water (0.5 ml) were added to the reaction to hydrolyze the one remaining triflate from the product. The reaction was stirred at 85° C. for 2 h and left at room temperature for 12 h. The reaction was then diluted with ethyl acetate (100 ml), filtered, extracted with sat. aq. $NaHCO_3$ (6×30 ml), brine (30 ml), dried with $Na_2SO_4$, filtered, and concentrated under reduced pressure. The product [6-(2,4-dichlorophenyl)-5-imidazol-2-yl(2-pyridyl)]{2-[(5-nitro(2-pyridyl))amino]ethyl}amine (79859) was obtained as a yellow glass weighing 143 mg in 85% yield.

HPLC: 22.1 min (>95% purity)

MS: M+H=470.2 ($C_{21}H_{17}Cl_2N_7O_2$+H=470)

Example 138

Preparation of give [4-(2,4-dichlorophenyl)-2-({2-[(5-nitro(2-pyridyl))amino]ethyl}amino)pyrimidin-5-yl]methan-1-ol To a stirred solution of a suspension of 2.13 g (4.68 mmol) ethyl 4-(2,4-dichloro-phenyl)-2-({2-[(tert-butoxy)carbonylamino]ethyl}amino)pyrimidine-5-carboxylate in 10 mL THF at room temperature under nitrogen was added 25 mL of DIBAL-H (1 M in THF, 25.0 mmol) dropwise. During this addition the suspension gradually turned into a homogenous yellow solution. After 1 h the resulting solution was heated to 70° C. for an additional 7 h. The reaction was then cooled and the reaction was quenched by the addition of Rochelle's salt. The resulting suspension was partitioned between methylene chloride and water. The aqueous layer was extracted twice with methylene chloride and the combined organic layers washed with brine and dried with sodium sulfate. Concentration gave 2.05 g of a yellow foam. Chromatography on silica gel (110 g) using 5% methanol/ether as eluent gave 430 mg (22%) of N-(2-{[4-(2,4-dichlorophenyl)-5-(hydroxymethyl)pyrimidin-2-yl]amino}ethyl)(tert-butoxy)carboxamide as a colorless foam.

HPLC [Method AZ-S], 9.42 min (100%); MS (m+H/z), 413.

N-(2-{[4-(2,4-dichlorophenyl)-5-(hydroxymethyl)pyrimidin-2-yl]amino}ethyl)(tert-butoxy)carboxamide (372 mg, 0.90 mmol) was dissolved in 2 mL of anhdyrous trifluoroacetic acid and stirred at room temperature for 2 h. Evaporation of the solvent afforded {2-[(2-aminoethyl)amino]-4-(2,4-dichlorophenyl)pyrimidin-5-yl}methan-1-ol, as its trifluoracetate salt, in quantitative yield.

{2-[(2-aminoethyl)amino]-4-(2,4-dichlorophenyl)pyrimidin-5-yl}methan-1-ol was dissolved in 3 mL of anhydrous THF and 1.47 g (4.50 mmol) of anhydrous cesium carbonate was added. 2-chloro-5-nitro-6-aminopyridine (143 mg, 0.9 mmol) was added in one portion and the yellow suspension heated at 70° C. for 18 h. The reaction mixture was filtered, concentrated and the residue chromatographed (silica gel, 5% methanol/methylene chloride) to give [4-(2,4-dichlorophenyl)-2-({2-[(5-nitro(2-pyridyl))amino]ethyl}amino)pyrimidin-5-yl]methan-1-ol, 216 mg (53%), as a yellow solid.

HPLC [Method AZ-S], 6.92 min (100%); MS (m+H/z), 450.

Example 139

Preparation of [4-(2,4-dichlorophenyl)-2-({2-[(5-nitro(2-pyridyl))amino]ethyl}amino)pyrimidin-5-yl]methan-1-ol The process of Example 140 is repeated using 2-chloro-5-nitro-pyridine and {2-[(2-aminoethyl)amino]-4-(2,4-dichlorophenyl)pyrimidin-5-yl}methan-1-ol. Chromatography of the residue (silica gel, 5% methanol/methylene chloride) afforded 200 mg (51%) of [4-(2,4-dichlorophenyl)-2-({2-[(5-nitro(2-pyridyl))amino]ethyl}amino)pyrimidin-5-yl]methan-1-ol as a yellow solid.

HPLC [Method AZ-S], 7.85 min (100%); MS (m+H/z), 435.

Example 140

Preparation of [4-(2,4-dichlorophenyl)-5-(morpholin-4-ylmethyl)pyrimidin-2-yl]{2-[(5-nitro(2-pyridyl))amino]ethyl}amine Using the method of Swern, et al., 100 mg of N-(2-{[4-(2,4-dichlorophenyl)-5-(hydroxymethyl)pyrimidin-2-yl]amino}ethyl)(tert-butoxy)carboxamide was dissolved in 1 mL of anhydrous methylene chloride and added to a solution of oxalyl chloride (30.7 μL, 0.363 mmol) and DMSO (51.6 μL, 0.726 mmol) which had been stirring at −78° C. for 15 min. The resulting solution was stirred for an additional 30 min, at which time 202 μL (1.45 mmol) of triethyl amine was added. The resulting suspension was allowed to warm to room temperature after 15 min and 1 mL of water was added and the layers separated. The aqueous layer was extracted with methylene chloride and the combined organic layers dried (sodium sulfate) and concentrated to afford N-(2-{[4-(2,4-dichlorophenyl)-5-formylpyrimidin-2-yl]amino}ethyl)(tert-butoxy)carboxamide as a light yellow foam. This product proved to be air sensitive and was used without further manipulation.

HPLC [Method AZ-S], 11.41 min (95%); MS (m+H/z), 411.

N-(2-{[4-(2,4-dichlorophenyl)-5-formylpyrimidin-2-yl]amino}ethyl)(tert-butoxy)carboxamide (50 mg, 0.121 mmol) was dissolved in 5 mL of THF, 242 μL of sodium cyanoborohydride (1 M in THF) and 5 μL of glacial acetic acid added and the mixture was heated to 70° C. for 18 h. Following slow addition of 1 mL of water to decompose excess reagent, the mixture was partitioned between ethyl acetate and saturated citric acid solution. The organic layer was discarded, and aqueous layer was carefully basified with sodium hydoxide to PH 9, then extracted with ethyl acetate twice. The combined organic layers was dried (sodium sulfate), concentrated, and purified by chromatography (selica gel, 10% methanol/methylene chloride) to afford N-(2-{[4-(2,4-dichlorophenyl)-5-(morpholin-4-ylmethyl)pyrimidin-2-yl]amino}ethyl)(tert-butoxy)carboxamide, 30 mg (52%).

HPLC [Method AZ-S], 8.28 min (95%); MS (m+H/z), 482.

Using the conditions described in Step 1.2 above, N-(2-{[4-(2,4-dichlorophenyl) 5-(morpholin-4-ylmethyl)pyrimidin-2-yl]amino}ethyl)(tert-butoxy)carboxamide was treated with anhydrous trifluouroacetic acid to afford (2-aminoethyl)[4-(2,4-dichlorophenyl)-5-(morpholin-4-ylmethyl)pyrimidin-2-yl]amine in near quantitative yield.

HPLC [Method AZ-S], 3.97 min (95%); MS (m+H/z), 382.

Using the conditions described in the previous example, (2-aminoethyl)[4-(2,4-dichlorophenyl)-5-(morpholin-4-ylmethyl)pyrimidin-2-yl]amine and 9.7 mg (0.061 mmol) of 2-chloro-5-nitropyridine gave [4-(2,4-dichlorophenyl)-5-(morpholin-4-ylmethyl)pyrimidin-2-yl]{2-[(5-nitro(2-pyridyl))amino]ethyl}amine in 60% yield following chromatography (silica gel, 5% methanol/methylene chloride).

HPLC [Method AZ-S], 7.43 min (100%); MS (m+H/z), 504.

Example 141

Preparation of [4-(2,4-dichlorophenyl)-5-(morpholin-4-ylmethyl)pyrimidin-2-yl]{2-[(5-nitro-6-amino(2-pyridyl))amino]ethyl}amine Using the conditions described in Example 139, (2-aminoethyl)[4-(2,4-dichlorophenyl)-5-(morpholin-4-ylmethyl)pyrimidin-2-yl]amine and 10.6 mg (0.061 mmol) of 2-chloro-5-nitro-6-aminopyridine afforded 191 mg (60%) of [4-(2,4-dichlorophenyl)-5-(morpholin-4-ylmethyl)pyrimidin-2-yl]{2-[(5-nitro-6-amino(2-pyridyl))amino]ethyl}amine as a yellow solid following chromatography (silica gel, 5% methanol/methylene chloride).

HPLC [Method AZ-S], 6.49 min (100%); MS (m+H/z), 519.

Example 142

Preparation of [4-(2,4-dichlorophenyl)-5-(morpholin-4-ylmethyl)pyrimidin-2-yl]{2-[(5-nitro-6-amino(2-pyridyl))amino]ethyl}amine and related compounds A suspension of 0.44 g (2.59 mmol) of 2,2,2-trifluoro-N-[2-(methylamino)ethyl]acetamide (prepared according to *Syn. Comm.*, 26:3633–3636 (1996)) and 0.38 g (2.59 mmol) of 1-pyrazolocarboxamidine hydrochloride in 5 mL anhydrous THF was stirred at room temperature for 3 h. Concentration of this suspension afforded a white solid which was found by 1H NMR analysis to consist of the desired guanidine, N-[2-(amidinomethylamino)ethyl]-2,2,2-trifluoroacetamide hydrochloride, and pyrazole. This was used without further purification in the next step.

A solution of 0.60 g (2.3 mmol) 2,4-dichloro-2-(1-imidazoyl)ethan-1-one, 0.38 mL (2.82 mmol) dimethyformamide dimethylacetal and 5 mL THF was refluxed for 2 h. Concentration afforded 1-(2,4-dichlorophenyl)-2-(1-imidazoyl)-3-dimethylaminoprop-2-en-1-one as a light red solid in quantitative yield. This solid was redissolved in 5 mL THF, 1.0 g (3.06 mmol) of anhydrous cesium carbonate and the residue containing N-[2-(amidinomethylamino) ethyl]-2,2,2-trifluoroacetamide hydrochloride described above were added and the resulting mixture heated to 70° C. for 18 h. After cooling, water was added and the resulting mixture extracted with methylene chloride. The aqueous layer was extracted with methylene chloride and the combined organics washed with brine, dried and concentrated to afford 1.56 g of a brown oil. Chromatography (silica gel, 5% methanol/methylene chloride) afforded 0.35 g of the desired pyrimidine, N-(2-{[4-(2,4-dichlorophenyl)-5-imidazolylpyrimidin-2-yl]methylamino}ethyl)-2,2,2-trifluoroacetamide as a brown solid.

HPLC [Method AZ-S], 7.68 min (85%); MS (m+H/z), 459.

The aforementioned pyrimidine, N-(2-{[4-(2,4-dichlorophenyl)-5-imidazolyl-pyrimidin-2-yl]methylamino}ethyl)-2,2,2-trifluoroacetamide (114 mg, 0.25 mmol) was dissolved in 2 mL methanol and potassium hydroxide (40 mg, 1 mmol) added. This suspension was stirred at room temperature for 1 hour. Water was added, and the solution extracted with methylene chloride. The aqueous layer was thoroughly extracted with methylene chloride and the organic layers washed with brine, dried and concentrated to give the deprotected primary amine, (2-aminoethyl)[4-(2,4-dichlorophenyl)-5-imidazolylpyrimidin-2-yl]methylamine, in quantitative yield.

HPLC [Method AZ-S], 4.43 min (90%); MS (m+H/z), 363.

Using the procedure described above in Example 139, reaction of (2-aminoethyl) [4-(2,4-dichlorophenyl)-5-imidazolylpyrimidin-2-yl]methylamine and 2-chloro-5-nitropyridine were reacted to afford [4-(2,4-dichlorophenyl)-5-imidazolylpyrimidin-2-yl]methyl{2-[(5-nitro(2-pyridyl))amino]ethyl}amine (73174).

HPLC [Method AZ-S], 7.82 min (100%); MS (m+H/z), 485.

Using the procedure described above, reaction of (2-aminoethyl)[4-(2,4-dichlorophenyl)-5-imidazolylpyrimidin-2-yl]methylamine and 2-chloro-5-nitro-6-amino-pyridine were reacted to afford [4-(2,4-dichlorophenyl)-5-imidazolylpyrimidin-2-yl]methyl{2-[(5-nitro-6-amino(2-pyridyl))amino]ethyl}amine.

HPLC [Method AZ-S], 6.73 min (100%); MS (m+H/z), 500.

Using the procedure described above in Example 139, reaction of (2-aminoethyl) [4-(2,4-dichlorophenyl)-5-imidazolylpyrimidin-2-yl]methylamine and 2-chloro-5-cyanopyridine were reacted to afford [4-(2,4-dichlorophenyl)-5-imidazolylpyrimidin-2-yl]methyl{2-[(5-cyano(2-pyridyl))amino]ethyl}amine.

HPLC [Method AZ-S], 6.49 min (100%); MS (m+H/z), 465.

A solution of 0.60 g (2.3 mmol) 2,4-dichloro-2-(2-imidazoyl)ethan-1-one, 0.38 mL (2.82 mmol) dimethyformamide dimethylacetal and 5 mL THF was refluxed for 2 h. Concentration afforded 1-(2,4-dichlorophenyl)-2-(2-imidazoyl)-3-(dimethylamino)prop-2-en-1-one as a light red solid in quantitative yield. This solid was redissolved in 5 mL THF, 1.0 g (3.06 mmol) of anhydrous cesium carbonate and N-[2-(amidinomethylamino) ethyl]-2,2,2-trifluoroacetamide hydrochloride (vide supra) were added and the resulting mixture heated to 70° C. for 18 h. After cooling, water was added and the resulting mixture extracted with methylene chloride. The aqueous layer was extracted with methylene chloride and the combined organics washed with brine, dried and concentrated to afford a brown oil. Chromatography (silica gel, 5% methanol/methylene chloride) afforded 0.30 g of the desired pyrimidine, N-(2-{[4-(2,4-dichlorophenyl)-5-imidazol-2-ylpyrimidin-2-yl]methylamino}ethyl)-2,2,2-trifluoroacetamide, as a brown solid.

HPLC [Method AZ-S], 7.25 min (100%); MS (m+H/z), 459.

The aforementioned pyrimidine, N-(2-{[4-(2,4-dichlorophenyl)-5-imidazol-2-ylpyrimidin-2-yl]methylamino}ethyl)-2,2,2-trifluoroacetamide (114 mg, 0.25 mmol) was dissolved in 2 mL methanol and potassium hydroxide (40 mg, 1 =mol) added. This suspension was stirred at room temperature for 1 hour. Water was added, and the solution extracted with methylene chloride. The aqueous layer was thoroughly extracted with methylene chloride and the organic layers washed with brine, dried and concentrated to give the deprotected primary amine, (2-aminoethyl)[4-(2, 4-dichlorophenyl)-5-imidazol-2-ylpyrimidin-2-yl]methylamine in quantitative yield.

HPLC [Method AZ-S], 3.92 min (100%); MS (m+H/z), 363.

Using the procedure described above in Example 139, reaction of (2-aminoethyl)[4-(2,4-dichlorophenyl)-5-imidazol-2-ylpyrimidin-2-yl]methylamine and 2-chloro-5-cyano-pyridine were reacted to afford [4-(2,4-dichlorophenyl)-5-imidazol-2-ylpyrimidin-2-yl]methyl{2-[(5-cyano(2-pyridyl))amino]ethyl}amine.

HPLC [Method AZ-S], 5.98 min (100%); MS (m+H/z), 465.

Using the procedure described above in Example 139, reaction of (2-aminoethyl)[4-(2,4-dichlorophenyl)-5-imidazol-2-ylpyrimidin-2-yl]methylamine and 2-chloro-5-nitro-pyridine were reacted to afford [4-(2,4-dichlorophenyl)-5-imidazol-2-ylpyrimidin-2-yl]methyl{2-[(5-nitro(2-pyridyl))amino]ethyl}amine.

HPLC [Method AZ-S], 7.31 min (100%); MS (m+H/z), 485.

Using the procedure described above in Example 139, reaction of (2-aminoethyl)[4-(2,4-dichlorophenyl)-5-imidazol-2-ylpyrimidin-2-yl]methylamine and 2-chloro-5-nitro-6-aminopyridine were reacted to afford [4-(2,4-dichlorophenyl)-5-imidazol-2-ylpyrimidin-2-yl]methyl{2-[(5-nitro-6-amino(2-pyridyl))amino]ethyl}amine.

HPLC [Method AZ-S], 5.85 min (100%); MS (m+H/z), 500.

Example 143

Preparation of {2-[4-(2,4-dichlorophenyl)-5-imidazolylpyrimidin-2-yloxy]ethyl}(5-nitro(2-pyridyl))amine (76062) and related compounds A suspension of 1.50 g (4.84 mmol) 1-(2,4-dichlorophenyl)-2-(1-imidazoyl)-3-dimethylaminoprop-2-en-1-one (prepared as described in Step 3.1 above), 0.673 g (2.42 mmol) of S-methylisothiourea nitrate and 2.05 g (6.29 mmol) in 30 mL of N-methylpyrrolidinone (NMP) was heated to 80° C. for 2 h. Water was added and the mixture extracted with ethyl acetate. The aqueous layer was further extracted with additional ethyl acetate. The combined organic layers were thoroughly washed with water, brine and dried with sodium sulfate. Concentration and chromatography of the residue (silica gel, 2% methanol/methylene chloride) afforded 800 mg (50%) of the desired pyrimidine, 4-(2,4-dichlorophenyl)-5-imidazolyl-2-methylthiopyrimidine.

HPLC [Method AZ-S], 7.40 min (100%); MS (m+H/z), 337.

4-(2,4-dichlorophenyl)-5-imidazolyl-2-methylthiopyrimidine (219 mg, 0.65 mmol) was dissolved in 2 mL anhydrous methylene chloride and 590 mg (57–86%, 1.95 mmol) of m-chloroperoxybenzoic acid added at room temperature and stirred for 2 h. Saturated sodium carbonate was added and the organic layer separated and washed with 10% aqueous sodium sulfite. Drying (sodium sulfate) and concentration afforded 240 mg (100%) of 4-(2,4-dichlorophenyl)-5-imidazolyl-2-(methylsulfonyl) pyrimidine as a yellow solid which was used without further purification.

HPLC [Method AZ-S], 5.47 min (100%); MS (m+H/z), 369.

To a stirred suspension of 1.58 g 2-chloro-5-nitropyridine (10.0 mmol) in 10 mL acetonitrile was added 1.81 mL (30 mmol) of ethanolamine dropwise at room temperature. After heating at 80° C. for 0.5 h, the reaction was cooled, water was added, followed by the addition of ether. Cooling this biphasic mixture at 5° C. led to the formation of a yellow solid, which was collected and identified as 2-[(5-nitro-2-pyridyl)amino]ethan-1-ol.

HPLC [Method AZ-S], 1.74 min (100%); MS (m+H/z), 184.

1.74 g 2-chloro-5-nitro-6-aminopyridine (10.0 mmol) was reacted at 80° C. with 1.81 mL (30 mmol) of ethanolamine. Cooling the reaction mixture led to the formation of a yellow solid, which was collected and identified as 2-[(6-amino-5-nitro-2-pyridyl)amino]ethan-1-ol.

HPLC [Method AZ-S], 1.32 min (100%); MS (m+H/z), 199.

1.38 g 2-chloro-5-cyanopyridine (10.0 mmol) was reacted with 1.81 mL (30 mmol) of ethanolamine at 80° C. for 0.5 h. The reaction was cooled, water was added, followed by the addition of ether. Cooling this biphasic mixture at 5° C. led to the formation of a yellow solid, which was collected and identified as 6-[(2-hydroxyethyl)amino]pyridine-3-carbonitrile.

HPLC [Method AZ-S], 1.13 min (100%); MS (m+H/z), 164.

To a stirred solution of 37.2 mg (0.203 mmol) of 2-(5-nitro-2-aminopyridyl)ethanolamine in 1 mL anydrous THF at room temperature was added 244 μL of a 1M solution of sodium hexamethyldisilazide (1M in toluene, 0.244 mmol). This solution was stirred for 1 h, and a solution of 4-(2,4-dichlorophenyl)-5-imidazolyl-2-(methylsulfonyl) pyrimidine in 1 mL anhydrous THF was added dropwise. After stirring for 4 h, water was added and the reaction mixture thoroughly extracted with ethyl acetate. The combined organics were washed with brine, dried (sodium sulfate), concentrated and chromatographed (silica gel, 5% methanol/methylene chloride) to give 15.7 mg of {2-[4-(2,4-dichlorophenyl)-5-imidazolylpyrimidin-2-yloxy]ethyl}(5-nitro(2-pyridyl))amine (76062) as a yellow solid.

HPLC [Method AZ-S], 7.44 min (85%); MS (m+H/z), 472.

As described above, {2-[4-(2,4-dichlorophenyl)-5-imidazolylpyrimidin-2-yloxy]ethyl}(5-nitro-6-amino(2-pyridyl))amine (76063) was synthesized using 4-(2,4-dichlorophenyl)-5-imidazolyl-2-(methylsulfonyl) pyrimidine and 2-(5-nitro-6-amino-2-pyridyl)ethanolamine to afford 24.3 mg of {2-[4-(2,4-dichlorophenyl)-5-imidazolylpyrimidin-2-yloxy]ethyl}(5-nitro-6-amino(2-pyridyl))amine as a light yellow solid.

HPLC [Method AZ-S], 6.47 min (90%); MS (m+H/z), 487.

As described in above, {2-[4-(2,4-dichlorophenyl)-5-imidazolylpyrimidin-2-yloxy]ethyl}(5-cyano(2-pyridyl)) amine (76064) was synthesized using 4-(2,4-dichlorophenyl)-5-imidazolyl-2-(methylsulfonyl)pyrimidine and 6-[(2-hydroxyethyl)amino]pyridine-3-carbonitrile to afford 27.6 mg of {2-[4-(2,4-dichlorophenyl)-5-imidazolylpyrimidin-2-yloxy]ethyl}(5-cyano(2-pyridyl)) amine as a light yellow solid.

HPLC [Method AZ-S], 6.37 min (95%); MS (m+H/z), 452.

Example 144

Preparation of [2-(dimethylamino)ethoxy]-N-[4-(4-cyanophenyl)-2-({2-[(5-nitro(2-pyridyl))amino] ethyl}amino)pyrimidin-5-yl]carboxamide A solution of 50 mg (0.12 mmol) of 4-(4-cyanophenyl)-2-({2-[(5-nitro(2-pyridyl))amino]ethyl}amino)pyrimidine- 5-carboxylic acid, 26.2 ide (0.12 mmol, DPPA), 17.2 μL of triethylamine (0.12 mmol) in 2 mL of THF was heated to 75° C. for 24 hours. After cooling, the solution was concentrated and the residue chromatographed (silica, 5% methanol/methylene chloride) to give 40.2 mg (68%) of the desired carbamate, [2-(dimethylamino)ethoxy]-N-[4-(4-cyanophenyl)-2-({2-[(5-nitro(2-pyridyl))amino]ethyl}amino)pyrimidin-5-yl]carboxamide, as a colorless solid.

HPLC [Method AZ-S], 6.23 min (100%); MS (m+H/z), 492.

Example 145

Preparation of Additional Compounds

The compounds described in detail below were synthesized using the following general procedures:

Step A. Alkylation 1 mmol of aryl substituted phenacyl chloride in DMF was added drop wise to 2 mmol of amine and 2 mmol of $Cs_2CO_3$ in DMF at room temperature for fourteen hours. The reaction mixture was concentrated in vacuo and diluted with water and ethyl acetate. The solution was extracted three times with ethyl acetate, dried over sodium sulfate, and purified by column chromatography or trituration.

Step B. Enaminone Formation 1 mmol of substrate was heated to 80° C. in neat DMF-DMA for six hours. Product was concentrated in vacou and purified by trituration with diethyl ether.

Step C. Pyrimidine Formation 1 mmol of substrate, 1 mmol of guanadine, and 3 mmol of $Cs_2CO_3$ was dissolved in DMF and heated to 90° C. for fourteen hours. The reaction mixture was concentrated in vacuo and diluted with water and ethyl acetate. The solution was extracted three times with ethyl acetate, dried over sodium sulfate, and purified by column chromatography with 5–10% methanol in methylenechloride.

Step D. Cyclization to Imide 1 mmol of substrate was heated to 120° C. in acetic acid for four hours and then concentrated in vacuo and purified by column chromatography with 5–10% methanol in methylenechloride.

Step E. Phthalimide Cleavage 1 mmol of substrate and 20 mmol of hydrazine were stirred in ethanol at 75° C. The Ethanol was removed from the reaction mixture in vacuo and then methylene chloride was added the solution was filtered. The filtrate was collected and concentrated in vacuo.

Step F. Acid Coupling 1 mmol of substrate, 2 mmol of carboxylic acid, 2 mmol of HBTU, and 3 mmol of Diisopropylethyl amine were stirred in THF. The reaction mixture was concentrated in vacuo and diluted with water and ethyl acetate. The solution was extracted three times with ethyl acetate, dried over sodium sulfate, and purified by column chromatography with 5–10% methanol in methylenechloride.

Step G. Boc Deprotection 1 mmol of substrate was stir in a mixture of 1 ml methylenechloride and 1 ml trifloroacetic acid at 40° C. for 30 min. and concentrated in vacuo.

Step H. SnAr Tail Piece 1 mmol of substrate, 1.5 mmol of a substituted 2-chloropyridine, and 4 mmol of Diisopropylethyl amine were stirred in 2 ml of DMF at 80° C. for fourteen hours. The reaction mixture was concentrated in vacuo and diluted with water and ethyl acetate. The solution was extracted three times with ethyl acetate, dried over sodium sulfate, and purified by column chromatography with 5–10% methanol in methylenechloride.

Step I. Bromination 20 mmol of aryl substituted acetiphenone, 1 ml conc. HCl were mixed in 20 ml diethyl ether at 0° C. under nitrogen. To this solution a solution of 20 mmol $Br_2$ in 20 ml chloroform was added drop wise and left for four hours and then concentrated in vacuo.

Step J. SnAr on Ketone 1 mmol of 1-(4-fluorophenyl)-2-imidazolylethan-1-one, 0.3 mmol of an amine, and 1 mmol of $K_2CO_3$ were heated at 100° C. for 14 hours. The reaction mixture was poured over ice, then filtered, and the solid was collected.

Step K. Anhydride Coupling 1 mmol of substrate and 1 mmol of anhydride were stirred at room temperature for four hours in THF. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

Step L. Suzuki Reaction 1 mmol of a 2,6-dichloro-pyridine, 1.05 mmol of boronic acid, and 3 mmol of $Na_2CO_3$ were dissolved in 1.5 ml THF and 0.5 ml water and purged with nitrogen. 0.05 mmol of [1,1'-Bis(diphenylphosphino)ferrocne]dichloropalladium (II) was added to reaction and stirred at room temperature under nitrogen for 14 hours. The reaction mixture was diluted with water and ethyl acetate. The solution was extracted three times with ethyl acetate, dried over sodium sulfate, and purified by column chromatography with 10% ethylacetate 90% hexanes.

Step M. SnAr Reaction 1 mmol of substrate is taken with 2 mmol of amine and 3 mmol of Diisopropylethyl amine in 2 ml of DMF at 80° C. for two hours. The reaction mixture was concentrated in vacuo and diluted with water and ethyl acetate. The solution was extracted three times with ethyl acetate, dried over sodium sulfate, and purified by column chromatography 30% ethylacetate 70% hexanes.

Step N. Nitro Reduction 1 mmol of substrate was taken with an equal weight of 5% Pd-C with 20 mmol $N_2H_4$ and dissolved in THF. The reaction was stirred at reflux for 24 hrs and then filtered through celite and purified by column chromatography.

Step O. Ethanol Nitro Reduction 1 mmol of substrate was taken with an equal weight of 5% Pd-C and dissolved in ethanol. The reaction was placed in a Parr shaker under 35 PSI of hydrogen for six hours, then filtered through celite, and purified by column chromatography.

Example 145-4

Preparation of [4-(2,4-difluorophenyl)-5-imidazolylpyrimidin-2-yl]{2-[(5-nitro(2-pyridyl))amino]ethyl}amine

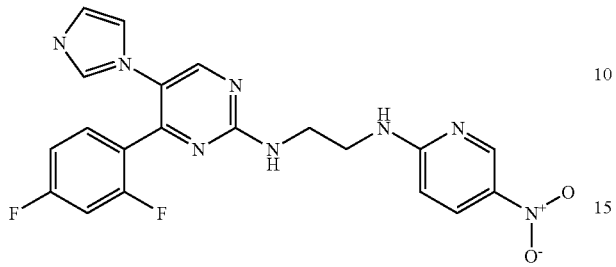

[4-(2,4-difluorophenyl)-5-imidazolylpyrimidin-2-yl]{2-[(5-nitro(2-pyridyl))amino]ethyl}amine was made in accordance with the foregoing procedures using 1-(2,4-difluorophenyl)-2-chloroethan-1-one and imidazole in step A, step B and amino{2-[(5-nitro(2-pyridyl))amino]ethyl}carboxamidine in step C.

HPLC: 7.150 min.

MS: MH$^+$=439.1

Example 145-2

Preparation of [5-imidazolyl-4-(4-methylphenyl)pyrimidin-2-yl]{2-[(5-nitro(2-pyridyl))amino]ethyl}amine

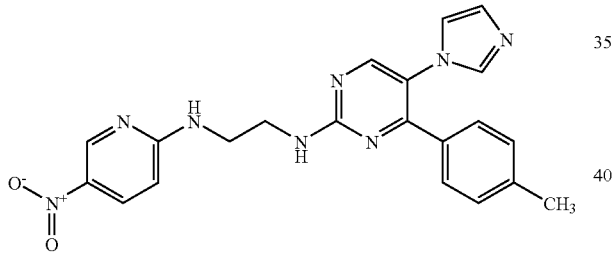

[5-imidazolyl-4-(4-methylphenyl)pyrimidin-2-yl]{2-[(5-nitro(2-pyridyl))amino]ethyl}amine was made in accordance with the foregoing procedures using 2-bromo-1-(4-methylphenyl)ethan-1-one and imidazole in step A, step B and amino{2-[(5-nitro(2-pyridyl))amino]ethyl}carboxamidine in step C.

HPLC: 7.333 min.

MS: MH$^+$=417.2

Example 145-3

Preparation of [4-(2-chlorophenyl)-5-imidazolylpyrimidin-2-yl]{2-[(5-nitro(2-pyridyl))amino]ethyl}amine

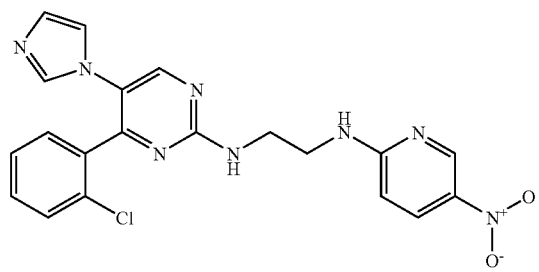

[4-(2-chlorophenyl)-5-imidazolylpyrimidin-2-yl]{2-[(5-nitro(2-pyridyl))amino]ethyl}amine was made in accordance with the foregoing procedures through step I, using 1-(2-chlorophenyl)ethan-1-one and imidazole in step A, step B and amino{2-[(5-nitro(2-pyridyl))amino]ethyl}carboxamidine in step C.

HPLC: 7.233 min.

MS: MH$^{3O}$ =437.1

Example 145-4

Preparation of tert-butyl 4-{4-[5-imidazolyl-2-({2-[(5-nitro(2-pyridyl))amino]ethyl}amino)pyrimidin-4-yl]phenyl}piperazinecarboxylate

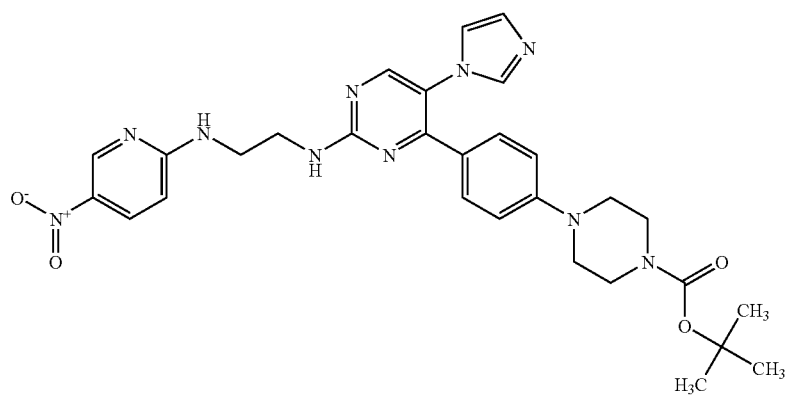

tert-butyl 4-{4-[5-imidazolyl-2-({2-[(5-nitro(2-pyridyl)) amino]ethyl}amino)pyrimidin-4-yl]phenyl}piperazinecarboxylate was made in accordance with the foregoing procedures using 2-bromo-1-(4-fluorophenyl)ethan-1-one and imidazole in step A, step J using tert-butyl piperazinecarboxylate, step B and amino{2-[(5-nitro(2-pyridyl))amino]ethyl}carboxamidine in step C.

HPLC: 9.670 min.

MS: MH$^+$=587.2

Example 145–5

Preparation of {5-imidazolyl-4-[4-(trifluoromethyl)phenyl]pyrimidin-2-yl}{2-[(5-nitro(2-pyridyl))amino]ethyl}amine

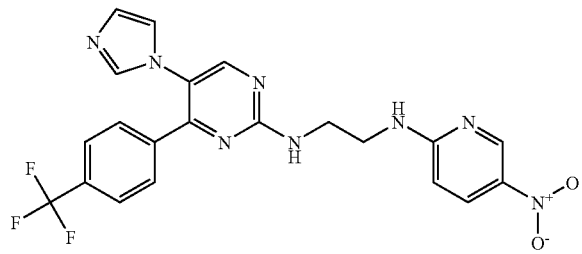

{5-imidazolyl-4-[4-(trifluoromethyl)phenyl]pyrimidin-2-yl}{2-[(5-nitro(2-pyridyl))amino]ethyl}amine was made in accordance with the foregoing procedures through step I using 1-[4-(trifluoromethyl)phenyl]ethan-1-one, A using imidazole, B, and C using amino{2-[(5-nitro(2-pyridyl))amino]ethyl}carboxamidine.

HPLC: 8.533 min.

MS: MH$^+$=471.2

Example 145-6

Preparation of [4-(4-ethylphenyl)-5-imidazolylpyrimidin-2-yl]{2-[(5-nitro(2-pyridyl))amino]ethyl}amine

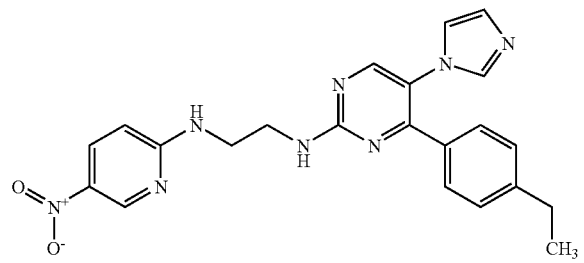

[4-(4-ethylphenyl)-5-imidazolylpyrimidin-2-yl]{2-[(5-nitro(2-pyridyl))amino]ethyl}amine was made in accordance with the foregoing procedures through steps I using 1-(4-ethylphenyl)ethan-1-one, A using imidazole, B, and C using amino{2-[(5-nitro(2-pyridyl))amino]ethyl}carboxamidine.

HPLC: 8.267 min.

MS: MH$^+$=431.2

Example 145-7

Preparation of [4-(3,5-dichloro(2-thienyl))-5-imidazolylpyrimidin-2-yl]{2-[(5-nitro(2-pyridyl))amino]ethyl}amine

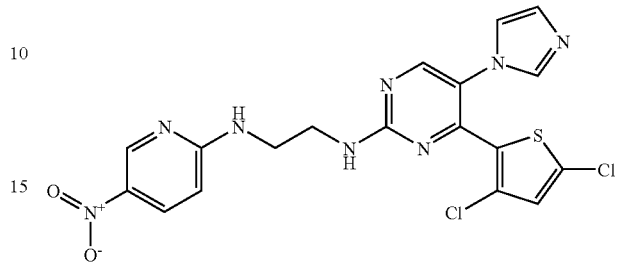

[4-(3,5-dichloro(2-thienyl))-5-imidazolylpyrimidin-2-yl]{2-[(5-nitro(2-pyridyl))amino]ethyl}amine was made in accordance with the foregoing procedures through steps I using 1-(3,5-dichloro-2-thienyl)ethan-1-one, A using imidazole, B, and C using amino{2-[(5-nitro(2-pyridyl))amino]ethyl}carboxamidine.

HPLC: 8.167 min.

MS: MH$^+$=477.1

Example 145-8

Preparation of [5-imidazolyl-4-(4-piperazinylphenyl)pyrimidin-2-yl]{2-[(5-nitro(2-pyridyl))amino]ethyl}amine

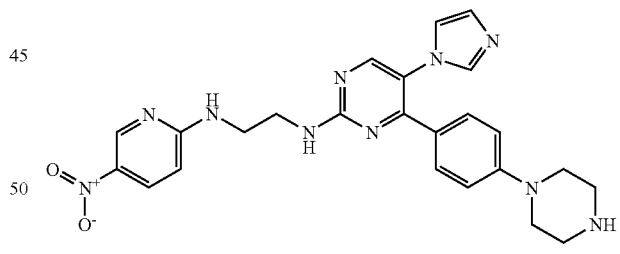

[5-imidazolyl-4-(4-piperazinylphenyl)pyrimidin-2-yl]{2-[(5-nitro(2-pyridyl))amino]ethyl}amine was made in accordance with the foregoing procedures through steps A using 2-bromo-1-(4-fluorophenyl)ethan-1-one and imidazole, J using tert-butyl piperazinecarboxylate, B, C using amino{2-[(5-nitro(2-pyridyl))amino]ethyl}carboxamidine, and G.

HPLC:

MS: MH$^+$=487.3

Example 145–9

Preparation of 2-{N-[4-(2,4-dichlorophenyl)-2-({2-[(5-nitro(2-pyridyl))amino]ethyl}amino)pyrimidin-5-yl]carbamoyl}benzoic acid

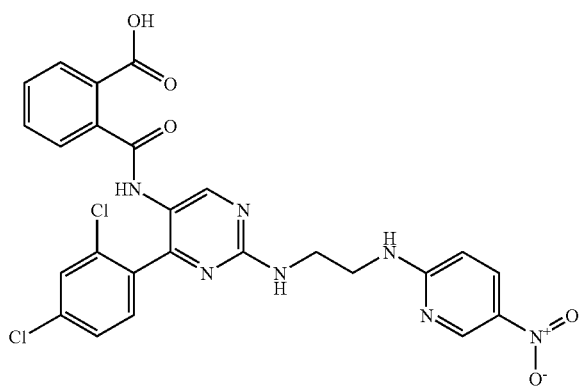

2-{N-[4-(2,4-dichlorophenyl)-2-({2-[(5-nitro(2-pyridyl))amino]ethyl}amino)pyrimidin-5-yl]carbamoyl}benzoic acid was made in accordance with the foregoing procedures through steps A using 1-(2,4-dichlorophenyl)-2-chloroethan-1-one and phthalimide, B, and C using amino{2-[(5-nitro(2-pyridyl))amino]ethyl}carboxamidine.

HPLC: 11.433 min.

MS: MH⁺=568.1

Example 145–10

Preparation of 5-[5-imidazolyl-2-({2-[(5-nitro(2-pyridyl))amino]ethyl}amino)pyrimidin-4-yl]thiophene-2-cabonitrile

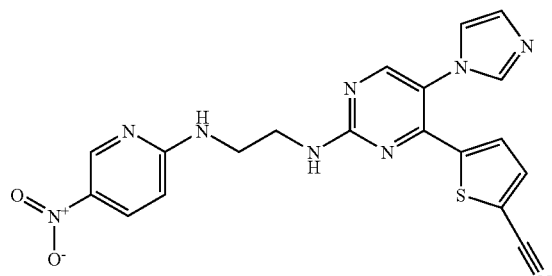

5-[5-imidazolyl-2-({2-[(5-nitro(2-pyridyl))amino]ethyl}amino)pyrimidin-4-yl]thiophene-2-carbonitrile was made in accordance with the foregoing procedures through steps I using 5-acetylthiophene-2-carbonitrile, A using imidazole, B, and C using amino {2-[(5-nitro(2-pyridyl))amino]ethyl}carboxamidine.

HPLC 7.517 min.

MS: MH⁺=434.1

Example 145-11

Preparation of {5-imidazolyl-4-[4-(4-methylpiperazinyl)phenyl]pyrimidin-2-yl}{2-[(5-nitro(2-pyridyl))amino]ethyl}amine

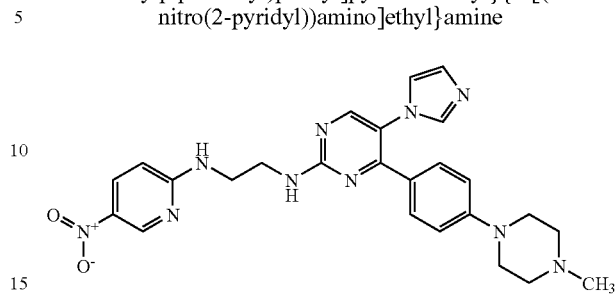

{5-imidazolyl-4-[4-(4-methylpiperazinyl)phenyl]pyrimidin-2-yl}{2-[(5-nitro(2-pyridyl))amino]ethyl}amine was made in accordance with the foregoing procedures through steps A using 2-bromo-1-(4-fluorophenyl)ethan-1-one and imidazole, J using methylpiperazine, B, and C using amino{2-[(5-nitro(2-pyridyl))amino]ethyl}carboxamidine.

HPLC: 5.417 min.

MS: MH⁺=501.3

Example 145-12

Preparation of [5-imidazolyl-4-(4-piperidylphenyl)pyrimidin-2-yl]{2-[(5-nitro(2-pyridyl))amino]ethyl}amine

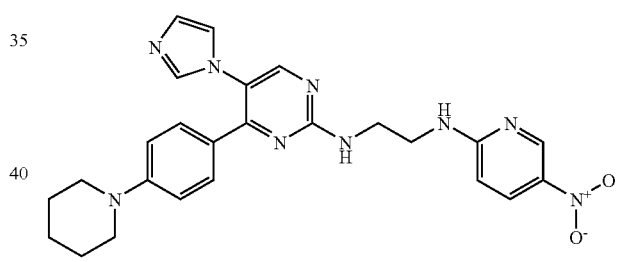

[5-imidazolyl-4-(4-piperidylphenyl)pyrimidin-2-yl]{2-[(5-nitro(2-pyridyl))amino]ethyl}amine was made in accordance with the foregoing procedures through steps A using 2-bromo-1-(4-fluorophenyl)ethan-1-one and imidazole, J using piperidine, B, and C using amino{2-[(5-nitro(2-pyridyl))amino]ethyl}carboxamidine.

HPLC: 6.300 min.

MS: MH⁺=486.2

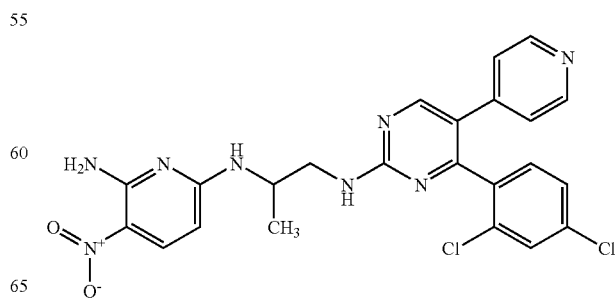

Example 145-13

Preparation of N-{2-[(6-amino-5-nitro(2-pyridyl))amino]ethyl}-N-[4-(2,4-dichlorophenyl)-5-(3,5-dioxomorpholin-4-yl)pyrimidin-2-yl]acetamide

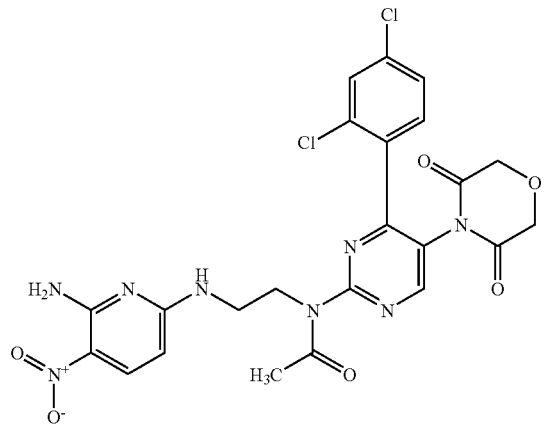

N-{2-[(6-amino-5-nitro(2-pyridyl))amino]ethyl}-N-[4-(2,4-dichlorophenyl)-5-(3,5-dioxomorpholin-4-yl)pyrimidin-2-yl]acetamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and K using 1,4-dioxane-2,6-dione and then an excess of acetic anhydride.

HPLC: 13.117 min.

MS: MH$^+$=575.1

Example 145-14

Preparation of N-[2-({2-[(6-amino-5-nitro(2-pyridyl))amino]ethyl}amino)-4-(2,4-dichlorophenyl)pyrimidin-5-yl]acetamide

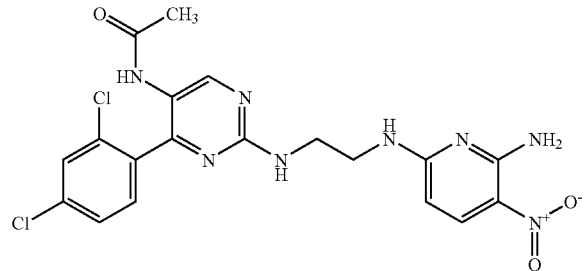

N-[2-({2-[(6-amino-5-nitro(2-pyridyl))amino]ethyl}amino)-4-(2,4-dichlorophenyl)pyrimidin-5-yl]acetamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and K using acetic anhydride.

HPLC: 10.200 min.

MS: MH$^+$=477.0

Example 145-15

Preparation of 4-[2-({2-[(6-amino-5-nitro(2-pyridyl))amino]ethyl}amino)-4-(2,4-dichlorophenyl)pyrimidin-5-yl]morpholine-3,5-dione

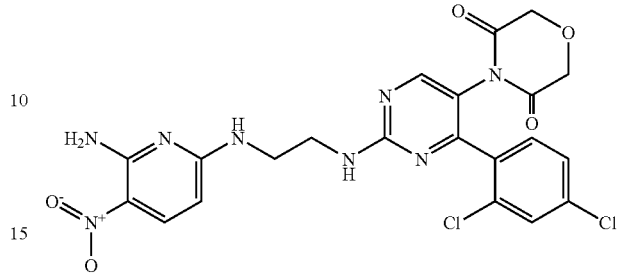

4-[2-({2-[(6-amino-5-nitro(2-pyridyl))amino]ethyl}amino)-4-(2,4-dichlorophenyl)pyrimidin-5-yl]morpholine-3,5-dione was made in accordance with the foregoing procedures through steps steps A using 1-(2,4-dichlorophenyl)-2-chloroethan-1-one and phthalimide, B, C using amino{2-[(6-amino-5-nitro(2-pyridyl))amino]ethyl}carboxamidine, D, E, K using 1,4-dioxane-2,6-dione, and F.

HPLC: 9.317 min.

MS: MH$^+$=533.1

Example 145-16

Preparation of N-[2-({2-[(6-amino-5-nitro(2-pyridyl))amino]ethyl}amino)-4-(2,4-dichlorophenyl)pyrimidin-5-yl]-2-(dimethylamino)acetamide

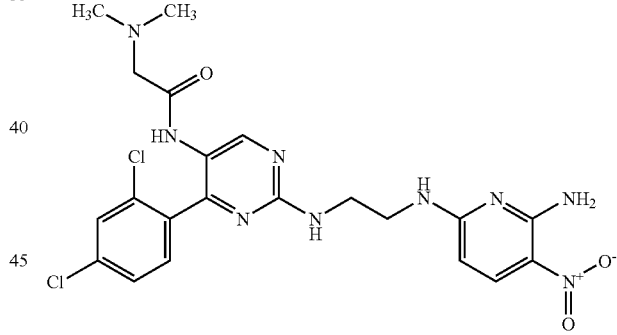

N-[2-({2-[(6-amino-5-nitro(2-pyridyl))amino]ethyl}amino)-4-(2,4-dichlorophenyl)pyrimidin-5-yl]-2-(dimethylamino)acetamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and F using 2-(dimethylamino)acetic acid.

HPLC: 6.567 min.

MS: MH$^+$=520.2

Example 145-17

Preparation of 1-[2-({2-[(6-amino-5-nitro(2-pyridyl))amino]ethyl}amino)-4-(2,4-dichlorophenyl)pyrimidin-5-yl]-3-pyrroline-2,5-dione 1-[2-({2-[(6-amino-5-nitro(2-pyridyl))amino]ethyl}amino)-4-(2,4-dichlorophenyl)pyrimidin-5-yl]-3- pyrroline-2,5-dione was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, K using malic anhydride, and F.

HPLC: 10.083 min.
MS: MH$^+$=515.1

Example 145-18

Preparation of 4-[4-(2,4-dichlorophenyl)-2-({2-[(5-nitro(2-pyridyl))amino]ethyl}amino)pyrimidin-5-yl]morpholine-3,5-dione 4-[4-(2,4-dichlorophenyl)-2-({2-[(5-nitro(2-pyridyl))amino]ethyl}amino)pyrimidin-5-yl]morpholine-3,5-dione was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, K using 1,4-dioxane-2,6-dione, and F.

HPLC:
MS: MH$^+$=518.1

Example 145-19

Preparation of N-[2-({2-[(6-amino-5-nitro(2-pyridyl))amino]ethyl}amino)-4-(2,4-dichlorophenyl)pyrimidin-5-yl]-4-morpholin-4-ylbutanamide N-[2-({2-[(6-amino-5-nitro(2-pyridyl))amino]ethyl}amino)-4-(2,4-dichlorophenyl)pyrimidin-5-yl]-4-morpholin-4-ylbutanamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, F using 4-chlorobutanoic acid. 1mmol of N-[2-({2-[(6-amino-5-nitro(2-pyridyl))amino]ethyl}amino)-4-(2,4-dichlorophenyl)pyrimidin-5-yl]-4-bromobutanamide, 2 mmol of morpholine, 3 mmol Diisopropylethyl amine, and 0.1 mmol of tetrabutylammonium iodide were stirred at room temperature for fourteen hours. The reaction mixture was concentrated in vacuo and diluted with water and ethyl acetate. The solution was extracted three times with ethyl acetate, dried over sodium sulfate, and purified by column chromatography with 5–10% methanol in methylenechloride.

HPLC: 4.837 min.
MS: MH$^+$=590.2

Example 145-20

Preparation of 1-[2-({2-[(6-amino-5-nitro(2-pyridyl))amino]ethyl}amino)-4-(2,4-dichlorophenyl)pyrimidin-5-yl]piperazine-2,6-dione 1-[2-({2-[(6-amino-5-nitro(2-pyridyl))amino]ethyl}amino)-4-(2,4-dichlorophenyl)pyrimidin-5-yl]piperazine-2,6-dione was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, F using 2-[(tert-butoxy)-N-(carboxymethyl)carbonylamino]acetic acid, and G.

HPLC: 5.825 min.
MS: MH$^+$=532.2

Example 145-21

Preparation of tert-butyl 4-[2-({2-[(6-amino-5-nitro(2-pyridyl))amino]ethyl}amino)-4-(2,4-dichlorophenyl)pyrimidin-5-yl]-3,5-dioxopiperazinecarboxylate

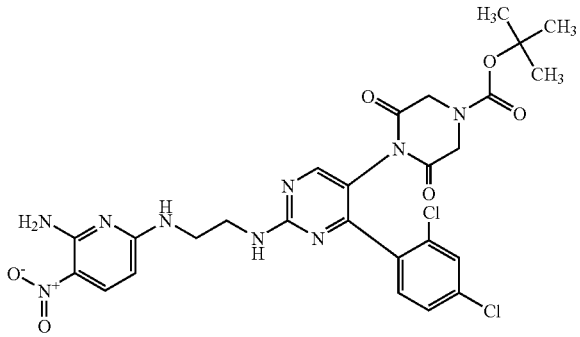

tert-butyl 4-[2-({2-[(6-amino-5-nitro(2-pyridyl))amino]ethyl}amino)-4-(2,4-dichlorophenyl)pyrimidin-5-yl]-3,5-dioxopiperazinecarboxylate was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and F using 2-[(tert-butoxy)-N-(carboxy-methyl)carbonylamino]acetic acid.

HPLC: 9.137 min.
MS: MH$^+$=632.2

Example 145-22

Preparation of tert-butyl 4-[4-(2,4-dichlorophenyl)-2-({2-[(5-nitro(2-pyridyl))amino]ethyl}amino)pyrimidin-5-yl]-3,5-dioxopiperazinecarboxylate

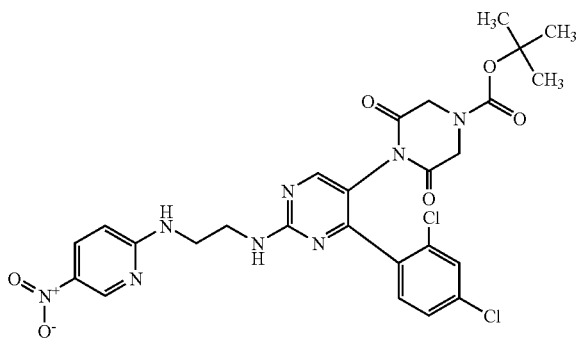

tert-butyl 4-[4-(2,4-dichlorophenyl)-2-({2-[(5-nitro(2-pyridyl))amino]ethyl}amino)pyrimidin-5-yl]-3,5-dioxopiperazinecarboxylate was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, and F using 2-[(tert-butoxy)-N-(carboxymethyl)carbonylamino]acetic acid.

HPLC: 9.861 min.
MS: MH$^+$=617.2

Example 145-23

Preparation of 1-[4-(2,4-dichlorophenyl)-2-({2-[(5-nitro(2-pyridyl))amino]ethyl}amino)pyrimidin-5-yl]piperazine-2,6dione

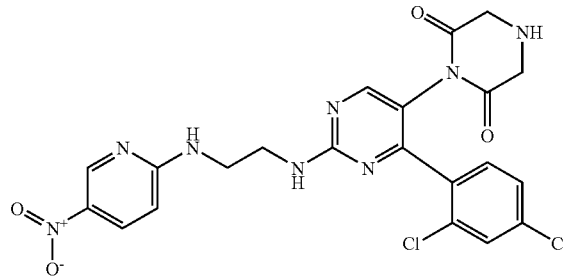

1-[4-(2,4-dichlorophenyl)-2-({2-[(5-nitro(2-pyridyl))amino]ethyl}amino)pyrimidin-5-yl]piperazine-2,6-dione was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, F using 2-[(tert-butoxy)-N-(carboxymethyl)carbonylamino]acetic acid, and G.

HPLC: 6.554 min.
MS: MH$^+$=517.2

Example 145-24

Preparation of tert-butyl 4-[2-({2-[(6-amino-5-nitro(2-pyridyl))amino]ethyl}amino)-4-(2,4-dichlorophenyl)pyrimidin-5-yl]-2,6-dimethylpiperazinecarboxylate

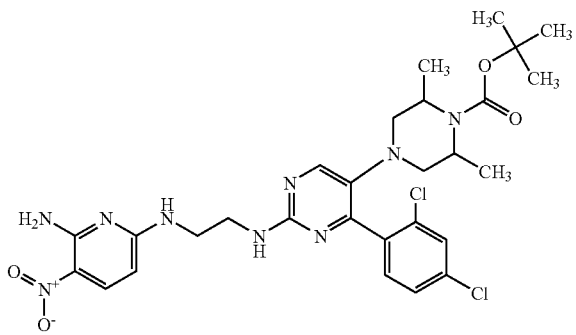

tert-butyl 4-[2-({2-[(6-amino-5-nitro(2-pyridyl))amino]ethyl}amino)-4-(2,4-dichlorophenyl)pyrimidin-5-yl]-2,6-dimethylpiperazinecarboxylate was made in accordance with the foregoing procedures through steps A using 1-(2,4-dichlorophenyl)-2-chloroethan-1-one and 2,6-dimethylpiperazine. 1 mmol of this product, 1 mmol of tert-butyl (tert-butoxycarbonyloxy)formate, and 2 mmol of triethylamine were stirred at room temperature in methylenechloride for four hours. The reaction mixture was concentrated in vacuo and diluted with water and ethyl acetate. The solution was extracted three times with ethyl acetate, dried over sodium sulfate, and purified by column chromatography with 5–10% methanol in methylenechloride. This product was taken on to steps B and C using amino{2-[(6-amino-5-nitro(2-pyridyl))amino]ethyl}carboxamidine.

HPLC: 10.96 min.
MS: MH$^+$=632.3

Example 145-25

Preparation of tert-butyl 4-[4-(2,4-dichlorophenyl)-2-({2-[(5-nitro(2-pyridyl))amino]ethyl}amino)pyrimidin-5-yl]-2,6-dimethylpiperazinecarboxylate

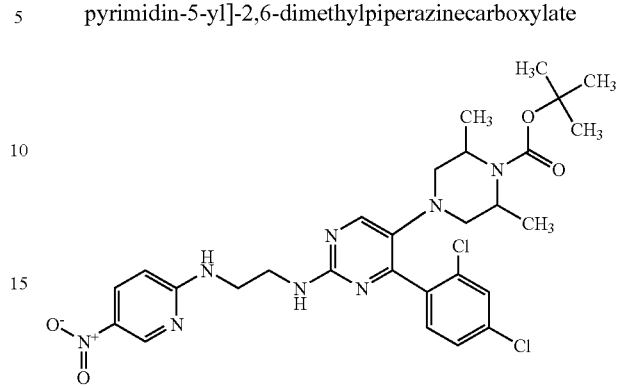

tert-butyl 4-[4-(2,4-dichlorophenyl)-2-({2-[(5-nitro(2-pyridyl))amino]ethyl}amino)pyrimidin-5-yl]-2,6-dimethylpiperazinecarboxylate was made in accordance with the foregoing procedures through steps A using 1-(2,4-dichlorophenyl)-2-chloroethan-1-one and 2,6-dimethylpiperazine. 1 mmol of this product, 1 mmol of tert-butyl (tert-butoxycarbonyloxy)formate, and 2 mmol of triethylamine were stirred at room temperature in methylenechloride for four hours. The reaction mixture was concentrated in vacuo and diluted with water and ethyl acetate. The solution was extracted three times with ethyl acetate, dried over sodium sulfate, and purified by column chromatography with 5–10% methanol in methylenechloride. This product was taken on to steps B and C using amino{2-[(5-nitro(2-pyridyl))amino]ethyl}carboxamidine.

HPLC: 11.713 min.
MS: MH$^+$=617.2

Example 145-26

Preparation of {2-[(6-amino-5-nitro(2-pyridyl))amino]ethyl}[4-(2,4-dichlorophenyl)-5-(3,5-dimethylpiperazinyl)pyrimidin-2-yl]amine

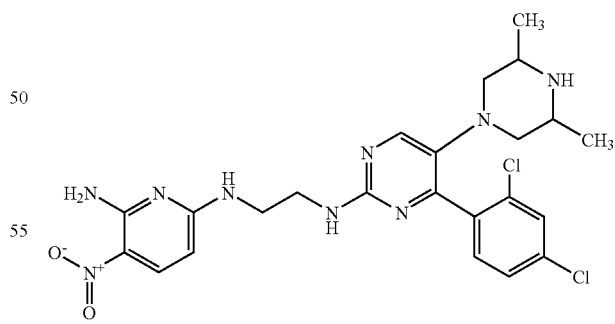

{2-[(6-amino-5-nitro(2-pyridyl))amino]ethyl}[4-(2,4-dichlorophenyl)-5-(3,5-dimethylpiperazinyl)pyrimidin-2-yl]amine was made in accordance with the foregoing procedures through steps A using 1-(2,4-dichlorophenyl)-2-chloroethan-1-one and 2,6-dimethylpiperazine. 1 mmol of this product, 1 mmol of tert-butyl (tert-butoxy-carbonyloxy)

formate, and 2 mmol of triethylamine were stirred at room temperature in methylenechloride for four hours. The reaction mixture was concentrated in vacuo and diluted with water and ethyl acetate. The solution was extracted three times with ethyl acetate, dried over sodium sulfate, and purified by column chromatography with 5–10% methanol in methylenechloride. This product was taken on to steps B, C using amino{2-[(6-amino-5-nitro(2-pyridyl))amino]ethyl}carboxamidine, and G.

HPLC: 5.653 min.

MS: MH$^+$=532.6

Example 145-27

Preparation of [4-(2,4-dichlorophenyl)-5-(3,5-dimethylpiperazinyl)pyrimidin-2-yl]{2-[(5-nitro(2-pyridyl))amino]ethyl}amine

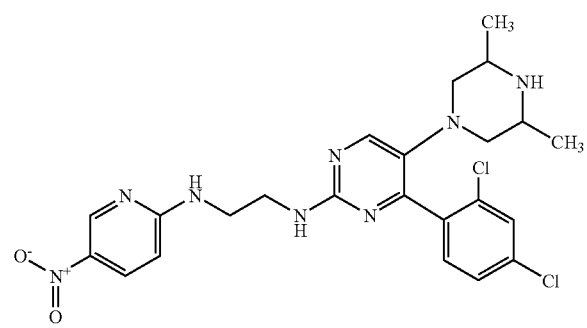

[4-(2,4-dichlorophenyl)-5-(3,5-dimethylpiperazinyl)pyrimidin-2-yl]{2-[(5-nitro(2-pyridyl))amino]ethyl}amine was made in accordance with the foregoing procedures through steps A using 1-(2,4-dichlorophenyl)-2-chloroethan-1-one and 2,6-dimethylpiperazine. 1 mmol of this product, 1 mmol of tert-butyl (tert-butoxycarbonyloxy)formate, and 2 mmol of triethylamine were stirred at room temperature in methylenechloride for four hours. The reaction mixture was concentrated in vacuo and diluted with water and ethyl acetate. The solution was extracted three times with ethyl acetate, dried over sodium sulfate, and purified by column chromatography with 5–10% methanol in methylenechloride. This product was taken on to steps B, C using amino{2-[(5-nitro(2-pyridyl))amino]ethyl}carboxamidine, and G.

HPLC: 6.193 min.

MS: MH$^+$=517.6

Example 145-28

Preparation of N-[4-(2,4-dichlorophenyl)-2-({2-[(5-nitro(2-pyridyl))amino]ethyl}amino)pyrimidin-5-yl]-4-hydroxybutanamide

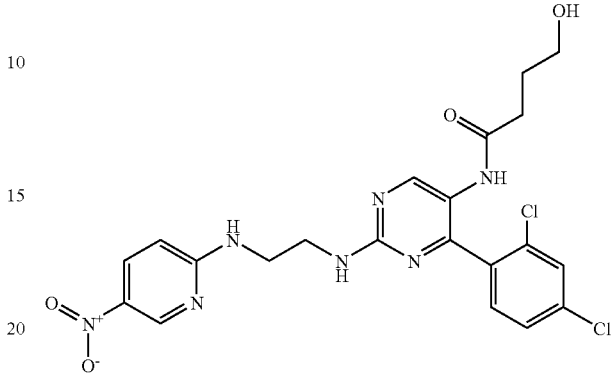

N-[4-(2,4-dichlorophenyl)-2-({2-[(5-nitro(2-pyridyl))amino]ethyl}amino)pyrimidin-5-yl]-4-hydroxybutanamide (74814) was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, F using 4-bromobutanoic acid.

HPLC: 5.688 min.

MS: MH$^+$=506.2

Example 145-29

Preparation of [5-((1E)-1-aza-2-pyrrolidinylprop-1-enyl)-4-(2,4-dichlorophenyl)pyrimidin-2-yl]{2-[(6-amino-5-nitro(2-pyridyl))amino]ethyl}amine

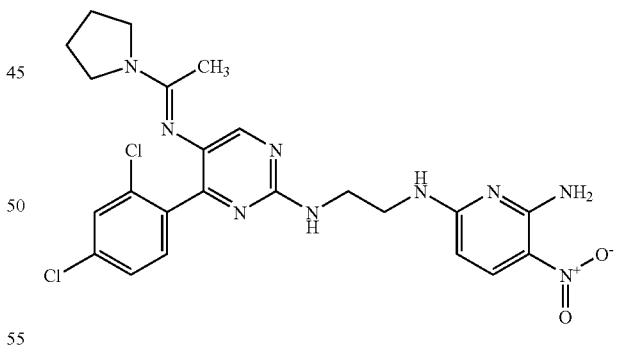

[5-((1E)-1-aza-2-pyrrolidinylprop-1-enyl)-4-(2,4-dichlorophenyl)pyrimidin-2-yl]-{2-[(6-amino-5-nitro(2-pyridyl))amino]ethyl}amine was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamnidine, D, E, and K using acetic anhydride. 1 mmol of N-[2-({2-[(6-amino-5-nitro(2-pyridyl))amino]ethyl}amino)-4-(2,4-dichlorophenyl)pyrimidin-5-yl]acetamide and 2 mmol of Lawesson's reagent were stirred in 2 ml of DME at 80° C. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride. 1 mmol of 1-{[2-({2-[(6-amino-5-nitro(2-pyridyl))amino]ethyl}amino)-4-(2,4-dichlorophenyl)pyrimidin-5-yl]amino}ethane-1-thione was heated to 85° C. in pyrrolidine and purified by column chromatography eluting with 5–10% methanol/methylene chloride.

HPLC: 6.032 min.

MS: MH⁺=530.3

Example 145-30

Preparation of {5-[(1E)-1-aza-2-(cyclopropylamino)prop-1-enyl]-4-(2,4-dichlorophenyl)pyrimidin-2-yl}{2-[(6-amino-5-nitro(2-pyridyl))amino]ethyl}amine {5-[(1E)-1-aza-2-(cyclopropylamino)prop-1-enyl]-4-(2,4-dichlorophenyl)pyrimidin-2-yl}{2-[(6-amino-5-nitro(2-pyridyl))amino]ethyl}amine was made in accordance with the foregoing procedures through steps A using 1-(2,4-dichlorophenyl)-2-chloroethan-1-one and phthalimide, B, C using amino{2-[(6-amnino-5-nitro(2-pyridyl))amino]ethyl}carboxamidine, D, E, and K using acetic anhydride. 1 mmol of N-[2-({2-[(6-amino-5-nitro(2-pyridyl))amino]ethyl}amino)-4-(2,4-dichlorophenyl)pyrimidin-5-yl]acetamide and 2 mmol of Lawesson's reagent were stirred in 2 ml of DME at 80° C. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride. 1 mmol of 1-{[2-({2-[(6-amino-5-nitro(2-pyridyl))amino]ethyl}amino)-4-(2,4-dichlorophenyl)pyrimidin-5-yl]amino}ethane-1-thione was heated to 40° C. in cyclopropylamine and purified by column chromatography eluting with 5–10% methanol/methylene chloride.

HPLC: 5.781 min.

MS: MH⁺=516.2

Example 145-31

Preparation of 1-[2-({2-[(6-amino-5-nitro(2-pyridyl))amino]ethyl}amino)-4-(2,4-dichlorophenyl)pyrimidin-5-yl]-3-(4-methylpiperazinyl)pyrrolidine-2,5-dione 1-[2-({2-[(6-amino-5-nitro(2-pyridyl))amino]ethyl}amino)-4-(2,4-dichlorophenyl)pyrimidin-5-yl]-3-(4-methylpiperazinyl)pyrrolidine-2,5-dione was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, K using malic anhydride, and F. Large excess of morpholine was added to clean fractions of 1-[2-({2-[(6-amino-5-nitro(2-pyridyl))amino]ethyl}amino)-4-(2,4-dichlorophenyl)pyrimidin-5-yl]-3-pyrroline-2,5-dione concentrated in vacuo, and purified by column chromatography eluting with 5–10% methanol/methylene chloride.

HPLC: 4.897 min.

MS: MH⁺=546.3

Example 145-32

Preparation of [6-(2,4-dichlorophenyl)-5-nitro(2-pyridyl)]{2-[(5-nitro(2-pyridyl))amino]ethyl}amine

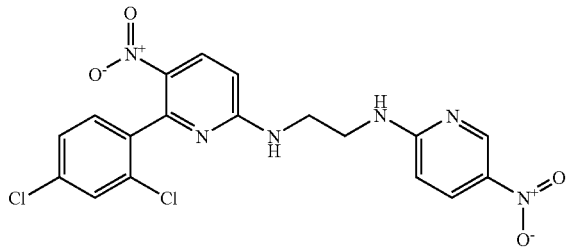

[6-(2,4-dichlorophenyl)-5-nitro(2-pyridyl)]{2-[(5-nitro(2-pyridyl))amino]ethyl}amine was made in accordance with the foregoing procedures through steps L using 2,6-dichloro-3-nitropyridine and 2,4-dichlorobenzeneboronic acid, and step M using (2-aminoethyl)(5-nitro(2-pyridyl))amine.

HPLC: 9.598 min.

MS: MH⁺=448.8

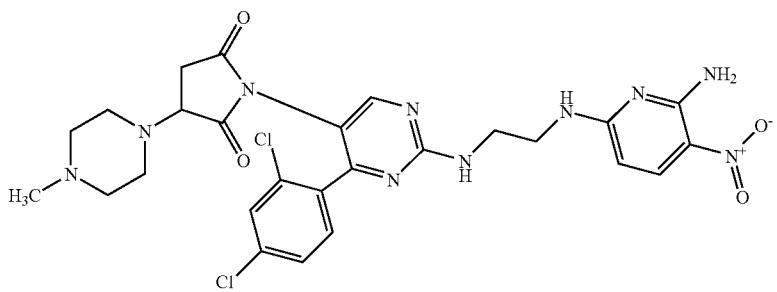

Example 145-33

Preparation of N-[6-({2-[(6-amino-5-nitro(2-pyridyl))amino]ethyl}amino)-2-(2,4-dichlorophenyl)(3-pyridyl)]-N-ethylacetamide

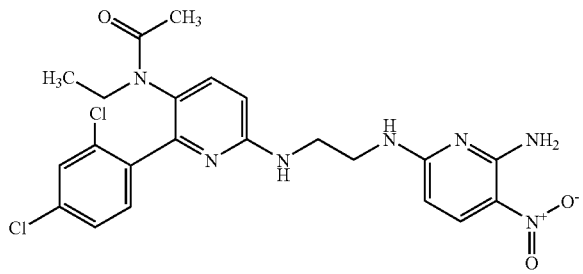

N-[6-({2-[(6-amino-5-nitro(2-pyridyl))amino]ethyl}amino)-2-(2,4-dichloro-phenyl)(3-pyridyl)]-N-ethylacetamide was made in accordance with the foregoing procedures through steps L using 2,6-dichloro-3-nitropyridine and 2,4-dichlorobenzeneboronic acid, M using N-(2-aminoethyl)(tert-butoxy)carboxamide, O, K using acetic anhydride, G, and H using 6-chloro-3-nitro-2-pyridylamine.

HPLC: 6.223 min.
MS: MH$^+$=504.2

Example 145-34

Preparation of {5-[(6-amino-5-nitro(2-pyridyl))amino]-6-(2,4-dichlorophenyl)(2-pyridyl)}{2-[(6-amino-5-nitro(2-pyridyl))amino]ethyl}amine {5-[(6-amino-5-nitro(2-pyridyl))amino]-6-(2,4-dichlorophenyl)(2-pyridyl)}{2-[(6-amino-5-nitro(2-pyridyl))amino]ethyl}amine was made in accordance with the foregoing procedures through steps L using 2,6-dichloro-3-nitropyridine and 2,4-dichlorobenzeneboronic acid, M N-(2-aminoethyl)(tert-butoxy)carboxamide, N, H using 6-chloro-3-nitro-2-pyridylamine, G, and H using 6-chloro-3-nitro-2-pyridylamine.

HPLC: 7.467 min.
MS: MH$^+$=571.0

Example 145-35

Preparation of {2-[(6-amino-5-nitro(2-pyridyl))amino]ethyl}[6-(2,4-dichlorophenyl)-5-(ethylamino)(2-pyridyl)]amine

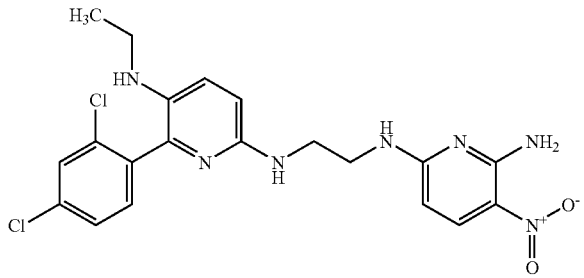

{2-[(6-amino-5-nitro(2-pyridyl))amino]ethyl}[6-(2,4-dichlorophenyl)-5-(ethylamino)(2-pyridyl)]amine was made in accordance with the foregoing procedures through steps L using 2,6-dichloro-3-nitropyridine and 2,4-dichlorobenzeneboronic acid, M using N-(2-aminoethyl)(tert-butoxy)carboxamide, O, G, and H using 6-chloro-3-nitro-2-pyridylamine.

HPLC: 5.263 min.
MS: MH$^+$=462.0

Example 145-36

Preparation of [6-(2,4-dichlorophenyl)-3-nitro(2-pyridyl)]{2-[(5-nitro(2-pyridyl))amino]ethyl}amine

[6-(2,4-dichlorophenyl)-3-nitro(2-pyridyl)]{2-[(5-nitro(2-pyridyl))amino]ethyl}amine was made in accordance with the foregoing procedures through steps L using 2,6-dichloro-3-nitropyridine and 2,4-dichlorobenzeneboronic acid collecting minor product, and step M using (2-aminoethyl)(5-nitro(2-pyridyl))amine.

HPLC: 12.003 min.
MS: MH$^+$=449.0

Example 145-37

Preparation of 2-(2,4-dichlorophenyl)-4-methyl-6-({2-[(5-nitro(2-pyridyl))amino]ethyl}amino)pyridine-3-carbonitrile

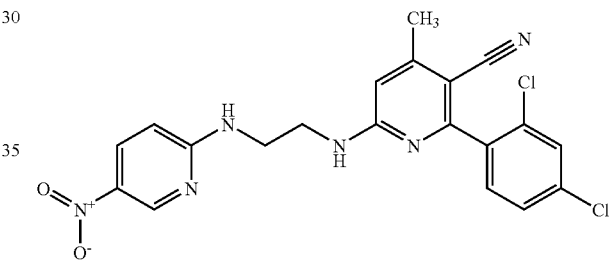

2-(2,4-dichlorophenyl)-4-methyl-6-({2-[(5-nitro(2-pyridyl))amino]ethyl}amino)pyridine-3-carbonitrile was made in accordance with the foregoing procedures through steps L using 2,6-dichloro-4-methylpyridine-3-carbonitrile and 2,4-dichloro-benzeneboronic acid, and step M using (2-aminoethyl)(5-nitro(2-pyridyl))amine.

HPLC: 12.183 min.
MS: MH$^+$=443.0

Example 145-38

Preparation of {2-[(6-amnino-5-nitro(2-pyridyl))amino]ethyl}[6-(2,4-dichlorophenyl)-3-nitro(2-pyridyl)]amine {2-[(6-amino-5-nitro(2-pyridyl))amino]ethyl}[6-(2,4-dichlorophenyl)-3-nitro(2-pyridyl)]amine was made in accordance with the foregoing procedures through steps L using 2,6-dichloro-3-nitropyridine and 2,4-dichlorobenzeneboronic acid collecting minor product, M using N-(2-aminoethyl)(tert-butoxy)carboxamide, G, and H using 6-chloro-3-nitro-2-pyridylamine.

HPLC: 10.682 min.
MS: MH$^+$=464.0

Example 145-39

Preparation of {2-[(6-amino-5-nitro(2-pyridyl))amino]ethyl}[6-(4-ethylphenyl)-5-nitro(2-pyridyl)]amine

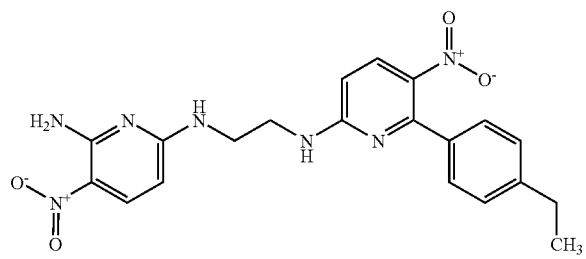

{2-[(6-amino-5-nitro(2-pyridyl))amino]ethyl}[6-(4-ethylphenyl)-5-nitro(2-pyridyl)]amine was made in accordance with the foregoing procedures through steps L using 2,6-dichloro-3-nitropyridine and 4-ethylbenzeneboronic acid, M using N-(2-aminoethyl)(tert-butoxy)carboxamide, G, and H using 6-chloro-3-nitro-2-pyridylamine.

HPLC: 9.354 min.

MS: MH$^+$=424.1

Example 145-40

Preparation of N-{1-[2-({2-[(6-amino-5-nitro(2-pyridyl))amino]ethyl}amino)-4-(2,4-dichlorophenyl)pyrimidin-5-yl]-2,6-dioxo(3-piperidyl)}(tert-butoxy)carboxamide

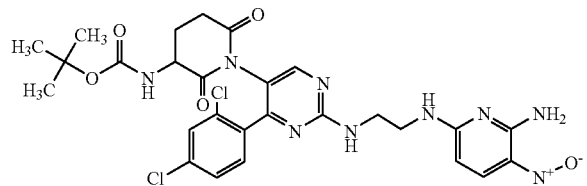

N-{1-[2-({2-[(6-amino-5-nitro(2-pyridyl))amino]ethyl}amino)-4-(2,4-dichlorophenyl)pyrimidin-5-yl]-2,6-dioxo(3-piperidyl)}(tert-butoxy)carboxamide was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, and F using 1-[(tert-butoxy) carbonyl-amino]propane-1,3-dicarboxylic acid.

HPLC: 9.152 min.

MS: MH$^+$=646.4

Example 145-41

Preparation of 3-amino-1-[2-({2-[(6-amino-5-nitro(2-pyridyl))amino]ethyl}amino)-4-(2,4-dichlorophenyl)pyrimidin-5-yl]piperidine-2,6-dione

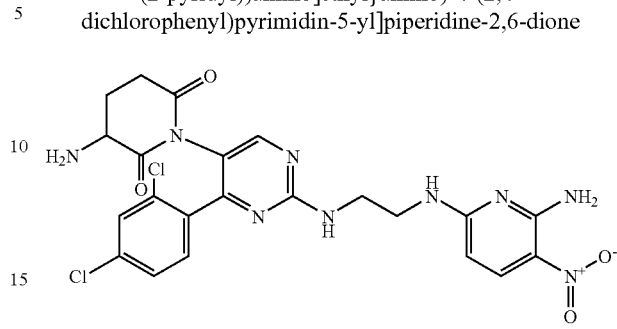

3-amino-1-[2-({2-[(6-amino-5-nitro(2-pyridyl))amino]ethyl}amino)-4-(2,4-dichlorophenyl)pyrimidin-5-yl]piperidine-2,6-dione was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, D, E, F using 1-[(tert-butoxy)carbonylamino]propane-1,3-dicarboxylic acid, and G.

HPLC: 5.247 min.

MS: MH$^+$=546.3

Example 145-42

Preparation of N-[2-({2-[(6-amino-5-nitro(2-pyridyl))amino]ethyl}amino)-4-(2,4-dichlorophenyl)pyrimidin-5-yl]-2-[(tert-butoxy)-N-methylcarbonylamino]

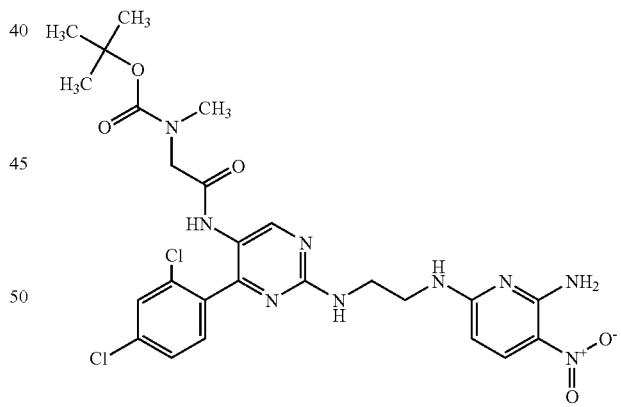

N-[2-({2-[(6-amino-5-nitro(2-pyridyl))amino]ethyl}amino)-4-(2,4-dichloro-phenyl)pyrimidin-5-yl]-2-[(tert-butoxy)-N-methylcarbonylamino]acetamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and F using 2-[(tert-butoxy)-N-methylcarbonylamino]acetic acid.

HPLC: 8.346 min.

MS: MH$^+$=606.2

Example 145-43

Preparation of N-[2-({2-[(6-amino-5-nitro(2-pyridyl))amino]ethyl}amino)-4-(2,4-dichlorophenyl)pyrimidin-5-yl]-2-(methylamino)acetamide

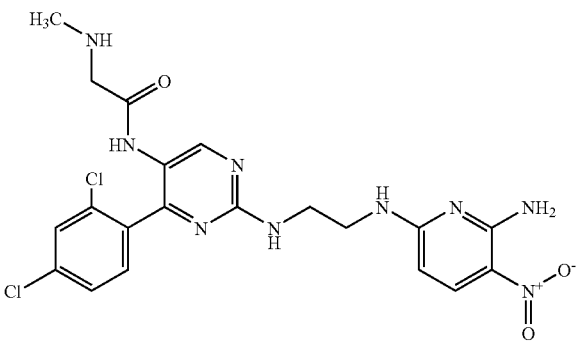

N-[2-({2-[(6-amino-5-nitro(2-pyridyl))amino]ethyl}amino)-4-(2,4-dichlorophenyl)pyrimidin-5-yl]-2-(methylamino)acetamide was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, F using 2-[(tert-butoxy)-N-methylcarbonylamino]acetic acid, and G.

HPLC: 4.716 min.
MS: MH+=506.1

Example 145-44

Preparation of 1-[6-({2-[(6-amino-5-nitro(2-pyridyl))amino]ethyl}amino)-2-(4-ethylphenyl)-3-pyridyl]pyrrolidine-2,5-dione

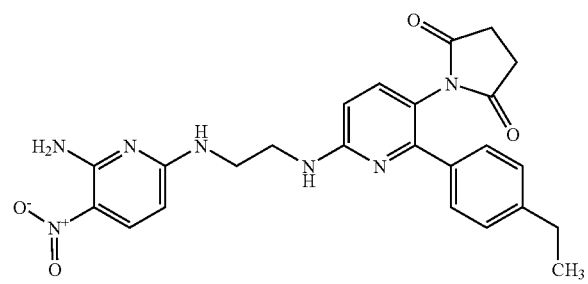

1-[6-({2-[(6-amino-5-nitro(2-pyridyl))amino]ethyl}amino)-2-(4-ethylphenyl)-3-pyridyl]pyrrolidine-2,5-dione was made in accordance with the foregoing procedures through steps L using 2,6-dichloro-3-nitropyridine and 4-ethylbenzeneboronic acid, M using N-(2-aminoethyl)(tert-butoxy)carboxamide, F using ethane-1,2-dicarboxylic acid, G, and H using 6-chloro-3-nitro-2-pyridylamine.

HPLC: 6.072 min.
MS: MH+=476.2

Example 145-45

Preparation of 2-[4-(2,4-dichlorophenyl)-2-({2-[(5-nitro(2-pyridyl))amino]ethyl}amino)pyrimidin-5-yl]isoindoline-1,3-dione 2-[4-(2,4-dichlorophenyl)-2-({2-[(5-nitro(2-pyridyl))amino]ethyl}amino)pyrimidin-5-yl]isoindoline-1,3-dione was made in accordance with the foregoing procedures through steps A using 1-(2,4-dichlorophenyl)-2-chloroethan-1-one and phthalimide, B, C using amino{2-[(5-nitro(2-pyridyl))amino]ethyl}carboxamidine, and D.

HPLC: 12.12 min.
MS: MH+=549.8

Example 145-46

Preparation of 2-[2-({2-[(6-amino-5-nitro(2-pyridyl))amino]ethyl}amino)-4-(2,4-dichlorophenyl)pyrimidin-5-yl]-3-pyrrolino[3,4-c]pyridine-1,3-dione 2-[2-({2-[(6-amino-5-nitro(2-pyridyl))amino]ethyl}amino)-4-(2,4-dichlorophenyl)pyrimidin-5-yl]-3-pyrrolino[3,4-c]pyridine-1,3-dione was made in accordance with the foregoing procedures through steps A using 1-(2,4-dichlorophenyl)-2-chloroethan-1-one and 3-pyrrolino[3,4-c]pyridine-1,3-dione, B, C using amino{2-[(6-amino-5-nitro(2-pyridyl))amino]ethyl}carboxamidine, and D.

HPLC: 9.85 min.
MS: MH+=566.1

Example 145-47

Preparation of 1-{[2-({2-[(6-amino-5-nitro(2-pyridyl))amino]ethyl}amino)-4-(2,4-dichlorophenyl)pyrimidin-5-yl]amino}ethane-1-thione 1-{[2-({2-[(6-amino-5-nitro(2-pyridyl))amino]ethyl}amino)-4-(2,4-dichloro-phenyl)pyrimidin-5-yl]amino}ethane-1-thione was made in accordance with the foregoing procedures through steps A using 1-(2,4-dichlorophenyl)-2-chloroethan-1-one and phthalimide, B, C using amino{2-[(6-amino-5-nitro(2-pyridyl))amino]ethyl}carboxamidine, D, E, and K using acetic anhydride. 1 mmol of N-[2-({2-[(6-amino-5-nitro(2-pyridyl))amino]ethyl}amino)-4-(2,4-dichlorophenyl)pyrimidin-5-yl]acetamide and 2 mmol of Lawesson's reagent were stirred in 2 ml of DME at 80° C. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

HPLC: 11.63 min.
MS: MH+=493.1

Example 146

Preparation of 4-[5-imidazol-2-yl-2-({2-[(5-nitro(2-pyridyl))amino]ethyl}amino)pyrimidin-4-yl]benzenecarbonitrile

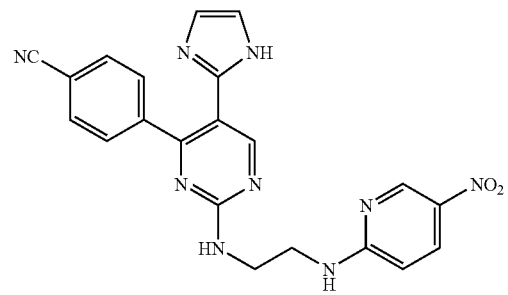

4-[5-imidazol-2-yl-2-({2-[(5-nitro(2-pyridyl))amino]ethyl}amino)pyrimidin-4-yl]benzenecarbonitrile was prepared from 4-cyanobenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 21.9 min (>95% purity)

MS: M+H=428.1 ($C_{21}H_{17}N_9O_2$+H=428)

Example 147

Preparation of 6-[(2-{[4-(2,4-dichlorophenyl)-5-imidazol-2-ylpyrimidin-2-yl]amino}ethyl)amino]pyridine-3-carbonitrile

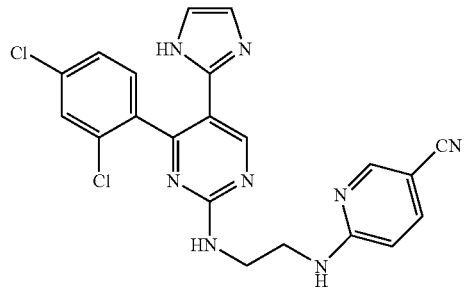

6-[(2-{[4-(2,4-dichlorophenyl)-5-imidazol-2-ylpyrimidin-2-yl]amino}ethyl)amino]pyridine-3-carbonitrile was prepared from 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 18.2 min (>95% purity)

MS: M+H=451.1 ($C_{21}H_{16}C_{12}N_8$+H=451)

Example 148

Preparation of [4-(2,4-dichlorophenyl)-5-imidazol-2-ylpyrimidin-2-yl](2-{[5-(trifluoromethyl)(2-pyridyl)]amino}ethyl)amine

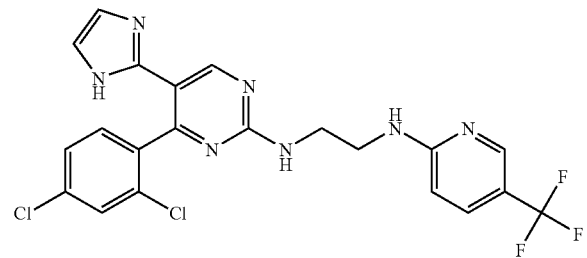

[4-(2,4-dichlorophenyl)-5-imidazol-2-ylpyrimidin-2-yl](2-{[5-(trifluoromethyl) (2-pyridyl)]amino}ethyl)amine (71480) was prepared from 2-chloro-5-(trifluoro-methyl) pyridine using the general method for [4-(2,4-dichlorophenyl)-5-imidazol-2-ylpyrimidin-2-yl]{2-[(5-nitro(2-pyridyl))amino]ethyl}amine.

HPLC: 18.9 min (>95% purity)

MS: M+H=494.1 ($C_{21}H_{16}Cl_2F_3N_7$+H=494)

Example 149

Preparation of [4-(2,4-dichlorophenyl)-5-(1-methylimidazol-2-yl)pyrimidin-2-yl]{2-[(5-nitro(2-pyridyl))amino]ethyl}amine

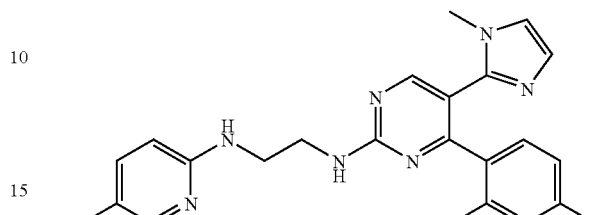

[4-(2,4-dichlorophenyl)-5-(1-methylimidazol-2-yl)pyrimidin-2-yl]{2-[(5-nitro(2-pyridyl))amino]ethyl}amine was prepared from 1,2-dimethylimidazole using the general method for [4-(2,4-dichlorophenyl)-5-imidazol-2-ylpyrimidin-2-yl]{2-[(5-nitro(2-pyridyl))amino]ethyl}amine.

HPLC: 21.9 min (>95% purity)

MS: M+H=485.1 ($C_{21}H_{18}Cl_2N_8O_2$+H=485)

Example 150

Preparation of {5-imidazol-2-yl-4-[4-(trifluoromethyl)phenyl]pyrimidin-2-yl}{2-[(5-nitro(2-pyridyl))amino]ethyl}amine

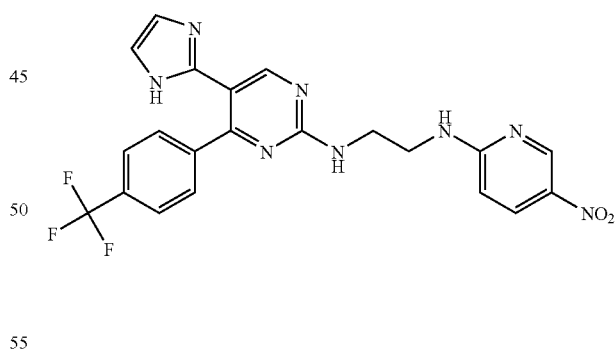

{5-imidazol-2-yl-4-[4-(trifluoromethyl)phenyl]pyrimidin-2-yl}{2-[(5-nitro(2-pyridyl))amino]ethyl}amine was prepared from 4-(trifluoromethyl)benzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 22.0 min (>95% purity)

MS: M+H=471.2 ($C_{21}H_{17}F_3N_8O_2$+H=471)

Example 151

Preparation of 6-{[2-({5-imidazol-2-yl-4-[4-(trifluoromethyl)phenyl]pyrimidin-2-yl}amino)ethyl]amino}pyridine-3-carbonitrile

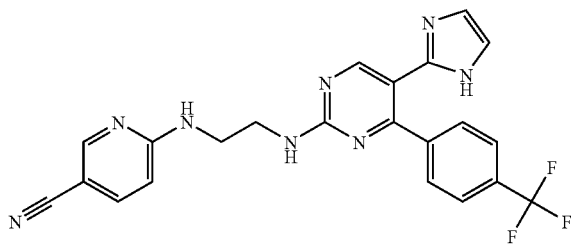

6-{[2-({5-imidazol-2-yl-4-[4-(trifluoromethyl)phenyl]pyrimidin-2-yl}amino)ethyl]amino}pyridine-3-carbonitrile was prepared from 4-(trifluoromethyl)benzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.3 min (>95% purity)

MS: M+H=451.2 ($C_{22}H_{17}F_3N_8$+H=451)

Example 152

Preparation of {5-imidazol-2-yl-4-[4-(trifluoromethyl)phenyl]pyrimidin-2-yl}(2-{[5-(trifluoromethyl)(2-pyridyl)]amino}ethyl)amine

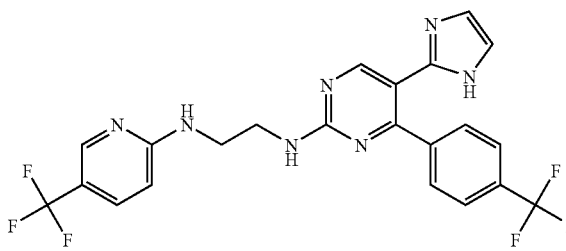

{5-imidazol-2-yl-4-[4-(trifluoromethyl)phenyl]pyrimidin-2-yl}(2-{[5-(trifluoro-methyl)(2-pyridyl)]amino}ethyl)amine was prepared from 4-(trifluoromethyl)benzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 20.0 min (>95% purity)

MS: M+H=494.2 ($C_{22}H_{17}F_6N_7$+H=494)

Example 153

Preparation of 6-[(2-{[4-dichlorophenyl)-5-(1-methylimidazol-2-yl)pyrimidin-2-yl]amino}ethyl)amino]pyridine-3-carbonitrile

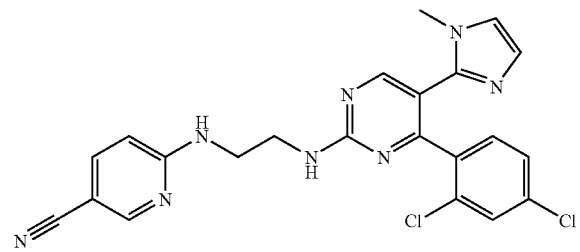

6-[(2-{[4-(2,4-dichlorophenyl)-5-(1-methylimidazol-2-yl)pyrimidin-2-yl]amino}ethyl)amino]pyridine-3-carbonitrile was prepared from 1,2-dimethylimidazole and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.0 min (>95% purity)

MS: M+H=465.1 ($C_{22}H_{18}Cl_2N_8$+H=465)

Example 154

Preparation of [4-(2,4-dichlorophenyl)-5-(1-methylimidazol-2-yl)pyrimidin-2-yl](2-{[5-(trifluoromethyl)(2-pyridyl)]amino}ethyl)amine

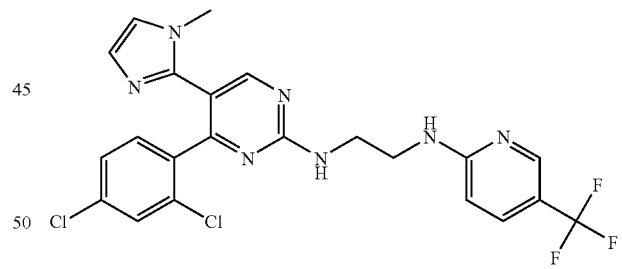

[4-(2,4-dichlorophenyl)-5-(1-methylimidazol-2-yl)pyrimidin-2-yl](2-{[5-(trifluoro-methyl)(2-pyridyl)]amino}ethyl)amine was prepared from 1,2-dimethylimidazole and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 20.0 min (>95% purity)

MS: M+H=508.1 ($C_{22}H_{18}Cl_2F_3N_7$+H=508)

Example 155

Preparation of [4-(2-chlorophenyl)-5-imidazol-2-ylpyrimidin-2-yl]{2-[(5-nitro(2-pyridyl))amino]ethyl}amine

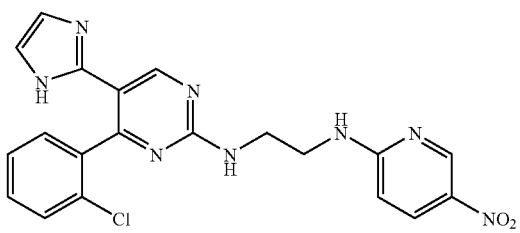

[4-(2-chlorophenyl)-5-imidazol-2-ylpyrimidin-2-yl]{2-[(5-nitro(2-pyridyl))amino]ethyl}amine was prepared from 2-chlorobenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 18.5 min (>95% purity)

MS: M+H=437.1 ($C_{20}H_{17}ClN_8O_2$+H=437)

Example 156

Preparation of 6-[(2-{[4-(2-chlorophenyl)-5-imidazol-2-ylpyrimidin-2-yl]amino}ethyl)amino]pyridine-3-carbonitrile

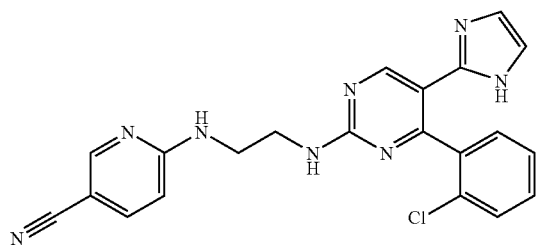

6-[(2-{[4-(2-chlorophenyl)-5-imidazol-2-ylpyrimidin-2-yl]amino}ethyl)amino]pyridine-3-carbonitrile was prepared from 2-chlorobenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 15.3 min (>95% purity)

MS: M+H=417.2 ($C_{21}H_{17}ClN_8$+H=417)

Example 157

Preparation of [4-(2-chlorophenyl)-5-imidazol-2-ylpyrimidin-2-yl](2-{[5-(trifluoromethyl)(2-pyridyl)]amino}ethyl)amine

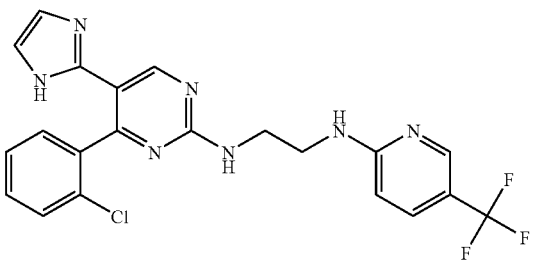

[4-(2-chlorophenyl)-5-imidazol-2-ylpyrimidin-2-yl](2-{[5-(trifluoromethyl)(2-pyridyl)]amino}ethyl)amine was prepared from 2-chlorobenzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 16.8 min (>95% purity)

MS: M+H=460.2 ($C_{21}H_{17}ClF_3N_7$+H=460)

Example 158

Preparation of [4-(2-chloro-4-fluorophenyl)-5-imidazol-2-ylprimidin-2-yl]{2-[(5-nitro(2-pyridyl))amino]ethyl}amine

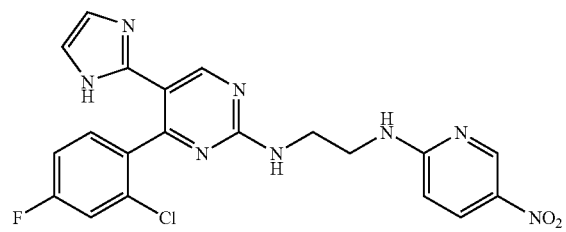

[4-(2-chloro-4-fluorophenyl)-5-imidazol-2-ylpyrimidin-2-yl]{2-[(5-nitro(2-pyridyl))amino]ethyl}amine was prepared from 2-chloro-4-fluorobenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 19.4 min (>95% purity)

MS: M+H=455.1 ($C_{20}H_{16}ClFN_8O_2$+H=455)

Example 159

Preparation of {4-[4-fluoro-2-(trifluoromethyl)phenyl]-5-imidazol-2-ylpyrimidin-2-yl}{2-[(5-nitro(2-pyridyl))amino]ethyl}amine

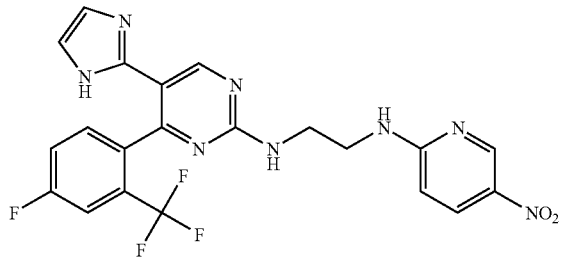

{4-[fluoro-2-(trifluoromethyl)phenyl]-5-imidazol-2-ylpyrimidin-2yl}{2-[(5-nitro(2-pyridyl))amino]ethyl}amine was prepared from 4-fluoro-2-(trifluoromethyl)benzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 21.0 min (>95% purity)

MS: M+H=489.2 ($C_{21}H_{16}F_4N_8O_2$+H=489)

Example 160

Preparation of {4-[4-fluoro-2-(trifluoromethyl)phenyl]-5-imidazol-2-ylpyrimidin-2-yl}{2-[(5-nitro(2-pyridyl))amino]ethyl}amine

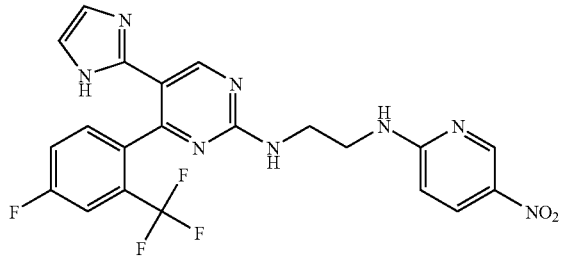

{4-[4-fluoro-2-(trifluoromethyl)phenyl]-5-imidazol-2-ylpyrimidin-2-yl}{2-[(5-nitro(2-pyridyl))amino]ethyl}amine was prepared from 4-fluoro-2-(trifluoromethyl)benzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 21.2 min (>95% purity)

MS: M+H=431.3 ($C_{21}H_{16}F_4N_8O_2$+H=431)

Example 161

Preparation of [4-(4-ethylphenyl)-5-imidazol-2-ylpyrimidin-2-yl](2-{[5-(trifluoromethyl)(2-pyridyl)]amino}ethyl)amine

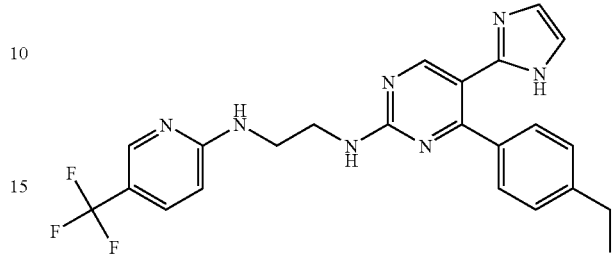

[4-(4-ethylphenyl)-5-imidazol-2-ylpyrimidin-2-yl](2-{[5-(trifluoromethyl)(2-pyridyl)]amino}ethyl)amine was prepared from 4-ethylbenzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.4 min (>95% purity)

MS: M+H=454.3 ($C_{23}H_{22}F_3N_7$+H=454)

Example 162

Preparation of {4-[2-fluoro-4-(trifluoromethyl)phenyl]-5-imidazol-2-ylpyrimidin-2-yl}{2-[(5-nitro(2-pyridyl))amino]ethyl}amine

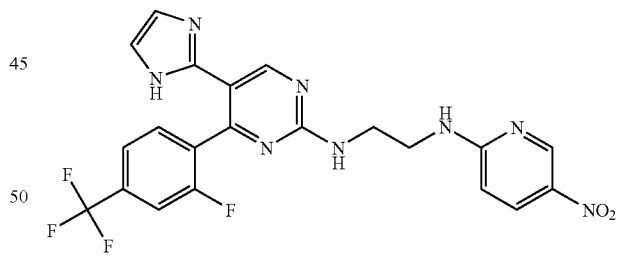

{4-[2-fluoro-4-(trifluoromethyl)phenyl]-5-imidazol-2-ylpyrimidin-2-yl}{2-[(5-nitro(2-pyridyl))amino]ethyl}amine was prepared from 2-fluoro-4-(trifluoromethyl)benzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 22.2 min (>95% purity)

MS: M+H=489.2 ($C_{21}H_{16}F_4N_8O_2$+H=489)

Example 163

Preparation of 6-[(2-{[4-(2-chloro-4-fluorophenyl)-5-imidazol-2-ylpyrimidin-2-yl]amino}ethyl)amino]pyridine-3-carbonitrile

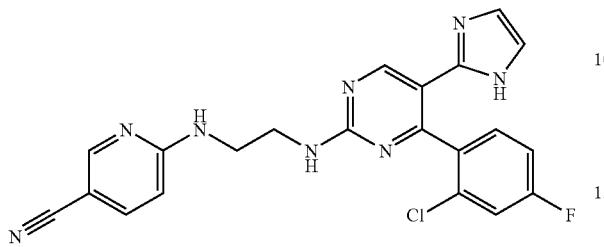

6-[(2-{[4-(2-chloro-4-fluorophenyl)-5-imidazol-2-ylpyrimidin-2-yl]amino}ethyl)amino]pyridine-3-carbonitrile was prepared from 2-chloro-4-fluorobenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 16.3 min (>95% purity)

MS: M+H=435.2 ($C_{21}H_{16}ClFN_8$+H=435)

Example 164

Preparation of [4-(2-chloro-4-fluorophenyl)-5-imidazol-2-ylpyrimidin-2-yl](2-{[5-(trifluoromethyl)(2-pyridyl)]amino}ethyl)amine

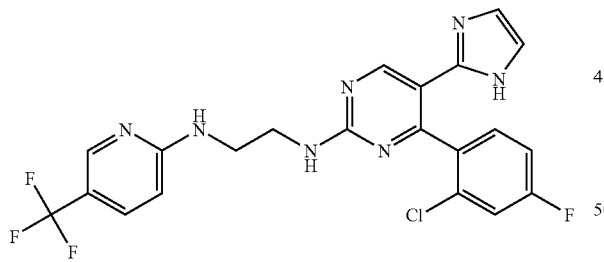

[4-(2-chloro-4-fluorophenyl)-5-imidazol-2-ylpyrimidin-2-yl](2-{[5-(trifluoromethyl)(2-pyridyl)]amino}ethyl)amine was prepared from 2-chloro-4-fluorobenzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 17.7 min (>95% purity)

MS: M+H=478.2 ($C_{21}H_{16}ClF_4N_7$+H=478)

Example 165

Preparation of 6-{[2-({4-[4-fluoro-2-(trifuoromethyl)phenyl]-5-imidazol-2-ylpyrimidin-2-yl}amino)ethyl]amino}pyridine-3-carbonitrile

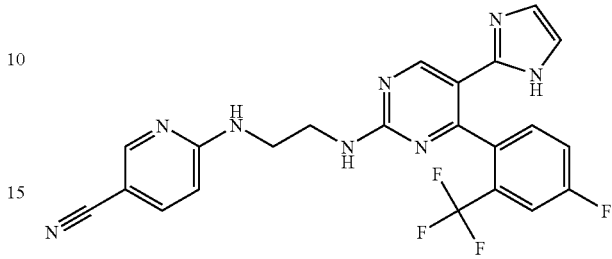

6-{[2-({4-[4-fluoro-2-(trifluoromethyl)phenyl]-5-imidazol-2-ylpyrimidin-2-yl}amino)ethyl]amino}pyridine-3-carbonitrile was prepared from 4-fluoro-2-(trifluoromethyl)benzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 18.1 min (>95% purity)

MS: M+H=469.2 ($C_{22}H_{16}F_4N_8$+H=469)

Example 165

Preparation of {4-[4-fluoro-2-(trifluoromethyl)phenyl]-5-imidazol-2-ylpyrimidin-2-yl}(2-{[5-(trifluoromethyl)(2-pyridyl)]amino}ethyl)amine

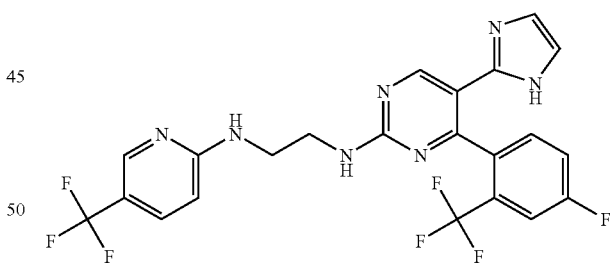

{4-[4-fluoro-2-(trifluoromethyl)phenyl]-5-imidazol-2-ylpyrimidin-2-yl }(2-{[5-(trifluoromethyl)(2-pyridyl)]amino}ethyl)amine was prepared from 4-fluoro-2-(trifluoromethyl)benzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 18.8 min (>95% purity)

MS: M+H=512.2 ($C_{22}H_{16}F_7N_7$+H=512)

Example 166

Preparation of 6-[(2-{[4-(4-ethylphenyl)-5-imidazol-2-ylpyrimidin-2-yl]amino}ethyl)amino]pyridine-3-carbonitrile

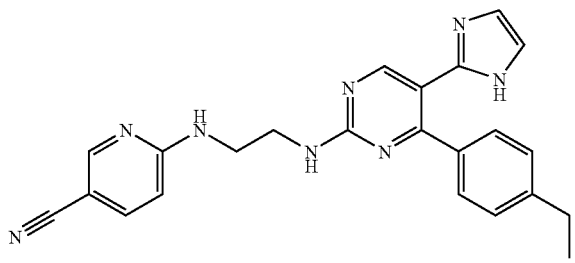

6-[(2-{[4-(4-ethylphenyl)-5-imidazol-2-ylpyrimidin-2-yl]amino}ethyl)amino]pyridine-3-carbonitrile was prepared from 4-ethylbenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 17.9 min (>95% purity)

MS: M+H=411.2 ($C_{23}H_{22}N_8$+H=411)

Example 167

Preparation of [4-(4-chlorophenyl)-5-imidazol-2-ylpyrimidin-2-yl]{2-[(5-nitro(2-pyridyl))amino]ethyl}amine

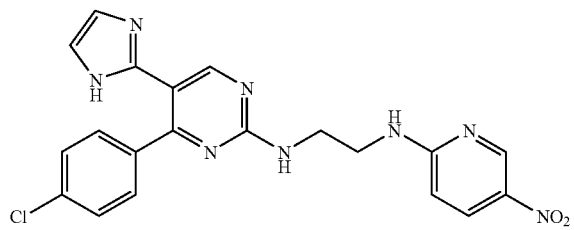

[4-(4-chlorophenyl)-5-imidazol-2-ylpyrimidin-2-yl]{2-[(5-nitro(2-pyridyl))amino]ethyl}amine was prepared from 4-chlorobenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 20.0 min (>95% purity)

MS: M+H=437.1 ($C_{20}H_{17}ClN_8O_2$+H=437)

Example 168

Preparation of 6-[(2-{[4-(4-chlorophenyl)-5-imidazol-2-ylpyrimidin-2-yl]amino}ethyl)amino]pyridine-3-carbonitrile

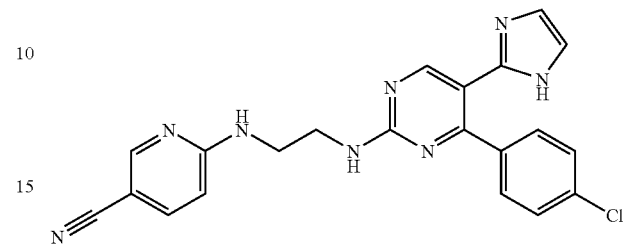

6-[(2-{[4-(4-chlorophenyl)-5-imidazol-2-ylpyrimidin-2-yl]amino}ethyl)amino]pyridine-3-carbonitrile was prepared from 4-chlorobenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 17.1 min (>95% purity)

MS: M+H=417.2 ($C_{21}H_{17}ClN_8$+H=417)

Example 169

Preparation of [4-(4-chloro-2-methylphenyl)-5-imidazol-2-ylpyrimidin-2-yl]{2-[(5-nitro(2-pyridyl))amino]ethyl}amine

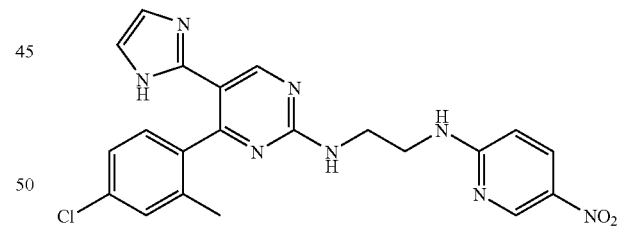

[4-(4-chloro-2-methylphenyl)-5-imidazol-2-ylpyrimidin-2-yl]{2-[(5-nitro(2-pyridyl))amino]ethyl}amine was prepared from 4-chloro-2-methylbenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 20.8 min (>95% purity)

MS: M+H=451.2 ($C_{21}H_{19}ClN_8O_2$+H=451)

Example 170

Preparation of [4-(4-chloro-2-methylphenyl)-5-imidazol-2-ylpyrimidin-2-yl](2-{[5-(trifluoromethyl)(2-pyridyl)]amino}ethyl)amine

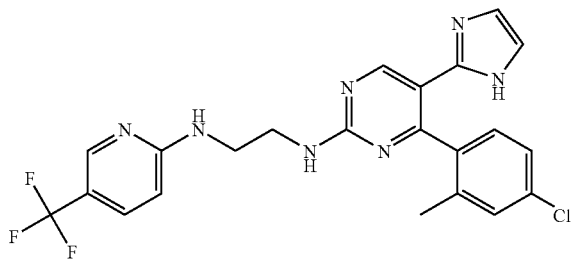

[4-(4-chloro-2-methylphenyl)-5-imidazol-2-ylpyrimidin-2-yl](2-{[5-(trifluoro-methyl)(2-pyridyl)]amino}ethyl)amine was prepared from 4-chloro-2-methylbenzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.2 min (>95% purity)

MS: M+H=474.2 ($C_{22}H_{19}ClF_3N_7$+H=474)

Example 171

Preparation of 6-{[2-({4-[2-fluoro-4-(trifluoromethyl)phenyl]-5-imidazol-2-ylpyrimidin-2-yl}amino)ethyl]amino}pyridine-3-carbonitrile

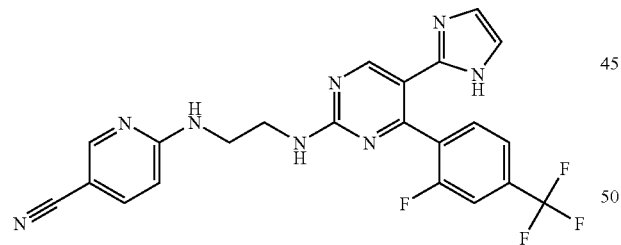

6-{[2-({4-[2-fluoro-4-(trifluoromethyl)phenyl]-5-imidazol-2-ylpyrimidin-2-yl}amino)ethyl]amino}pyridine-3-carbonitrile was prepared from 2-fluoro-4-(trifluoromethyl)benzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.7 min (>95% purity)

MS: M+H=469.3 ($C_{22}H_{16}F_4N_8$+H=469)

Example 172

Preparation of [4-(2-fluorophenyl)-5-imidazol-2-ylpyrimidin-2-yl]{2-[(5-nitro(2-pyridyl))amino]ethyl}amine

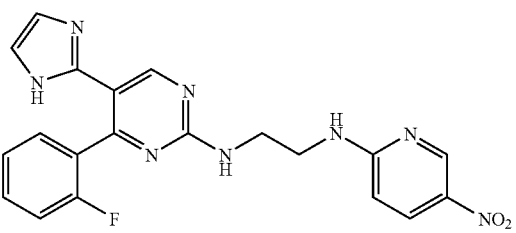

[4-(2-fluorophenyl)-5-imidazol-2-ylpyrimidin-2-yl]{2-[(5-nitro(2-pyridyl))amino]ethyl}amine was prepared from 2-fluorbenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 17.9 min (>95% purity)

MS: M+H=421.2 ($C_{20}H_{17}FN_8O_2$+H=421)

Example 173

Preparation of 6-[(2-{[4-(2-fluorophenyl)-5-imidazol-2-ylpyrimidin-2-yl]amino}ethyl)amino]pyridine-3-carbonitrile

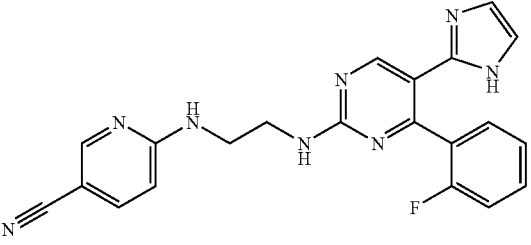

6-[(2-{[4-(2-fluorophenyl)-5-imidazol-2-ylpyrimidin-2-yl]amino}ethyl)amino]pyridine-3-carbonitrile was prepared from 2-fluorbenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 14.7 min (>95% purity)

MS: M+H=401.2 ($C_{21}H_{17}FN_8$+H=401)

Example 174

Preparation of [4-(4-chloro-2-methoxyphenyl)-5-imidazol-2-ylpyrimidin-2-yl]{2-[(5-nitro(2-pyridyl))amino]ethyl}amine

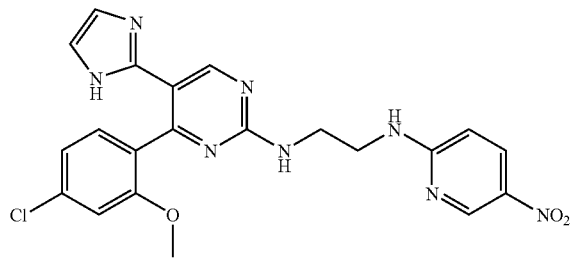

[4-(4-chloro-2-methoxyphenyl)-5-imidazol-2-ylpyrimidin-2-yl]{2-[(5-nitro(2-pyridyl))amino]ethyl}amine was prepared from 4-chloro-2-methoxybenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 19.9 min (>95% purity)

MS: M+H=467.3 ($C_{21}H_{19}ClN_8O_3$+H=467)

Example 175

Preparation of 6-[(2-{[4-(4-chloro-2-methoxyphenyl)-5-imidazol-2-ylpyrimidin-2-yl]amino}ethyl)amino]pyridine-3-carbonitrile

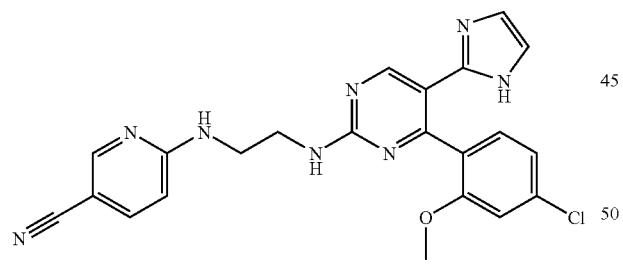

6-[(2-{[4-(4-chloro-2-methoxyphenyl)-5-imidazol-2-ylpyrimidin-2-yl]amino}ethyl)amino]pyridine-3-carbonitrile was prepared from 4-chloro-2-methoxybenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 16.9 min (>95% purity)

MS: M+H=447.3 ($C_{22}H_{19}ClN_8O$+H=447)

Example 176

Preparation of 6-[(2-{[4-(4-chloro-2-methylphenyl)-5-imidazol-2-ylpyrimidin-2-yl]amino}ethyl)amino]pyridine-3-carbonitrile

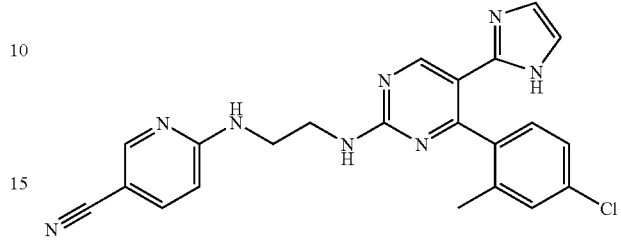

6-[(2-{[4-(2-chloro-4-fluorophenyl)-5-imidazol-2-ylpyrimidin-2-yl]amino}ethyl)amino]pyridine-3-carbonitrile was prepared from 4-chloro-2-methylbenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 17.9 min (>95% purity)

MS: M+H=430.8 ($C_{22}H_{19}ClN_8$+H=430)

Example 177

Preparation of [4-(4-bromo-2-chlorophenyl)-5-imidazol-2-ylpyrimidin-2-yl]{2-[(5-nitro(2-pyridyl))amino]ethyl}amine

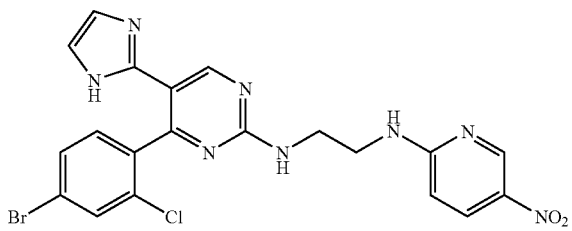

[4-(4-bromo-2-chlorophenyl)-5-imidazol-2-ylpyrimidin-2-yl]{2-[(5-nitro(2-pyridyl))amino]ethyl}amine was prepared from 4-bromo-2-chlorolbenzoyl chloride using the general method for [4-(2,4-dichlorophenyl)-5-imidazol-2-ylpyrimidin-2-yl]{2-[(5-nitro(2-pyridyl))amino]ethyl}amine.

HPLC: 21.5 min (>95% purity)

MS: M+H=515.2 ($C_{20}H_{16}BrClN_8O_2$+H=515)

Example 178

Preparation of 6-[(2-{[4-(4-bromo-2-chlorophenyl)-5-imidazol-2-ylpyrimidin-2-yl]amino}ethyl)amino]pyridine-3-carbonitrile

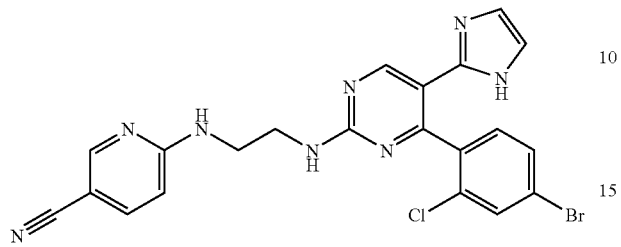

6-[(2-{[4-(4-bromo-2-chlorophenyl)-5-imidazol-2-ylpyrimidin-2-yl]amino}ethyl)amino]pyridine-3-carbonitrile was prepared from 4-bromo-2-chlorobenzoyl chloride and 2-chloro-5-(cyano)pyridine using the general method for [4-(2,4-dichlorophenyl)-5-imidazol-2-ylpyrimidin-2-yl]{2-[(5-nitro(2-pyridyl))amino]ethyl}amine.

HPLC: 17.7 min (>95% purity)

MS: M+H=495 ($C_{21}H_{16}BrClN_8$+H=495)

Example 179

Preparation of [4-(4-bromo-2-chlorophenyl)-5-imidazol-2-ylpyrimidin-2-yl](2-{[5-(trifluoromethyl)(2-pyridyl)]amino}ethyl)amine

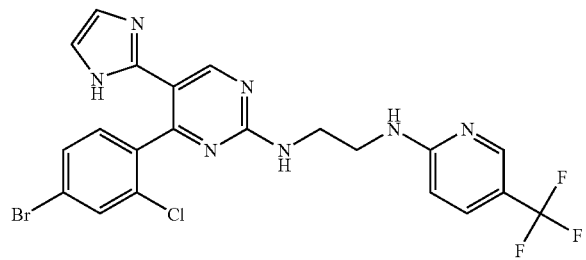

[4-(4-bromo-2-chlorophenyl)-5-imidazol-2-ylpyrimidin-2-yl](2-{[5-(trifluoro-methyl)(2-pyridyl)]amino}ethyl)amine was prepared from 4-bromo-2-chlorobenzoyl chloride and 2-chloro-5-(trifluoromethyl)pyridine using the general method for [4-(2,4-dichlorophenyl)-5-imidazol-2-ylpyrimidin-2-yl]{2-[(5-nitro(2-pyridyl))amino]ethyl}amine.

HPLC: 19.7 min (>95% purity)

MS: M+H=538.2 ($C_{21}H_{16}BrClF_3N_7$+H=538)

Example 180

Preparation of 4-[2-({2-[(6-amino-5-nitro(2-pyridyl))amino]ethyl}amino)-5-imidazol-2-ylpyrimidin-4-yl]benzenecarbonitrile

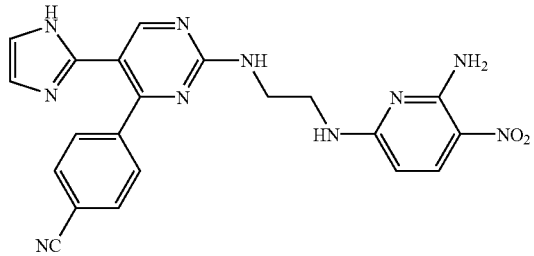

4-[2-({2-[(6-amino-5-nitro(2-pyridyl))amino]ethyl}amino)-5-imidazol-2-ylpyrimidin-4-yl]benzenecarbonitrile was prepared from 4-cyanobenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 20.0 min (>95% purity)

MS: M+H=443.1 ($C_{21}H_{18}N_{10}O_2$+H=443)

Example 181

Preparation of {2-[(6-amino-5-nitro(2-pyridyl))amino]ethyl}{5-imidazol-2-yl-4-[4-(trifluoromethyl)phenyl]pyrimidin-2-yl}amine

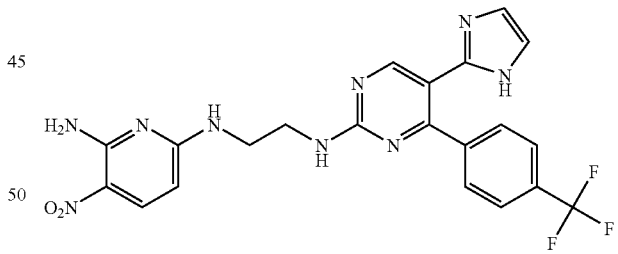

{2-[(6-amino-5-nitro(2-pyridyl))amino]ethyl}{5-imidazol-2-yl-4-[4-(trifluoro-methyl)phenyl]pyrimidin-2-yl}amine was prepared from 4-(trifluoromethyl)benzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 20.2 min (>95% purity)

MS: M+H=486.2 ($C_{21}H_{18}F_3N_9O_2$+H=486)

Example 182

Preparation of {2-[(6-amino-5-nitro(2-pyridyl))amino]ethyl}[4-(2,4-dichlorophenyl)-5-(1-methylimidazol-2-yl)pyrimidin-2-yl]amine

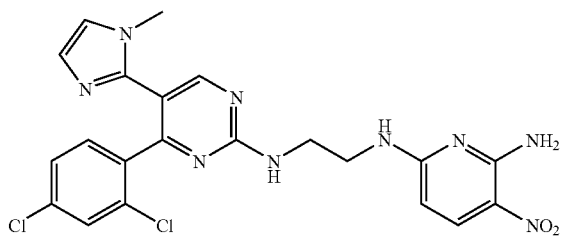

{2-[(6-amino-5-nitro(2-pyridyl))amino]ethyl}[4-(2,4-dichlorophenyl)-5-(1-methyl-imidazol-2-yl)pyrimidin-2-yl]amine was prepared from 1,2-dimethylimidazole using the general method for {2-[(4-amino-5-nitro(2-pyridyl))amino]ethyl}[4-(2,4-dichlorophenyl)-5-imidazol-2-ylpyrimidin-2-yl]amine.

HPLC: 19.6 min (>95% purity)

MS: M+H=500.2 ($C_{21}H_{19}Cl_2N_9O_2$+H=500)

Example 183

Preparation of {2-[(6-amino-5-nitro(2-pyridyl))amino]ethyl}[4-(2-chlorophenyl)-5-imidazol-2-ylpyrimidin-2-yl]amine

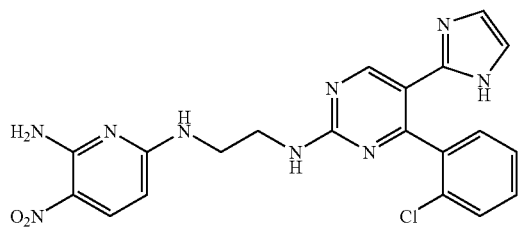

{2-[(6-amino-5-nitro(2-pyridyl))amino]ethyl}[4-(2-chlorophenyl)-5-imidazol-2-yl-pyrimidin-2-yl]amine was prepared from 2-chlorobenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 16.4 min (>95% purity)

MS: M+H=452.7 ($C_{20}H_{18}ClN_9O_2$+H=452)

Example 184

Preparation of {2-[(6-amino-5-nitro(2-pyridyl))amino]ethyl}[4-(2-chloro-4-fluorophenyl)-5-imidazol-2-ylpyrimidin-2-yl]amine

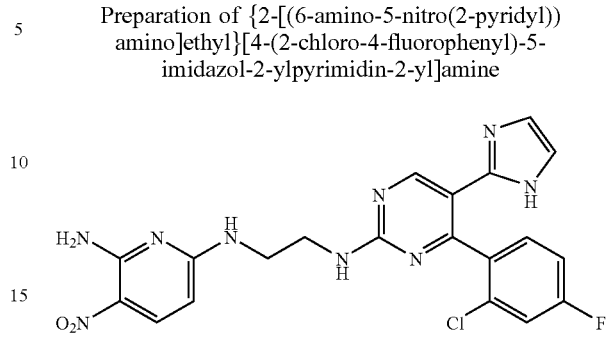

{2-[(6-amino-5-nitro(2-pyridyl))amino]ethyl}[4-(2-chloro-4-fluorophenyl)-5-imidazol-2-ylpyrimidin-2-yl]amine was prepared from 2-chloro-4-fluorobenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 17.3 min (>95% purity)

MS: M+H=470.2 ($C_{20}H_{17}ClFN_9O_2$+H=470)

Example 185

Preparation of {2-[(6-amino-5-nitro(2-pyridyl))amino]ethyl}{4-[4-fluoro-2-(trifluoromethyl)phenyl]-5-imidazol-2-ylpyrimidin-2-yl}amine

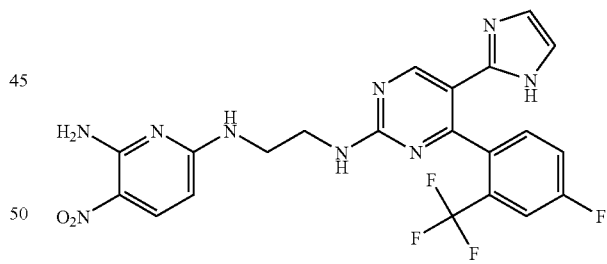

{2-[(6-amino-5-nitro(2-pyridyl))amino]ethyl}{4-[4-fluoro-2-(trifluoromethyl)phenyl]-5-imidazol-2-ylpyrimidin-2-yl}amine was, prepared from 4-fluoro-2-(trifluoromethyl)benzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 18.4 min (>95% purity)

MS: M+H=504.3 ($C_{21}H_{17}F_4N_9O_2$+H=504)

Example 186

Preparation of {2-[(6-amino-5-nitro(2-pyridyl))amino]ethyl}[4-(4-chlorophenyl)-5-imidazol-2-ylpyrimidin-2-yl]amine

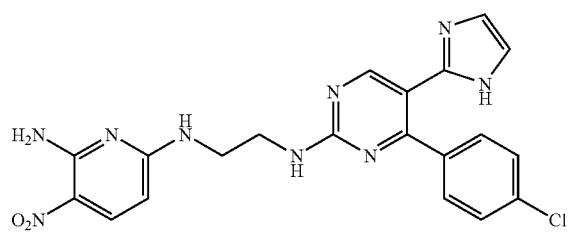

{2-[(6-amino-5-nitro(2-pyridyl))amino]ethyl}[4-(4-chlorophenyl)-5-imidazol-2-ylpyrimidin-2-yl]amine was prepared from 4-chlorobenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 18.0 min (>95% purity)

MS: M+H=452.2 ($C_{20}H_{18}ClN_9O_2$+H=452)

Example 187

Preparation of {2-[(6-amino-5-nitro(2-pyridyl))amino]ethyl}[4-(4-chloro-2-methylphenyl)-5-imidazol-2-ylpyrimidin-2-yl]amine

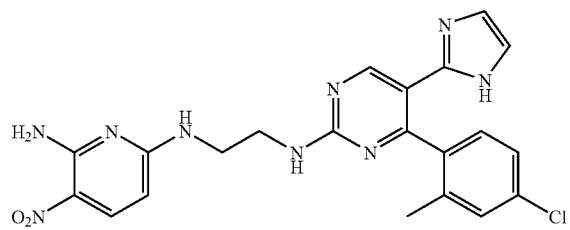

{2-[(6-amino-5-nitro(2-pyridyl))amino]ethyl}[4-(4-chloro-2-methylphenyl)-5-imidazol-2-ylpyrimidin-2-yl]amine was prepared from 4-chloro-2-methylbenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 18.7 min (>95% purity)

MS: M+H=466.1 ($C_{21}H_{20}ClN_9O_2$+H=466)

Example 188

Preparation of {2-[(6-amino-5-nitro(2-pyridyl))amino]ethyl}[4-(4-chloro-2-methoxyphenyl)-5-imidazol-2-ylpyrimidin-2-yl]amine

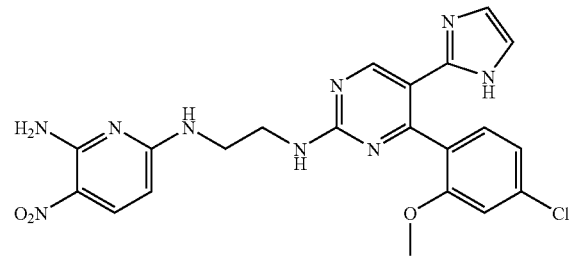

{2-[(6-amino-5-nitro(2-pyridyl))amino]ethyl}[4-(4-chloro-2-methoxyphenyl)-5-imidazol-2-ylpyrimidin-2-yl]amine was prepared from 4-chloro-2-methoxybenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 17.8 min (>95% purity)

MS: M+H=482.1 ($C_{21}H_{20}ClN_9O_3$+H=482)

Example 189

Preparation of {2-[(6-amino-5-nitro(2-pyridyl)amino]ethyl}[4-(4-bromo-2-chlorophenyl)-5-imidazol-2-ylpyrimidin-2-yl]amine

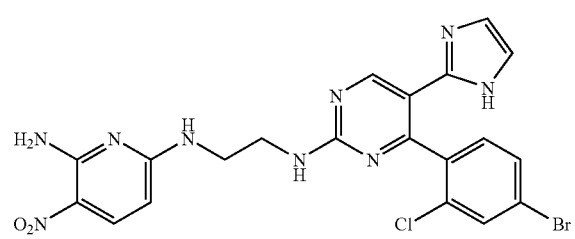

{2-[(6-amino-5-nitro(2-pyridyl))amino]ethyl}[4-(4-chloro-2-methoxyphenyl)-5-imidazol-2-ylpyrimidin-2-yl]amine was prepared from 4-bromo-2-chlorolbenzoyl chloride using the general method for {2-[(4-amino-5-nitro(2-pyridyl))amino]ethyl}[4-(2,4-dichlorophenyl)-5-imidazol-2-ylpyrimidin-2-yl]amine.

HPLC: 19.4 min (>95% purity)

MS: M+H=530 ($C_{20}H_{17}BrClN_9O_2$+H=530)

Example 190

Preparation of {2-[(6-amino-5-nitro(2-pyridyl))amino]ethyl}[4-(4-bromo-2-chlorophenyl)-5-(4-methylimidazol-2-yl)pyrimidin-2-yl]amine

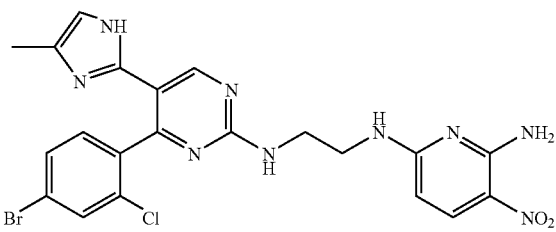

{2-[(6-amino-5-nitro(2-pyridyl))amino]ethyl}[4-(4-bromo-2-chlorophenyl)-5-(4-methylimidazol-2-yl)pyrimidin-2-yl]amine was prepared from 4-bromo-2-chlorolbenzoyl chloride and 2-amino-6-chloro-3-nitropyridine using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 19.4 min (>95% purity)

MS: M+H=544.1 ($C_{21}H_{19}BrClN_9O_2$+H=544)

Example 191

Preparation of 6-[(2-{[4-(4-bromo-2-chlorophenyl)-5-(4-methylimidazol-2-yl)pyrimidin-2-yl]amino}ethyl)amino]pyridine-3-carbonitrile

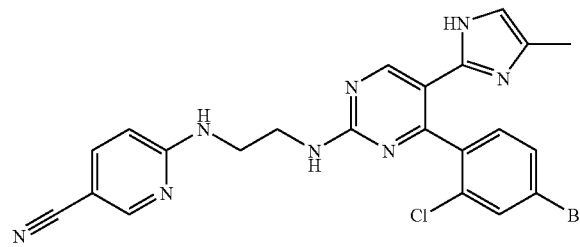

6-[(2-{[4-(4-bromo-2-chlorophenyl)-5-(4-methylimidazol-2-yl)pyrimidin-2-yl]amino}ethyl)amino]pyridine-3-carbonitrile was prepared from 4-bromo-2-chlorolbenzoyl chloride using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 18.7 min (>95% purity)

MS: M+H=509.1 ($C_{22}H_{18}BrClN_8$+H=509)

Example 192

Preparation of {2-[(6-amino-5-nitro(2-pyridyl))amino]ethyl}[4-(2-chloro-4-fluorophenyl)-5-(4-methylimidazol-2-yl)pyrimidin-2-yl]amine

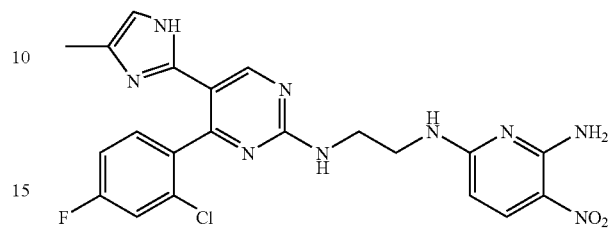

{2-[(6-amino-5-nitro(2-pyridyl))amino]ethyl}[4-(2-chloro-4-fluorophenyl)-5-(4-methylimidazol-2-yl)pyrimidin-2-yl]amine was prepared from 4-fluoro-2-chlorobenzoyl chloride and 2-amino-6-chloro-3-nitropyridine using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 17.7 min (>95% purity)

MS: M+H=484.3 ($C_{21}H_{19}ClFN_9O_2$+H=484)

Example 193

Preparation of 6-[(2-{[4-(2-chloro-4-fluorophenyl)-5-(4-methylimidazol-2-yl)pyrimidin-2-yl]amino}ethyl)amino]pyridine-3-carbonitrile

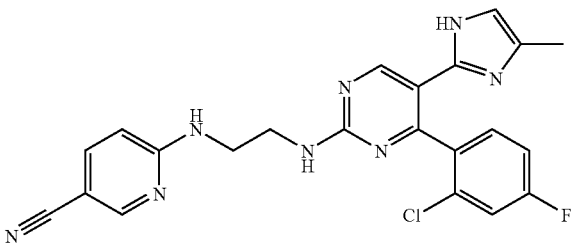

6-[(2-{[4-(2-chloro-4-fluorophenyl)-5-(4-methylimidazol-2-yl)pyrimidin-2-yl]amino}ethyl)amino]pyridine-3-carbonitrile was prepared from 4-fluoro-2-chlorobenzoyl chloride using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 16.7 min (>95% purity)

MS: M+H=449.3 ($C_{22}H_{18}ClFN_8$+H=449)

Example 194

Preparation of [4-(2,4-dichlorophenyl)-5-(4-methylimidazol-2-yl)pyrimidin-2-yl]{2-[(5-nitro(2-pyridyl))amino]ethyl}amine

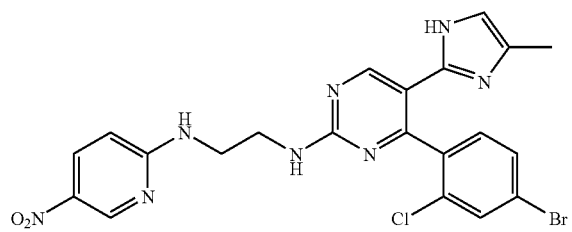

[4-(2,4-dichlorophenyl)-5-(4-methylimidazol-2-yl)pyrimidin-2-yl]{2-[(5-nitro(2-pyridyl))amino]ethyl}amine was prepared from 6-chloro-3-nitropyridine using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 21.9 min (>95% purity)

MS: M+H=485.6 ($C_{21}H_{18}Cl_2N_8O_2$+H=485)

Example 195

Preparation of {2-[(6-amino-5-nitro(2-pyridyl))amino]ethyl}[4-(2,4-dichlorophenyl)-5-(4-methylimidazol-2-yl)pyrimidin-2-yl]amine

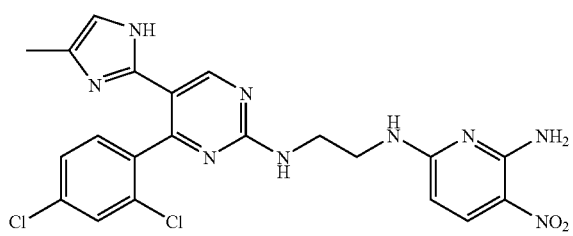

{2-[(6-amino-5-nitro(2-pyridyl))amino]ethyl}[4-(2,4-dichlorophenyl)-5-(4-methyl-imidazol-2-yl)pyrimidin-2-yl]amine was prepared from 2-amino-6-chloro-3-nitropyridine using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 19.8 min (>95% purity)

MS: M+H=500.2 ($C_{21}H_{19}Cl_2N_9O_2$+H=500)

Example 196

Preparation of [4-(2,4-dichlorophenyl)-5-(4-methylimidazol-2-yl)pyrimidin-2-yl](2-{[5-(trifluoromethyl)(2-pyridyl)]amino}ethyl)amine

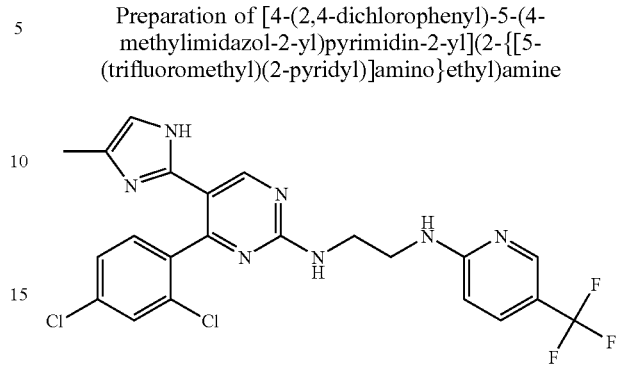

[4-(2,4-dichlorophenyl)-5-(4-methylimidazol-2-yl)pyrimidin-2-yl](2-{[5-(trifluoro-methyl)(2-pyridyl)]amino}ethyl)amine was prepared from 2-chloro-5-(trifluoromethyl)pyridine using the general method for 6-[(2-{[4-(2,4-dichlorophenyl)-5-(4-methylimidazol-2-yl)pyrimidin-2-yl]amino}ethyl)amino]pyridine-3-carbonitrile.

HPLC: 20.0 min (>95% purity)

MS: M+H=508.1 ($C_{22}H_{18}Cl_2F_3N_7$+H=508)

Example 197

Preparation of 4-[2-({2-[(6-chloropyrimidin-4-yl)amino]ethyl}amino)-5-imidazolylpyrimidin-4-yl]benzenecarbonitrile

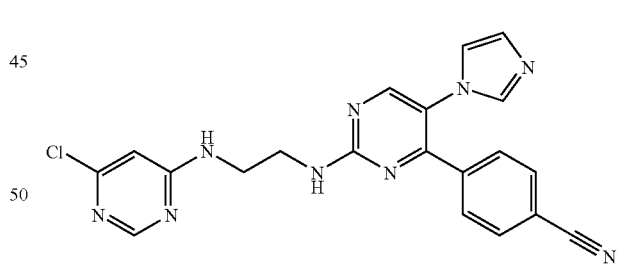

4-[2-({2-[(6-chloropyrimidin-4-yl)amino]ethyl}amino)-5-imidazolylpyrimidin-4-yl]benzenecarbonitrile was prepared from 4,6-dichloropyrimidine using the general method for 4-{5-imidazolyl-2-[(2-{[5-(trifluoromethyl)(2-pyridyl)]amino}ethyl)amino]pyrimidin-4-yl}benzenecarbonitrile.

HPLC: 16.1 min (>95% purity)

MS: M+H=418.1 ($C_{20}H_{16}ClN_9$+H=418)

Example 198

Preparation of 4-amino-2-[(2-{[4-(4-cyanophenyl)-5-imidazolylpyrimidin-2-yl]amino}ethyl)amino]pyrimidine-5-carbonitrile

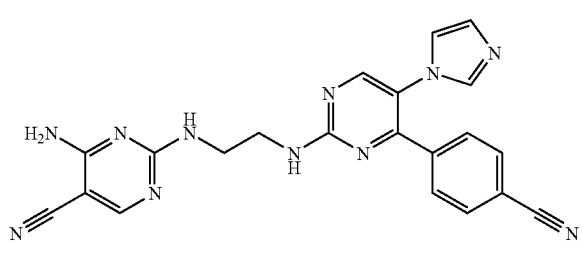

4-amino-2-[(2-{[4-(4-cyanophenyl)-5-imidazolylpyrimidin-2-yl]amino}ethyl)amino]pyrimidine-5-carbonitrile was prepared from 4-amino-2-chloropyrimidine-5-carbonitrile using the general method for 4-{5-imidazolyl-2-[(2-{[5-(trifluoromethyl) (2-pyridyl)]amino}ethyl)amino]pyrimidin-4-yl}benzenecarbonitrile.

HPLC: 17.5 min (>95% purity)

MS: M+H=436.2 ($C_{21}H_{17}N_{11}$+H=436)

Example 199

Preparation of [6-(2,4-dichlorophenyl)-5-(4-methylimidazolyl)(2-pyridyl)]{2-[(5-nitro(2-pyridyl))amino]ethyl}amine

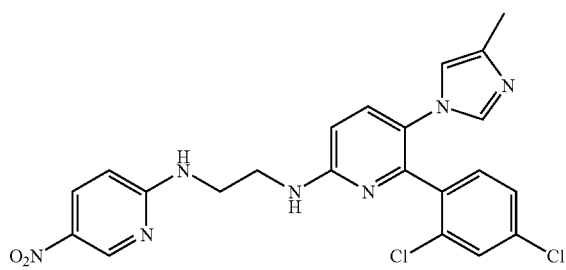

[6-(2,4-dichlorophenyl)-5-(4-methylimidazolyl)(2-pyridyl)]{2-[(5-nitro(2-pyridyl))amino]ethyl}amine was prepared from 4-methyimidazole (the isomers were separated using a slica gel column) and 2-chloro-5-nitropyridine using the general method for {2-[(6-amino-5-nitro(2-pyridyl))amino]ethyl}[6-(2,4-dichlorophenyl)-5-imidazolyl (2-pyridyl)]amine.

HPLC: 22.8 min (>95% purity)

MS: M+H=484.2 ($C_{22}H_{19}Cl_2N_7O_2$+H=484)

Example 200

Preparation of [6-(2,4-dichlorophenyl)-5-(4-methylimidazolyl)(2-pyridyl)](2-{[5-(trifluoromethyl)(2-pyridyl)]amino}ethyl)amine

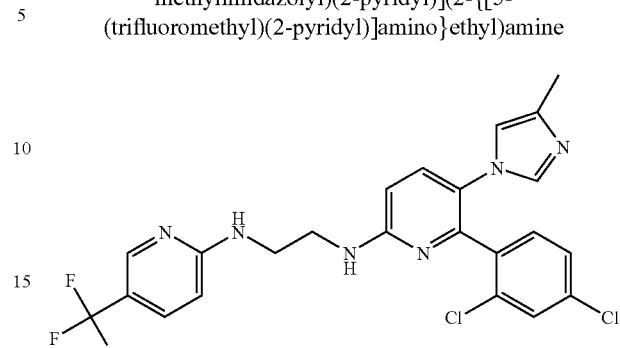

[6-(2,4-dichlorophenyl)-5-(4-methylimidazolyl)(2-pyridyl)](2-{[5-(trifluoro-methyl)(2-pyridyl)]amino}ethyl)amine was prepared from 4-methyimidazole (the isomers were separated using a slica gel column) and 2-chloro-5-(trifluoromethyl)pyridine using the general method for {2-[(6-amino-5-nitro(2-pyridyl))amino]ethyl}[6-(2,4-dichlorophenyl)-5-imidazolyl(2-pyridyl)]amine.

HPLC: 21.0 min (>95% purity)

MS: M+H=507 ($C_{23}H_{19}Cl_2F_3N_6$+H=507)

Example 201

Preparation of 1-[2-(2,4-dichlorophenyl)-6-({2-pyridyl))amino]ethyl}amino)-3-pyridyl]hydropyridin-2-one

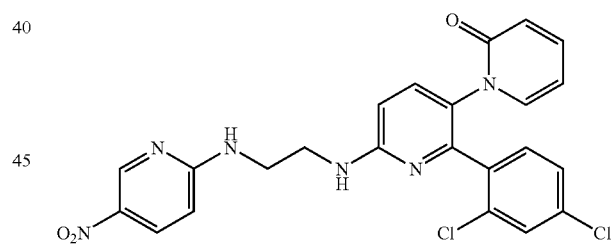

1-[2-(2,4-dichlorophenyl)-6-({2-[(5-nitro(2-pyridyl))amino]ethyl}amino)-3-pyridyl]hydropyridin-2-one was prepared following the same procedures as the method for {2-[(6-amino-5-nitro(2-pyridyl))amino]ethyl}[6-(2,4-dichlorophenyl)-5-imidazolyl (2-pyridyl)]amine with the following exceptions. 1-[2-(2,4-dichlorophenyl)-2-oxoethyl]hydropyridin-2-one was made by heating 2-hydroxypyridine with 2 equivalents of Hünig's base in acetonitrile until dissolved followed by addition of 1-(2,4-dichlorophenyl)-2-chloroethan-1-one. The reaction was heated at 65° C. for 18 hours and purified by slica gel column. Also, 2-chloro-5-nitropyridine was used for the final step.

HPLC: X min (>95% purity)

MS: M+H=X ($C_{23}H_{18}Cl_2N_6O_3$+H=X)

Example 202

Preparation of 1-[6-({2-[(6-amino-5-nitro(2-pyridyl))amino]ethyl}amino)-2-(2,4-dichlorophenyl)-3-pyridyl]hydropyridin-2-one

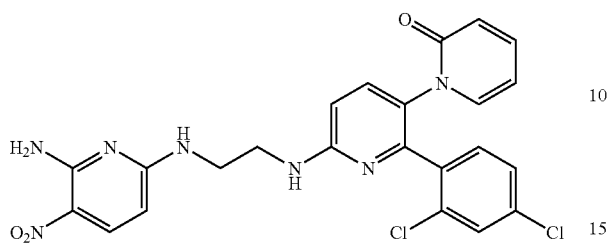

1-[6-({2-[(6-amino-5-nitro(2-pyridyl))amino]ethyl}amino)-2-(2,4-dichlorophenyl)-3-pyridyl]hydropyridin-2-one was prepared following the same procedures as the method for {2-[(6-amino-5-nitro(2-pyridyl))amino]ethyl}[6-(2,4-dichlorophenyl)-5-imidazolyl(2-pyridyl)]amine with the following exceptions. 1-[2-(2,4-dichlorophenyl)-2-oxoethyl]hydropyridin-2-one was made by heating 2-hydroxypyridine with 2 equivalents of Hünig's base in acetonitrile until dissolved followed by addition of 1-(2,4-dichlorophenyl)-2-chloroethan-1-one. The reaction was heated at 65° C. for 18 hours and purified by slica gel column.

HPLC: X min (>95% purity)

MS: M+H=X ($C_{23}H_{19}Cl_2N_7O_3$+H=X)

Example 203

Preparation of 6-[(2-{[6-(2,4-dichlorophenyl)-5-(2-oxohydropyridyl)-2-pyridyl]amino}ethyl)amino]pyridine-3-carbonitrile

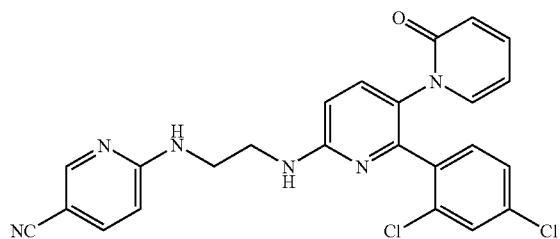

6-[(2-{[6-(2,4-dichlorophenyl)-5-(2-oxohydropyridyl)-2-pyridyl]amino}ethyl)amino]pyridine-3-carbonitrile was prepared following the same procedures as the method for {2-[(6-amino-5-nitro(2-pyridyl))amino]ethyl}[6-(2,4-dichlorophenyl)-5-imidazolyl(2-pyridyl)]amine with the following exceptions. 1-[2-(2,4-dichlorophenyl)-2-oxoethyl]hydropyridin-2-one was made by heating 2-hydroxypyridine with 2 equivalents of Hünig's base in acetonitrile until dissolved followed by addition of 1-(2,4-dichlorophenyl)-2-chloroethan-1-one. The reaction was heated at 65° C. for 18 hours and purified by slica gel column. Also, 2-chloro-5-cyanopyridine was used for the final step.

HPLC: X min (>95% purity)

MS: M+H=X ($C_{24}H_{18}Cl_2N_6O$+H=X)

Example 204

Preparation of ethyl 6-({2-[(5-nitro(2-pyridyl))amino]ethyl}amino)-2-phenylpyridine-3-carboxylate

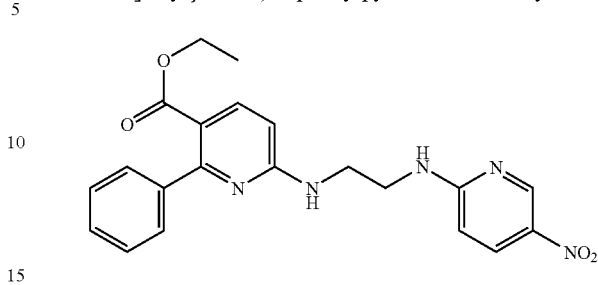

ethyl 6-({2-[(5-nitro(2-pyridyl))amino]ethyl}amino)-2-phenylpyridine-3-carboxylate was prepared from ethyl 3-oxo-3-phenylpropanoate as the starting material and DDQ in the oxidation step. The final product is achieved directly from the chloropyridine by reacting ethyl 6-chloro-2-phenylpyridine-3-carboxylate with 2-(2-aminoethylamine)-5-nitropyridine in CH$_3$CN and Hüing's base at 80° C. for 18 hours. The procedures are analogous to the general method for {2-[(6-amino-5-nitro(2-pyridyl))amino]ethyl}[6-(2,4-dichlorophenyl)-5-imidazolyl(2-pyridyl)]amine.

HPLC: 24.5 min (>95% purity)

MS: M+H=408.1 ($C_{21}H_{21}N_5O_4$+H=408.1)

Example 205

Preparation of ethyl 2-(2,4-dichlorophenyl)-6-({2-[(5-nitro(2-pyridyl))amino]ethyl}amino)pyridine-3-carboxylate

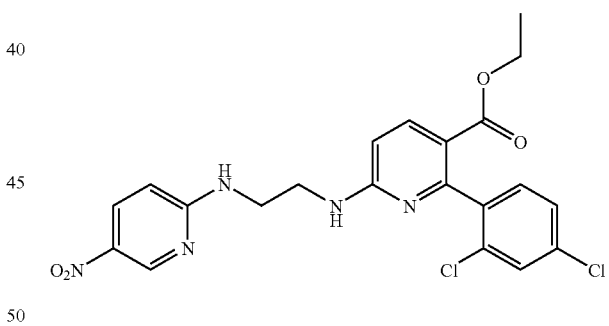

Ethyl 2-(2,4-dichlorophenyl)-6-({2-[(5-nitro(2-pyridyl))amino]ethyl}amino)pyridine-3-carboxylate was prepared from ethyl 3-(2,4-dichlorophenyl)-3-oxopropanoate (ref. Wemple, J.; et. al. *Synthesis* 1993, 290–292.) as the starting material and THF/ethanol ratio of 3:1 as the solvent in the first step. The oxidation uses DDQ. The final product is achieved directly from the chloropyridine by reacting ethyl 6-chloro-2-phenylpyridine-3-carboxylate with 2-(2-aminoethylarnine)-5-nitropyridine in CH$_3$CN and Hüing's Hüing's base at 120° C. for 18 hours. The procedures are analogous to the general method for {2-[(6-amino-5-nitro(2-pyridyl))amino]ethyl}[6-(2,4-dichlorophenyl)-5-imidazolyl(2-pyridyl)]amine.

HPLC: 31 min (>95% purity)

MS: M+H=476.1 ($C_{21}H_{19}Cl_2N_5O_4$+H=476)

Example 206

Preparation of ethyl 2-(4-cyanophenyl)-6-({2-[(5-nitro(2-pyridyl))amino]ethyl}amino)pyridine-3-carboxylate

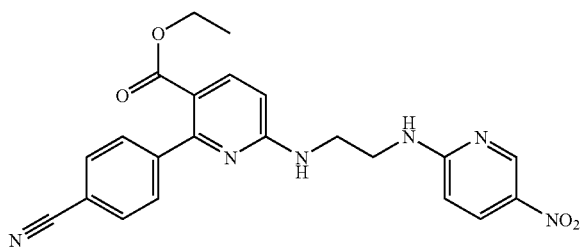

ethyl 2-(4-cyanophenyl)-6-({2-[(5-nitro(2-pyridyl))amino]ethyl}amino)pyridine-3-carboxylate (62258) was prepared from ethyl 3-(4-cyanophenyl)-3-oxopropanoate (ref. Wemple, J.; et. al. *Synthesis* 1993, 290–292.) as the starting material and THF/ethanol ratio of 1:5 as the solvent in the first step. The oxidation uses DDQ in toluene. The final product is achieved directly from the chloropyridine by reacting ethyl 6-chloro-2-phenylpyridine-3-carboxylate with 2-(2-aminoethylamine)-5-nitropyridine in DMA and Hüing's base at 120° C. for 18 hours. The procedures are analogous to the general method for {2-[(6-amino-5-nitro(2-pyridyl))amino]ethyl}[6-(2,4-dichlorophenyl)-5-imidazolyl(2-pyridyl)]amine.

HPLC: 26.8 min (>95% purity)

MS: M+H=433.1 ($C_{22}H_{20}N_6O_4$+H=433)

Example 207

Preparation of 4-[3-imidazolyl-6-({2-[(5-nitro(2-pyridyl))amino]ethyl}amino)-2-pyridyl]benzenecarbonitrile

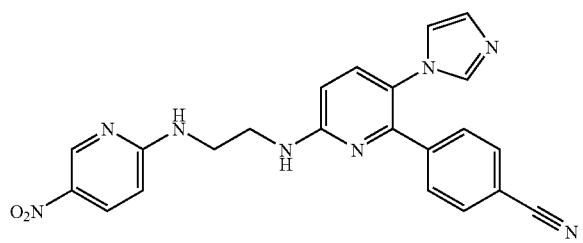

4-[3-imidazolyl-6-({2-[(5-nitro(2-pyridyl))amino]ethyl}amino)-2-pyridyl]benzene-carbonitrile was prepared from 4-cyanophenacyl bromide, CAN for the oxidation (1:1 acetic acid and water with heating at 80° C. for 1 hour), and 2-chloro-5-nitropyridine using the general method for {2-[(6-amino-5-nitro(2-pyridyl))amino]ethyl}[6-(2,4-dichlorophenyl)-5-imidazolyl(2-pyridyl)]amine.

HPLC: 19.5 min (>95% purity)

MS: M+H=427.2 ($C_{22}H_{18}N_8O_2$+H=427)

Example 208

Preparation of ethyl 6-({2-[(5-nitro(2-pyridyl))amino]ethyl}amino)-2-[4-(trifluoromethyl)phenyl]pyridine-3-carboxylate

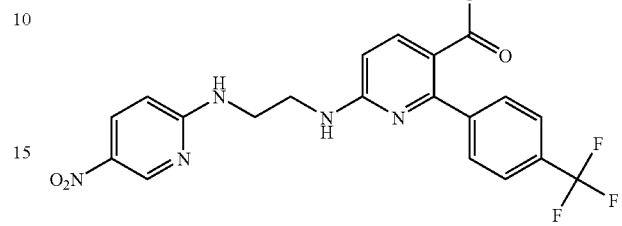

ethyl 6-({2-[(5-nitro(2-pyridyl))amino]ethyl}amino)-2-[4-(trifluoromethyl) phenyl]pyridine-3-carboxylate was prepared from ethyl 3-oxo-3[4-(trifluoromethyl)phenyl]propanoate (ref. Wemple, J.; et. al. *Synthesis* 1993, 290–292.) as the starting material. The oxidation was accomplished using 4 equivalents of chlorotrimethysilane and 1 equivalent of bromine in dichlormethane. The product was obtained directly from ethyl 6-chloro-2-[4-(trifluoromethyl)phenyl]pyridine-3-carboxylate by reacting it with 2-(2-aminoethylamine)-5-nitropyridine in DMA and Hünig's base at 70° C. for 72 hours. These procedures are analogous to the general method for {2-[(6-amino-5-nitro(2-pyridyl))amino]ethyl}[6-(2,4-dichlorophenyl)-5-imidazolyl(2-pyridyl)]amine.

HPLC: 30.4 min (>95% purity)

MS: M+H=476.2 ($C_{22}H_{20}F_3N_5O_4$+H=476)

Example 209

Preparation of 6-({2-[(5-nitro(2-pyridyl))amino]ethyl}amino)-2-[4-(trifluoromethyl)phenyl]pyridine-3-carboxylic acid

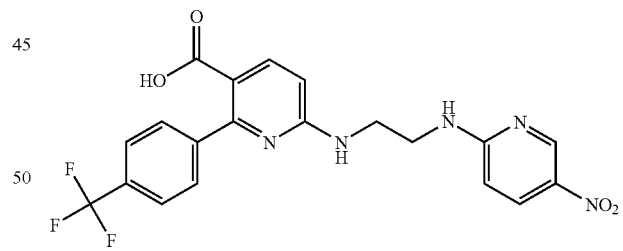

6-({2-[(5-nitro(2-pyridyl))amino]ethyl}amino)-2-[4-(trifluoromethyl) phenyl]pyridine-3-carboxylic acid was made by hydrolyzing ethyl 6-({2-[(5-nitro(2-pyridyl))amino]ethyl}amino)-2-[4-(trifluoromethyl)phenyl]pyridine-3-carboxylate (71477) which was made following the general method for {2-[(6-amino-5-nitro(2-pyridyl))amino]ethyl}[6-(2,4-dichlorophenyl)-5-imidazolyl(2-pyridyl)]amine. The hydrolyze was carried out using a solution of 1:1 water and concentrated hydrochloric acid and heating to 80° C. overnight.

HPLC: 24.0 min (>95% purity)

MS: M+H=448.1 ($C_{20}H_{16}F_3N_5O_4$+H=448)

Example 210

Preparation of 2-(2,4-dichlorophenyl)-6-({2-[(5-nitro(2-pyridyl))amino]ethyl}amino)pyridine-3-carboxylic acid

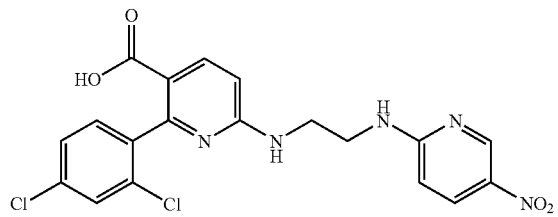

2-(2,4-dichlorophenyl)-6-({2-[(5-nitro(2-pyridyl))amino]ethyl}amino)pyridine-3-carboxylic acid was made by hydrolyzing ethyl 2-(2,4-dichlorophenyl)-6-({2-[(5-nitro(2-pyridyl))amino]ethyl}amino)pyridine-3-carboxylate (62257) which was made following the general method for {2-[(6-amino-5-nitro(2-pyridyl))amino]ethyl}[6-(2,4-dichlorophenyl)-5-imidazolyl(2-pyridyl)]amine. The hydrolize was carried out using a solution of 1:1 water and concentrated hydrochloric acid and heating to 80° C. overnight.

HPLC: 23.6 min (>95% purity)

MS: M+H=448.1 ($C_{19}H_{15}Cl_2N_5O_4$+H=448)

Example 211

Preparation of [6-(2,4-dichlorophenyl)-5-imidazolyl(2-pyridyl)]{2-[(5-nitro(2-pyridyl))amino]ethyl}amine

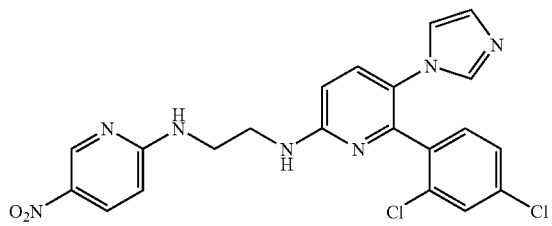

[6-(2,4-dichlorophenyl)-5-imidazolyl(2-pyridyl)]{2-[(5-nitro(2-pyridyl)) amino]ethyl}amine was prepared from 2-chloro-5-(nitro)pyridine using the general method for {2-[(6-amino-5-nitro(2-pyridyl))amino]ethyl}[6-(2,4-dichlorophenyl)-5-imidazolyl(2-pyridyl)]amine.

HPLC: 22.9 min (>95% purity)

MS: M+H=470.1 ($C_{21}H_{17}Cl_2N_7O_2$+H=470)

Example 212

Preparation of 6-[(2-{[6-(2,4-dichlorophenyl)-5-imidazolyl-2-pyridyl]amino}ethyl)amino]pyridine-3-carbonitrile

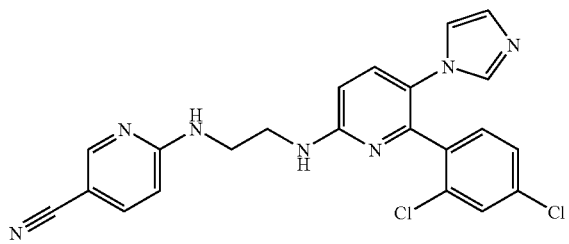

6-[(2-{[6-(2,4-dichlorophenyl)-5-imidazolyl-2-pyridyl]amino}ethyl)amino]pyridine-3-carbonitrile was prepared from 2-chloropyridine-5-carbonitrile using the general method for {2-[(6-amino-5-nitro(2-pyridyl))amino]ethyl}[6-(2,4-dichlorophenyl)-5-imidazolyl(2-pyridyl)]amine.

HPLC: 18.8 min (>95% purity)

MS: M+H=450 ($C_{22}H_{17}Cl_2N_7$+H=450)

Example 213

Preparation of {2-[(6-amino-5-nitro(2-pyridyl))amino]ethyl}[6-(2,4-dichlorophenyl)-5-(4-methylimidazolyl)(2-pyridyl)]amine

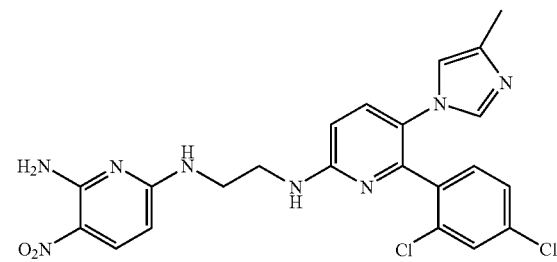

{2-[(6-amino-5-nitro(2-pyridyl))amino]ethyl}[6-(2,4-dichlorophenyl)-5-(4-methyl-imidazolyl)(2-pyridyl)]amine was prepared from 4-methylimidazole (the isomers were separated using a slica gel column) using the general method for {2-[(6-amino-5-nitro(2-pyridyl))amino]ethyl}[6-(2,4-dichlorophenyl)-5-imidazolyl(2-pyridyl)]amine.

HPLC: 21.5 min (>95% purity)

MS: M+H=499.3 ($C_{22}H_{20}Cl_2N_8O_2$+H=499)

Example 214

Preparation of 6-[(2-{[6-(2,4-dichlorophenyl)-5-(4-methylimidazolyl)-2-pyridyl]amino}ethyl)amino]pyridine-3-carbonitrile

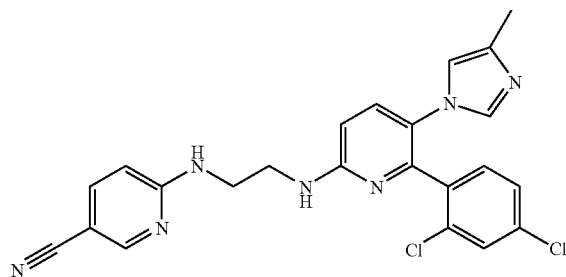

6-[(2-{[6-(2,4-dichlorophenyl)-5-(4-methylimidazolyl)-2-pyridyl]amino}ethyl)amino]pyridine-3-carbonitrile was prepared from 4-methyimidazole (The isomers were separated using a slica gel column.) and 2-chloropyridine-5-carbonitrile using the general method for {2-[(6-amino-5-nitro(2-pyridyl))amino]ethyl}[6-(2,4-dichlorophenyl)-5-imidazolyl(2-pyridyl)]amine.

HPLC: 20.7 min (>95% purity)

MS: M+H=464.2 ($C_{23}H_{19}Cl_2N_7$+H=464)

Example 215

Preparation of {2-[(6-amino-5-nitro(2-pyridyl))amino]ethyl}[6-(2,4-dichlorophenyl)-5-imidazol-2-yl(2-pyridyl)]amine

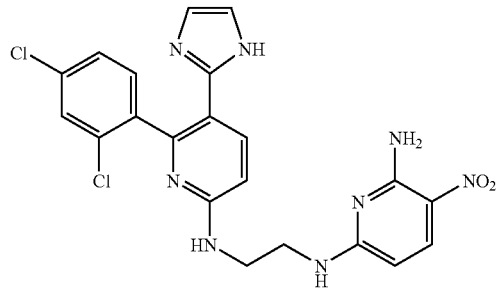

{2-[(6-amino-5-nitro(2-pyridyl))amino]ethyl}[6-(2,4-dichlorophenyl)-5-imidazol-2-yl(2-pyridyl)]amine was prepared from (2-aminoethyl)(6-amino-5-nitro(2-pyridyl))amine using the general method for [6-(2,4-dichlorophenyl)-5-imidazol-2-yl(2-pyridyl)]{2-[(5-nitro(2-pyridyl))amino]ethyl}amine.

HPLC: 20.1 min (>95% purity)

MS: M+H=485.4 ($C_{21}H_{18}Cl_2N_8O_2$+H=485)

Example 216

Preparation of [6-(2,4-dichlorophenyl)-5-imidazol-2-yl(2-pyridyl)](2-{[5-(trifluoromethyl)(2-pyridyl)]amino}ethyl)amine

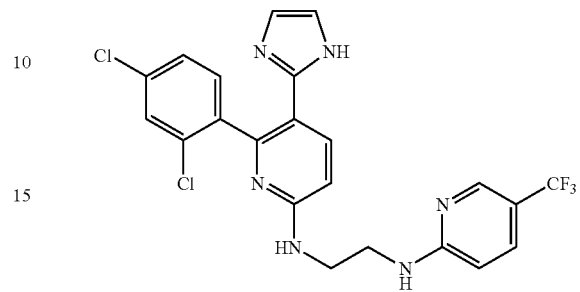

[6-(2,4-dichlorophenyl)-5-imidazol-2-yl(2-pyridyl)](2-{[5-(trifluoromethyl) (2-pyridyl)]amino}ethyl)amine was prepared from (2-aminoethyl)[5-(trifluoromethyl)(2-pyridyl)]amine using the general method for [6-(2,4-dichlorophenyl)-5-imidazol-2-yl(2-pyridyl)]{2-[(5-nitro(2-pyridyl))amino]ethyl}amine.

HPLC: 20.3 min (>95% purity)

MS: M+H=493.3 ($C_{22}H_{17}Cl_2F_3N_6$+H=493)

Example 217

Preparation of 6-[(2-{[6-(2,4-dichlorophenyl)-5-imidazol-2-yl-2-pyridyl]amino}ethyl)amino]pyridine-3-carbonetrile

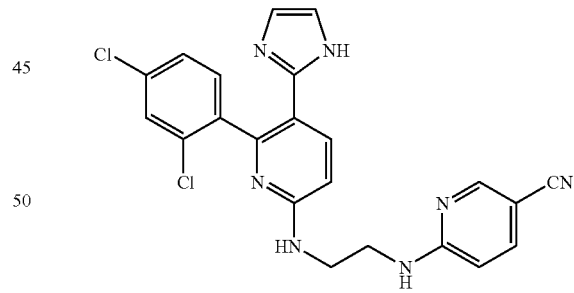

6-[(2-{[6-(2,4-dichlorophenyl)-5-imidazol-2-yl-2-pyridyl]amino}ethyl)amino]pyridine-3-carbonitrile was prepared from 6-[(2-aminoethyl)amino]pyridine-3-carbonitrile using the general method for [6-(2,4-dichlorophenyl)-5-imidazol-2-yl(2-pyridyl)]{2-[(5-nitro(2-pyridyl))amino]ethyl}amine.

HPLC: 18.9 min (>95% purity)

MS: M+H=450.4 ($C_{22}H_{17}Cl_2N_7$+H=450)

Example 218

Preparation of 1-(2,4-Dichlorophenyl)-2-pyrazolylethan-1-one

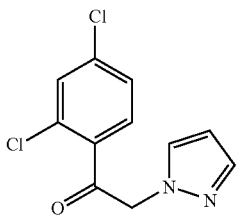

To a solution of 2',4'-dichlorophenacyl chloride (2.0 g, 8.9 mmol) and dry MeCN (50 mL) at 23° C. was added pyrazole (3.1 g, 44.8 mmol). The resulting solution was heated at 80° C. for 5 h then cooled to 23° C. The MeCN was removed under reduced pressure and CH2Cl2 (50 mL) was added. The resulting solution was washed with H2O (2×15 mL) and the organic layer was dried (Na2SO4) and concentrated under reduced pressure. The resulting residue was purified on silica gel (40% EtOAc/hexanes) to yield a light yellow solid.

m/z 256 (MH+)

Example 219

Preparation of 1-(2,4-Dichlorophenyl)-2-(4-methylimidazolyl)ethan-1-one

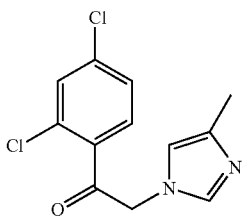

Made using the same procedure as for 1-(2,4-dichlorophenyl)-2-pyrazolylethan-1-one except that 4-methylimidazole,(3.7 g, 44.8 mmol) was used in place of pyrazole. The crude residue was purified on silica gel (5% MeOH/CH2Cl2) to yield a light yellow solid.

m/z 270 (MH+).

Example 220

Preparation of 1-(2,4-Dichlorophenyl)-2-(2,4-dimethylimidazole)ethan-1-one

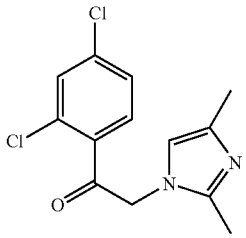

Made using the same procedure as for 1-(2,4-dichlorophenyl)-2-pyrazolylethan-1-one except that 2,4-dimethylimidazole (4.3 g, 44.8 mmol) was used in place of pyrazole. The crude residue was purified on silica gel (5% MeOH/CH2Cl2) to yield a light yellow solid m/z 284 (MH+)

Example 221

Preparation of 1-[2-(2,4-Dichlorophenyl)-2-oxoethyl]hydropyridin-2-one

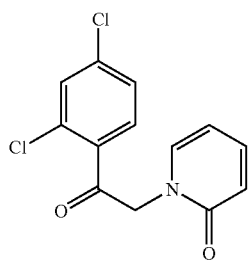

To a solution of 2', 4'-dichlorophenacyl chloride (1.0 g, 4.5 mmol) and dry MeCN (20 mL) at 23° C. was added polystyrene-bound 1,5,7-triazabicyclo[4.4.0]dec-5-ene (2.6 g, 6.7 mmol) and 2-hydroxypyridine (428 mg, 4.5 mmol) and the resulting mixture was shaken at 23° C. for 20 h. The mixture was filtered and the resin was washed with MeCN (10 mL). The MeCN was removed under reduced pressure and the resulting residue was purified on silica gel (5% MeOH/CH2Cl2) to yield a light yellow solid.

m/z 283 (MH+)

Example 222

Preparation of 2-Benzimidazolyl-1-(2,4-dichlorophenyl)ethan-1-one

Made using the same procedure as for 1-(2,4-dichlorophenyl)-2-pyrazolylethan-1-one except that benzimidazole (5.3 g, 44.8 mmol) was used in place of pyrazole. The crude residue was purified on silica gel (50% EtOAc/hexanes) to yield a light yellow solid m/z 306 (MH+)

Example 223

Preparation of 1-(2,4-Dichlorophenyl)-2-(2-methylimidazolyl)ethan-1-one

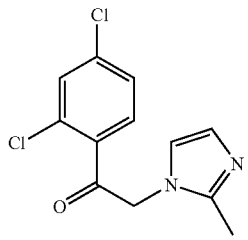

Made using the same procedure as for 1-(2,4-dichlorophenyl)-2-pyrazolylethan-1-one except that 2-methylimidazole (3.7 g, 44.8 mmol) was used in place of pyrazole. The crude residue was purified on silica gel (5% MeOH/CH2Cl2) to yield a light yellow solid.

m/z 270 (MH+)

Example 224

Preparation of 1-(2,4-Dichlorophenyl)-2-(4-phenylimidazolyl)ethan-1-one

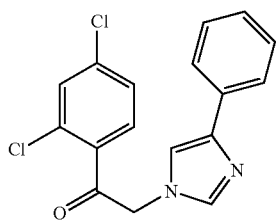

Made using the same procedure as for 1-(2,4-dichlorophenyl)-2-pyrazolylethan-1-one except that 4-phenylimidazole (6.5 g, 44.8 mmol) was used in place of pyrazole. The crude residue was purified on silica gel (50% EtOAc/hexanes) to yield a light yellow solid. m/z 332 (MH+)

Example 225

Preparation of 1-(2,4-Dichlorophenyl)-2-imidazolylethan-1-one

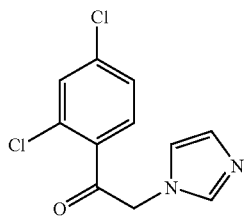

Made using the same procedure as for 1-(2,4-dichlorophenyl)-2-pyrazolylethan-1-one except that imidazole (3.1 g, 44.8 mmol) was used in place of pyrazole. The crude residue was purified on silica gel (5% MeOH/CH2Cl2) to yield a light yellow solid.

m/z 256 (MH+)

Example 226

Preparation of 1-[2-(2,4-Dichlorophenyl)-2-oxoethyl]-5-chlorohydropyridin-2-one

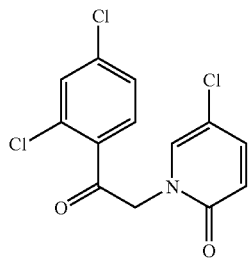

Made using the same procedure as for 1-[2-(2,4-dichlorophenyl)-2-oxoethyl]hydropyridin-2-one except that 5-chloro-2-hydroxypyridine (583 mg, 4.5 mmol) was used in place of 2-hydroxypyridine. The crude residue was purified on silica gel (5% MeOH/CH2Cl2) to yield a light yellow solid.

m/z 317 (MH+)

Example 227

Preparation of 1-(2,4-Dichlorophenyl)-3-(dimethylamino)-2-pyrazolylprop-2-en-1-one

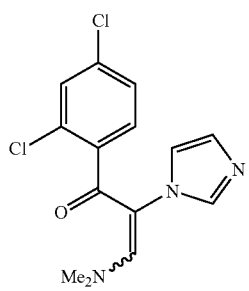

A solution of 1-(2,4-dichlorophenyl)-2-pyrazolylethan-1-one (I, 1.0 g, 3.9 mmol) and dimethylfornamidedimethyl acetal (10 mL, 75 mmol) was heated at 100° C. for 2 h. The resulting red-brown solution was concentrated under reduced pressure to yield a dark red-brown oil which was used without further purification.

m/z 311 (MH+)

Example 228

Preparation of 1-(2,4-Dichlorophenyl)-3-(dimethylamino)-2-(4-methylimidazolyl)prop-2-en-1-one

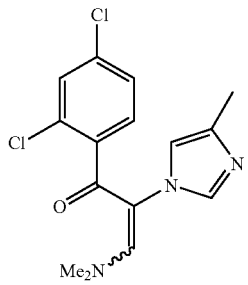

Made using the same procedure as for 1-(2,4-dichlorophenyl)-3-(dimethylamino)-2-pyrazolylprop-2-en-1-one except that 1-(2,4-dichlorophenyl)-2-(4-methylimidazolyl) ethan-1-one (II, 1.0 g, 3.7 mmol) was used. The crude residue was used without purification.

m/z 325 (MH+)

Example 229

Preparation of 1-(2,4-Dichlorophenyl)-3-(dimethylamino)-2-(2,4-dimethylimidazolyl)prop-2-en-1-one

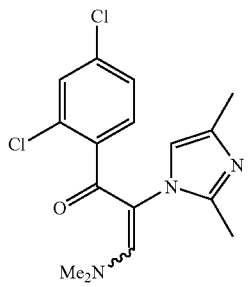

Made using the same procedure as for 1-(2,4-dichlorophenyl)-3-(dimethylamino)-2-pyrazolylprop-2-en-1-one except that 1-(2,4-dichlorophenyl)-2-(2,4-dimethylimidazole)ethan-1-one (III, 1.0 g, 3.5 mmol) was used. The crude residue was used without purification.

m/z 339 (MH+)

Example 230

Preparation of 1-(2,4-Dichlorophenyl)-3-(dimethylamino)-2-(2-oxohydropyridyl)prop-2-en-1-one

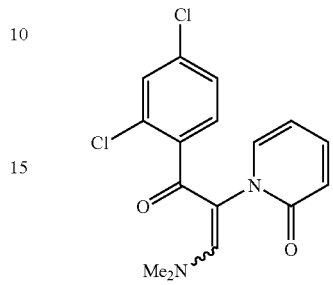

A solution of 1-[2-(2,4-dichlorophenyl)-2-oxoethyl] hydropyridin-2-one (IV, 1.0 g, 3.5 mmol), dry THF (25 mL) and dimethylformamidedimethyl acetal (10 mL, 75 mmol) was heated at 75° C. for 2.5 h. The resulting dark solution was concentrated under reduced pressure and the oily residue was used without purification.

m/z 338 (MH+)

Example 231

Preparation of 2-Benzimidazolyl-1-(2,4-dichlorophenyl)-3-(dimethylamino)prop-2-en-1-one

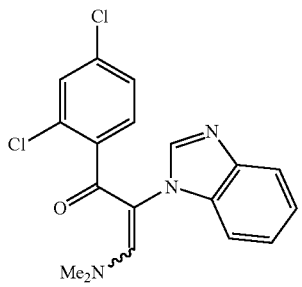

Made using the same procedure as for 1-(2,4-dichlorophenyl)-3-(dimethylamino)-2-pyrazolylprop-2-en-1-one except that 2-benzimidazolyl-1-(2,4-dichlorophenyl) ethan-1-one (V, 1.0 g, 3.3 mmol) was used. The crude residue was used without purification.

m/z 361 (MH+)

Example 232

Preparation of 1-(2,4-Dichlorophenyl)-3-(dimethylamino)-2-(2-methylimidazolyl)prop-2-en-1-one

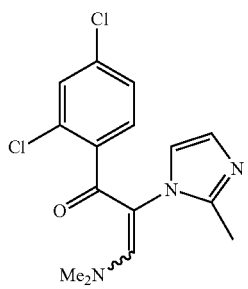

Made using the same procedure as for 1-(2,4-dichlorophenyl)-3-(dimethylamino)-2-pyrazolylprop-2-en-1-one except that 1-(2,4-dichlorophenyl)-2-(2-methylimidazolyl) ethan-1-one (VI, 1.0 g, 3.7 mmol) was used. The crude residue was used without purification.

m/z 325 (MH+)

Example 233

Preparation of 1-(2,4-Dichlorophenyl)-3-(dimethylamino)-2-(4-phenylimidazolyl)prop-2-en-1-one

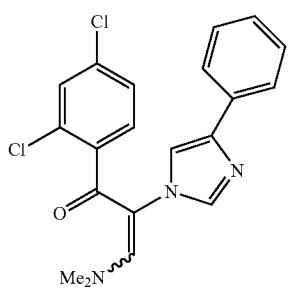

Made using the same procedure as for 1-(2,4-dichlorophenyl)-3-(dimethylamino)-2-(2-oxohydropyridyl)prop-2-en-1-one except that 1-(2,4-dichlorophenyl)-2-(4-phenyl-imidazolyl)ethan-1-one (VII, 1.0 g, 3.0 mmol) was used. The crude residue was used without purification.

m/z 387 (MH+)

MS:

Example 234

Preparation of 1-(2,4-Dichlorophenyl)-3-(dimethylamino)-2-imidazolylprop-2-en-1-one

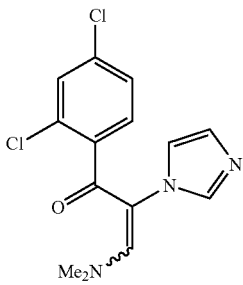

Made using the same procedure as for 1-(2,4-dichlorophenyl)-3-(dimethylamino)-2-(2-oxohydropyridyl)prop-2-en-1-one except that 1-(2,4-dichlorophenyl)-2-imidazolylethan-1-one (VIII, 1.0 g, 3.9 mmol) was used. The crude residue was used without purification.

m/z 311 (MH+)

Example 235

Preparation of 1-{2-(2,4-Dichlorophenyl)-1-[(dimethylamino)methylene]-2-oxoethyl}-5-chlorohydropyridin-2-one

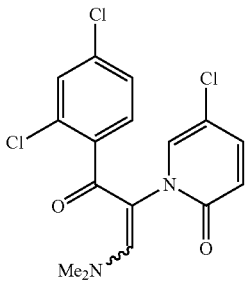

Made using the samne procedure as for 1-(2,4-dichlorophenyl)-3-(dimethylamino)-2-(2-oxohydropyridyl)prop-2-en-1-one except that 1-[2-(2,4-dichlorophenyl)-2-oxoethyl]-5-chlorohydropyridin-2-one (IX, 1.0 g, 3.2 mmol) was used. The crude residue was used without purification.

m/z 372 (MH+)

Example 236

Preparation of [4-(2,4-Dichlorophenyl)-5-pyrazolylpyrimidin-2-yl]{2-[(5-nitro(2-pyridyl))amino]ethyl}amine dihydrochloride

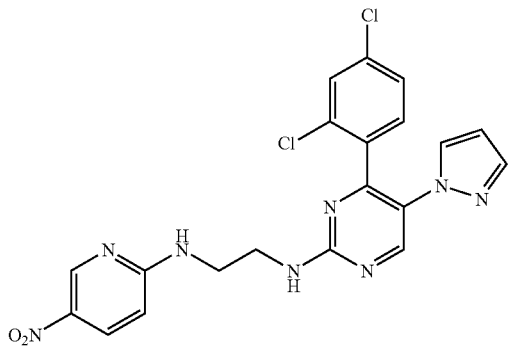

To a solution of 1-(2,4-dichlorophenyl)-3-(dimethylamino)-2-pyrazolylprop-2-en-1-one (X, 400 mg, 1.3 mmol) and EtOH (10 mL) at 23° C. was added amino{2-[(5-nitro(2-pyridyl))amino]ethyl}carboxamidine hydrochloride (365 mg, 1.4 mmol) followed by NaOEt in EtOH (1.6 mL, 1.6 mmol) and the resulting solution was heated at 90° C. for 16 h. The EtOH was removed under reduced pressure and the resulting residue was purified on silica gel (1–5% MeOH/CH2Cl2) to yield a yellow solid which was dissolved in MeCN/0.5M HCl (3 mL, 1:1), frozen and lyophilized to yield a yellow solid.

m/z 472 (MH+)

Example 237

Preparation of [4-(2,4-Dichlorophenyl)-5-(4-methylimidazolyl)pyrimidin-2-yl]{2-[(5-nitro(2-pyridyl))amino]ethyl}amine dihydrochloride

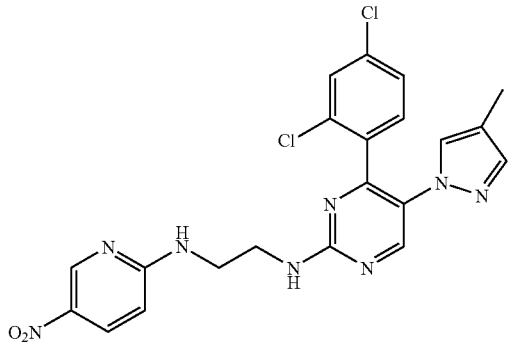

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(4-methylimidazolyl)prop-2-en-1-one (XI, 421 mg, 1.3 mmol) was used.

m/z 486 (MH+)

Example 238

Preparation of [4-(2,4-Dichlorophenyl)-5-(2,4-dimethylimidazolyl)pyrimidin-2-yl]{2-[(5-nitro(2-pyridyl))amino]ethyl}amine dihydrochloride

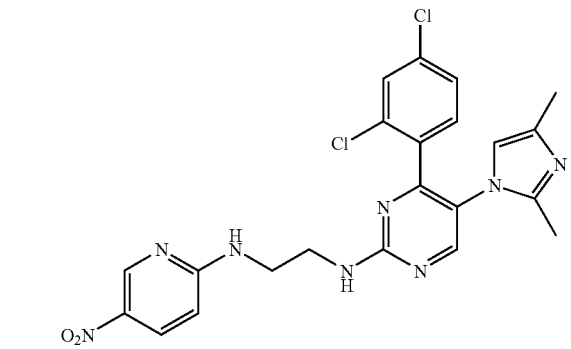

Made using the same procedure as for XIX except that 1-(2,4-dichlorophenyl)-3-(dimethylamino)-2-(2,4-dimethylimidazolyl)prop-2-en-1-one (XII, 439 mg, 1.3 mmol) was used.

m/z 500 (MH+)

Example 239

Preparation of 1-[4-(2,4-Dichlorophenyl)-2-({2-[(5-nitro(2-pyridyl))amino]ethyl}amino)pyrimidin-5-yl]hydropyridin-2-one hydrochloride

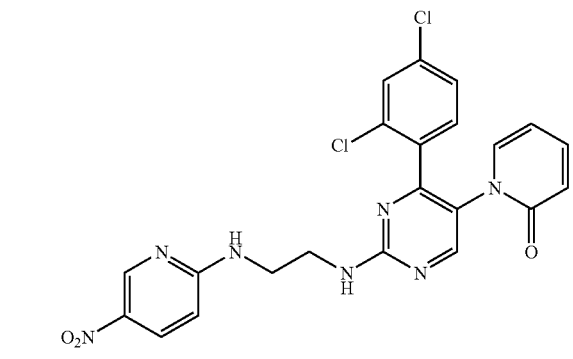

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(2-oxohydropyridyl)prop-2-en-1-one (438 mg, 1.3 mmol) was used and the crude product was purified by recrystallization (CH2Cl2/Et2O/hexanes)

m/z 499 (MH+)

Example 240

Preparation of [5-Benzimidazolyl-4-(2,4-dichlorophenyl)pyrimidin-2-yl]{2-[(5-nitro(2-pyridyl))amino]ethyl}amine dihydrochloride

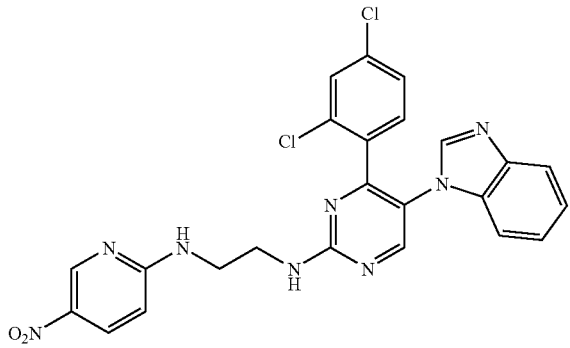

Made using the same procedure as for [4-(2,4-dichlorophenyl)-5-pyrazolylpyrimidin-2-yl]{2-[(5-nitro(2-pyridyl))amino]ethyl}amnine dihydro chloride except that 2-benzimidazolyl-1-(2,4-dicelorophenyl)-3-(dimethylamino)prop-2-en-1-one (XIV, 468 mg, 1.3 mmol) was used and the crude product was purified by recrystallization (CH$_2$Cl$_2$/Et$_2$O/hexanes).

m/z 522 (MH+)

Example 241

Preparation of [4-(2,4-Dichlorophenyl)-5-(2-methylimidazolyl)pyrimidin-2-yl]{2-[(5-nitro(2-pyridyl))amino]ethyl}amine dihydrochloride

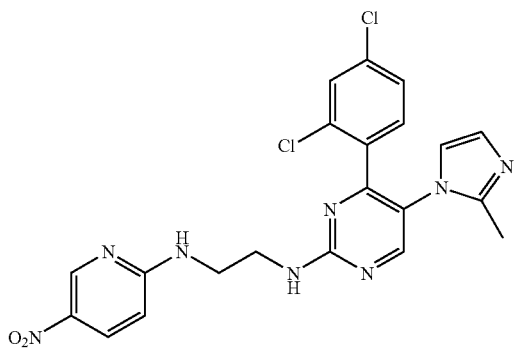

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(2-methylimidazolyl)prop-2-en-1-one (XV, 421 mg, 1.3 mmol) was used. m/z 486 (MH+)

Example 242

Preparation of {2-[(6-Amino-5-nitro(2-pyridyl))amino]ethyl}[4-(2,4-dichlorophenyl)-5-(2-methylimidazolyl)pyrimidin-2-yl]amine dihydrochloride

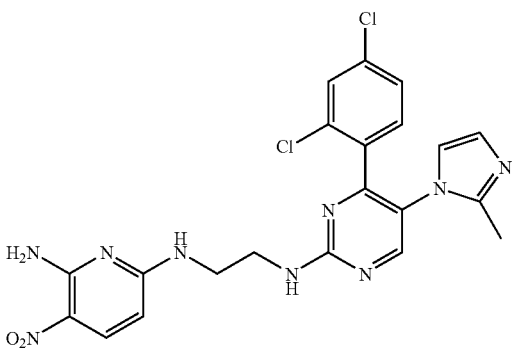

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(2-methylimidazolyl)prop-2-en-1-one (XV, 421 mg, 1.3 mmol) and amino{2-[(6-amino-5-nitro(2-pyridyl))amino]ethyl}carboxamidine hydrochloride (386 mg, 1.4 mmol) were used.

m/z 501 (MH+)

Example 243

Preparation of {2-[(6-Amino-5-nitro(2-pyridyl))amino]ethyl}[4-(2,4-dichlorophenyl)-5-(4-phenylimidazolyl)pyrimidin-2-yl]amine dihydrochloride

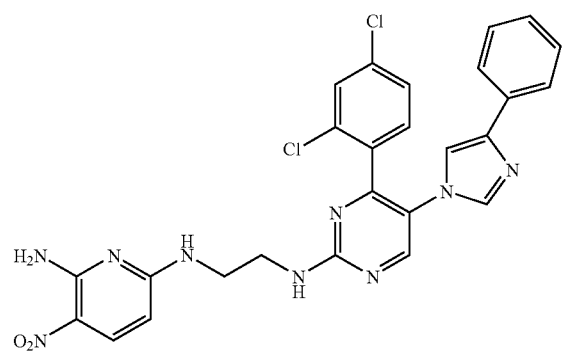

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(4-phenylimidazolyl)prop-2-en-1-one (502 mg, 1.3 mmol) and amino{2-[(6-amino-5-nitro(2-pyridyl)) amino]ethyl}carboxamidine hydrochloride (386 mg, 1.4 mmol) were used and the crude product was purified on silica gel (5% MeOH/CH$_2$Cl$_2$)

m/z 563 (MH+)

Example 244

Preparation of {2-[(6-Amino-5-nitro(2-pyridyl))amino]ethyl}[4-(2,4-dichlorophenyl)-5-(2,4-dimethylimidazolyl)pyrimidin-2-yl]amine dihydrochloride

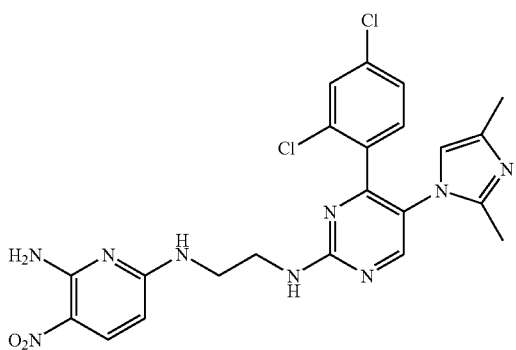

Made using the same procedure as for [4-(2,4-dichlorophenyl)-5-pyrazolylpyrimidin-2-yl]{2-[(5-nitro(2-pyridyl))amino]ethyl}amine dihydrochloride except that 1-(2,4-dichlorophenyl)-3-(dimethylamino)-2-(2,4-dimethylimidazolyl)prop-2-en-1-one (439 mg, 1.3 mmol) and amino{2-[(6-amino-5-nitro(2-pyridyl))amino]ethyl}carboxamidine hydrochloride (386 mg, 1.4 mmol) were used and the crude product was purified by reversed-phase HPLC (gradient of 95:5 $H_2O$:MeCN to 5:95 $H_2O$:MeCN).

m/z 515 (MH+)

Example 245

Preparation of Polymer-bound N-BOC-ethylenediamine

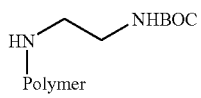

To a suspension of Merrifield resin (30 g, 21 mmol) and NMP (200 mL) was added 4-hydroxy-2-methoxybenzaldehyde (6.4 g, 42 mmol) and $K_2CO_3$ (8.7 g, 63 mmol). The resulting mixture was heated at 120° C. with shaking for 16 h. The resulting light brown mixture was filtered and the resin was washed with $H_2O$, NMP and $CH_2Cl_2$. The resin was dried under vacuum at 40° C. for 12 h.

To a suspension of the resin-bound aldehyde (30 g, 21 mmol) and $(MeO)_3CH$ (200 mL) was added N-BOC-ethylenediamine (6.7 mL, 42 mmol). The resulting mixture was shaken at 23° C. for 12 h, filtered and washed with $CH_2Cl_2$. The resin-bound imine was used immediately, slightly moist with $CH_2Cl_2$.

To a suspension of the resin-bound imine (30 g, 21 mmol) and MeOH/$CH_2Cl_2$/HOAc (200 mL, 2:2:1) was added borane-pyridine complex (6.8 mL, 67 mmol). The resulting mixture was shaken at 23° C. for 12 h, filtered and washed with NMP and $CH_2Cl_2$. The resin was dried under vacuum at 30° C. for 12 h to yield polymer-bound N-BOC-ethylenediamine.

Example 246

Preparation of Polymer-bound (2aminoethyl)(5-nitro(2-pyridyl))amine

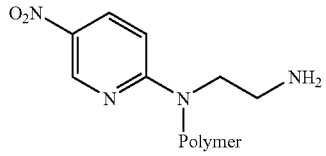

To a suspension of polymer-bound N-BOC-ethylenediamine (30 g, 21 mmol), NMP (200 mL) and $iPr_2NEt$ (18.3 mL, 105 mmol) at 23° C. was added 2-chloro-5-nitropyridine (16.6 g, 105 mmol). The resulting mixture was heated at 120° C. with shaking for 12 h, filtered and washed with NMP, $H_2O$ and $CH_2Cl_2$.

To the resin-bound, N-BOC-protected amine was added a solution of 2,6-lutidine and $CH_2Cl_2$ (100 mL, 150 mmol), followed by a solution of TMSOTf and $CH_2Cl_2$ (100 niL, 100 mmol). The resulting mixture was shaken at 23° C. for 3 h, filtered and washed with MeOH, $Et_3N$ and $CH_2Cl_2$. The resin was air dried to yield polymer-bound (2aminoethyl)(5-nitro(2-pyridyl))amine.

The air dried resin (10 mg) was suspended in 80% TFA/CH2Cl2 (1 mL) for 1 h, filtered, washed with $CH_2Cl_2$ (1 mL) and concentrated under a stream of air to yield a light yellow residue.

m/z 183 (MH+)

Example 247

Preparation of Polymer-bound {2-[(5-nitro(2-pyridyl))amino]ethyl}[(2-nitrophenyl)sulfonyl]amine

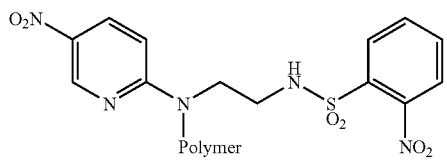

To a suspension of resin-bound (2aminoethyl)(5-nitro(2-pyridyl))amine (30 g, 21 mmol), $CH_2Cl_2$ (250 mL) and iPr2NEt (18.3 mL, 105 mmol) at 23° C. was added 2-nitrobenzenesulfonyl chloride (23.3 g, 105 mmol). The resulting mixture was shaken at 23° C. for 6 h, filtered, washed with NMP, $H_2O$ and $CH_2Cl_2$ and air dried to yield polymer-bound {2-[(5-nitro(2-pyridyl))amino]ethyl}[(2-nitrophenyl)sulfonyl]amine.

The air dried resin (10 mg) was suspended in 80% TFA/$CH_2Cl_2$ (1 mL) for 1 h, filtered, washed with $CH_2Cl_2$ (1 mL) and concentrated under a stream of air to yield a light yellow residue.

m/z 368 (MH+)

Example 248

Preparation of Polymer-bound [2-(dimethylamino)ethyl]{2-[(5-nitro(2-pyridyl))amino]ethyl}[(2-nitrophenyl)sulfonyl]amine

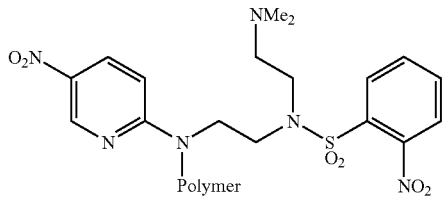

To a solution of Ph3P (11 g, 42 mmol) and CH$_2$Cl$_2$ (20 mL) at 23° C. was added DIAD (6.6 mL, 42 mmol) and the resulting yellow solution was maintained at 23° C. for 30 min. To this solution was added 2-(dimethylamino)ethanol (4.2 mL, 42 mmol) and the resulting solution was maintained at 23° C. for 5 min. then added to a suspension of resin-bound {2-[(5-nitro(2-pyridyl))amino]ethyl}[(2-nitrophenyl)sulfonyl]amine (3.0 g, 2.1 mmol) and CH2Cl2 (30 mL). The resulting mixture was shaken at 23° C. for 12h, filtered, washed with NMP, H$_2$O and CH2Cl2 and air dried to yield polymer-bound [2-(dimethylamino)ethyl]{2-[(5-nitro(2-pyridyl))amino]ethyl}[(2-nitrophenyl)sulfonyl]amine.

The air dried resin (10 mg) was suspended in 80% TFA/CH$_2$Cl$_2$ (1 mL) for 1 h, filtered, washed with CH$_2$Cl$_2$ (1 mL) and concentrated under a stream of air to yield a light yellow residue m/z 439 (MH+)

Example 249

Preparation of Polymer-bound dimethyl[2-({2-[(5-nitro(2-pyridyl))amino]ethyl}amino)ethyl]amine

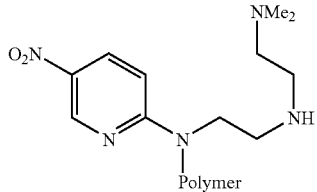

To a suspension of resin-bound [2-(dimethylamino)ethyl]{2-[(5-nitro(2-pyridyl))amino]ethyl}[(2-nitrophenyl)sulfonyl]amine (3.0 g, 2.1 mmol) and DMF (30 mL) at 23° C. was added H$_2$O (2 drops), K$_2$CO$_3$ (2.9 g, 21 mmol) and PhSH (2.2 mL, 21 mmol). The resulting mixture was shaken at 23° C. for 12 h, filtered, washed with NMP, H$_2$O and CH$_2$Cl$_2$ and air dried to yield polymer-bound dimethyl [2-({2-[(5-nitro(2-pyridyl))amino]ethyl}amino)ethyl]amine.

The air dried resin (10 mg) was suspended in 80% TFA/CH$_2$Cl$_2$ (1 mL) for 1 h, filtered, washed with CH$_2$Cl$_2$ (1 mL) and concentrated under a stream of air to yield a light yellow residue.

m/z 254 (MH+)

Example 250

Preparation of Polymer-bound amino[2-(dimethylamino)ethyl]{2-[(5-nitro(2-pyridyl))amino]ethyl}carboxamidine hydrochloride

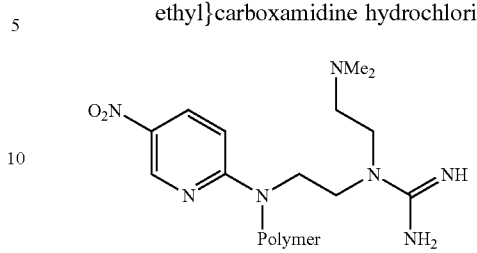

To a suspension of polymer-bound dimethyl [2-({2-[(5-nitro(2-pyridyl))amino]ethyl}amino)ethyl]amine (3.0 g, 2.1 mmol), NMP (30 mL) and iPr$_2$NEt (3.7 mL, 21 mmol) at 23° C. was added 1H-pyrazole-1-carboxamidine hydrochloride (3.1 g, 21 mmol). The resulting mixture was heated at 90° C. for 18 h, filtered, washed with NMP, H$_2$O and CH$_2$Cl$_2$ and air dried to yield polymer-bound amino [2-(dimethylamino)ethyl]{2-[(5-nitro(2-pyridyl))amino]ethyl}carboxamidine hydrochloride.

The air dried resin (10 mg) was suspended in 80% TFA/CH$_2$Cl$_2$ (1 mL) for 1 h, filtered, washed with CH$_2$Cl$_2$ (1 mL) and concentrated under a stream of air to yield a light yellow residue m/z 296 (MH+)

Example 251

Preparation of [4-(2,4-Dichlorophenyl)-5-imidazolylpyrimidin-2-yl][2-(dimethylamino)ethyl]{2-(5-nitro(2-pyridyl))amino]ethyl}amine trihydrochloride

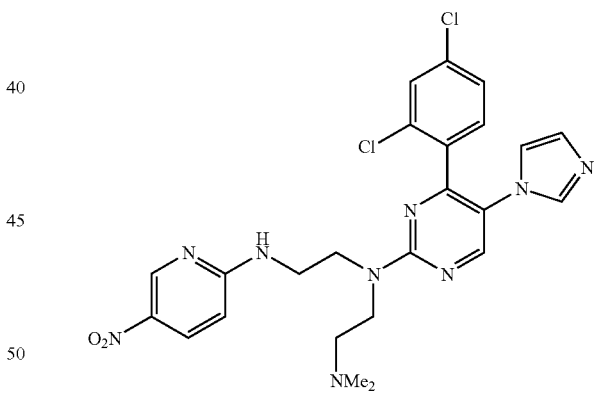

To a suspension of resin-bound amino [2-(dimethylamino)ethyl]{2-[(5-nitro(2-pyridyl))amino]ethyl}carboxamidine hydrochloride (3.0 g, 2.1 mmol) and NMP (30 mL) at 23° C. was added 7-methyl-1,5,7-triazabicyclo[4.4.0]dec-5-ene (1.5 mL, 10.5 mmol) and 1-(2,4-dichlorophenyl)-3-(dimethylamino)-2-imidazolylprop-2-en-1-one (XVII, 1.3 g, 4.2 mmol). The resulting mixture was heated at 120° C. for 20 h, filtered, washed with NMP, H$_2$O and CH$_2$Cl$_2$ and air dried to yield resin-bound [4-(2,4-dichlorophenyl)-5-imidazolylpyrimidin-2-yl][2-(dimethylamino)ethyl]{2-[(5-nitro(2-pyridyl))amino]ethyl}amine trihydrochloride.

The resin was suspended in 80% TFA/CH$_2$Cl$_2$ (30 mL) and shaken at 23° C. for 1.5 h, filtered and concentrated under a stream of air. The resulting crude material was purified by reversed-phase HPLC (gradient of 95:5 H$_2$O:MeCN to 5:95 H$_2$O:MeCN) and the recovered material was dissolved in MeCN/0.5M HCl (3 mL, 1:1), frozen and lyophilized to yield a yellow solid.

m/z 543 (MH+)

Example 252

Preparation of Polymer-bound {2-[(5-nitro(2-pyridyl))amino]ethyl}[(2-nitrophenyl)sulfonyl](2-pyrrolidinylethyl)amine

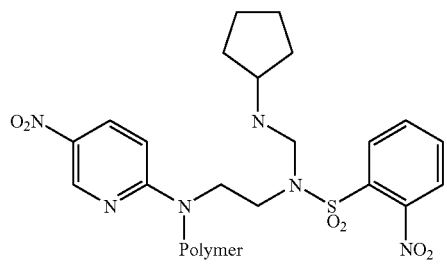

Made using the same procedure as for polymer-bound [2-(dimethylamino) ethyl]{2-[(5-nitro(2-pyridyl))amino]ethyl}[(2-nitrophenyl)sulfonyl]amine except that 1-(2-hydroxy-ethyl)pyrrolidine (4.9 mL, 42 mmol) was used.

m/z 465 (MH+)

Example 253

Preparation of Polymer-bound (5-nitro(2-pyridyl)){2[(2-pyrrolidinylethyl)amino]ethyl}amine

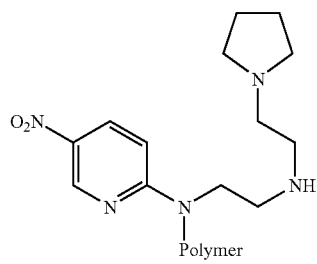

Made using the same procedure as for polymer-bound dimethyl [2-({2-[(5-nitro(2-pyridyl))amino]ethyl}amino) ethyl]amine except that resin-bound {2-[(5-nitro(2-pyridyl))amino]ethyl}[(2-nitrophenyl)sulfonyl](2-pyrrolidinylethyl)amine was used.

m/z 280 (MH+)

Example 254

Preparation of Polymer-bound amino{2-[(5-nitro(2-pyridyl))amino]ethyl}(2-pyrrolidinylethyl)carboxamidine hydrochloride

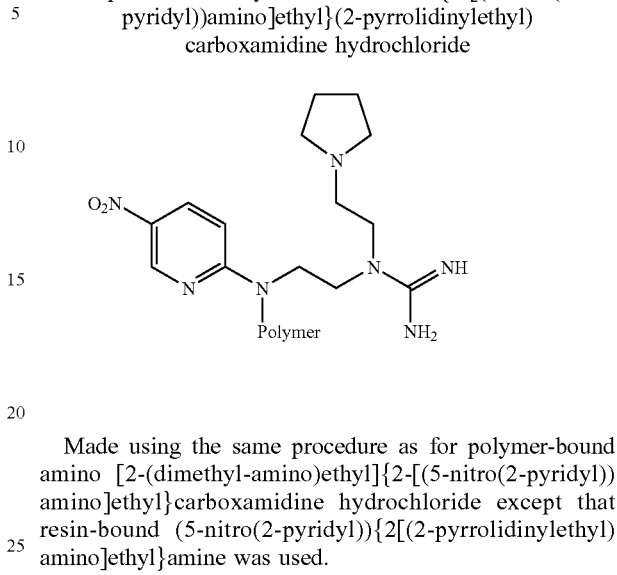

Made using the same procedure as for polymer-bound amino [2-(dimethyl-amino)ethyl]{2-[(5-nitro(2-pyridyl))amino]ethyl}carboxamidine hydrochloride except that resin-bound (5-nitro(2-pyridyl)){2[(2-pyrrolidinylethyl)amino]ethyl}amine was used.

m/z 322 (MH+)

Example 255

Preparation of [4-(2,4-Dichlorophenyl)-5-imidazolylpyrimidin-2-yl]{2-[(5-nitro(2-pyridyl))amino]ethyl}(2-pyrrolidinylethyl)amine trihydrochloride

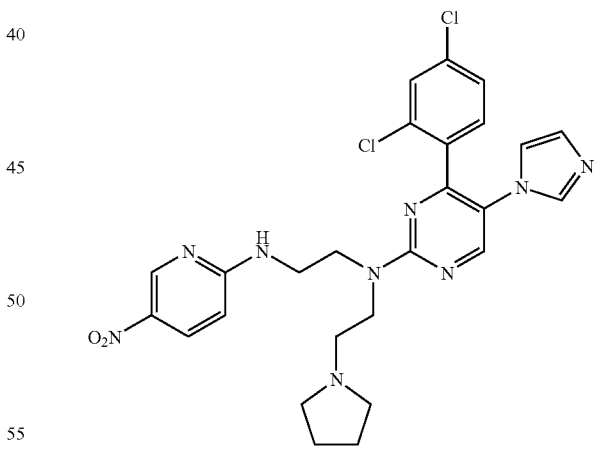

Made using the same procedure as for [4-(2,4-dichlorophenyl)-5-imidazolylpyrimidin-2-yl][2-(dimethylamino)ethyl]{2-[(5-nitro(2-pyridyl))amino]ethyl}amine trihydrochloride except that resin-bound amino{2-[(5-nitro(2-pyridyl))amino]ethyl}(2-pyrrolidinylethyl)carboxamidine hydrochloride was used.

m/z 569 (MH+)

Example 256

Preparation of Polymer-bound (2-morpholin-4-ylethyl){2-[(5-nitro(2-pyridyl))amino]ethyl}[(2-nitrophenyl)sulfonyl]amine

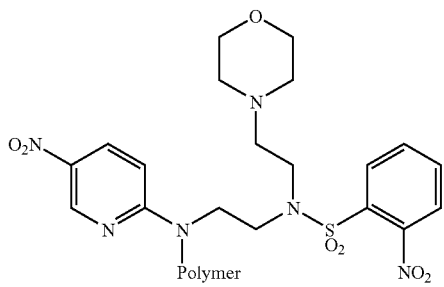

Made using the same procedure as for polymer-bound [2-(dimethylamino)ethyl]{2-[(5-nitro(2-pyridyl))amino]ethyl}[(2-nitrophenyl)sulfonyl]amine except that 4-(2-hydroxy-ethyl)morpholine (5.1 mL, 42 mmol) was used.

m/z 481 (MH+)

Example 257

Preparation of Polymer-bound {2-[(2-morpholin-4-ylethyl)amino]ethyl}(5-nitro(2-pyridyl))amine

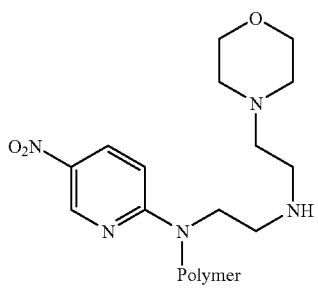

Made using the same procedure as for polymer-bound dimethyl [2-({2-[(5-nitro(2-pyridyl))amino]ethyl}amino)ethyl]amine except that resin-bound (2-morpholin-4-ylethyl){2-[(5-nitro(2-pyridyl))amino]ethyl}[(2-nitrophenyl)sulfonyl]amine was used.

m/z 296 (MH+)

Example 258

Preparation of Polymer-bound amino{2-morpholin-4-ylethyl){2-[(5-nitro(2-pyridyl))amino]ethyl}carboxamidine hydrochloride

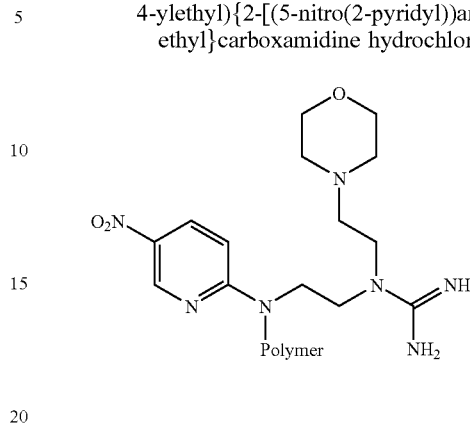

Made using the same procedure as for polymer-bound amino [2-(dimethyl-amino)ethyl]{2-[(5-nitro(2-pyridyl))amino]ethyl}carboxamidine hydrochloride except that resin-bound {2-[(2-morpholin-4-ylethyl)amino]ethyl}(5-nitro(2-pyridyl))amine was used.

m/z 338 (MH+)

Example 259

Preparation of [4-(2,4-Dichlorophenyl)-5-imidazolylpyrimidin-2-yl](2-morpholin-4-ylethyl){2-[(5-nitro(2-pyridyl))amino]ethyl}amine trihydrochloride

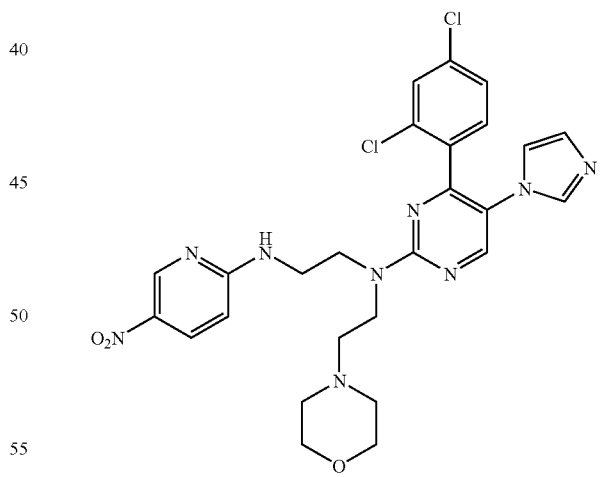

Made using the same procedure as for [4-(2,4-dichlorophenyl)-5-imidazolylpyrimidin-2-yl][2-(dimethylamino)ethyl]{2-[(5-nitro(2-pyridyl)) amino]ethyl}amine trihydrochloride except that resin-bound amino{2-morpholin-4-ylethyl){2-[(5-nitro(2-pyridyl))amino]ethyl}carboxamidine hydrochloride was used.

m/z 585 (MH+)

Example 260

Preparation of 6-[(2-{[4-(2,4-Dichlorophenyl)-5-(5-chloro-2-oxohydropyridyl)pyrimidin-2-yl]amino}ethyl)amino]pyridine-3-carbonitrile hydrochloride

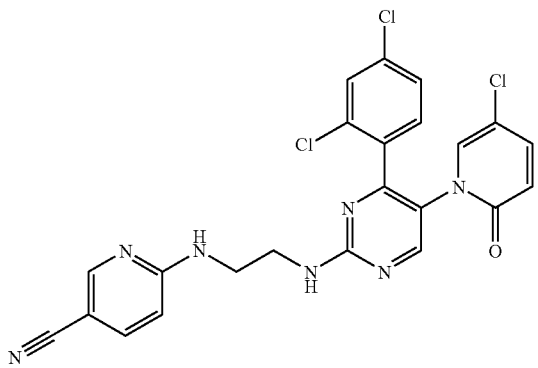

To a solution of 1-{2-(2,4-dichlorophenyl)-1-[(dimethylamino)methylene]-2-oxoethyl}-5-chlorohydropyridin-2-one (XVIII, 482 mg, 1.3 mmol) and DMF (10 mL) at 23° C. was added amino{2-[(5-cyano(2-pyridyl))amino]ethyl}carboxamidine hydrochloride (337 mg, 1.4 mmol) followed by Cs2CO3(652 mg, 2.0 mmol) and the resulting mixture was heated at 100° C. for 16 h. The DMF was removed under reduced pressure and the resulting residue was purified by recrystallization (CH2Cl2/Et2O/hexanes) to yield a yellow solid which was dissolved in MeCN/0.5M HCl (3 mL, 1:1), frozen and lyophilized to yield a yellow solid.

m/z 513 (MH+)

Example 261

Preparation of ethyl 6-({2-[(5-nitro(2-pyridyl))amino]ethyl}amino)-4-phenylpyridine-3-carboxylate

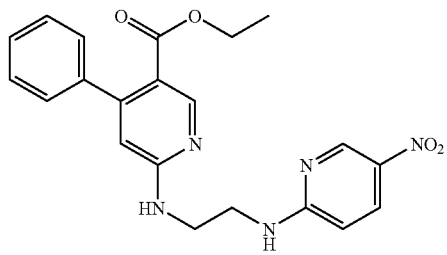

1. Preparation of diethyl (2Z)-3-phenylpent-2-ene-1,5-dioate.

A solution of iodobenzene (1.08 ml, 9.67 mmol) in DMA (5 ml) was added dropwise to a solution of diethylglutaconate (2 g, 10.74 mmol), Pd(OAc)2 (250 mg, 1.07 mmol), NaOAc (880 mg, 10.74 mmol) in DMA (5 ml) at 115° C. under argon. After heating for 8 hours at 130° C., the reaction was cooled, diluted with CH2Cl2 (60 ml), and washed with water (4×10 ml). The organic layer was washed with sat. aq. NaHCO3 (20 ml), brine (20 ml), dried with Na2SO4, filtered, and concentrated under reduced pressure. The dark oil was purified by column chromatography using CH2Cl2 as the eluent. The product oil was dried overnight in vacuo giving diethyl (2Z)-3-phenylpent-2-ene-1,5-dioate in 28% yield.

2. Preparation of diethyl (3E)-2-(hydroxymethylene)-3-phenylpent-3-ene-1,5-dioate.

A stirred mixture of NaH (158.4 mg, 6.6 mmol) and ethyl formate (1.07 ml, 13.2 mmol) in Et2O (5 ml) were refluxed under argon for 15 min. Diethyl (2Z)-3-phenylpent-2-ene-1,5-dioate in Et2O (5 ml) was added dropwise to the above solution over 5 min at rt. The reaction was heated to reflux for 12 hours. The heterogeneous yellow mixture was diluted with Et2O (100 ml), washed with sat. NH4Cl (40 ml), half sat. NH4Cl (40 ml), brine (20 ml), dried with Na2SO4, filtered, and concentrated under reduced pressure. The product diethyl (3E)-2-(hydroxymethylene)-3-phenylpent-3-ene-1,5-dioate was obtained in 97% yield and could be used without further purification.

3. Preparation of ethyl 6-oxo-4-phenylhydropyridine-3-carboxylate.

A mixture of diethyl (3E)-2-(hydroxymethylene)-3-phenylpent-3-ene-1,5-dioate (0.62 g, 2.13 mmol) was dissolved in gla. acetic acid (1 ml), toluene (1 ml), and abs. ethanol (3 ml). Ammonium acetate (0.07 g, 9.08 mmol) and flame dried 4 Å powder molecular sieves (0.4 g) were added to the stirred solution. The resulting mixture was stirred for 44–46 hours at 90–95° C. under argon. After 24 hours of heating, additional reagents were added including ammonium acetate (0.07 g, 9.08 mmol), acetic acid (1 ml), and flame dried 4 Å powder molecular sieves (0.4 g). On cooling EtOAc (80 ml) was added with stirring for 15 minutes. The sieves were filtered and washed with EtOAc (2×10 ml). The filtrate was concentrated under reduce pressure. To the crude material was added EtOAc (100 ml). The organic layer was then washed with distilled water (2×30 ml), sat. aq. NaHCO3 (30 ml), water (30 ml), brine (30 ml), dried with Na2SO4, filtered, and concentrated under reduced pressure. The oil was purified by column chromatography using 5% MeOH in CH2Cl2 as the eluent. The product oil was dried overnight in vacuo giving ethyl 6-oxo-4-phenylhydropyridine-3-carboxylate in 72% yield.

4. Preparation of ethyl 6-chloro-4-phenylpyridine-3-carboxylate.

To the dry ethyl 6-oxo-4-phenylhydropyridine-3-carboxylate (141 mg, 0.58 mmol) was added phosphorous oxychloride (10 ml) followed by NN-dimethylacetamide (1 drop). The reaction mixture was stirred for 12 hours at 100° C. under argon. The phosphorous oxychloride was removed under reduced pressure. The crude product was taken up in dichloromethane (2×25 ml), and the solvent was removed under vacuum. The glass was dried in vacuo 3–4 hour giving ethyl 6-chloro-4-phenylpyridine-3-carboxylate in 97% yield. The crude material is contaminated with phosphorous residue and is used with out further purification.

5. Preparation of ethyl 6-({2-[(5-nitro(2-pyridyl))amino]ethyl}amino)-4-phenylpyridine-3-carboxylate The crude material above, ethyl 6-chloro-4-phenylpyridine-3-carboxylate (140 mg, 0.56 mmol) was mixed with (2-aminoethyl)(5-nitro(2-pyridyl))amine (408 mg, 2.24 mmol), Hünig's base (390 ul), and DMA (2 ml) for 48 hours at 70–75° C. with stirring under argon. The reaction was followed by TLC and HPLC. When judged complete, the reaction was diluted with EtOAc (100 ml) and washed with sat. aq. NaHCO3 (5×30 ml), brine (30 ml), dried with Na2SO4, filtered, and concentrated under reduced pressure. The yellow solid was purified by column chromatography using 5% MeOH in CH2Cl2 as the eluent. The product was dried overnight in vacuo giving ethyl 6-({2-[(5-nitro(2-pyridyl))amino]ethyl}amino)-4-phenylpyridine-3-carboxylate in 70% yield.

HPLC: 3.52 min (>95% purity) (HP-1 method)

MS: M+H=408.2 ($C_{21}H_{21}N_5O_4$+H=408)

Example 262

Preparation of [5-((1E)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine

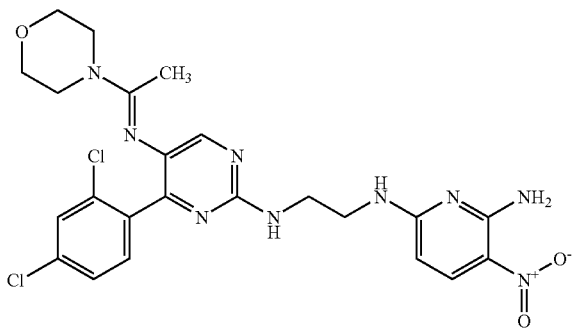

A. 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and then the reaction mixture was concentrated in vacuo and diluted with water and ethyl acetate. The ethyl acetate layer was concentrated and then purified by trituration with diethyl ether.

B. 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dione was heated to 80° C. in N,N-dimethylformamidedimethyl acetal for six hours. The reaction mixture was concentrated in vacuo and purified by trituration with diethyl ether.

C. 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl))amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate.

D. 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid was heated to 120° C. in glacial acetic acid for four hours and concentrated in vacuo.

E. [5-amino-4-(2,4-dichlorophenyl)pyrimidin-2-yl]{2-[(6-amino- 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and purified by column chromatography eluting with 5–10% methanol/methylene chloride.

F. N-[2-({2-[(6-amino-5-nitro(2-pyridyl))amino]ethyl}amino)-4-(2,4-dichlorophenyl)pyrimidin-5-yl]acetamide 1 mmol of [5-amino-4-(2,4-dichlorophenyl)pyrimidin-2-yl]{2-[(6-amino-5-nitro(2-pyridyl))amino]ethyl}amine and 1 mmol of acetic anhydride were stirred at room temperature for four hours in THF. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

G. 1-{[2-({2-[(6-amino-5-nitro(2-pyridyl))amino]ethyl}amino)-4-(2,4-dichlorophenyl)pyrimidin-5-yl]amino}ethane-1-thione 1 mmol of N-[2-({2-[(6-amino-5-nitro(2-pyridyl))amino]ethyl}amino)-4-(2,4-dichlorophenyl)pyrimidin-5-yl]acetamide and 2 mmol of Lawesson's reagent were stirred in 2 ml of DME at 80° C. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

H. [5-((1Z)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine 1 mmol of 1-{[2-({2-[(6-amino-5-nitro(2-pyridyl))amino]ethyl}amino)-4-(2,4-dichlorophenyl)pyrimidin-5-yl]amino}ethane-1-thione was heated to 90° C. in morpholine and purified by column chromatography eluting with 5–10% methanol/methylene chloride.

HPLC: 9.75 min. (100% purity)

MS: $MH^+$=546.3

Example 263

Preparation of {2-[(6-amino-5-nitro(2-pyridyl))amino]ethyl}[6-(2,4-dichlorophenyl)-5-nitro(2-pyridyl)]amine

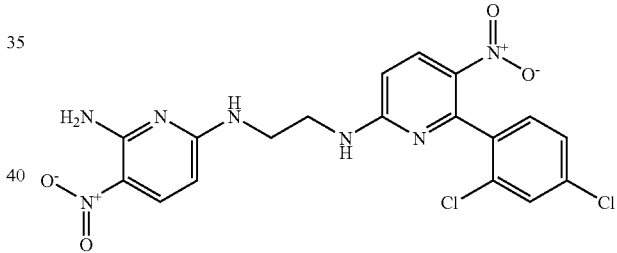

A. 2-(2,4-dichlorophenyl)-6-chloro-3-nitropyridine 1 mmol 2,6-dichloro-3-nitropyridine, 1.05 mmol of 2,4-dichlorobenzeneboronic acid, and 3 mmol of $Na_2CO_3$, were dissolved in 1.5 ml THF and 0.5 ml water and purged with nitrogen. 0.05 mmol of [1,1'-Bis(diphenylphosphino)ferrocne]dichloropalladium(II) was added to reaction and stirred at room temperature under nitrogen for fourteen hours. The reaction mixture was concentrated in vacuo and diluted with water and ethyl acetate. The solution was extracted three times with ethyl acetate, dried over sodium sulfate, and purified by column chromatography eluting with 10% ethylacetate 90% hexanes.

B. (2-aminoethyl)(6-amino-5-nitro(2-pyridyl))amine 1 mmol of 2-amino-6-chloro-3-nitropyridine and 15 amnol of 1,2-diaminoethane were stirred at reflux for fourteen hours. The reaction mixture was concentrated in vacuo and solution of 1.5 mmol of NaOH in water was added. This solution was extracted twice with 95%/5% methylene chloride/methanol. The aqueous was then saturated with salt and extracted twice with 95%/5% acetonitrile/methanol and then finally extrated twice with 95%/5% ethylacetate/methanol. All organic fractions were combined and dried over sodium sulfate.

C. {2-[(6-amino-5-nitro(2-pyridyl))amino]ethyl}[6-(2,4-dichlorophenyl)-5-nitro(2-pyridyl)]amine 1 mmol of 2-(2,4-dichlorophenyl)-6-chloro-3-nitropyridine was taken with 2 mmol of (2-aminoethyl)(6-amino-5-nitro(2-pyridyl))amine and 3 mmol of N,N-diisopropylethylamine in 2 ml of DMF at 80° C. for two hours. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

HPLC: 8.698 min. (100% purity)
MS: MH⁺=464.1

Example 264

Preparation of 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione

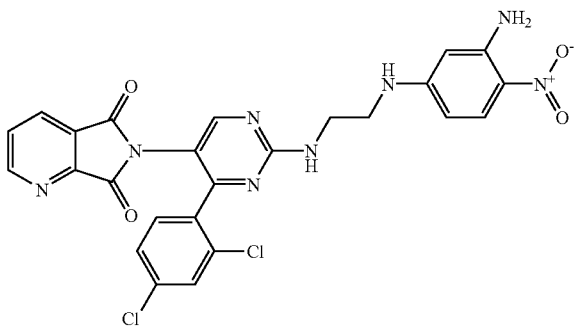

A. 2-[2-(2,4-dichlorophenyl)-2-oxoethyl]isoindoline-1,3-dione 1 mmol of 2,4-dichlorophenacyl chloride in DMF was added drop wise to 2 mmol of phthalimide and 2 mmol of $Cs_2CO_3$ in DMF at room temperature for fourteen hours and then the reaction mixture was concentrated in vacuo and diluted with water and ethyl acetate. The ethyl acetate layer was concentrated and then purified by trituration with diethyl ether.

B. 2-{2-(2,4-dichlorophenyl)-1-[(dimethylamino)methylene]-2-oxoethyl}isoindoline-1,3-dione 1 mmol of 2-[2-(2,4-dichlorophenyl)-2-oxoethyl]isoindoline-1,3-dion was heated to 80° C. in neat N,N-dimethylformamidedimethyl acetal for six hours. The reaction mixture was concentrated in vacuo and purified by trituration with diethyl ether.

C. 2-{N-[2-({2-[(6-amino-5-nitro(2-pyridyl))amino]ethyl}amino)-4-(2,4-dichlorophenyl)pyrimidin-5-yl]carbamoyl}benzoic acid 1 mmol of 2-{2-(2,4-dichlorophenyl)-1-[(dimethylamino)methylene]-2-oxoethyl}isoindoline-1,3-dione, 1 mmol of amino{2-[(6-amino-5-nitro(2-pyridyl)) amino]ethyl}carboxamidine, and 3 mmol of $Cs_2CO_3$ were dissolved in DMF and heated to 90° C. for fourteen hours. The reaction mixture was concentrated in vacuo and diluted with water and ethyl acetate. The solution was extracted three times with ethyl acetate and dried over sodium sulfate.

D. 2-[2-({2-[(6-amino-5-nitro(2-pyridyl))amino]ethyl}amino)-4-(2,4-dichlorophenyl)pyrimidin-5-yl]isoindoline-1,3-dione 1 mmol of 2-{N-[2-({2-[(6-amino-5-nitro(2-pyridyl))amino]ethyl}amino)-4-(2,4-dichlorophenyl)pyrimidin-5-yl]carbamoyl}benzoic acid was heated to 120° C. in glacial acetic acid for four hours and then concentrated in vacuo.

E. [5-amino-4-(2,4-dichlorophenyl)pyrimidin-2-yl]{2-[(6-amino-5-nitro(2-pyridyl))amino]ethyl}amine 1 mmol of 2-[2-({2-[(6-amino-5-nitro(2-pyridyl))amino]ethyl}amino)-4-(2,4-dichlorophenyl)pyrimidin-5-yl]isoindoline-1,3-dione and 20 mmol of hydrazine were stirred in ethanol at 75° C. for two hours and then purified by column chromatography eluting with 5–10% methanol/methylene chloride.

F. 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione 1 mmol of [5-amino-4-(2,4-dichlorophenyl)pyrimidin-2-yl]{2-[(6-amino-5-nitro(2-pyridyl))amino]ethyl}amine, and 2 mmol of furano[3,4-b]pyridine-5,7-dione were stirred at room temperature for four hours. 2 mmol of HBTU, and 3 mmol of N,N-diisopropylethylamine were added to solution and left for six hours at room temperature. The reaction mixture was concentrated in vacuo and diluted with water and ethyl acetate. The solution was extracted three times with ethyl acetate, dried over sodium sulfate, and purified by column chromatography eluting with 5–10% methanol/methylene chloride.

HPLC: 7.829 min. (97.32% purity)
MS: MH⁺=566.0

Example 265

Screening for GSK3 Inhibitory Activity Using a Cell-Free Assay

Pyriridine and pyridine compounds of the present invention were dissolved in DMSO, then tested for inhibition of human GSK3β (the nucleotide sequence for human GSK3β appears in GenBank under Accession No. L33801). Expression of GSK3β is described, for example, in Hughes et al., *Eur. J Biochem.*, 203:305–11 (1992), which is incorporated herein by reference.

An aliquot of 300 μl of substrate buffer (30 mM tris-HCl, 10 mM $MgCl_2$, 2 mM DTT, 3 μg/ml GSK3β and 0.5 μM biotinylated prephosphorylated SGSG-linked CREB peptide (Chiron Technologies PTY Ltd., Clayton, Australia) was dispensed into wells of a 96 well polypropylene microtiter plate. 3.5 μl /well of DMSO containing varying concentrations of each compound to be assayed or staurosporine (a known kinase inhibitor used as a positive control, or a negative control (i.e., DMSO only), was added and mixed thoroughly. The reactions were then initiated by adding 50 μl/well of 1 μM unlabeled ATP and $1–2×10^7$ cpm γ³³P-labeled ATP, and the reaction was allowed to proceed for about three hours at room temperature.

While the reaction was proceeding, streptavidin-coated Labsystems "Combiplate 8" capture plates (Labsystems, Helsinki, Finland) were blocked by incubating them with 300 μl/well of PBS containing 1% bovine serum albumin for at least one hour at room temperature. The blocking solution was then removed by aspiration, and the capture plates were filled with 100 μl/well of stopping reagent (50 μM ATP/20 mM EDTA).

When the three hour enzyme reaction was finished, triplicate 100 μl aliquots of each reaction mix were transferred to three wells containing stopping solution, one well on each of the three capture plates, and the well contents were mixed well. After one hour at room temperature, the wells of the capture plates were emptied by aspiration and washed five times using PBS and a 12 channel Corning 430474 ELISA plate washer. Finally, 200 μl of Microscint-20 scintillation fluid was added to each well of the plate. The plates were coated with plate sealers, then left on a shaker for 30 minutes. Each capture plate was counted in a Packard TopCount scintillation counter (Meridian, Conn.) and the results were plotted as a function of compound concentration.

Compounds of the present invention were then screened for inhibitory activity against GSK3 according to this assay. The following compounds exhibited $IC_{50}$s of 10 μM or less with respect to GSK3 in this cell-free assay: (4-phenylpyrimidin-2-yl)(2-(2-pyridyl)ethyl)amine, (4-phenylpyrimidin-2-yl)[2-(2-pyridylamino)ethyl]amine, [2-(2-pyridylamino)ethyl](4-(3-pyridyl)pyrimidin-2-yl) amine, 4-{2-[(2-(2-pyridyl)ethyl)amino]pyrimidin-4-yl}benzenecarbonitrile, 4-{2-[(4-pyridylmethyl)amino]pyrimidin-4-yl}benzamide, 4-{2-[(3-imidazol-5-ylethyl) amino]pyrimidin-4-yl}benzamide, 4-(2-{[2-(2-pyridylamino)ethyl]amino}pyrimidin-4-yl)benzenecarbonitrile,4-methyl-2-({2-[(5-nitro(2-pyridyl)) amino]ethyl}amino)pyrimidine-5-carboxylic acid, 4-(2-{[(3-methylphenyl)methyl]amino}pyrimidin-4-yl) benzamide, 4-(2-{[(4-aminophenyl)methyl] amino}pyrimidin-4-yl)benzamide, (5-ethyl-4-phenylpyrimidin-2-yl)[2-(2-pyridylamino) ethyl]amine, 4-(2-{[(5-methylpyrazin-2-yl)methyl]aamino}pyrimidin-4-yl)benzamide, 4-{2-[(3-phenoxypropyl)amino]pyrimidin-4-yl}phenol, 4-{2-[(3-imidazolylpropyl) amino]pyrimidin-4-yl}benzamide, [4-(3,4-difluorophenyl)pyrimidin-2-yl][2-(2-pyridylamino)ethyl]amine, 4-(2-{[(4-cyanophenyl)methyl] amino}pyrimidin-4-yl)benzamide,4-{2-[(2-phenoxyethyl) amino]pyrimidin-4-yl}benzamide, 4-(2-{[(3-methoxyphenyl) methyl]amino}pyrimidin-4-yl)benzamide, 4-(2-{[(4-methoxyphenyl)methyl]amino}pyrimidin-4-yl) benzamide, 4-(2-{[2-(4-fluorophenyl)ethyl] amino}pyrimidin-4-yl)benzamide, [2-(2,5-dimethoxyphenyl)ethyl](4-(3-pyridyl)pyrimidin-2-yl) amine, [4-(4-nitrophenyl) pyrimidin-2-yl][2-(2-pyridylamino)ethyl]amine,{2-[(5-nitro(2-pyridyl))amino] ethyl}(4-pyrazin-2-ylpyrimidin-2-yl)amine, ethyl 4-(2-furyl)-2-[(2-(2-pyridyl)ethyl)amino]pyrimidine-5-carboxylate, 4-(2-{[(3-chlorophenyl)methyl] amino}pyrimidin-4-yl)benzamide, [4-(4-chlorophenyl)-5-methylpyrimidin-2-yl][2-(2-pyridylamino)ethyl]amine, 4-{2-[(3-benzimidazolylpropyl)amino]pyrimidin-4-yl}phenol, 4-{2-[(4-phenylbutyl) amino]pyrimidin-4-yl}benzamide, 4-(2-{[2-(3-methoxyphenyl)ethyl] amino}pyrimidin-4-yl)benzamide, 4-{2-[(3-phenoxypropyl)amino]pyrimidin-4-yl}benzamide, 4-(2-{[(3-nitro-phenyl)methyl]amino}pyrimidin-4-yl)benzamide, 4-[2-({2-[(5-nitro-2-pyridyl)amino]ethyl}amino)pyrimidin-4-yl]phenol, 3-[2-({2-[(5-nitro-2-pyridyl)amino]ethyl}amino)pyrimidin-4-yl]phenol, 4-(2-{[2-(3-chlorophenyl)ethyl]amino}pyrimidin-4-yl)benzamide, 4-{2-[(naphthylmethyl)amino]pyrimidin-4-yl}benzamide, [5-(4-fluoro-phenyl)pyrimidin-2-yl]{2-[(5-nitro(2-pyridyl))amino]ethyl}amine, 4-(2-{[3-(4-chloro-phenoxy)propyl]amino}pyrimidin-4-yl)phenol, [4-(4-imidazolylphenyl)pyrimidin-2-yl][2-(2-pyridylamino)ethyl]amine, 4-(2-{[3-(2-aminobenzimidazolyl)propyl]amino}pyrimidin-4-yl) phenol, 4-(2-{[2-(2,5-dimethoxyphenyl)ethyl] amino}pyrimidin-4-yl)benzene-carbonitrile, [4-(2,4-dichlorophenyl)pyrimidin-2-yl][2-(2-pyridylamino)ethyl] amine, 3-[2-({2-[(5-nitro-2-pyridyl)amino]ethyl}amino) pyrimidin-4-yl]benzenecarbonitrile, 4-(2-{[3-(3-methylphenoxy)propyl]amino}pyrimidin-4-yl)benzamide, 4-{2-[(2-(2H-benzo[3,4-d]1,3-dioxolen-5-yl)ethyl)amino] pyrimidin-4-yl }benzamide, 4-(2-{[2-(4-nitrophenyl)ethyl] amino}pyrimidin-4-yl)benzamide, 4-(2-{[(2,6-dimethoxyphenyl)methyl]amino}pyrimidin-4-yl) benzamide, 4-(2-{[(3,4-dimethoxyphenyl)methyl] amino}pyrimidin-4-yl)benzamide, [2-({2-[(5-nitro(2-pyridyl))amino]ethyl}amino)pyrimidin-4-yl]benzylamine, ethyl 4-(4-fluorophenyl)-2-[(2-(2-pyridyl)ethyl)amino] pyrimidine-5-carboxylate, [4-(2,4-dimethyl(1,3-thiazol-5-yl))pyrimidin-2-yl]{2-[(5-nitro(2-pyridyl))amino] ethyl}amine, [4-(4-methyl-1-phenylpyrazol-3-yl)pyrimidin-2-yl][2-(2-pyridyl-amino)ethyl]amine, 4-[2-({[3-(trifluoromethyl)phenyl]methyl}amino)pyrimidin-4-yl] benzamide, 4-[2-({[4-(trifluoromethyl)phenyl] methyl}amino)pyrimidin-4-yl]benzamide, 4-(2-{[(3,5-dichlorophenyl)methyl]amino}pyrimidin-4-yl)benzamide, 4-{2-[4-benzylpiperazinyl]pyrimidin-4-yl}benzamide, 4-(2-{[(2,4-dichlorophenyl) methyl]amino}pyrimidin-4-yl) benzamide, ethyl 4-(4-cyanophenyl)-2-[(2-(2-pyridyl)ethyl) amino]pyrimidine-5-carboxylate, [2-(2-pyridylamino)ethyl] {4-[4-(trifluoromethoxy)phenyl]pyrimidin-2-yl}amine,{6-[(2-methoxyethyl)amino]-5-nitro(2-pyridyl)}{2-[(5-nitro(2-pyridyl))amino]ethyl}amine, 4-(2-{[3-(3-methoxyphenoxy) propyl]amino}pyrimidin-4-yl)benzamide, ethyl 4-(4-methoxyphenyl)-2-[(2-(2-pyridyl)ethyl)amino]pyrimidine-5-carboxylate, [(3-methylphenyl)methyl][2-({2-[(5-nitro-(2-pyridyl))amino]ethyl}amino)pyrimidin-4-yl]amine, 4-(2-{[3-(4-phenylimidazolyl)propyl]amino}pyrimidin-4-yl) benzenecarbonitrile, 4-{2-[(3-benzimidazolylpropyl)amino] pyrimidin-4-yl}-2-chlorophenol, 4-[2-({3-[4-(2,4-dichlorophenyl) imidazolyl]propyl}amino)pyrimidin-4-yl] benzamide, 4-[2-({3-[4-(3-methoxyphenyl) imidazolyl] propyl}amino)pyrimidin-4-yl]benzamide, (3-benzimidazolylpropyl)[4-(4-imidazolyl-phenyl) pyrimidin-2-yl]amine, N-{4-[2-({2-[(5-nitro-2-pyridyl) amino]ethyl}amino)pyrimidin-4-yl]phenyl}acetamide, 4-(2-{[3-(4-chlorophenoxy)propyl]amino}pyrimidin-4-yl) benzamide, 4-(2-{[(4-bromophenyl)methyl] amino}pyrimidin-4-yl)benzamide, 4-[2-({[4-(4-fluorophenyl)phenyl]methyl}amino)pyrimidin-4-yl] benzamide, 4-(2-{[(3-bromophenyl)methyl] amino}pyrimidin-4-yl)benzamide, 6-{[2-({5-nitro-6-[benzylamino]-2-pyridyl}amino)ethyl]amino}pyridine-3-carbonitrile, ethyl 4-(4-cyanophenyl)-2-{[2-(pyrimidin-2-ylamino) ethyl]amino}pyrimidine-5-carboxylate, 4-{2-[4-(2-methoxy-phenyl)piperazinyl]pyrimidin-4-yl}benzamide, 4-(2-{[2-(benzothiazol-2-ylamino)ethyl]amino}pyrimidin-4-yl)benzamide, ethyl 4-(3-nitrophenyl)-2-[(2-(2-pyridyl) ethyl)amino]pyrimidine-5-carboxylate, 6-methyl-2-({2-[(5-nitro(2-pyridyl))amino]ethyl}amino)-4-phenylpyrimidine-5-carboxylic acid, 4-{2-[(2,2-diphenylethyl)amino] pyrimidin-4-yl}benzamide, 4-(2-{[(3,4,5-trimethoxyphenyl)methyl]aamino}pyrimidin-4-yl) benzamide, methyl 2-({2-[(5-nitro(2-pyridyl))amino] ethyl}amino)-4-(3-pyridyl)pyrimidine-5-carboxylate, 4-[2-({[3-(3-aminophenyl)phenyl]methyl}amino)pyrimidin-4-yl]benzamide, 4-[2-({[4-(3-aminophenyl)phenyl] methyl}amino)pyrimidin-4-yl]benzamide, 4-{2-[(3-(2-naphthyloxy)propyl)amino]pyrimidin-4-yl}benzamide, 4-{2-[(3-(6-quinolyloxy)propyl)-amino]pyrimidin-4-yl}benzamide, [(3-chlorophenyl)methyl][2-({2-[(5-nitro(2-pyridyl))-amino]ethyl}amino)pyrimidin-4-yl]amine, [(4-chlorophenyl)methyl][2-({2-[(5-nitro(2-pyridyl))amino] ethyl}amino)pyrimidin-4-yl]amine, ethyl 4-(4-cyanophenyl)-2-{[2-(3-methoxyphenyl)ethyl] amino}pyrimidine-5-carboxylate, ethyl 2-({2-[(5-amino(2-pyridyl))amino]ethyl}amino)-4-(4-cyanophenyl) pyrimidine-5-carboxylate, 4-[5-nitro-2-({2-[(5-nitro(2- pyridyl))amino]ethyl}amino)pyrimidin-4-yl] benzenecarbonitrile, ethyl 4-[2-({2-[(5-nitro-2-pyridyl)amino]ethyl}amino)pyrimidin-4-yl]benzoate, ethyl 4-(3-nitrophenyl)-2-{[2-(2-pyridylamino)ethyl]amino}pyrimidine-5-carboxylate, N-benzyl(4-{2-[(2-(2-pyridyl)ethyl)amino]pyrimidin-4-yl}phenyl)carboxamide, {2-[(5-nitro(2-pyridyl))amino]ethyl}{5-nitro-6-[benzylamino](2-pyridyl)}amine, 4-(2-methoxyphenyl)-2-({2-[(5-nitro(2-pyridyl))amino]ethyl}amino)pyrimidine-5-carboxylic acid, 4-[2-({[3-(3-methoxyphenyl)phenyl]methyl}amino)pyrimidin-4-yl]benzamide, 4-[2-({2-[(5-nitro-2-pyridyl)amino]ethyl}amino)pyrimidin-4-yl]benzenesulfonamide, 4-(2-{[3-(2,4-dichloro-phenoxy)propyl]amino}pyrimidin-4-yl)benzamide, 4-(2-{[3-(3,4-dichlorophenoxy)propyl]amino}pyrimidin-4-yl)benzamide, 4-(2-{[3-(3-phenylphenoxy) propyl]amino}pyrimidin-4-yl)benzamide, 4-(2-{[(3-{3-[(methylamino)methyl]phenyl}phenyl)methyl]amino}pyrimidin-4-yl)benzamide, ethyl 4-(3-fluorophenyl)-2-({2-[(5-nitro(2-pyridyl))amino]ethyl}amino)pyrimidine-5-carboxylate, [4-phenyl-5-benzyl-pyrimidin-2-yl][2-(2-pyridylamino)ethyl]amine, 4-(2-{[3-(3-bromophenoxy) propyl]amino}pyrimidin-4-yl) benzamide, 4-[2-({2-[(5-nitro(2-pyridyl))amino]ethyl}amino)-5-phenylpyrimidin-4-yl]phenol, 4-(2,4-dichlorophenyl)-2-({2-[(5-nitro(2-pyridyl)) amino] ethyl}amino)pyrimidine-5-carbonitrile, 4-(3,4-dichlorophenyl)-2-({2-[(5-nitro(2-pyridyl))amino]ethyl}amino)pyrimidine-5-carbonitrile, 6-[(2-{[4-(4-cyanophenyl)-5-(ethoxycarbonyl)pyrimidin-2-yl]amino}ethyl)amino]pyridine-3-carboxylic acid, ethyl 4-(3-cyanophenyl)-2-({2-[(5-nitro(2-pyridyl))amino]ethyl}amino)pyrimidine-5-carboxylate, [(3,5-dichlorophenyl)methyl][2-({2-[(5-nitro(2-pyridyl))amino]ethyl}amino)pyrimidin-4-yl]amine, [(2,4-dichlorophenyl)methyl][2-({2-[(5-nitro(2-pyridyl))amino]ethyl}amino) pyrimidin-4-yl]amine, ethyl 4-(4-carbamoylphenyl)-6-ethyl-2-{[2-(2-pyridylamino) ethyl]amino}pyrimidine-5-carboxylate, ethyl 4-(4-carbamoylphenyl)-6-ethyl-2-{[2-(pyrimidin-2-ylamino)ethyl]amino}pyrimidine-5-carboxylate, ethyl 4-(3,4-dimethylphenyl)-2-({2-[(5-nitro(2-pyridyl))amino]ethyl}amino)pyrimidine-5-carboxylate, N-(2-methoxyethyl){4-[2-({2-[(5-nitro(2-pyridyl))amino]ethyl}amino) pyrimidin-4-yl]phenyl}carboxamide, 4-{2-[({3-[3-(acetylamino)phenyl]phenyl}methyl)amino]pyrimidin-4-yl}benzamide, ethyl 4-(4-cyanophenyl)-2-{[2-(2-quinolylamino) ethyl]amino}pyrimidine-5-carboxylate, 4-[2-({[3,5-bis(trifluoromethyl)phenyl]methyl}amino)pyrimidin-4-yl]benzamide, ethyl 4-(2,4-difluorophenyl)-2-({2-[(5-nitro(2-pyridyl))amino]ethyl}amino)pyrimidine-5-carboxylate, (4-{[(3-bromophenyl)methyl]amino}pyrimidin-2-yl){2-[(5-nitro(2-pyridyl))amino]ethyl}amine, 2-({2-[(6-amino-5-nitro(2-pyridyl))amino]ethyl}amino)-4-(3,4-dichlorophenyl)pyrimidine-5-carbonitrile,methyl 6-[(2-{[4-(4-cyanophenyl)-5-(ethoxycarbonyl)pyrimidin-2-yl]amino}ethyl)amino]pyridine-3-carboxylate, 4-{2-[({3-[3-(trifluoromethyl)phenyl]phenyl}methyl)amino]pyrimidin-4-yl}benzamide, [4-(4-benzimidazolylphenyl)pyrimidin-2-yl]{2-[(5-nitro(2-pyridyl))amino]ethyl}amine, ethyl 2-({2-[(5-nitro(2-pyridyl))amino]ethyl}amino)-4-(3-nitrophenyl)pyrimidine-5-carboxylate, ethyl 4-naphthyl-2-({2-[(5-nitro(2-pyridyl))amino]ethyl}amino)pyrimidine-5-carboxylate, ethyl 2-({2-[(5-nitro(2-pyridyl))amino]ethyl}amino)-4-(3-quinolyl)pyrimidine-5-carboxylate, ethyl 4-(4-cyanophenyl)-2-(2-{[5-(N-ethylcarbamoyl)(2-pyridyl)]amino}ethyl)amino) pyrimidine-5-carboxylate, benzyl{[4-(2-{[2-(2-pyridylamino) ethyl]amino}pyrimidin-4-yl)phenyl] sulfonyl}amine, ethyl 4-(4-cyanophenyl)-2-[(2-{[6-(methylamino)-5-nitro(2-pyridyl)]amino}ethyl)amino] pyrimidine-5-carboxylate,{4-[2-({2-[(5-nitro(2-pyridyl))amino]ethyl}amino)pyrimidin-4-yl]phenyl}-N-(oxolan-2-ylmethyl)carboxamide, N-(1-carbamoyl-2-phenylethyl)[4-methyl-2-({2-[(5-nitro(2-pyridyl))amino]ethyl}amino)pyrimidin-5-yl]carboxamide, N-(1-carbamoyl-2-phenylethyl)(4-{2-[(2-(2-pyridyl)ethyl)amino]pyrimidin-4-yl}phenyl)carboxamide, ethyl 4-(3,4-dimethoxyphenyl)-2-({2-[(5-nitro(2-pyridyl))amino]ethyl}amino)pyrimidine-5-carboxylate,{4-[2-({2-[(5-nitro(2-pyridyl))amino]ethyl}amino)pyrimidin-4-yl]phenyl}-N-benzylcarboxamide,{4-[2-({2-[(5-nitro(2-pyridyl))amino]ethyl}amino)pyrimidin-4-yl]phenyl}-N-(3-pyridylmethyl)carboxamide,{4-[4-(4,5-dichloroimidazol-2-yl)phenyl]pyrimidin-2-yl}{2-[(5-nitro(2-pyridyl))amino]ethyl}amine, ethyl 4-(4-butoxyphenyl)-2-({2-[(5-nitro(2-pyridyl))amino]ethyl}amino)pyrimidine-5-carboxylate, ethyl 4-{[(2-chlorophenyl)methyl]amino}-2-({2-[(5-nitro(2-pyridyl))amino]ethyl}amino)pyrimidine-5-carboxylate, 6-(2-fluorophenyl)-2-({2-[(5-nitro(2-pyridyl))amino]ethyl}amino)-4-phenyl-pyrimidine-5-carboxylic acid,{4-[2-({2-[(5-nitro(2-pyridyl))amino]ethyl}amino)pyrimidin-4-yl]phenyl}-N-(2-thienylmethyl)carboxamide, ethyl 2-({2-[(5-nitro(2-pyridyl))amino]ethyl}amino)-4-[3-(trifluoromethyl)phenyl]pyrimidine-5-carboxylate, ethyl 4-(3,4-dichlorophenyl)-2-({2-[(5-nitro(2-pyridyl))amino]ethyl}amino)pyrimidine-5-carboxylate, ethyl 4-(3,5-dichlorophenyl)-2-({2-[(5-nitro(2-pyridyl))amino]ethyl}amino)pyrimidine-5-carboxylate,{4-[2-({2-[(5-nitro(2-pyridyl))amino]ethyl}amino)pyrimidin-4-yl]phenyl}-N-(4-piperidylmethyl)carboxamide, (6-{[(2,4-dichlorophenyl)methyl]amino}-5-nitro(2-pyridyl)){2-[(5-nitro(2-pyridyl))amino]ethyl}amine, ethyl 4-(4-carbamoylphenyl)-6-ethyl-2-({2-[(3-nitro(2-pyridyl))amino]ethyl}amino)pyrimidine-5-carboxylate, ethyl 4-[4-(diethylamino)phenyl]-2-({2-[(5-nitro(2-pyridyl))amino]ethyl}amino)pyrimidine-5-carboxylate,{4-[2-({2-[(5-nitro(2-pyridyl))amino]ethyl}amino)pyrimidin-4-yl]phenyl}-N-(2-phenylethyl)carboxamide, N-[(3-methylphenyl) methyl]{4-[2-({2-[(5-nitro(2-pyridyl))amino]ethyl}amino)pyrimidin-4-yl]phenyl}carboxamide, 2-({2-[(5-nitro(2-pyridyl))amino]ethyl}amino)-4-(2,4,6-trichlorophenyl)pyrimidine-5-carboxylic acid, ethyl 2-({2-[(5-nitro(2-pyridyl))amino]ethyl}amino)-4-(4-phenylphenyl) pyrimidine-5-carboxylate,{4-[2-({2-[(6-amino-5-nitro(2-pyridyl))amino]ethyl}amino) pyrimidin-4-yl]phenyl}-N-benzylcarboxamide, N-[(5-methylpyrazin-2-yl)methyl]{4-[2-({2-[(5-nitro(2-pyridyl))amino]ethyl}amino) pyrimidin-4-yl]phenyl}carboxamide, N-[(3-fluorophenyl)methyl]{4-[2-({2-[(5-nitro(2-pyridyl))amino]ethyl}amino)pyrimidin-4-yl]phenyl}carboxamide, ethyl 2-({2-[(5-nitro(2-pyridyl))amino]ethyl}amino)-4-(4-sulfamoyl-phenyl)pyrimidine-5-carboxylate, N-[(4-fluorophenyl)methyl]{4-[2-({2-[(5-nitro(2-pyridyl))amino]ethyl}amino)pyrimidin-4-yl]phenyl}carboxamide, [4-(2-{[(3-bromo-phenyl)methyl]amino}pyrimidin-4-yl)phenyl]-N-[(3-methylphenyl)methyl]carboxamide, ethyl 4-(5-bromo(3-pyridyl))-2-({2-[(5-nitro(2-pyridyl))amino]ethyl}amino)pyrimidine-5-carboxylate, N-(3-imidazolylpropyl){4-[2-({2-[(5-nitro(2-pyridyl))amino]ethyl}amino)pyrimidin-4-yl]phenyl}carboxamide, tert-butyl 6-[(2-{[4-(4-cyanophenyl)-5-(ethoxycarbonyl)pyrimidin-2-yl]amino}ethyl)amino]pyridine-3-carboxylate, N-[(3-bromophenyl)methyl](4-{2-[(3-imidazolylpropyl)amino]pyrimidin-4-yl}phenyl)carboxamide, ethyl 4-[(2,4-dichlorophenyl)amino]-2-({2-[(5-nitro(2-pyridyl)) amino]ethyl}amino)pyrimidine-5- carboxylate, ethyl 4-(4-carbamoylphenyl)-6-ethyl-2-({3-[(5-nitro(2-pyridyl))amino]propyl}amino)pyrimidine-5-carboxylate, {4-[2-({2-[(5-nitro(2-pyridyl))amino]ethyl}amino)pyrimidin-4-yl]phenyl}-N-(2-phenylcyclopropyl)carboxamide, N-[(4-methoxyphenyl)methyl]{4-[2-({2-[(5-nitro(2-pyridyl))amino]ethyl}amino)pyrimidin-4-yl]phenyl}carboxamide, 2-({2-[(5-nitro(2-pyridyl))amino]ethyl}amino)-6-(4-nitrophenyl)-4-phenylpyrimidine-5-carboxylic acid, 2-({2-[(5-nitro(2-pyridyl))amino]ethyl}amino)-6-(4-nitrophenyl)-4-(4-pyridyl)pyrimidine-5-carboxylic acid, ethyl 4-(4-carbamoylphenyl)-6-ethyl-2-[(2-{[5-(trifluoromethyl)(2-pyridyl)]amino}ethyl)amino]pyrimidine-5-carboxylate, ethyl 4-(4-cyanophenyl)-2-[(2-{[5-(morpholin-4-ylcarbonyl)(2-pyridyl)]amino}ethyl)amino]pyrimidine-5-carboxylate, N-[(3-chlorophenyl)methyl]{4-[2-({2-[(5-nitro(2-pyridyl))amino]ethyl}amino)pyrimidin-4-yl]phenyl}carboxamide, N-[(3,4-difluorophenyl)methyl]{4-[2-({2-[(5-nitro(2-pyridyl))amino]ethyl}amino) pyrimidin-4-yl]phenyl}carboxamide, ethyl 4-[4-(4-methylpiperazinyl)phenyl]-2-({2-[(5-nitro(2-pyridyl))amino]ethyl}amino)pyrimidine-5-carboxylate, 4-cyclohexyl-2-({2-[(5-nitro(2-pyridyl))amino]ethyl}amino)-6-(4-nitrophenyl)pyrimidine-5-carboxylic acid,{4-[2-({2-[(5-nitro(2-pyridyl))amino]ethyl}amino)pyrimidin-4-yl]phenyl}-N-[(3-nitrophenyl)methyl]carboxamide, ethyl 4-{[(3-bromophenyl)methyl]amino}-2-({2-[(5-nitro(2-pyridyl))amino]ethyl}amino)pyrimidine-5-carboxylate, N-[(3-bromophenyl)methyl][4-(2-{[2-(3-methoxyphenyl)ethyl]amino}pyrimidin-4-yl)phenyl]carboxamide, N-(naphthyl-methyl){4-[2-({2-[(5-nitro(2-pyridyl))amino]ethyl}amino)pyrimidin-4-yl]phenyl}carboxamide, 4-(3-cyanophenyl)-2-({2-[(5-nitro(2-pyridyl))amino]ethyl}amino)-6-(4-nitrophenyl)pyrimidine-5-carboxylic acid, N-[(3,4-dimethoxyphenyl)methyl]{4-[2-({2-[(5-nitro(2-pyridyl))amino]ethyl}amino)pyrimidin-4-yl]phenyl}carboxamide, N-[(2,3-dimethoxyphenyl)methyl]{4-[2-({2-[(5-nitro(2-pyridyl))amino]ethyl}amino)pyrimidin-4-yl]phenyl}carboxamide, 4-(4-methoxyphenyl)-2-({2-[(5-nitro(2-pyridyl))amino]ethyl}amino)-6-(4-nitrophenyl)pyrimidine-5-carboxylic acid, N-[(3-bromophenyl)methyl]{4-[2-({2-[(6-methoxy(2-pyridyl))amino]ethyl}amino) pyrimidin-4-yl]phenyl}carboxamide, {4-[2-({2-[(5-nitro(2-pyridyl))amino]ethyl}amino)pyrimidin-4-yl]phenyl}-N-{[3-(trifluoromethyl)phenyl]methyl}carboxamide, N-[(3,5-dichlorophenyl)methyl]{4-[2-({2-[(5-nitro(2-pyridyl))amino]ethyl}amino)pyrimidin-4-yl]phenyl}carboxamide, N-[(3,4-dichlorophenyl)methyl]{4-[2-({2-[(5-nitro(2-pyridyl))amino]ethyl}amino)pyrimidin-4-yl]phenyl}carboxamide, ethyl 4-(4-cyanophenyl)-2-{[2-({5-nitro-6-[benzylamino](2-pyridyl)}amino)ethyl]amino}pyrimidine-5-carboxylate, ethyl 4-[3,5-bis(trifluoromethyl)phenyl]-2-({2-[(5-nitro(2-pyridyl))amino]ethyl}amino)pyrimidine-5-carboxylate, 4,6-bis(4-nitrophenyl)-2-({2-[(5-nitro(2-pyridyl))amino]ethyl}amino)pyrimidine-5-carboxylic acid, [4-(2-{[2-(2,5-dimethoxyphenyl)ethyl]amino}pyrimidin-4-yl)phenyl]-N-[(3-bromophenyl)methyl]carboxamide, 2-({2-[(5-nitro(2-pyridyl))amino]ethyl}amino)-4-(3-nitrophenyl)-6-(4-nitrophenyl)pyrimidine-5-carboxylic acid, N-[(3-bromophenyl)methyl]{4-[2-({2-[(4-nitrophenyl)amino]ethyl}amino)pyrimidin-4-yl]phenyl}carboxamide, N-[(3-bromophenyl)methyl]{4-[2-({2-[(5-nitro(2-pyridyl))amino]ethyl}amino)pyrimidin-4-yl]phenyl}carboxamide, N-[(4-bromophenyl)methyl]{4-[2-({2-[(5-nitro(2-pyridyl))amino]ethyl}amino)pyrimidin-4-yl]phenyl}carboxamide,{4-[2-({2-[(5-nitro(2-pyridyl))amino]ethyl}amino)pyrimidin-4-yl]phenyl}-N-[(4-sulfamoylphenyl)methyl]carboxamide, N-[2-(2,4-dichlorophenyl)ethyl]{4-[2-({2-[(5-nitro(2-pyridyl))amino]ethyl}amino)pyrimidin-4-yl]phenyl}carboxamide, N-[(3-bromophenyl)methyl][4-(2-{[2-(2-quinolylamino)ethyl]amino}pyrimidin-4-yl)phenyl]carboxamide, 2-({2-[(5-nitro(2-pyridyl))amino]ethyl}amino)-6-(4-nitrophenyl)-4-(4-quinolyl)pyrimidine-5-carboxylic acid, N-(2,2-diphenylethyl){4-[2-({2-[(5-nitro(2-pyridyl))amino]ethyl}amino) pyrimidin-4-yl]phenyl}carboxamide, N-[(3-bromophenyl)methyl]{4-[2-({3-[(5-nitro(2-pyridyl))amino]propyl}amino)pyrimidin-4-yl]phenyl}carboxamide,{4-[2-({2-[(6-amino-5-nitro(2-pyridyl))amino]ethyl}aamino)pyrimidin-4-yl]phenyl}-N-[(3-bromophenyl) methyl]carboxamide, 2-({2-[(5-nitro(2-pyridyl))amino]ethyl}amino)-6-(4-nitrophenyl)-4-[4-(trifluoromethyl)phenyl]pyrimidine-5-carboxylic acid, N-[(3-bromophenyl)methyl](4-{2-[(2-{[5-(trifluoromethyl)(2-pyridyl)]amino}ethyl)amino]pyrimidin-4-yl}phenyl)carboxamide, [(3-bromophenyl)methyl]({4-[2-({2-[(5-nitro(2-pyridyl)) amino]ethyl}amino)pyrimidin-4-yl]phenyl}sulfonyl)amine, and N-[(3-iodophenyl)methyl]{4-[2-({2-[(5-nitro(2-pyridyl))amino]ethyl}amino)pyrimidin-4-yl]phenyl}carboxamide, 1-[2-{[2-({6-amino-5-[hydroxy(oxido)amino]-2-pyridinyl}amino)ethyl]aamino}-4-(2,4-dichlorophenyl)-5-pyrimidinyl]-2-piperazinone, 1-[2-{[2-({6-amino-5-[hydroxy(oxido)amino]-2-pyridinyl}amino)ethyl]amino}-4-(2,4-dichlorophenyl)-5-pyrimidinyl]-4-ethyl-3-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-methyl-2-piperazinone, 1-[2-{[2-({6-amino-5-[hydroxy(oxido)amino]-2-pyridinyl}amino)ethyl]amino}-4-(2,4-dichlorophenyl)-5-pyrimidinyl]-4-methyl-2-piperazinone, 6-[(2-{[6-(2,4-dichlorophenyl)-5-(4-methyl-2-oxo-1-piperazinyl)-2-pyridinyl]amino}ethyl)amino]nicotinonitrile, 1-[6-{[2-({6-amino-5-[hydroxy(oxido)amino]-2-pyridinyl}amino)ethyl]amino}-2-(4-ethylphenyl)-3-pyridinyl]-4-methyl-2-piperazinone, 6-[(2-{[6-(4-ethylphenyl)-5-(4-methyl-2-oxo-1-piperazinyl)-2-pyridinyl]amino}ethyl)amino]nicotinonitrile, 6-({2-[[6-(4-ethylphenyl)-5-(4-methyl-2-oxo-1-piperazinyl)-2-pyridinyl](methyl)amino]ethyl}amino)nicotinonitrile, 6-[(2-{[4-(2,4-dichlorophenyl)-5-(4-methyl-2-oxo-1-piperazinyl)-2-pyrimidinyl]amino}ethyl)amino]nicotinonitrile, 1-[6-{[2-({6-amino-5-[hydroxy(oxido)amino]-2-pyridinyl}amino)ethyl]amino}-2-(2,4-difluorophenyl)-3-pyridinyl]-4-methyl-2-piperazinone, 4-[6-{[2-({6-amino-5-[hydroxy(oxido)amino]-2-pyridinyl}amino)ethyl]aamino}-3-(4-methyl-2-oxo-1-piperazinyl)-2-pyridinyl]benzonitrile, 1-[6-{[2-({6-amino-5-[hydroxy(oxido)amino]-2-pyridinyl}amino)ethyl]amino}-2-(2,4-dichlorophenyl)-3-pyridinyl]-4-isopropyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-ethyl-2-piperazinone, 1-{6-{[2-({6-amino-5-[hydroxy(oxido)amino]-2-pyridinyl }amino)ethyl]amino}-2-[2-(trifluoromethyl) phenyl]-3-pyridinyl-}4-methyl-2-piperazinone, 1-[6-{[2-({6-amino-5-[hydroxy(oxido)amino]-2-pyridinyl}amino)ethyl]amino}-2-(2-bromophenyl)-3-pyridinyl]-4-methyl-2-piperazinone, 1-[6-{[2-({6-amino-5-[hydroxy(oxido)amino]-2-pyridinyl}amino)propyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)propyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)-1-methylethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)-1-methylethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)-1,1-dimethylethyl]amino}-2-(2,4-dichloro-phenyl)-3-pyridinyl]-4-methyl-2-piperazinone, 1-[6-{[2-({6-amino-5-[hydroxy(oxido)amino]-2-pyridinyl}amino)ethyl][2-(1-pyrrolidinyl)ethyl]amino}-2-(2,4-dichlorophenyl)-3-pyridinyl]-4-methyl-2-piperazinone, 1-[6-[3-({6-amino-5-[hydroxy(oxido)amino]-2-pyridinyl}amino)propyl]-2-(2,4-dichlorophenyl)-3-pyridinyl-4-methyl-2-piperazinone, 1-[6-[[2-({6-amino-5-[hydroxy(oxido)amino]-2-pyridinyl}amino)ethyl](methyl)amino]-2-(2,4-dichlorophenyl)-3-pyridinyl]-4-methyl-2-piperazinone, 1-[6-[2-({6-amino-5-[hydroxy(oxido)amino]-2-pyridinyl}amino)ethoxy]-2-(2,4-dichlorophenyl)-3-pyridinyl]-4-methyl-2-piperazinone, 1-[6-{[2-({6-amino-5-[hydroxy(oxido)amino]-2-pyridinyl}oxy)ethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)ethyl][2-(4-morpholinyl) ethyl]amino}-2-(2,4-dichlorophenyl)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-cyclopropyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-cyclohexyl-2-piperazinone, 1-[6-{[2-({6-amino-5-[hydroxy(oxido)amino]-2-pyridinyl}aamino)ethyl]amino}-2-(4-bromophenyl)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-3,4-dimethyl-2-piperazinone, 1-(2-(2,4-dichlorophenyl)-6-{[2-({5-[hydroxy(oxido)amino]-6-methoxy-2-pyridinyl}amino)ethyl]amino}-3-pyridinyl)-4-methyl-2-piperazinone, 1-(2-(2,4-dichlorophenyl)-6-{[2-({5-[hydroxy(oxido)amino]-2-pyridinyl }amino)ethyl]amino}-3-pyridinyl)-4-methyl-2-piperazinone, 4-[6-{[2-({6-amino-5-[hydroxy(oxido)amino]-2-pyridinyl}amino)ethyl]amino}-3-(4-methyl-2-oxo-1-piperazinyl)-2-pyridinyl]benzamide, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-3(4H)-one, 1-[6-{[2-({6-amino-5-[hydroxy(oxido)amino]-2-pyridinyl}amino)ethyl]amino}-2-(2,4-dichlorophenyl)-3-pyridinyl]-4-(methylsulfonyl)-2-piperazinone, 4-acetyl-1-[6-{[2-({6-amino-5-[hydroxy(oxido)amino]-2-pyridinyl}amino)ethyl]amino}-2-(2,4-dichlorophenyl)-3-pyridinyl]-2-piperazinone, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-3(4H)-one, 2-[6-{[2-({6-amino-5-[hydroxy(oxido)amino]-2-pyridinyl}amino)ethyl]amino}-2-(2,4-dichlorophenyl)-3-pyridinyl]hexahydropyrrolo[1,2-a]pyrazin-1(2H)-one, 2-[6-{[2-({6-amino-5-[hydroxy(oxido) amino]-2-pyridinyl}amino)ethyl]amino}-2-(2,4-dichlorophenyl)-3-pyridinyl]hexahydropyrrolo-[1,2-a]pyrazin-1(2H)-one, 1-[6-{[2-({6-amino-5-[hydroxy(oxido)amino]-2-pyridinyl}amino)ethyl]amino}-2-(2,4-difluorophenyl)-3-pyridinyl]-4-ethyl-2-piperazinone, 4-[6-{[2-({6-amino-5-[hydroxy(oxido)amino]-2-pyridinyl}amino)ethyl]amino}-3-(4-ethyl-2-oxo-1-piperazinyl)-2-pyridinyl]benzonitrile, 1-[6-{[2-({6-amino-5-[hydroxy(oxido)amino]-2-pyridinyl}amino)propyl]amino}-2-(2,4-dichlorophenyl)-3-pyridinyl]-4-ethyl-2-piperazinone, 1-(6-{[2-({6-amino-5-[hydroxy(oxido)amino]-2-pyridinyl}amino)ethyl]amino}-2-phenyl-3-pyridinyl)-4-methyl-2-piperazinone, 1-[6-{[2-({6-amino-5-[hydroxy(oxido)amino]-2-pyridinyl}amino)ethyl]amino}-2-(4-chlorophenyl)-3-pyridinyl]-4-methyl-2-piperazinone, 3-amino-i -[6-{[2-({6-amino-5-[hydroxy(oxido)amino]-2-pyridinyl}amino)ethyl]amino}-2-(2,4-dichlorophenyl)-3-pyridinyl]-2-piperidinone, 1-[6-{[2-({6-amino-5-[hydroxy(oxido)amino]-2-pyridinyl}amino)ethyl]amino}-2-(3-chlorophenyl)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenoxy)-3-pyridinyl]-4-methyl-2-piperazinone, 1-[6-{[2-({6-amino-5-[hydroxy(oxido)amino]-2-pyridinyl}amino)ethyl]amino}-2-(2,4-dichlorophenyl)-3-pyridinyl]-4-(2,2,2-trifluoroethyl)-2-piperazinone, 4-[6-{[2-({6-amino-5-[hydroxy(oxido)amino]-2-pyridinyl}amino)ethyl]amino}-2-(2,4-dichloro-phenyl)-3-pyridinyl]-3-morpholinone, 1-{6-[2-(6-Amino-5-nitro-pyridin-2-ylamino)ethylamino]-[2,3']bipyridinyl-3-yl}-4-methyl-piperazin-2-one, 1-[6-{[2-({6-amino-5-[hydroxy(oxido)amino]-2-pyridinyl }amino)ethyl]amino}-2-(2,4-dichlorophenyl)-3-pyridinyl]-2-piperidinone, 1-[6-{[2-({6-amino-5-[hydroxy(oxido)amino]-2-pyridinyl}amino)ethyl]amino}-2-(4-chloro-2-methylphenyl)-3-pyridinyl]-4-methyl-2-piperazinone, 1-[6-{[2-({6-amino-5-[hydroxy(oxido)amino]-2-pyridinyl}amino)ethyl]amino}-2-(4-methoxyphenyl)-3-pyridinyl]-4-methyl-2-piperazinone, and 1-[6-{[2-({6-amino-5-[hydroxy(oxido)amino]-2-pyridinyl}amino)ethyl]amino}-2-(3-furyl)-3-pyridinyl]-4-methyl-2-piperazinone.

The following compounds exhibited IC$_{50}$s of 1 μM or less with respect to GSK3 in this cell-free assay: 4-{2-[(2-(2-pyridyl)ethyl)amino]pyrimidin-4-yl}benzamide, 4-{2-[(2-phenylpropyl)amino]pyrimidin-4-yl}benzamide, 4-(2-{[2-(2-pyridylamino) ethyl]amino}pyrimidin-4-yl)benzamide, 4-(2-{[2-(pyrimidin-2-ylamino)ethyl]amino}pyrimidin-4-yl)benzamide, (5-nitro-4-phenylpyrimidin-2-yl)[2-(2-pyridylamino)ethyl]amine, 4-(2-{[3-(4-nitroimidazolyl)propyl]amino}pyrimidin-4-yl)phenol, 4-(2-{[2-(2-methoxyphenyl)ethyl]amino}pyrimidin-4-yl)benzamide, 4-[2-({2-[(5-cyano-2-pyridyl) amino]ethyl}amino) pyrimidin-4-yl]benzamide, 2-({2-[(5-nitro(2-pyridyl))amino]ethyl}amino)-4-phenylpyrimidine-5-carbonitrile, 4-[2-({2-[(6-methoxy-2-pyridyl)amino]ethyl}amino) pyrimidin-4-yl]benzamide, 4-(2-{[3-(4,5-dichloroimidazolyl)propyl]amino}pyrimidin-4-yl)phenol, 4-(2-{[3-(4-nitroimidazolyl)propyl]amino}pyrimidin-4-yl)benzamide, 4-{2-[(3-benzimidazolylpropyl)amino]pyrimidin-4-yl}benzamide, 4-[2-({2-[(4-amino-5-cyano-pyrimidin-2-yl)amino]ethyl}amino)pyrimidin-4-yl] benzamide, 4-{2-[(3-benzimidazolylpropyl)amino]pyrimidin-4-yl}-2-methoxphenol, 4-(2-{[2-(2,5-dimethoxyphenyl)ethyl]amino}pyrimidin-4-yl)benzamide, 4-(2-{[2-(2,3-dimethoxy-phenyl)ethyl]amino}pyrimidin-4-yl)benzamide, 4-(2-{[3-(4-methoxyphenoxy) propyl]amino}pyrimidin-4-yl)benzamide, 4-[2-({2-[(5-nitro-2-pyridyl)amino]ethyl}amino)pyrimidin-4-yl]benzamide,{2-[(5-nitro(2-pyridyl))amino]ethyl}(5-nitro-4-phenyl-pyrimidin-2-yl)amine, 4-(2-{[2-(2-quinolylamino) ethyl]amino}pyrimidin-4-yl)benzamide, 4-(4-cyanophenyl)-2-({2-[(5-nitro(2-pyridyl))amino]ethyl}amino)pyrimidine-5-carbonitrile, 4-(2-{[3-(4,5-dichloroimidazolyl)propyl]amino}pyrimidin-4-yl)benzamide, 4-{2-[(2-{[5-

(aminothioxomethyl)-2-pyridyl]amino}ethyl)amino] pyrimidin-4-yl}benzamide, 4-[2-({3-[(5-nitro-2-pyridyl) amino]propyl}amino)pyrimidin-4-yl]benzamide, 4-(2-{[3-(4-phenylimidazolyl)propyl]amino}pyrimidin-4-yl) benzamide, 4-{2-[(3-naphthyloxypropyl)amino]pyrimidin-4-yl}benzamide, 4-(2-{[3-(5,6-dimethylbenzimidazolyl) propyl]amino}pyrimidin-4-yl)benzamide, [4-(4-imidazolylphenyl)pyrimidin-2-yl]{2-[(5-nitro(2-pyridyl)) amino]ethyl}amine, 4-{2-[(2-{[5-(trifluoromethyl)-2-pyridyl]amino}ethyl)amino]pyrimidin-4-yl}benzamide, 4-(4-cyanophenyl)-2-({2-[(5-nitro(2-pyridyl))amino] ethyl}amino)pyrimidine-5-carboxamide, 4-(4-cyanophenyl)-2-({2-[(5-nitro(2-pyridyl))amino] ethyl}amino)pyrimidine-5-carboxylic acid, 2-({2-[(6-amino-5-nitro(2-pyridyl))amino]ethyl}aamino)-4-(2,4-dichlorophenyl)pyrimidine-5-carboxylic acid, ethyl 2-({2-[(5-nitro(2-pyridyl))amino]ethyl}amino)-4-(4-pyridyl) pyrimidine-5-carboxylate, ethyl 2-({2-[(5-cyano(2-pyridyl)) amino]ethyl}amino)-4-(4-cyanophenyl)pyrimidine-5-carboxylate, 4-[2-({3-[3-(trifluoromethyl)phenoxy] propyl}amino)pyrimidin-4-yl]benzamide, [4-(4-cyanophenyl)-2-({2-[(5-nitro(2-pyridyl))amino] ethyl}amino)pyrimidin-5-yl]-N-methylcarboxamide, methyl 4-(4-cyanophenyl)-2-({2-[(5-nitro(2-pyridyl)) amino]ethyl}amino)pyrimidine-5-carboxylate, [4-(4-morpholin-4-ylphenyl)pyrimidin-2-yl]{2-[(5-nitro(2-pyridyl))amino]ethyl}amine, ethyl 4-(4-methylphenyl)-2-({2-[(5-nitro(2-pyridyl))amino]ethyl}amino)pyrimidine-5-carboxylate, {2-[(6-amino-5-nitro(2-pyridyl))amino] ethyl}{5-nitro-6-[benzylamino](2-pyridyl)}amine, 2-({2-[(5-nitro-(2-pyridyl))amino]ethyl}amino)-4-(4-nitrophenyl) pyrimidine-5-carboxylic acid, ethyl 4-(4-fluorophenyl)-2-({2-[(5-nitro(2-pyridyl))amino]ethyl}amino)pyrimidine-5-carboxylate, 4-[5-imidazolyl-2-({2-[(5-nitro(2-pyridyl)) amino]ethyl}amino)pyrimidin-4-yl]benzene-carbonitrile, 4-[5-imidazol-2-yl-2-({2-[(5-nitro(2-pyridyl))amino] ethyl}amino)pyrimidin-4-yl]benzenecarbonitrile, ethyl 2-({2-[(4-amino-5-cyanopyrimidin-2-yl)amino] ethyl}amino)-4-(4-cyanophenyl)pyrimidine-5-carboxylate, [4-(2,4-dimethyl-phenyl)-5-imidazolylpyrimidin-2-yl]{2-[(5-nitro(2-pyridyl))amino]ethyl}amine, 2-({2-[(6-amino-5-nitro(2-pyridyl))amino]ethyl}amino)-4-(2,4-dichlorophenyl)pyrimidine-5-carbonitrile, ethyl 4-(4-cyanophenyl)-2-({2-[(4-nitrophenyl)amino]ethyl}amino) pyrimidine-5-carboxylate, [4-(4-cyanophenyl)-2-({2-[(5-nitro(2-pyridyl))amino]ethyl}amino)pyrimidin-5-yl]-N,N-dimethylcarboxamide, ethyl 4-(4-cyanophenyl)-2-({2-[(5-nitro(2-pyridyl))amino]ethyl}amino)pyrimidine-5-carboxylate, [4-(2,4-dichlorophenyl)-5-ethylpyrimidin-2-yl] {2-[(5-nitro(2-pyridyl))amino]ethyl}amine, ethyl 4-(4-ethylphenyl)-2-({2-[(5-nitro(2-pyridyl))amino] ethyl}amino) pyrimidine-5-carboxylate, ethyl 4-(4-methoxyphenyl)-2-({2-[(5-nitro(2-pyridyl))amino] ethyl}amino)pyrimidine-5-carboxylate, 4-[5-(methylsulfonyl)-2-({2-[(5-nitro(2-pyridyl))amino] ethyl}amino)pyrimidin-4-yl]benzenecarbonitrile, 4-(2-{[3-(5,6-dichlorobenzimidazolyl)propyl]amino}pyrimidin-4-yl) benzamide, 4-[2-({2-[(6-amino-5-nitro(2-pyridyl))amino] ethyl}amino)-5-imidazolyl-pyrimidin-4-yl] benzenecarbonitrile, 4-[2-({2-[(6-amino-5-nitro(2-pyridyl)) amino]ethyl}amino)-5-imidazol-2-ylpyrimidin-4-yl] benzenecarbonitrile, N-(cyanomethyl)[4-(4-cyanophenyl)-2-({2-[(5-nitro(2-pyridyl))amino]ethyl}amino)pyrimidin-5-yl]carboxamide, 4-[5-(3-methyl(1,2,4-oxadiazol-5-yl))-2-({2-[(5-nitro(2-pyridyl)) amino]ethyl}amino)pyrimidin-4-yl]benzenecarbonitrile, ethyl 4-(4-chlorophenyl)-2-({2-[(5-nitro(2-pyridyl))amino]ethyl}amino)pyrimidine-5-carboxylate, ethyl 4-(3,4-difluoro-phenyl)-2-({2-[(5-nitro (2-pyridyl))amino]ethyl}amino)pyrimidine-5-carboxylate, N-(2-aminoethyl)[4-(4-cyanophenyl)-2-({2-[(5-nitro(2-pyridyl))amino]ethyl}amino)pyrimidin-5-yl]carboxamide, ethyl 4-(4-cyanophenyl)-2-({2-[(4-methyl-5-nitro(2-pyridyl))amino]ethyl}amino)pyrimidine-5-carboxylate, ethyl 2-({2-[(6-amino-5-nitro(2-pyridyl))amino] ethyl]amino)-4-(4-cyanophenyl)pyrimidine-5-carboxylate, [4-(4-cyanophenyl)-2-({2-[(5-nitro(2-pyridyl))amino] ethyl}amino) pyrimidin-5-yl]-N-(2-hydroxyethyl) carboxamide, 2-hydroxyethyl 4-(4-cyanophenyl)-2-({2-[(5-nitro(2-pyridyl))amino]ethyl}amino)pyrimidine-5-carboxylate, ethyl 2-({2-[(4-amino-5-nitropyrimidin-2-yl) amino]ethyl}amino)-4-(4-cyanophenyl)pyrimidine-5-carboxylate, ethyl 4-[4-(methylethyl)phenyl]-2-({2-[(5-nitro(2-pyridyl))amino]ethyl}amino)pyrimidine-5-carboxylate, ethyl 4-[4-(dimethylamino)phenyl]-2-({2-[(5-nitro(2-pyridyl))amino]ethyl}amino)pyrimidine-5-carboxylate, ethyl 4-(2H-benzo[3,4-d]1,3-dioxolen-5-yl)-2-({2-[(5-nitro(2-pyridyl))amino]ethyl}amino)pyrimidine-5-carboxylate, ethyl 2-({2-[(5-nitro(2-pyridyl))amino] ethyl}amino)-4-(4-nitrophenyl)pyrimidine-5-carboxylate, ethyl 4-(4-methylthiophenyl)-2-({2-[(5-nitro(2-pyridyl)) amino]ethyl}amino)pyrimidine-5-carboxylate, ethyl 4-(4-cyanophenyl)-2-[(2-{[5-(trifluoromethyl)(2-pyridyl)] amino}ethyl)amino]pyrimidine-5-carboxylate, ethyl 4-(2-naphthyl)-2-({2-[(5-nitro(2-pyridyl)) amino]ethyl}amino) pyrimidine-5-carboxylate, N-butyl[4-(4-cyanophenyl)-2-({2-[(5-nitro(2-pyridyl))amino]ethyl}amino)pyrimidin-5-yl]carboxamide, N-(tert-butyl)[4-(4-cyano-phenyl)-2-({2-[(5-nitro(2-pyridyl))amino]ethyl}amino)pyrimidin-5-yl] carboxamide, ethyl 4-(4-carbamoylphenyl)-2-({2-[(5-cyano (2-pyridyl))amino]ethyl}amino)-6-ethyl-pyrimidine-5-carboxylate, tert-butyl 4-(4-cyanophenyl)-2-({2-[(5-nitro(2-pyridyl)) amino]ethyl}amino)pyrimidine-5-carboxylate, N-(carbamoylmethyl)[4-(4-cyanophenyl)-2-({2-[(5-nitro(2-pyridyl))amino]ethyl}amino)pyrimidin-5-yl]carboxamide, ethyl 4-(4-cyano-phenyl)-6-ethyl-2-({2-[(5-nitro(2-pyridyl))amino]ethyl}amino)pyrimidine-5-carboxylate, butyl 4-(4-cyanophenyl)-2-({2-[(5-nitro(2-pyridyl))amino] ethyl}amino)pyrimidine-5-carboxylate, ethyl 4-{[(4-cyanophenyl)methyl]amino}-2-({2-[(5-nitro(2-pyridyl)) amino]ethyl}amino)pyrimidine-5-carboxylate, ethyl 4-{[(3-cyanophenyl)methyl]amino}-2-({2-[(5-nitro(2-pyridyl)) amino]ethyl}amino)pyrimidine-5-carboxylate, ethyl 4-[4-(tert-butyl)phenyl]-2-({2-[(5-nitro(2-pyridyl))amino] ethyl}amino)pyrimidine-5-carboxylate, 4-[2-({2-[(5-nitro (2-pyridyl))amino]ethyl}amino)-5-[benzylamino] pyrimidin-4-yl]benzene-carbonitrile, [4-(2,4-dichlorophenyl)-5-imidazolylpyrimidin-2-yl]{2-[(5-nitro(2-pyridyl))amino]ethyl}amine, [4-(2,4-dichlorophenyl)-5-imidazol-2-ylpyrimidin-2-yl]{2-[(5-nitro(2-pyridyl))amino] ethyl}amine, 4-(4-cyanophenyl)-6-(3-fiuryl)-2-({2-[(5-nitro (2-pyridyl))amino]ethyl}amino)pyrimidine-5-carboxylic acid, 4-[2-({2-[(5-nitro(2-pyridyl)) amino]ethyl}amino)-5-(piperazinylcarbonyl)pyrimidin-4-yl]benzenecarbonitrile, ethyl 4-(4-imidazolylphenyl)-2-({2-[((5-nitro(2-pyridyl)) amino]ethyl}amino)pyrimidine-5-carboxylate, 4-[5-(morpholin-4-ylcarbonyl)-2-({2-[(5-nitro(2-pyridyl)) amino]ethyl}amino)pyrimidin-4-yl]benzenecarbonitrile, ethyl 4-(4-(2-furyl)phenyl)-2-({2-[(5-nitro(2-pyridyl)) amino]ethyl}amino)pyrimidine-5-carboxylate, ethyl 2-({2-[(5-nitro(2-pyridyl))amino]ethyl}amino)-4-(4-(1,3-oxazol-5-yl)phenyl)pyrimidine-5-carboxylate, ethyl 2-({2-[(5-nitro (2-pyridyl))amino]ethyl}amino)-4-(1,2,4-triazol-4-yl) phenyl) pyrimidine-5-carboxylate, N-[2-(dimethylamino) ethyl][4-(4-cyanophenyl)-2-({2-[(5-nitro(2-pyridyl))amino]

ethyl}amino)pyrimidin-5-yl]carboxamide, 2-(dimethylamino) ethyl 4-(4-cyano-phenyl)-2-({2-[(5-nitro(2-pyridyl))amino]ethyl}amino) pyrimidine-5-carboxylate, ethyl 2-({2-[(5-nitro(2-pyridyl))amino]ethyl}amino)-4-[4-(trifluoromethyl)phenyl]pyrimidine-5-carboxylate, ethyl 4-(2,4-dichlorophenyl)-2-({2-[(5-nitro(2-pyridyl))amino]ethyl}amino)pyrimidine-5-carboxylate, ethyl 4-(4-(1H-1,2,3,4-tetraazol-5-yl)phenyl)-2-({2-[(5-nitro(2-pyridyl))amino]ethyl}amino)pyrimidine-5-carboxylate, ethyl 4-(4-carbamoylphenyl)-6-ethyl-2-({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-phenylpyrimidine-5-carboxylic acid,{2-[(6-amino-5-nitro(2-pyridyl))amino]ethyl}[4-(2,4-dichlorophenyl)-5-imidazolylpyrimidin-2-yl]amine,{2-[(6-amino-5-nitro(2-pyridyl))amino]ethyl}[4-(2,4-dichlorophenyl)-5-imidazol-2-ylpyrimidin-2-yl]amine, ethyl 4-(4-bromophenyl)-2-({2-[(5-nitro(2-pyridyl))amino]ethyl}amino)pyrimidine-5-carboxylate, ethyl 4-[4-(methylsulfonyl)phenyl]-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(4-(1,3-oxazol-5-yl)phenyl)pyrimidine-5-carboxylate, N-[2-(dimethylamino)ethyl][4-(4-cyanophenyl)-2-({2-[(5-nitro(2-pyridyl))amino]ethyl}amino)pyrimidin-5-yl]-N-methylcarboxamide, N-(1-carbamoyl-2-hydroxyethyl)[4-(4-cyanophenyl)-2-({2-[(5-nitro(2-pyridyl))amino]ethyl}amino) pyrimidin-5-yl]carboxamide, 3-(dimethylamino)propyl 4-(4-cyanophenyl)-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(2,4-dichlorophenyl)pyrimidine-5-carboxylate, 2-(dimethylamino)ethyl 2-({2-[(6-amino-5-nitro(2-pyridyl))amino]ethyl}amino)-4-(4-cyanophenyl) pyrimidine-5-carboxylate, [2-(dimethyl-amino)ethoxy]-N-[4-(4-cyanophenyl)-2-({2-[(5-nitro(2-pyridyl))amino]ethyl}amino)pyrimidin-5-yl]carboxamide, ethyl 2-({2-[(5-nitro(2-pyridyl))amino]ethyl}amino)-4-[4-(trifluoromethoxy)phenyl]pyrimidine-5-carboxylate, ethyl 4-(4-morpholin-4-ylphenyl)-2-({2-[(5-nitro(2-pyridyl))amino]ethyl}amino)pyrimidine-5-carboxylate, [4-(4-cyanophenyl)-2-({2-[(5-nitro(2-pyridyl))amino]ethyl}amino) pyrimidin-5-yl]-N-benzyl-carboxamide, ethyl 4-(6-morpholin-4-yl(3-pyridyl))-2-({2-[(5-nitro(2-pyridyl))amino]ethyl}amino) pyrimidine-5-carboxylate, [4-(4-cyanophenyl)-2-({2-[(5-nitro(2-pyridyl))amino]ethyl}amino)pyrimidin-5-yl]-N-(4-pyridylmethyl)carboxamide, phenylmethyl 4-(4-cyanophenyl)-2-({2-[(5-nitro(2-pyridyl))amino]ethyl}amino)pyrimidine-5-carboxylate, 4-(4-cyanophenyl)-6-(4-fluorophenyl)-2-({2-[(5-nitro(2-pyridyl))amino]ethyl}amino)pyrimidine-5-carboxylic acid, N-[(3-methoxyphenyl)methyl]{4-[2-({2-[(5-nitro(2-pyridyl))amino]ethyl}amino)pyrimidin-4-yl]phenyl}carboxamide, 4-[5-{3-[2-(dimethylamino)ethyl](1,2,4-oxadiazol-5-yl)}-2-({2-[(5-nitro(2-pyridyl)) amino]ethyl}amino)pyrimidin-4-yl]benzenecarbonitrile, N-[(3-bromophenyl)methyl][4-(2-{[2-(pyrimidin-2-ylamino)ethyl]amino}pyrimidin-4-yl)phenyl]carboxamide, 4-(dimethyl-amino)butyl 4-(4-cyanophenyl)-2-({2-[(5-nitro(2-pyridyl))amino]ethyl}amino) pyrimidine-5-carboxylate, 4,6-bis(4-cyanophenyl)-2-({2-[(5-nitro(2-pyridyl))amino]ethyl}amino)pyrimidine-5-carboxylic acid, ethyl 2-({2-[(6-amino-5-nitro(2-pyridyl)) amino]ethyl}amino)-4-(4-morpholin-4-ylphenyl)pyrimidine-5-carboxylate, 4-(3-hydroxyphenyl)-2-({2-[(5-nitro(2-pyridyl))amino]ethyl}amino)-6-(4-nitrophenyl)pyrimidine-5-carboxylic acid, 2-morpholin-4-ylethyl 4-(4-cyanophenyl)-2-({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-(4-nitrophenyl)pyrimidine-5-carboxylic acid, 4-(4-cyanophenyl)-2-({2-[(5-nitro(2-pyridyl))amino]ethyl}amino)-6-(3-nitrophenyl)pyrimidine-5-carboxylic acid, N-[(3-bromophenyl)methyl]{4-[2-({2-[(5-cyano(2-pyridyl))amino]ethyl}amino)pyrimidin-4-yl]phenyl}carboxamide, ethyl 4-(4-carbamoylphenyl)-2-({2-[(5-nitro-(2-pyridyl))amino]ethyl})-6-(4-pyridyl)pyrimidine-5-carboxylate, 2-(dimethylamino)ethyl 2-({2-[(6-amino-5-nitro(2-pyridyl))amino]ethyl}amino)-4-(2,4-dichloro-phenyl)pyrimidine-5-carboxylate, 2-[bis(2-hydroxyethyl)amino]ethyl 4-(4-cyanophenyl)-2-({2-[(5-nitro(2-pyridyl))amino]ethyl}amino) pyrimidine-5-carboxylate,{4-[2-({2-[(4-amino-5-cyanopyrimidin-2-yl)amino]ethyl}amino)pyrimidin-4-yl]phenyl}-N-[(3-bromophenyl)methyl]carboxamide, 4-(4-carboxyphenyl)-2-({2-[(5-nitro(2-pyridyl)) amino]ethyl}amino)-6-(4-nitrophenyl)pyrimidine-5-carboxylic acid, 2-hydroxy-3-morpholin-4-ylpropyl 4-(4-cyanophenyl)-2-({2-[(5-nitro(2-pyridyl))amino]ethyl}amino)pyrimidine-5-carboxylate, ethyl 4-(4-cyanophenyl)-2-({2-[(5-nitro(2-pyridyl))amino]ethyl}amino)-6-(4-nitrophenyl)pyrimidine-5-carboxylate, (2-{5-[2-({2-[(6-amino-5-nitro(2-pyridyl)) amino]ethyl}amino)-4-(2,4-dichlorophenyl)pyrimidin-5-yl](1,2,4-oxadiazol-3-yl) }ethyl)dimethylamine, ethyl 4-(4-carbamoylphenyl)-2-({2-[(5-nitro(2-pyridyl))amino]ethyl}amino)-6-(4-nitrophenyl)pyrimidine-5-carboxylate, [4-(4-imidazolylphenyl)pyrimidin-2-yl]{2-[(5-nitro(2-pyridyl))amino]ethyl}amine, 4-[5-imidazolyl-2-({2-[(5-nitro(2-pyridyl))amino]ethyl}amino)pyrimidin-4-yl]benzenecarbonitrile, 4-[2-({2-[(6-amino-5-nitro(2-pyridyl))amino]ethyl}amino)-5-imidazolylpyrimidin-4-yl]benzenecarbonitrile, [4-(2,4-dichlorophenyl)-5-imidazolylpyrimidin-2-yl]{2-[(5-nitro(2-pyridyl))amino]ethyl}amine, 4-[2-({2-[(5-nitro-2-pyridyl)amino]ethyl}amino)-7a-hydro-1,2,4-triazolo[1,5-a]pyrimidin-7-yl]benzenecarbonitrile,{2-[(6-amino-5-nitro(2-pyridyl))amino]ethyl}[4-(2,4-dichloro-phenyl)-5-imidazolylpyrimidin-2-yl]amine, [4-(2,4-dichlorophenyl)-5-imidazol-2-yl-pyrimidin-2-yl]{2-[(5-nitro(2-pyridyl))amino]ethyl}amine, 6-[(2-{[4-(2,4-dichlorophenyl)-5-imidazolylpyrimidin-2-yl]amino}ethyl)amino]pyridine-3-carbonitrile, [5-benzotriazolyl-4-(2,4-dichlorophenyl)pyrimidin-2-yl]{2-[(5-nitro(2-pyridyl))amino]ethyl}amine, [2-({2-[(6-amino-5-nitro(2-pyridyl))amino]ethyl}amino)-4-(2,4-dichlorophenyl)pyrimidin-5-yl]methan-1-ol, [4-(2,4-dichlorophenyl)-2-({2-[(5-nitro(2-pyridyl))amino]ethyl}amino)-pyrimidin-5-yl]methan-1-ol, 2-[2-({2-[(6-amino-5-nitro(2-pyridyl))amino]ethyl}amino)-4-(2,4-dichlorophenyl)pyrimidin-5-yl]isoindoline-1,3-dione, [5-amino-4-(2,4-dichlorophenyl)pyrimidin-2-yl]{2-[(6-amino-5-nitro(2-pyridyl))amino]ethyl}amine, {2-[(6-amino-5-nitro(2-pyridyl))amino]ethyl}[4-(2,4-dichlorophenyl)-5-morpholin-4-yl-pyrimidin-2-yl]amine, {2-[(6-amino-5-nitro(2-pyridyl))aamino]ethyl}{4-(2,4-dichloro-phenyl)-5-[5-(trifluoromethyl)(1,2,3,4-tetraazolyl)]pyrimidin-2-yl}amine, 1-[2-({2-[(6-amino-5-nitro(2-pyridyl))amino]ethyl}amino)-4-(2,4-dichlorophenyl)pyrimidin-5-yl]pyrrolidine-2,5-dione, [4-(2,4-dichlorophenyl)-5-pyrazolylpyrimidin-2-yl]{2-[(5-nitro(2-pyridyl))amino]ethyl}amine, [4-(2,4-dichlorophenyl)-5-(4-methylimidazolyl)pyrimidin-2-yl]{2-[(5-nitro(2-pyridyl))amino]ethyl}aamine, [4-(2,4-dichlorophenyl)-5-(2,4-dimethylimidazolyl)pyrimidin-2-yl]{2-[(5-nitro(2-pyridyl))amino]ethyl}amine, 6-[(2-{[4-(2,4-dichlorophenyl)-5-imidazol-2-ylpyrimidin-2-yl]

amino}ethyl)amino]pyridine-3-carbonitrile,{2-[(6-amino-5-nitro(2-pyridyl))amino]ethyl}[4-(2,4-dichlorophenyl)-5-(morpholin-4-ylmethyl)pyrimidin-2-yl]amine,{2-[(6-amino-5-nitro(2-pyridyl)) amino]ethyl}[4-(2,4-dichlorophenyl)-5-piperazinylpyrimidin-2-yl]amine,{2-[(6-amino-5-nitro(2-pyridyl))amino]ethyl][4-(4-ethylphenyl)-5-imidazolylpyrimidin-2-yl]amine, 1-[4-(2,4-dichlorophenyl)-2-({2-[(5-nitro(2-pyridyl))amino]ethyl}amino) pyrimidin-5-yl]hydropyridin-2-one, [5-benzimidazolyl-4-(2,4-dichlorophenyl)pyrimidin-2-yl]{2-[(5-nitro-(2-pyridyl))amino]ethyl}amine,{2-[(6-amino-5-nitro(2-pyridyl))amino]ethyl}[4-(2,4-dichlorophenyl)-5-imidazolylpyrimidin-2-yl]methylamine, {2-[(6-amino-5-nitro(2-pyridyl))amino]ethyl}[4-(2,4-dichlorophenyl)-5-(4-pyridyl)pyrimidin-2-yl]amine,{2-[(6-amino-5-nitro(2-pyridyl))amino]ethyl}[4-(2,4-dichlorophenyl)-5-(4-methylpiperazinyl)pyrimidin-2-yl]amine, [4-(2,4-dichlorophenyl)-5-(2-methylimidazolyl)pyrimidin-2-yl]{2-[(5-nitro(2-pyridyl))amino]ethyl}amine,{2-[(6-amino-5-nitro(2-pyridyl))amino]ethyl}[4-(2,4-dichlorophenyl)-5-(2-methylimidazolyl)pyrimidin-2-yl]amine,{2-[(6-amino-5-nitro(2-pyridyl))amino]ethyl}[4-(2,4-dichlorophenyl)-5-(4-phenylimidazolyl)pyrimidin-2-yl]amine,{2-[(6-amino-5-nitro(2-pyridyl))amino]ethyl}[4-(2,4-dichlorophenyl)-5-(2,4-dimethylimidazolyl)pyrimidin-2-yl]amine, [4-(2,4-dichlorophenyl)-5-imidazol-2-ylpyrimidin-2-yl](2-{[5-(trifluoromethyl)(2-pyridyl)]amino}ethyl)amine, [4-(2,4-dichlorophenyl)-5-piperazinylpyrimidin-2-yl]{2-[(5-nitro(2-pyridyl))amino]ethyl}amine, [4-(2,4-dichlorophenyl)-5-imidazolylpyrimidin-2-yl][2-(dimethylamino)ethyl]{2-[(5-nitro(2-pyridyl))amino]ethyl}amine, 1-[2-({2-[(6-amino-5-nitro(2-pyridyl))amino]ethyl}amino)-4-(2,4-dichlorophenyl)pyrimidin-5-yl]-4-methylpiperazine-2,6-dione, [4-(2,4-dichlorophenyl)-5-(1-methylimidazol-2-yl)pyrimidin-2-yl]{2-[(5-nitro(2-pyridyl)) amino]ethyl}amine, 1-[2-({2-[(6-amino-5-nitro(2-pyridyl))amino]ethyl}amino)-4-(2,4-dichloro-phenyl)pyrimidin-5-yl]-3-morpholin-4-ylpyrrolidine-2,5-dione, 1-[4-(2,4-dichlorophenyl)-2-({2-[(5-nitro(2-pyridyl))amino]ethyl}amino)pyrimidin-5-yl]-4-methylpiperazine-2,6-dione, 1-[2-({2-[(6-amino-5-nitro(2-pyridyl))amino]ethyl}amino)-4-(2,4-dichlorophenyl)pyrimidin-5-yl]-3-(dimethylamino)pyrrolidine-2,5-dione, {5-imidazol-2-yl-4-[4-(trifluoromethyl)phenyl]pyrimidin-2-yl}{2-[(5-nitro(2-pyridyl))amino]ethyl}amine,{2-[(6-amino-5-nitro(2-pyridyl))amino]ethyl}[4-(2,4-dichlorophenyl)-5-(1-methylimidazol-2-yl)pyrimidin-2-yl]amine, [4-(2,4-dichlorophenyl)-5-(4-methylpiperazinyl)pyrimidin-2-yl]{2-[(5-nitro(2-pyridyl))amino]ethyl}amine, [4-(2,4-dichlorophenyl)-5-(morpholin-4-ylmethyl)pyrimidin-2-yl]{2-[(5-nitro(2-pyridyl))amino]ethyl}amine, [4-(2,4-dichlorophenyl)-5-(4-methylimidazol-2-yl)pyrimidin-2-yl]{2-[(5-nitro(2-pyridyl))amino]ethyl}amine, {2-[(6-amino-5-nitro(2-pyridyl)) amino]ethyl}[4-(2,4-dichlorophenyl)-5-(4-methylimidazol-2-yl)pyrimidin-2-yl]amine,{2-[(6-amino-5-nitro(2-pyridyl))amino]ethyl}[4-(2-chlorophenyl)-5-imidazol-2-ylpyrimidin-2-yl]amine, [4-(2-chloro-4-fluorophenyl)-5-imidazol-2-ylpyrimidin-2-yl]{2-[(5-nitro(2-pyridyl))amino]ethyl}amine, [4-(2,4-dichlorophenyl)-5-imidazolylpyrimidin-2-yl]{2-[(5-nitro(2-pyridyl))amino]ethyl}(2-pyrrolidinylethyl)amine, [4-(2,4-dichlorophenyl)-5-imidazolylpyrimidin-2-yl](2-morpholin-4-ylethyl){2-[(5-nitro(2-pyridyl))amino]ethyl}amine, 6-[(2-{[4-(2,4-dichlorophenyl)-5-(4-methylimidazol-2-yl)pyrimidinyl]amino}ethyl)amino]pyridine-3-carbonitrile, {2-[(6-amino-5-nitro(2-pyridyl))amino]ethyl}[4-(2-chloro-4-fluorophenyl)-5-imidazol-2-ylpyrimidin-2-yl]amine, [4-(4-ethylphenyl)-5-imidazol-2-ylpyrimidin-2-yl]{2-[(5-nitro(2-pyridyl))amino]ethyl}amine, [5-((1E)-1-aza-2-morpholin-4-ylprop-1-enyl)-4-(2,4-dichlorophenyl)pyrimidin-2-yl]{2-[(6-amino-5-nitro(2-pyridyl))amino]ethyl}amine, N-[4-(2,4-dichlorophenyl)-2-({2-[(5-nitro(2-pyridyl))amino]ethyl}amino)pyrimidin-5-yl]acetamide, [4-(2,4-dichlorophenyl)-5-imidazol-2-ylpyrimidin-2-yl]{2-[(6-methoxy-5-nitro(2-pyridyl))amino]ethyl}amine, 6-[(2-{[4-(2,4-dichlorophenyl)-5-imidazolyl-pyrimidin-2-yl]methylamino}ethyl)amino]pyridine-3-carbonitrile, 6-[(2-{[4-(2,4-dichloro-phenyl)-5-imidazol-2-ylpyrimidin-2-yl]methylamino}ethyl)amino]pyridine-3-carbonitrile, [4-(2,4-dichlorophenyl)-5-imidazol-2-ylpyrimidin-2-yl]methyl{2-[(5-nitro(2-pyridyl))amino]ethyl}amine, 6-[(2-{[4-(2-chloro-4-fluorophenyl)-5-imidazol-2-ylpyrimidin-2-yl]amino}ethyl)amino]pyridine-3-carbonitrile, [4-(4-chlorophenyl)-5-imidazol-2-ylpyrimidin-2-yl]{2-[(5-nitro(2-pyridyl))amino]ethyl}amine,{2-[(6-amino-5-nitro(2-pyridyl))amino]ethyl}[4-(4-chloro-2-methylphenyl)-5-imidazol-2-ylpyrimidin-2-yl]amine, {2-[(6-amino-5-nitro(2-pyridyl))amino]ethyl}[4-(4-bromo-2-chlorophenyl)-5-imidazol-2-ylpyrimidin-2-yl]amine, 6-[(2-{[4-(4-bromo-2-chlorophenyl)-5-imidazol-2-ylpyrimidin-2-yl]amino}ethyl)amino]pyridine-3-carbonitrile, 6-[2-({2-[(6-amino-5-nitro(2-pyridyl))amino]ethyl}amino)-4-(2,4-dichlorophenyl)pyrimidin-5-yl]-3-pyrrolino[3,4-b]pyridine-5,7-dione, N-[2-({2-[(6-amino-5-nitro(2-pyridyl))amino]ethyl}amino)-4-(2,4-dichlorophenyl)pyrimidin-5-yl]-2-(methylamino)acetamide,{2-[(6-amino-5-nitro(2-pyridyl))amino]ethyl}[4-(4-bromo-2-chlorophenyl)-5-(4-methylimidazol-2-yl)pyrimidin-2-yl]amine, 6-[(2{[4-(4-bromo-2-chlorophenyl)-5-(4-methylimidazol-2-yl)pyrimidin-2-yl]amino}ethyl)amino]pyridine-3-carbonitrile,{2-[(6-amino-5-nitro(2-pyridyl))amino]ethyl}[4-(2-chloro-4-fluorophenyl)-5-(4-methylimidazol-2-yl)pyrimidin-2-yl]amine, 6-[(2-{[4-(2,4-dichlorophenyl)-5-(5-chloro-2-oxohydropyridyl)pyrimidin-2-yl]amino}ethyl)amino]pyridine-3-carbonitrile, [6-(2,4-dichlorophenyl)-5-imidazolyl(2-pyridyl)]{2-[(5-nitro(2-pyridyl))amino]ethyl}amine,{2-[(6-amino-5-nitro(2-pyridyl))amino]ethyl}[6-(2,4-dichlorophenyl)-5-imidazolyl(2-pyridyl)]amine, 6-[(2-{[6-(2,4-dichlorophenyl)-5-imidazolyl-2-pyridyl]amino}ethyl)amino]pyridine-3-carbonitrile,{2-[(6-amino-5-nitro(2-pyridyl))amino]ethyl}[6-(2,4-dichlorophenyl)-5-nitro(2-pyridyl)]amine,{2-[(6-amino-5-nitro(2-pyridyl))amino]ethyl}[6-(2,4-dichlorophenyl)-5-(4-methylimidazolyl) (2-pyridyl)]amine, 6-[(2-{[6-(2,4-dichlorophenyl)-5-(4-methylimidazolyl)-2-pyridyl]amino}ethyl)amino]pyridine-3-carbonitrile, and [4-(4-bromo-2-chlorophenyl)-5-imidazol-2-ylpyrimidin-2-yl]{2-[(5-nitro(2-pyridyl))amino]ethyl}amine.

Accordingly, these results demonstrate that compounds of the present invention exhibit inhibitory activity against GSK3.

Example 266

Screening for GSK3 Inhibitory Activity Using a Cell-Based Glycogen Synthase Assay CHO-HIRC cells are maintained in 10 cm tissue culture plates in Ham's F12 medium/10% dialysed fetal bovine serum. Cells from a confluent 10 cm plate are harvested and divided into the 6 wells of a 6-well tissue culture plate to a final volume of 2 ml, of medium. The cells are left to grow at 37° C. for 24 hours. The cells are then washed three times in Ham's F12 medium containing no fetal bovine serum, and finally the cells are left for a further 24 hours at 37° C. in 2 ml of the serum-free medium.

At the end of this time, 20 µl of compound dissolved in DMSO is added to each well and incubated at 37° C. After 20 minutes the medium is removed and the cells are washed once in PBS at room temperature and then rapidly frozen in the plates in liquid nitrogen. Cells are then thawed on ice in the presence of 140 μl of lysis buffer (50 mM Tris pH 7.8; 1 mM EDTA, 100 mM NaF, 25 pg/ml leupeptin, 1 mM DTT, 1 mM PMSF) per well. Cells are scraped from the plates and frozen in Eppendorf tubes on dry ice. Lysates are then thawed and refrozen on dry ice.

After rethawing, lysates are spun at 14,000 g for 15 minutes. The supernatants are then removed and stored on ice. Each supernatant (45 μl) is added to 45 μl of reaction buffer (65 mM Tris pH 7.8; 26 mM EDTA, 32.5 mM KF, 9.3 mM UDP-glucose; 11 mg/ml glycogen; 500 nCi/ml $^{14}$C-UDP-glucose) and a further 45 μl is added to 45 μl reaction buffer/20 mM glucose-6-phosphate. Reactions are incubated at 30° C. for 30 minutes and then spotted onto a 2 cm square 31ET chromatograph paper (Whatman). Filter papers are washed twice for 20 minutes in 66% ethanol, rinsed briefly in acetone and dried for 1 hour at room temperature.

Filters are added to 5 ml of liquid scintillant and counted in a liquid scintillation counter. The percentage of the total glycogen synthase that is active in any lysate is expressed as 100×(cpm minus glucose-6-phosphate)/(cpm plus glucose-6-phosphate). Such values are determined in duplicate for 5 different concentrations of compound and for DMSO alone, and the values are then plotted against the logarithm of the concentration. The concentration of compound which stimulates glycogen synthase activity to 50% of the maximal level is determined by fitting a sigmoidal curve to the plotted data. The maximal level is defined as that level to which glycogen synthase activity tends asymtotically as the concentration of test compound increases substantially beyond the $EC_{50}$.

Example 267

Screening for Inhibition of Tau Protein Phosphorylation

A. Transient Transfection of COS Cells with GSK3 Expression Plasmid and Tau Expression Plasmid Construction COS cells are maintained in T25 tissue culture flasks in high glucose MEM medium/5% fetal bovine serum. Cells from a confluent T25 flask are harvested and 80,000 cells/well are seeded into Coming 6-well tissue culture plates in a fmal volume of 2 ml/well of medium. The cells are left to grow at 37° C. for 48 hours. The cells are then washed twice in Opti-MEM containing no fetal bovine serum, and finally the cells are left in 1 ml of Opti-MEM.

Polynucleotide encoding tau protein is subcloned into plasmid pSG5 under an early SV40 promoter to generate a tau expression plasmid. The cloning of cDNA encoding tau protein is generally described in Goedert et al., *EMBO Journal*, 8(2):393–399 (1989), which is incorporated herein by reference. A GSK3 expression plasmid is prepared by subdloning polynucleotide encoding GSK3β into pCG, which is an ApEVRF derivative described in Giese et al., *Genes & Development*, 9:995–1008 (1995) and Matthias et al., *Nucleic Acid Research*, 17:6418 (1989), both of which are incorporated herein by reference.

The following solutions are prepared in 1.5 ml Eppendorf tubes: Solution A: for each transfection, 2 μg of DNA (tau expression plasmid) and 0.7 μg of DNA (GSK3 expression plasmid) are diluted into 100 μl of Opti-MEM (Gibco BRL); Solution B: for each transfection, 8 μl of Lipofectamine reagent is diluted into 100 μl of Opti-MEM. The two solutions are combined, mixed gently, and incubated at room temperature for 45 minutes to allow DNA-liposome complexes to form. For each transfection, 0.8 ml of Opti-MEM is added to the tube containing the complexes. The diluted solution is mixed gently and overlaid onto the rinsed cells. The cells are incubated with the complexed DNA/Lipofectamine for 6 hours at 37° C. in a $CO_2$ incubator. Following incubation, 1 ml of growth medium (high glucose MEM) with 20% FBS is added to each well and incubated at 37° C. overnight. The medium is replaced with fresh, complete medium at 18 hours following the start of transfection, and the cells are left to grow at 37° C. for another 48 hours.

B. Tau Phosphorylation Inhibition Assay

Two hours before harvesting, 2 μl of test compound (GSK3 inhibitor) dissolved in DMSO is added to each well and incubated at 37° C. After 2 hours the medium is removed and the cells are rapidly frozen on the plates on dry ice and stored at −70° C. Cells are thawed on ice in the presence of 200 μl of lysing buffer (1% Triton® X-100, 20 mM Tris pH 7.5, 137 mM NaCl, 15% glycerol, 25 μg/ml leupeptin, 1 μg ml pepstatin-A, 1 μM PMSF, 21 μg/ml aprotinin, 50 mM NaF, 50 mM β-glycerophosphate, 15 mM sodium pyrophosphate, 1 mM sodium orthovanadate). The contents of each well are centrifuged at 14,000 g, 4° C. for 5 minutes and the supernatants transferred to clean tubes. At this point the lysates may be stored at −20° C.

C. ELISA to Detect Phosphorylated tau in Cell Lysates

Immulon 4 strips (Dynatech) are coated with monoclonal anti-phosphorylated tau (AT8, Polymedco, Inc.) at 5 μg/ml in PBS containing Ca++ and Mg++, 100 μl/well. After overnight incubation at 4° C., the strips are washed twice with washing buffer (PBS containing 0.05% Tween® 20) and blocked with PBS containing 1% BSA, 5% normal mouse serum and 0.05% Tween® 20 at room temperature for 1 hour. The strips are washed 5 times with washing buffer. Lysate (100 μl) diluted 1:10 in PBS containing 1% BSA, 0.1% $NaN_3$ is added into each well and incubated at room temperature for 1 hour. After washing, 100 μl of 0.5 μg/ml biotinylated monoclonal anti-(non-phosphorylated) tau (HT7, Polymedco, Inc.) in PBS-BSA is added into each well. Strips are washed 5 times and HRP-conjugated streptavidin is added, incubated at room temperature for 30 minutes and washed extensively with washing buffer. TMB substrate (Pierce) is used for color development and the reaction is stopped by adding an equal volume of 0.8 M sulfuric acid. Strips are read on an ELISA plate reader using a 450 nm filter. The concentration of compound that inhibits tau phosphorylation to 50% of the maximal level (i.e., $IC_{50}$) is determined by fitting a sigmoidal curve to the plotted data.

Example 268

Testing the Potential of GSK3 Inhibitors to Protect Primary Hippocampal Cells from Glutamate Excitotoxicity Hippocampi were dissected from embryonic day 18–19 rats. The tissue was collected in Hibernate TM media (Gibco BRL) and minced into approximately 1 mm pieces. Tissue was dissociated using the Papain Dissociation System (Worthington Biochemical Corporation). Following isolation the cells were resuspended in serum-free media composed of Neurobasal TM (Gibco BRL), 2% B27 supplement (GibcoBRL), L-glutamine and antibiotics. Cells were plated in 35 mm tissue culture dishes coated with poly-L-lysine at a concentration of 7.5×104 cells per dish. Following 10–14 days at 37° C. in 5% CO2 cells were rinsed and fed with fresh media. The next day representative compounds of the invention were added to the culture media to a final concentration of between 1 nM and 100 µM. Four to eight hours following compound addition the conditioned media was removed from cells and stored at 37° C. Cultures were rinsed twice with HEPES-buffered balanced salt solution (HBSS) containing 10 µM glycine. Grabb and Choi, *J. Neuroscience* 19:1657–62 (1999). Cultures were then exposed for 5 min at room temperature to 200 µM glutamic acid in the same HBSS. Following exposure, cultures were rinsed three times with the buffer and then returned to their original conditioned media containing the compounds. Twenty to twenty-four hours following glutamic acid exposure, cultures were rinsed in HBSS and exposed for 10 min to Trypan Blue. This dye is taken up by dead cells. The cultures were rinsed and then fixed for 30 min in 4% paraformaldehyde. The number of live and dead (blue nuclei) large neurons are counted (at least 200 cells from each culture) by phase contrast microscopy and photographed. Using this method, compounds of this invention have been shown to be capable of significantly reducing the potential of glutamate to induce neuronal cell death.

Example 269

Evaluation of Efficacy in Diabetic Rodents

The glucose Tolerance Test

Compound Formulation for Oral Dosing:

Test compounds were typically formulated for oral gavage as solutions in water or suspensions in 1% carboxymethylcellulose/0.1% tween-80 (both from Sigma Chem., MO) the day prior to administration. Some early compounds were formulated as solutions in 15% Captisol (a modified cyclodexytrin by CyDex Co., IL) following procedures common to those below. For water solutions, dry and lyophilized test compound powder is solubilized in distilled water and mixed well by vortexing and sonicating. If necessary, test solution is pH adjusted with 1 N NaOH or 1 N HCl and is finally sterile filtered through a syringe appended with a 0.2 micron cellulose acetate membrane (Millipore Co., MA). For oral suspensions, the test compound powder is mixed with a fresh suspension of 1% carboxymethylcellulose/0.1% tween-80 and extensively sonicated, pH adjusted if necessary as described above, and vortexed until particle size is homogeneous and <10 micron in size.

Diabetic Mouse Glucose Tolerance Test:

Obese db/db (female C57BlKs/J) mice were obtained from Jackson Labs (Bar Harbor, Me.) at 8 weeks of age and used for efficacy testing 1–2 weeks later. On the morning of a test, food was removed early in the morning (7–8 hrs prior to the glucose bolus). Local anesthetic (EMLA creme, Astra Pharm., MA) was applied to the end of the tail and 50–100 µl blood samples were obtained from snips of the tail tip and collected into eppendorf tubes containing 5 µl 500 U/ml sodium heparin (Elkins-Sinn, NJ) with subsequent isolation of plasma. Samples were obtained at various intervals throughout the day for a total of 6–8 time points. Mice were randomized into treatment groups and administered the first oral dose of test compound (0.2 ml volume) 4.5 hr prior to the glucose and again 0.5 hr prior to administration of 0.2 ml 50% dextrose (Abbott Lab., IL) via oral gavage (oGTT) or intraperitoneal injection. After the final blood sample about 2 hr following the glucose administration, food was returned to the animals.

Regulation of Basal Glycemia and Insulinemia:

Test compounds were typically orally administered to db/db mice (see above) or ZDF rats (Genetic Models, Inc.; Indianapolis, Ind.) in the context of a multi-day, multi-dose regimen or as a single bolus. The ZDF rats were received at 8 weeks of age and used for efficacy testing 1–2 weeks later. Food was removed about 30 min prior to dosing and a single bolus of test compound (dosing volume ranging from 1–8 mg/ml) was administered. Blood was sampled as described above at 1–6 time points over the next 2–3 hr. Food was returned to the animal cages following the blood sampling.

Primary Endpoints:

Glucose and insulin levels are measured from plasma and/or blood samples. Glucose levels are measured from whole blood by the One-Touch glucometer (Lifescan Co., CA) and from plasma by Beckman glucose analyzer. Glucose results typically reflect blood values for mouse and plasma values for rat studies. Measurement of insulin levels has been via ELISA (Crystal Chem. Co., IL) following the supplier's protocol.

Results Quantitation:

Efficacy may be expressed as mg/dL glucose or ng/ml insulin or represented as area under the curve (AUC) for plasma glucose (taken above the normoglycemic baseline of 100 mg/dL) and insulin (taken above the normoinsulinemic baseline of 1 ng/mL). Typically, when expressed as AUC, the results are actually represented as reduced AUC ([(vehicle control AUC—test group AUC)/vehicle control AUCX100]). Such expression provides a single quantitative expression of the magnitude of improved glucose disposal and/or reduced basal hyperglycemia or insulin conservation relative to the placebo control group.

Results:

Representative compounds of the invention exhibited good in vitro potency, and when formulated in captisol and administered s.c. to mice (30 mg/kg), exhibited high bioavailability and tissue penetrance in vivo. A significant reduction in basal hyperglycemia just prior to the glucose tolerance test, and significantly improved glucose disposal following glucose challenge were observed. A 45–50% reduction in the AUC relative to the control group was observed if the glucose response is quantitated by determining the area under the blood glucose curve (AUC) from −60 min to +120 min. This is comparable to the efficacy obtained with Troglitazone (when dosed orally for at least several days at either 60 or 100 mg/kg/day). Also of significance was the observation that insulin levels in treated animals remained lower than in control mice.

While preferred embodiments of the invention has been illustrated and described, it will be appreciated that various changes can be made therein without departing from the spirit and scope of the invention.

What which is claimed is:

1. A compound having the structure:

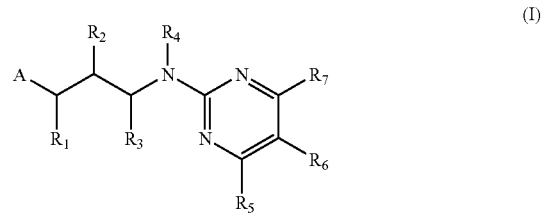

(I)

wherein:

A is selected from the group consisting of pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, and benzimidazolyl, which may be optionally substituted with from 0 to 3 substitution groups independently selected from the group consisting of nitro, amino, cyano, halo, thioamido, amidino, oxamidino, alkoxyamidino, imidino, guanidino, sulfonamido, carboxyl, formyl, loweralkyl, haloloweralkyl, loweralkoxy, haloloweralkoxy, loweralkoxyalkyl, loweralkylaminoloweralkoxy, loweralkylcarbonyl, loweraralkylcarbonyl, lowerheteroaralkylcarbonyl, alkylthia, aminoalkyl and cyanoalkyl;

$R_1$, $R_2$, $R_3$, and $R_4$ are independently selected from the group consisting of hydrogen, hydroxyl, and loweralkyl, cycloloweralkyl, cyclicaniinoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl;

$R_5$ and $R_7$ are independently selected from the group consisting of hydrogen, halo, loweralkyl, cycloalkyl, alkoxy, aminoalkoxy, alkylamino, aralkylamino, heteroaralkylamino, arylamino, heteroarylamino cycloimido, heterocycloimido, amidino, cycloamidino, heterocycloamidino, guanidinyl, aryl, biaryl, heteroaryl, heterobiaryl, heterocycloalkyl, and arylsulfonamido, which may be optionally substituted with from 0 to 5 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, atkylcarbonyl, arylcarbonyl, aralkylcarbonyl, heteroarylcarbonyl, heteroaralkylcarbonyl, alkylthio, aminoalkyl, and cyanoalkyl; and $R_6$ is selected from the group consisting of pyridyl, pyrimidinyl, piperazinyl, thiazolyl, indolyl, imidazolyl, oxadiazolyl, tetrazolyl, pyrazinyl, triazolyl, thienyl, furanyl, quinolinyl, pyrrolylpyridyl, benzothiazolyl, benzotriazolyl, and benzimidazolyl, which may he optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl;

or a pharmaceutically acceptable salt thereof.

2. A compound of claim 1 wherein A has the formula:

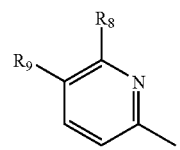

(II)

wherein $R_8$ and $R_9$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy, loweralkylcarbonyl, alkylthio, aryl and, aralkyl.

3. A compound of claim 1, wherein A is selected from the group consisting of aminopyridyl, nitropyridyl, aminonitropyridyl, cyanopyridyl, cyanothiazolyl, aminocyanopyridyl, trifluoromethylpyridyl, methoxypyridyl, methoxynitropyridyl, methoxycyanopyridyl and nitrothiazolyl.

4. A compound of claim 1, wherein at least one of $R_1$, $R_2$, $R_3$, and $R_4$ is loweralkyl selected from the group consisting of unsubstituted loweralkyl, haloloweralkyl, heterocycloaminoalkyl, and loweralkylaminoloweralkyl.

5. A compound of claim 4, wherein at least one of $R_1$, $R_2$, $R_3$, and $R_4$ is loweralkylaminoloweralkyl.

6. A compound of claim 4, wherein $R_1$, $R_2$, and $R_3$ are hydrogen and $R_4$ is selected from the group consisting of methyl, ethyl, aminoethyl, dimethylaminoethyl, pyridylethyl, piperidinyl, pyrrolidinylethyl, piperazinylethyl and morpholinylethyl.

7. A compound of claim 1, wherein at least one of $R_5$ and $R_7$ is selected from the group consisting of substituted and unsubstituted aryl, heteroaryl and biaryl.

8. A compound of claim 7, wherein at least one of $R_5$ and $R_7$ is a moiety of the formula:

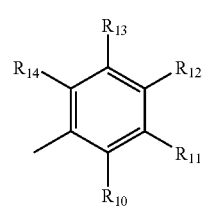

(III)

wherein $R_{10}$, $R_{11}$, $R_{12}$, $R_{13}$, and $R_{14}$ are independently selected from the group consisting of hydrogen, nitro, amino, cyano, halo, thioamido, carboxyl, hydroxy, loweralkyl, loweralkoxy, loweralkoxyalkyl, haloloweralkyl, haloloweralkoxy, aminoalkyl, alkylamino, aminoalkylalkynyl, alkylaminoalkylalkynyl, alkylthio, alkylcarbonylamino, aralkylcarbonylamino, heteroaralkylcarbonylamino, arylcarbonylamino, heteroarylcarbonylamino aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyloxyalkyl, and heteroaralkcarbonyloxyalkyl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl.

9. A compound of claim 8 wherein $R_{10}$, $R_{11}$, $R_{13}$, and $R_{14}$ are hydrogen and $R_{12}$ is selected from the group consisting of halo, loweralkyl, hydroxy, loweralkoxy, haloloweralkyl, aminocarbonyl, alkylaminocarbonyl and cyano.

10. A compound of claim 8 wherein $R_{11}$, $R_{13}$, and $R_{14}$ are hydrogen and $R_{10}$ and $R_{12}$ are independently selected from the group consisting of halo, loweralkyl, hydroxy, loweralkoxy, haloloweralkyl and cyano.

11. A compound of claim 8 wherein $R_{10}$, $R_{11}$, $R_{13}$, and $R_{14}$ are hydrogen and $R_{12}$ is heteroaryl.

12. A compound of claim 8 wherein $R_{10}$, $R_{11}$, $R_{13}$, and $R_{14}$ are hydrogen and $R_{12}$ is a heterocycloalkyl.

13. A compound of claim 8 wherein at least one of $R_{10}$, $R_{11}$, $R_{12}$, $R_{13}$, and $R_{14}$ are halo and the remainder of $R_{10}$, $R_{11}$, $R_{12}$, $R_{13}$, and $R_{14}$ are hydrogen.

14. A compound of claim 8 wherein at least one of $R_5$ and $R_7$ is selected from the group consisting of dichlorophenyl, difluorophenyl, trifluoromethylphenyl, chloro fluorophenyl, bromochlorophenyl, ethylphenyl, methylchlorophenyl, imidazolylphenyl, cyanophenyl, morphlinophenyl and cyanochlorophenyl.

15. A compound of claim 1, wherein $R_6$ is a monoketopiperazinyl group having the structure:

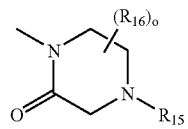

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloaryl-loweralkyl carbocyclic and heterocyclic; or $R_{16}$ can be taken with another $R_{16}$ or with $R_{15}$ to form a carbocyclic, heterocyclic or aryl ring; and o is an integer between 1 and 6.

16. A compound of claim 15, wherein $R_{15}$ is loweralkyl.

17. A compound of claim 16, wherein $R_{15}$ is selected from the group consisting of methyl, ethyl, n-propyl, isopropyl, cyclopropyl, n-butyl, isobutyl and t-butyl.

18. A compound of claim 15, wherein $R_{15}$ is taken with $R_{16}$ to form a group having the structure:

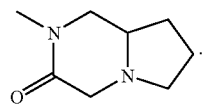

19. A compound of claim 15, wherein $R_{15}$ is taken with $R_{16}$ to form a group having the structure:

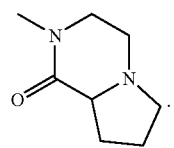

20. A compound having the structure:

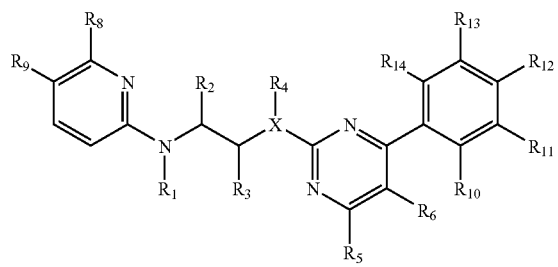

(IV)

wherein:

$R_1$, $R_2$, $R_3$ and $R_4$ are independently selected from the group consisting of hydrogen, hydroxyl, loweralkyl, cyclicaminoalkyl, alkylaminoallcyl, loweralkoxy, amino, alkylamino, alkylcarbonyl, arylcarbonyl, aralkylcarbonyl, heteroarylcarbonyl, heteroaralkylcarbonyl, aryl and heteroaryl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl;

$R_5$ is selected from the group consisting of hydrogen, halo, loweralkyl, cycloalkyl, alkoxy, aminoalkoxy, alkylamino, aralkylamino, heteroaralkylamino, arylamino, heteroarylamino cycloimido, heterocycloimido, amidino, cycloamidino, heterocycloamidino, guanidinyl, aryl, biaryl, heteroaryl, heterobiaryl, heterocycloalkyl, and arylsulfonamido, which may be optionally substituted with from 0 to 5 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkyle arbonyl, heteroarylcarbonyl, heteroaralkylcarbonyl, alkylthio, aminoalkyl, and cyanoalky;

$R_6$ is selected from the group consisting of pyridyl, pyrimidinyl, pyrrolidinyl, thiazolyl, indolyl, imidazolyl, oxadi azolyl, tetrazolyl, pyrazinyl, triazolyl, thienyl, furanyl, quinolinyl, pyrrolylpyridyl, benzothiazolyl, benzotriazolyl, and benzimidazolyl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl;

$R_8$ and $R_9$ are independently selected from the group consisting of hydrogen, hydroxy, nitro, amino, cyano, halo, thioamido, amidino, oxamidino, alkoxyamidino, imidino, guanidinyl, sulfonamido, carboxyl, formyl, loweralkyl, aminoloweralkyl, loweralkylaminoloweralkyl, haloloweralkyl, loweralkoxy, haloloweralkoxy, loweralkoxyalkyl, loweralkylaminoloweralkoxy loweralkylcarbonyl, loweraralkylcarbonyl, lowerheteroaralkylcarbonyl, alkylthio, aryl and, aralkyl; and $R_{10}$, $R_{11}$, $R_{12}$, $R_{13}$, and $R_{14}$ are independently selected from the group consisting of hydrogen, nitro, amino, cyano, halo, thioamido, carboxyl, hydroxy, loweralkyl, loweralkoxy, loweralkoxyalkyl, haloloweralkyl, haloloweralkoxy, aminoalkyl, alkylamino, alkylthio, alkylcarbonylamino, aralkylcarbonyl amino, heteroaralkylcarbonylamino, arylcarbonylamino, heteroarylcarbonylamino aminocarbonyl, loweralkylaminocarbonyl, aminoaralkyl, loweralkylaminoalkyl, aryl, heteroaryl, cycloheteroalkyl, aralkyl, and alkylcarbonyloxy, arylcarbonyloxy, aralkylcarbonyloxy, arylcarbonyloxyalkyl, alkyloxycarbonylalkyl, heteroarylcarbonyloxyalkyl, aralkycarbonyloxyalkyl, heteroaralkylcarbonyloxyalkyl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl;

wherein heteroaryl is selected from the group consisting of pyridyl, pyrimidinyl, thiazolyl, indolyl, imidazolyl, oxadiazolyl, tetrazolyl, pyrazinyl, triazolyl, thienyl, furanyl, quinolinyl, pyrrolyopyridyl, benzothiazolyl, benzotriazolyl, and benzimidazolyl, which may be optionally substituted with from 0 to 3 substitution groups independently selected from the group consisting of hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, and cyanoalkyl; and wherein heterocyclo is a cycloalkyl substituent having from 3 to 8 ring atoms comprising from 1 to 5 heteroatoms selected from the group consisting of N, O and S;

or a pharmaceutically acceptable salt thereof.

21. A compound of claim 20, wherein at least one of $R_8$ and $R_9$ is selected from the group consisting of nitro, amino, cyano, trifluoromethyl and loweralkoxy.

22. A compound of claim 20, wherein at least one of $R_1$, $R_2$, $R_3$ and $R_4$ is loweralkyl selected from the group consisting of hydrogen, unsubstituted loweralkyl, haloloweralkyl, heterocycloaminoalkyl, aminoloweralkyl and loweralkylaminoloweralkyl.

23. A compound of claim 20, wherein at least one of $R_1$, $R_2$, $R_3$ and $R_4$ is loweralkylaminoloweralkyl.

24. A compound of claim 20, wherein $R_1$, $R_2$, and $R_3$ are hydrogen and $R_4$ is selected from the group consisting of methyl, ethyl, aminoethyl, dimethylaminoethyl, pyridylethyl, piperidinyl, pyrrolidinylethyl, piperazinylethyl and morpholinylethyl.

25. A compound of claim 20, wherein $R_5$ is selected from the group consisting of hydrogen and substituted and unsubstituted aryl, heteroaryl and biaryl.

26. A compound of claim 20 wherein $R_{10}$, $R_{11}$, $R_{13}$, and $R_{14}$ are hydrogen and $R_{12}$ is selected from the group consisting of halo, loweralkyl, hydroxy, loweralkoxy, halolowcralkyl, aminocarbonyl, alkylaminocarbonyl and cyano.

27. A compound of claim 20 wherein $R_{11}$, $R_{13}$, and $R_{14}$ are hydrogen and $R_{10}$ and $R_{12}$ are independently selected from the group consisting of halo, loweralkyl, hydroxy, loweralkoxy, haloloweralkyl, aminocarbonyl and cyano.

28. A compound of claim 20 wherein $R_{10}$ is hydrogen or halo, $R_{11}$, $R_{13}$, and $R_{14}$ are hydrogen and $R_{12}$ is heteroaryl.

29. A compound of claim 20 wherein $R_{10}$ is hydrogen or halo, $R_{11}$, $R_{13}$, and $R_{14}$ are hydrogen and $R_{12}$ is a heterocycloalkyl.

30. A compound of claim 20 wherein at least one of $R_{10}$, $R_{11}$, $R_{12}$, $R_{13}$, and $R_{14}$ are halo and the remainder of $R_{10}$, $R_{11}$, $R_{12}$, $R_{13}$, and $R_{14}$ are hydrogen.

31. A compound of claim 20 wherein $R_{10}$, $R_{11}$, $R_{12}$, $R_{13}$, and $R_{14}$, taken together with the phenyl ring of structure IV, form a moiety selected from the group consisting of dieblorophenyl, difluorophenyl, trifluoromethyiphenyl, chlorofluoropheflyl, bromochlorophenyl, ethylphenyl, methylchiorophenyl, imidazolylphenyl, cyanophenyl, morpholinophenyl and cyanochlorophenyl.

32. A compound of claim 20, wherein $R_6$ is a monoketopiperazinyl group having the structure:

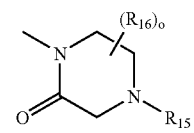

wherein $R_{15}$ and $R_{16}$ are independently selected from the group consisting of hydrogen, loweralkyl, loweralkynyl, aryl, heteroaryl, arylloweralkyl, loweralkylarylloweralkyl, haloloweralkyl, haloaryl-loweralkyl carbocyclic and heterocyclic; or $R_{16}$ can be taken with another $R_{16}$ or with $R_{15}$ to form a carbocyclic, heterocyclic or aryl ring; and o is an integer between 1 and 6.

33. A compound of claim 32, wherein $R_{15}$ is loweralkyl.

34. A compound of claim 33, wherein $R_{15}$ is selected from the group consisting of methyl, ethyl, n-propyl, isopropyl, cyclopropyl, n-butyl, isobutyl and t-butyl.

35. A compound of claim 32, wherein $R_{15}$ is taken with $R_{16}$ to form a group having the structure:

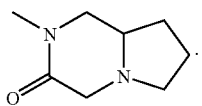

36. A compound of claim 32, wherein $R_{15}$ is taken with $R_{16}$ to form a group having the structure:

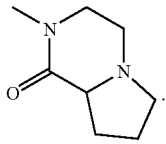

37. A composition comprising an amount of a compound of claim 1 effective to modulate GSK3 activity in a human or animal subject when administered thereto, together with a pharmaceutically acceptable carrier.

38. A composition comprising an amount of a compound of claim 20 effective to modulate GSK3 activity in a human or animal subject when administered thereto, together with a pharmaceutically acceptable carrier.

39. A method of inhibiting GSK3 activity in a human or animal subject, comprising administering to the human or animal subject in need of such treatment an effective amount of a composition of claim 37.

40. A method of inhibiting GSK3 activity in a human or animal subject, comprising administering to the human or animal subject in need of such treatment an effective amount of a composition of claim 38.

41. A method of treating a cell comprising administering to the cell an amount of a compound of claim 1 effective to inhibit GSK3 activity in the cell.

42. A method of treating a cell comprising administering to the cell an amount of a compound of claim 20 effective to inhibit GSK3 activity in the cell.

43. A method for treating diabetes or Alzheimer's disease in a human or animal subject, comprising administering to the human or animal subject in need of such treatment an amount of a composition of claim 37 effective to inhibit GSK3 activity in the subject.

44. A method of claim 43, wherein the composition is administered by a mode of administration selected from the group consisting of oral, subcutaneous, transdermal, transmucosal, iontophoretic, intravenous, intrathecal, buccal, sublingual, intranasal, and rectal administration.

\* \* \* \* \*

UNITED STATES PATENT AND TRADEMARK OFFICE
CERTIFICATE OF CORRECTION

PATENT NO. : 7,045,519 B2  Page 1 of 5
APPLICATION NO. : 09/949035
DATED : May 16, 2006
INVENTOR(S) : J.M. Nuss et al.

It is certified that error appears in the above-identified patent and that said Letters Patent is hereby corrected as shown below:

ON TITLE PAGE

| COLUMN | LINE | ERROR |
|---|---|---|
| Item (56) Pg. 5, col.1 | Refs. Cited (Other Publs.) | insert in appropriate order "CAS printout for Mills et al. (US 6,131,402).* |
| Item (56) Pg. 5, col. 1 | Refs. Cited (Other Publs., Item 64) | "GSK-62" should read --GSK-β-- |

| COLUMN | LINE | ERROR |
|---|---|---|
| 228 (Claim 1, (Structure I) | 50-60 line 2) | " |

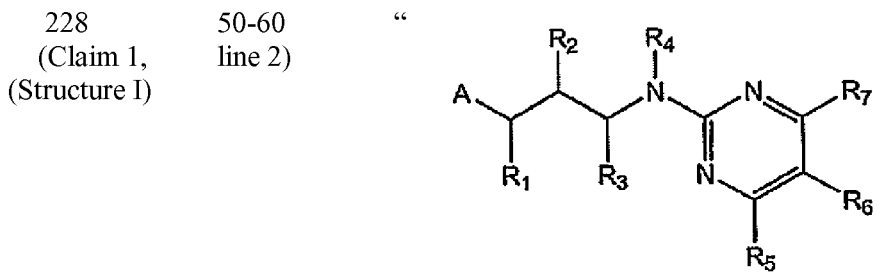

(I)"

should read --

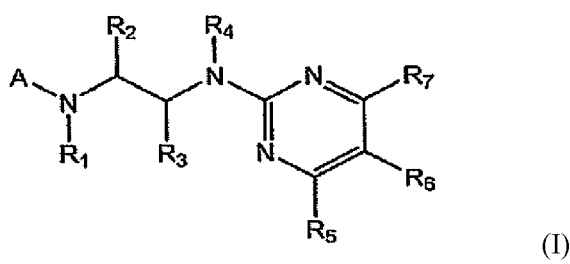

(I)--

UNITED STATES PATENT AND TRADEMARK OFFICE
CERTIFICATE OF CORRECTION

PATENT NO.        : 7,045,519 B2
APPLICATION NO.   : 09/949035
DATED             : May 16, 2006
INVENTOR(S)       : J.M. Nuss et al.

It is certified that error appears in the above-identified patent and that said Letters Patent is hereby corrected as shown below:

| COLUMN | LINE | ERROR |
|---|---|---|
| 229 (Claim 1, | 9 line 16 of text) | "alkylthia," should read --alkylthio,-- |
| 229 (Claim 1, | 12 line 19 of text) | "cyclicaniinoalkyl," should read --cyclicaminoalkyl,-- |
| 229 (Claim 1, | 45 line 48 of text) | "atkylcarbonyl," should read --alkycarbonyl,-- |
| 229 (Claim 1, | 54 line 56 of text) | "he" should read --be-- |
| 231 (Claim 8, | 2 line 19 of text) | "heteroaralkcarbonyloxyalkyl," should read --heteroaralkylcarbonyloxyalkyl,-- |
| 231 (Claim 14, | 29 line 1) | "$R_5$and" should read --$R_5$ and-- |
| 231 (Claim 14, | 31 line 3) | "chloro fluorophenyl," should read --chlorofluorophenyl,-- |
| 231 (Claim 14, | 35 line 6) | "cyanochiorophenyl." should read --cyanochlorophenyl.-- |

UNITED STATES PATENT AND TRADEMARK OFFICE
CERTIFICATE OF CORRECTION

PATENT NO. : 7,045,519 B2  
APPLICATION NO. : 09/949035  
DATED : May 16, 2006  
INVENTOR(S) : J.M. Nuss et al.

Page 3 of 5

It is certified that error appears in the above-identified patent and that said Letters Patent is hereby corrected as shown below:

| COLUMN | LINE | ERROR |
|---|---|---|
| 232 (Claim 20, | 10-20 line) | " 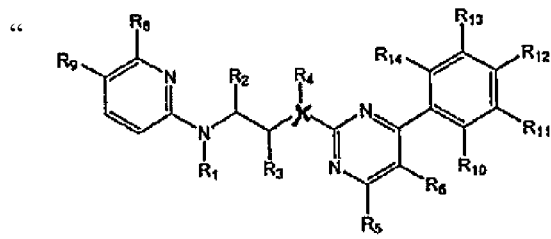 (IV)" should read -- 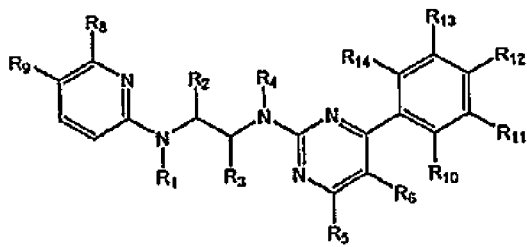 (IV) -- |
| 232 (Claim 20, | 27 line 5 of text) | before "cycliaminoalkyl," insert --cycloloweralkyl,-- |

UNITED STATES PATENT AND TRADEMARK OFFICE
CERTIFICATE OF CORRECTION

PATENT NO. : 7,045,519 B2
APPLICATION NO. : 09/949035
DATED : May 16, 2006
INVENTOR(S) : J.M. Nuss et al.

It is certified that error appears in the above-identified patent and that said Letters Patent is hereby corrected as shown below:

| COLUMN | LINE | ERROR |
|---|---|---|
| 232 (Claim 20, | 27 line 6 of text) | "alkylaminoallcyl," should read --alkylaminoalkyl,-- |
| 232 (Claim 20, | 56 line 34 of text) | "aralkyle arbonyl," should read --aralkylcarbonyl,-- |
| 232 (Claim 20, | 61 line 39 of text) | "oxadi azolyl," should read --oxadiazolyl,-- |
| 233 (Claim 20, | 23 line 68 of text) | "aralkylcarbonyl amino," should read --aralkylcarbonylamino,-- |
| 234 (Claim 26, | 19 line 4) | "halolowcralkyl," should read --haloloweralkyl,-- |
| 234 (Claim 31, | 38 line 4) | "dieblorophenyl," should read --dichlorophenyl,-- |
| 234 (Claim 31, | 38 line 4) | "trifluoromethyiphenyl," should read --trifluoromethylphenyl,-- |
| 234 (Claim 31, | 39 line 5) | "chlorofluoropheflyl," should read --chlorofluorophenyl,-- |

UNITED STATES PATENT AND TRADEMARK OFFICE
CERTIFICATE OF CORRECTION

PATENT NO. : 7,045,519 B2
APPLICATION NO. : 09/949035
DATED : May 16, 2006
INVENTOR(S) : J.M. Nuss et al.

It is certified that error appears in the above-identified patent and that said Letters Patent is hereby corrected as shown below:

| COLUMN | LINE | ERROR |
|---|---|---|
| 234 (Claim 31, | 40 line 6) | "methylchiorophenyl," should read --methylchlorophenyl,-- |

Signed and Sealed this

Sixteenth Day of January, 2007

JON W. DUDAS
*Director of the United States Patent and Trademark Office*